(12) United States Patent
Carpenter et al.

(10) Patent No.: US 11,168,079 B2
(45) Date of Patent: Nov. 9, 2021

(54) ALKENE COMPOUNDS AS FARNESOID X RECEPTOR MODULATORS

(71) Applicant: BRISTOL-MYERS SQUIBB COMPANY, Princeton, NJ (US)

(72) Inventors: Joseph E. Carpenter, Bountiful, UT (US); Matthias Broekema, New Hope, PA (US); Jianxin Feng, Bensalem, PA (US); Chunjian Liu, Pennington, NJ (US); Wei Wang, Princeton, NJ (US); Ying Wang, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/759,660

(22) PCT Filed: Oct. 31, 2018

(86) PCT No.: PCT/US2018/058323
§ 371 (c)(1),
(2) Date: Apr. 27, 2020

(87) PCT Pub. No.: WO2019/089670
PCT Pub. Date: May 9, 2019

(65) Prior Publication Data
US 2020/0283430 A1 Sep. 10, 2020

Related U.S. Application Data

(60) Provisional application No. 62/580,060, filed on Nov. 1, 2017.

(51) Int. Cl.
| C07D 401/14 | (2006.01) |
| A61K 31/4545 | (2006.01) |
| C07D 413/14 | (2006.01) |
| C07D 417/14 | (2006.01) |
| C07D 471/04 | (2006.01) |
| C07D 471/08 | (2006.01) |
| C07D 487/04 | (2006.01) |
| C07D 519/00 | (2006.01) |

(52) U.S. Cl.
CPC ......... *C07D 413/14* (2013.01); *C07D 417/14* (2013.01); *C07D 471/04* (2013.01); *C07D 471/08* (2013.01); *C07D 487/04* (2013.01); *C07D 519/00* (2013.01)

(58) Field of Classification Search
CPC .. C07D 401/14; C07D 413/14; C07D 417/14; C07D 471/04; A61K 31/4545; A61K 31/4525; A61K 31/4535; A61P 3/00; A61P 29/00; A61P 35/00
USPC ......... 546/194, 198, 209; 514/318, 321, 326
See application file for complete search history.

(56) References Cited

U.S. PATENT DOCUMENTS

| 8,158,665 | B2 | 4/2012 | Caldwell et al. |
| 8,907,095 | B2 | 12/2014 | Xia et al. |
| 9,539,244 | B2 | 1/2017 | Kinzel et al. |
| 9,751,874 | B2 | 9/2017 | Gege et al. |
| 2003/0130296 | A1 | 7/2003 | Bauer et al. |
| 2004/0048316 | A1 | 3/2004 | Haffner et al. |
| 2006/0258725 | A1 | 11/2006 | Boggs et al. |
| 2008/0096921 | A1 | 4/2008 | Navas, III et al. |
| 2008/0167356 | A1 | 7/2008 | Caldwell et al. |
| 2008/0306125 | A1 | 12/2008 | Bell et al. |
| 2009/0093524 | A1 | 4/2009 | Bell et al. |
| 2009/0270460 | A1 | 10/2009 | Bell et al. |
| 2010/0035918 | A1 | 2/2010 | Guckian et al. |
| 2010/0152166 | A1 | 6/2010 | Genin et al. |
| 2010/0184809 | A1 | 7/2010 | Kremoser et al. |
| 2010/0210660 | A1 | 8/2010 | Kremoser et al. |
| 2010/0249179 | A1 | 9/2010 | Deaton et al. |
| 2011/0034507 | A1 | 2/2011 | Akwabi-Ameyaw et al. |
| 2011/0092512 | A1 | 4/2011 | Ackermann et al. |
| 2011/0230493 | A1 | 9/2011 | Long et al. |
| 2012/0232116 | A1 | 9/2012 | Krernoser et al. |
| 2013/0261108 | A1 | 10/2013 | Tully et al. |
| 2013/0331349 | A1 | 12/2013 | Tully et al. |

(Continued)

FOREIGN PATENT DOCUMENTS

| CN | 106146483 A | 11/2016 |
| CN | 106632294 A | 5/2017 |

(Continued)

OTHER PUBLICATIONS

Claudel, Thierry et al., "The Farnesoid X Receptor: A Novel Drug Target?", Expert Opin. Investig. Drugs, vol. 13(9), pp. 1135-1148, (2004).

(Continued)

*Primary Examiner* — Charanjit Aulakh
(74) *Attorney, Agent, or Firm* — Gary Greenblatt

(57) ABSTRACT

The present invention provides compounds of Formula (I): Formula (I) or stereoisomers, tautomers, or pharmaceutically acceptable salts or solvates thereof, wherein all the variables are as defined herein. These compounds modulate the activity of farnesoid X receptor (FXR), for example, as agonists. This invention also relates to pharmaceutical compositions comprising these compounds and methods of treating a disease, disorder, or condition associated with FXR dysregulation, such as pathological fibrosis, transplant rejection, cancer, osteoporosis, and inflammatory disorders, by using the compounds and pharmaceutical compositions.

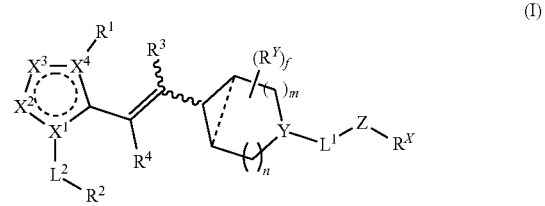

11 Claims, No Drawings

(56) References Cited

U.S. PATENT DOCUMENTS

| | | |
|---|---|---|
| 2014/0039007 A1 | 2/2014 | Tully et al. |
| 2014/0221659 A1 | 8/2014 | Kinzei et al. |
| 2015/0218187 A1 | 8/2015 | Koul et al. |
| 2015/0366856 A1 | 12/2015 | Tully et al. |
| 2016/0176861 A1 | 6/2016 | Gege et al. |
| 2017/0298068 A1 | 10/2017 | Gege et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2019/0002452 A1 | 1/2019 | Zhang et al. |

FOREIGN PATENT DOCUMENTS

| | | |
|---|---|---|
| CN | 107021958 A | 8/2017 |
| EP | 3034499 A1 | 6/2016 |
| EP | 3401315 A1 | 11/2018 |
| WO | WO199313101 A1 | 7/1993 |
| WO | WO199817276 A1 | 4/1998 |
| WO | WO2006006490 A1 | 1/2006 |
| WO | WO2008051942 A2 | 5/2008 |
| WO | WO2009009059 A1 | 1/2009 |
| WO | WO2009149795 A2 | 12/2009 |
| WO | WO2012087520 A1 | 6/2012 |
| WO | WO2013007387 A1 | 1/2013 |
| WO | WO2013186159 A1 | 12/2013 |
| WO | WO2017133521 A1 | 8/2017 |
| WO | WO2017145040 A1 | 8/2017 |
| WO | WO2017145041 A1 | 8/2017 |
| WO | WO2018059314 A1 | 4/2018 |

OTHER PUBLICATIONS

International Preliminary Report on Patentability for PCT/US2018/058323, dated May 5, 2020 for 12880-WO-PCT.

Matthew Lantz Crawley, "Farnesoid X receptor modulators: a patent review," Expert Opinion on Therapeutic Patents, (2010) 20:8, pp. 1047-1057.

Sepe, Valentina et al., "Farnesoid X Receptor Modulators 2014-present: A Patent Review", Expert Opinion on Therapeutic Patents, vol. 28, No. 5, pp. 351-364 (2018).

Tully, David C. et al., "Discovery of Tropifexor (LJN452), a Highly Potent Non-bile Acid FXR Agonist for the Treatment of Cholestatic Liver Diseases and Nonalcoholic Steatohepatitis (NASH)", Journal of Medicinal Chemistry, vol. 60, pp. 9960-9973 (2017).

ALKENE COMPOUNDS AS FARNESOID X RECEPTOR MODULATORS

CROSS REFERENCE

This application is a 371 application of International Application No. PCT/US2018/058323 filed on Oct. 31, 2018, which claims the benefit of U.S. Provisional Application Ser. No. 62/580,060, filed Nov. 1, 2017, the content of each is hereby fully incorporated by reference in its entirety for all purposes.

DESCRIPTION

The present invention relates generally to compounds useful as farnesoid X receptor (FXR) modulators, pharmaceutical compositions comprising such compounds and to their use in therapy, especially in the treatment or prophylaxis of diseases, disorders, and conditions for which an FXR modulator is indicated.

FXR or NR1H4 (nuclear receptor subfamily 1, group H, member 4) is a nuclear receptor that can activate the expression of specific target genes in a ligand-dependent manner. FXR is expressed in the liver, throughout the gastrointestinal tract, colon, ovary, adrenal gland, kidney, and in the gall bladder and biliary tree in humans. FXR forms a heterodimer with Retinoid X Receptor (RXR) and binds to specific response elements in target genes to regulate gene transcription (B. M. Forman et al., Cell 1995; 81: 687; W. Seol et al., Mol. Endocrinol. 1995; 9: 72). The FXR/RXR heterodimer typically binds to an inverted repeat of a consensus hexanucleotide sequence (AGGTCA) separated by a single nucleotide, i.e. an IR-1 sequence. The relevant physiological ligands of FXR are bile acids including chenodeoxycholic acid and its taurine-conjugate (D. J. Parks et al., Science 1999; 284: 1365; M. Makishima et al., Science 1999; 284: 1362). FXR activation regulates the expression of multiple genes that encode enzymes and transporters involved in bile acid synthesis, influx, and efflux from the liver and intestine resulting in a net decrease in total endogenous bile acids in a negative feedback loop. FXR is involved in paracrine and endocrine signaling by upregulating the expression of the cytokine Fibroblast Growth Factor 15 (rodents) or 19 (primates), which can also contribute to the regulation of bile acid concentrations (Holt et al., Genes Dev. 2003; 17: 1581; Inagaki et al., Cell Metab 2005; 2: 217). Therefore, FXR is considered to be a master regulator of bile acid homeostasis.

One use of FXR agonists is for the treatment of diseases in which bile acids are dysregulated, including cholestatic diseases (e.g. primary biliary cirrhosis and primary sclerosing cholangitis) that can lead to fibrosis, cirrhosis, cholangiocarcinoma, hepatocellular carcinoma, liver failure, and death. While elevated bile acid concentrations in the liver have deleterious effects, bile acids also affect the microflora and integrity of the small intestine. Obstruction of bile flow in humans or rodents causes proliferation of intestinal bacteria and mucosal injury, which can lead to bacterial translocation across the mucosal barrier and systemic infection (Berg, Trends Microbiol. 1995; 3: 149-154). Mice lacking FXR have increased ileal levels of bacteria and a compromised epithelial barrier, while activation of intestinal FXR plays an important role in preventing bacterial overgrowth and maintaining the integrity of the intestinal epithelium (Inagaki et al., Proc Natl Acad Sci 2006; 103: 3920-3925). Over time, FXR null mice spontaneously develop hepatocellular carcinoma, and this can be abrogated by selective re-activation of FXR in the intestine (Degirolamo et al., Hepatology 61: 161-170). Pharmacological activation of FXR with a small molecule agonist or transgenic expression of FXR in the intestine can normalize bile acid concentrations, decrease cellular proliferation in hepatic bile ducts, and reduce inflammatory cell infiltration, necrotic area, and liver fibrosis in rodent models of cholestasis (Liu et al., J. Clin. Invest. 2003; 112:1678-1687; Modica et al., Gastroenterology. 2012; 142: 355-365). Some of these beneficial effects observed in preclinical models of cholestasis have translated to human patients, and the FXR agonist, obeticholic acid (OCA or OCALIVA™), has been approved for the treatment of primary biliary cirrhosis (https://www.fda.gov/newsevents/newsroom/pressannouncements/ucm503964.htm).

In addition to controlling bile acid homeostasis, FXR agonists regulate the hepatic expression of hundreds of genes encoding proteins involved in cholesterol and lipid metabolism and transport, glucose homeostasis, inflammation, chemotaxis, and apoptosis among other pathways (Zhan et al., PLoS One 2014; 9: e105930; Ijssennagger et al., J Hepatol 2016; 64: 1158-1166). Consistent with these broad effects on gene expression, FXR agonists have also been investigated in preclinical models of fibrosis, cancer, inflammatory diseases, and metabolic disorders, including dyslipidemia, obesity, type 2 diabetes, nonalcoholic fatty liver disease (NAFLD) and metabolic syndrome (Crawley, Expert Opin. Ther. Patents 2010; 20:1047-1057).

FXR agonists are also being investigated in human clinical trials for the treatment of NAFLD, a more advanced form of fatty liver disease, nonalcoholic steatohepatitis (NASH), and associated complications. NAFLD is one of the most common causes of chronic liver disease in the world today (Vernon et al., Aliment Pharmacol Ther 2011; 34:274-285). The risk factors for developing NAFLD include obesity, type 2 diabetes mellitus (T2DM), insulin resistance, hypertension, and dyslipidemia. In a 6-week clinical trial in T2DM patients with NAFLD, the FXR agonist OCA statistically significantly improved insulin sensitivity and reduced body weight, showing beneficial effects on some of these risk factors (Mudaliar et al., Gastroenterology 2013; 145: 574-582). NASH is the most severe and progressive form of NAFLD and includes the histological findings of hepatic steatosis, inflammation, and ballooning degeneration with varying amounts of pericellular fibrosis (Sanyal et al., Hepatology 2015; 61:1392-1405). In a 72-week clinical trial in patients with NASH, OCA statistically significantly improved hepatic steatosis, lobular inflammation, hepatocyte ballooning, and fibrosis as assessed by histological analyses of liver biopsies (Neuschwander-Tetri et al., Lancet 2015; 385: 956-965). These data also suggest the potential for FXR agonists to show benefit on clinical outcomes given that NASH is the second leading cause of hepatocellular carcinoma (HCC) and liver transplantation in the United States (Wong et al., Hepatology 2014; 59: 2188-2195).

The present invention provides novel compounds for treating a disease, disorder, or condition associated with farnesoid X receptor (FXR) activity in a patient in need thereof.

SUMMARY OF THE INVENTION

In one aspect, the present invention provides compounds of Formula (I) and (II) as well as the subgenera and species thereof, including stereoisomers, tautomers, pharmaceutically acceptable salts, and solvates thereof, which are useful as FXR modulators.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with activity of farnesoid X receptor (FXR) in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used, either as a single agent or in combination with other agents, in the treatment of a disease, disorder, or condition selected from nonalcoholic steatohepatitis (NASH), non-alcoholic fatty liver disease (NAFLD), chronic kidney disease, diabetic kidney disease, primary sclerosing cholangitis (PSC), and primary biliary cirrhosis (PBC). The compounds of the invention may be used, either as a single agent or in combination with other agents, in the treatment of idiopathic pulmonary fibrosis (IPF).

The compounds of the invention may be used for the manufacture of a medicament for the treatment of a disease, disorder, or condition in a patient in need of such treatment.

Other features and advantages of the invention will be apparent from the following detailed description and claims.

DETAILED DESCRIPTION

The present application provides compounds, including all stereoisomers, solvates, prodrugs and pharmaceutically acceptable salt and solvate forms thereof, according to Formula (I). The present application also provides pharmaceutical compositions containing at least one compound according to Formula (I), or a stereoisomer, a tautomer, or a pharmaceutically acceptable salt or a solvate thereof, and optionally at least one additional therapeutic agent. Additionally, the present application provides methods for treating a patient suffering from a FXR-modulated disease or disorder such as for example, biliary fibrosis, liver fibrosis, renal fibrosis, Non-Alcoholic Fatty Liver Disease (NAFLD), Non-Alcoholic Steato-Hepatitis (NASH), primary sclerosing cholangitis (PSC), primary biliary cirrhosis (PBC), and pancreatic fibrosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

I. Compounds of the Invention

In one embodiment, the present invention provides a compound of Formula (I):

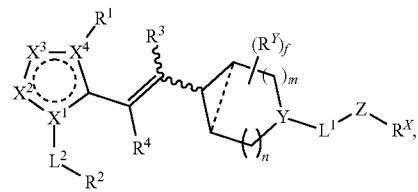

or a stereoisomer, a tautomer, or a pharmaceutically acceptable salt or solvate thereof; wherein:

$X^1$ and $X^4$ are each independently C or N;

$X^2$ and $X^3$ are each independently $CR^5$, N, $NR^6$, O, or S;

Y is $CR^7$, or N;

the dashed straight line is an optional covalent bond;

m and n are each independently an integer of 0, 1, or 2; provided that when m and n are both 0, then the optional covalent bond of the dashed line is absent;

f is an integer of 0, 1, 2, or 3;

Z is 6- to 10-membered aryl, 5- to 10-membered heteroaryl, 3- to 10-membered carbocyclyl, or 4- to 10-membered heterocyclyl, wherein the aryl, heteroaryl, carbocyclyl, and heterocyclyl are independently substituted with 0 to 5 $R^8$;

$L^1$ is a covalent bond, O, S, $NR^{17}$, —$S(O)_2$—, $C_{1-3}$ alkylene, $C_{1-3}$ heteroalkylene, $C_{2-4}$ alkenylene, $C_{2-4}$ alkynylene, aryl, or a 5- to 6-membered heteroaryl containing 1 to 4 heteroatoms independently selected from N, O, and S; wherein the alkylene, heteroalkylene, aryl, and heteroaryl are each independently substituted with 0 to 3 $R^{11}$;

$L^2$ is a covalent bond, O, S, $NR^{18}$, $C_{1-3}$ alkylene, or $C_{1-3}$ heteroalkylene, wherein the alkylene and heteroalkylene are independently substituted with 0 to 3 $R^{16}$;

$R^X$ is -$L^3$-R;

$L^3$ is a covalent bond, a $C_{1-3}$ alkylene, or —C(O)$NR^{12}$—$CH_2$—, wherein the $C_{1-3}$ alkylene is substituted with 0 to 3 $R^{15}$;

$R^Z$ is —CN, —C(O)$OR^{13}$, —C(O)$NR^{14a}R^{14b}$

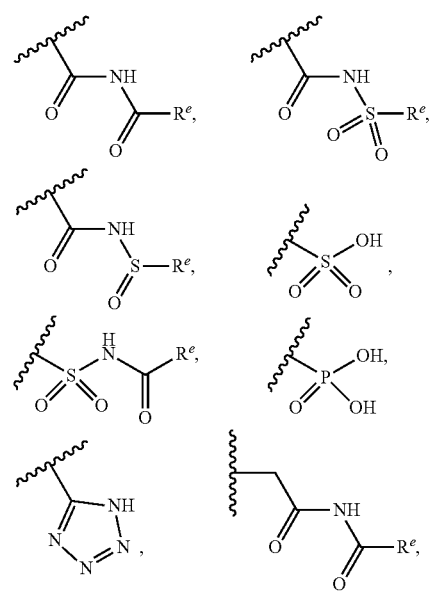

-continued

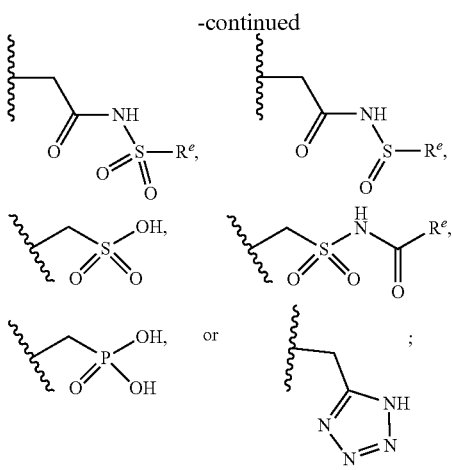

$R^e$ is $C_{1-6}$ alkyl, $C_{3-6}$ cycloalkyl, haloalkyl, hydroxyalkyl, aminoalkyl, alkoxyalkyl, or haloalkoxyalkyl;

each $R^Y$ is independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; or alternatively two $R^Y$, together with the carbon atoms to which they are attached, form a bridge moiety; and with the proviso that when Y is N and $R^Y$ is attached to a carbon atom adjacent to Y, then $R^Y$ is not halo, cyano, hydroxyl, amino, alkoxy, or haloalkoxy;

$R^1$ is $C_{1-6}$ alkyl, $C_{3-5}$ cycloalkyl, or $C_{4-6}$ heterocyclyl, wherein the alkyl and cycloalkyl are substituted with 0 to 3 $R^9$;

$R^2$ is 6- to 10-membered aryl, 5- to 10-membered heteroaryl, 3- to 10-membered carbocyclyl, or 4- to 10-membered heterocyclyl, wherein the aryl, heteroaryl, carbocyclyl, and heterocyclyl are independently substituted with 0 to 5 $R^{10}$;

$R^3$ and $R^4$ are each independently hydrogen, $C_{1-6}$ alkyl, haloalkyl, hydroxyalkyl, aminoalkyl, alkoxyalkyl, or haloalkoxyalkyl;

$R^5$ and $R^7$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^6$, $R^{17}$ and $R^{18}$ are each independently is hydrogen, $C_{1-6}$ alkyl, haloalkyl, hydroxyalkyl, aminoalkyl, alkoxyalkyl, or haloalkoxyalkyl;

$R^8$ and $R^{10}$ are each independently halo, cyano, hydroxyl, amino, oxo, $-OR^a$, $-SR^a$, $=S$, $-NR^cR^c$, $=NH$, $=N-OH$, $=NR^a$, $=N-OR^a$, $-NO_2$, $-S(O)_2R^a$, $-S(O)_2NHR^b$, $-S(O)_2NR^cR^c$, $-S(O)_2OR^b$, $-OS(O)_2R^b$, $-OS(O)_2OR^b$, $-P(O)(OR^b)(OR^b)$, $-C(O)R^b$, $-C(NR^b)R^b$, $-C(O)OR^b$, $-C(O)NR^cR^c$, $-C(NR^b)NR^cR^c$, $-OC(O)R^b$, $-NR^bC(O)R^b$, $-OC(O)OR^b$, $-NR^bC(O)OR^b$, $-OC(O)NR^cR^c$, $-NR^bC(O)NR^cR^c$, $-NR^bC(NR^b)R^b$, $-NR^bC(NR^b)NR^cR^c$, $C_{1-6}$ alkyl, $C_{1-6}$ haloalkyl, aryl, arylalkyl, heteroaryl, carbocyclyl, or heterocyclyl; wherein the alkyl, aryl, heteroaryl, carbocyclyl, and heterocyclyl, by themselves or as part of another group, are each independently substituted with 0 to 5 $R^d$;

$R^b$ is each independently hydrogen or $R^a$;

$R^c$ is each independently $R^b$ or alternatively, the two $R^c$ are taken together with the nitrogen atom to which they are bonded form a 4, 5, 6 or 7 membered heterocyclyl;

$R^d$ is each independently $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, $-OR^a$, $-SR^a$, $=S$, $-NR^cR^c$, $=NH$, $=N-OH$, $=NR^a$, $=N-OR^a$, $-NO_2$, $-S(O)_2R^a$, $-S(O)_2NHR^b$, $-S(O)_2NR^cR^c$, $-S(O)_2OR^b$, $-OS(O)_2R^b$, $-OS(O)_2OR^b$, $-P(O)(OR^b)(OR^b)$, $-C(O)R^b$, $-C(NR^b)R^b$, $-C(O)OR^b$, $-C(O)NR^cR^c$, $-C(NR^b)NR^cR^c$, $-OC(O)R^b$, $-NR^bC(O)R^b$, $-OC(O)OR^b$, $-NR^bC(O)OR^b$, $-NR^bC(O)NR^cR^c$, $-NR^bC(NR^b)R^b$, or $-NR^bC(NR^b)NR^cR^c$;

$R^9$ is each independently halo, cyano, hydroxyl, amino, or $C_{1-6}$ alkyl;

$R^{11}$ and $R^{16}$ are each independently halo, oxo, cyano, hydroxyl, amino, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy;

$R^{12}$ are each independently hydrogen or $C_{1-4}$ alkyl;

$R^{13}$ is hydrogen, $C_{1-10}$ alkyl, or glycosyl;

$R^{14a}$ and $R^{14b}$ are each independently hydrogen, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy; and $R^{15}$ are each independently halo, oxo, cyano, hydroxyl, amino, alkyl, alkoxy, or alkylamino; or alternatively, two $R^{15}$, taken together with the atom(s) to which they are attached, form a carbocyclyl or heterocyclyl moiety.

In any one of the preceding embodiments of Formula (I), $X^2$ is N or $NR^6$.

It should be understood by one skilled in the art that the dashed circle in Formula (I) denotes an aromatic ring formed by $X^1$, $X^2$, $X^3$, $X^4$, and the carbon atom; and the dashed straight line is an optional covalent bond; and the wavy or squiggly lines indicate the inclusion of geometric isomers, e.g., $R^3$ and $R^4$ can be at either cis or trans positions.

In one embodiment of Formula (I), the compound is represented by Formula (Ia):

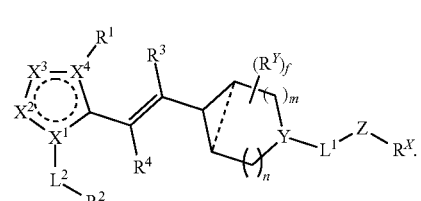

(Ia)

In one embodiment of Formula (I), the compound is represented by Formula (Ia):

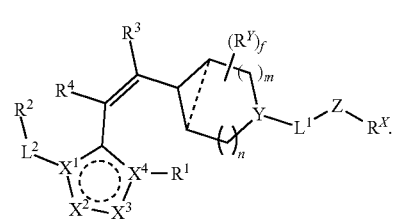

(Ib)

In any one of the preceding embodiments of Formula (I), Formula (Ia), or Formula (Ib), two $R^Y$, together form a $C_{1-3}$ alkylene bridge moiety. $(R^Y)_f$ denotes one or more optional substituent groups on any of the ring member atoms, and each of $R^Y$ is independent and can be the same or different.

In any one of the preceding embodiments of Formula (I), Formula (Ia), or Formula (Ib), the

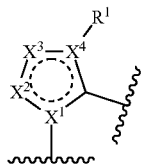

moiety is

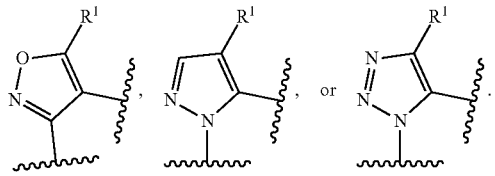

In any one of the preceding embodiments of Formula (I), Formula (Ia), or Formula (Ib), the

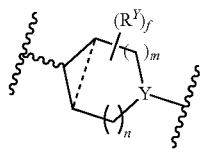

moiety is

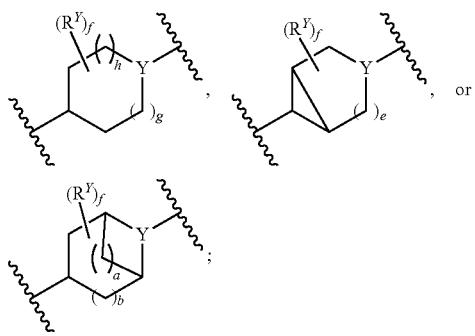

h and g are each independently an integer of 0 or 1;
e is an integer of 1 or 2;
a is an integer of 1 or 2;
b is an integer of 1 or 2;
f is an integer of 0, 1, or 2; and
each $R^Y$ is independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy.

In any one of the preceding embodiments of Formula (I), Formula (Ia), or Formula (Ib), the

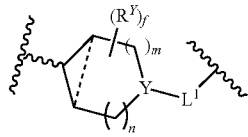

moiety is:

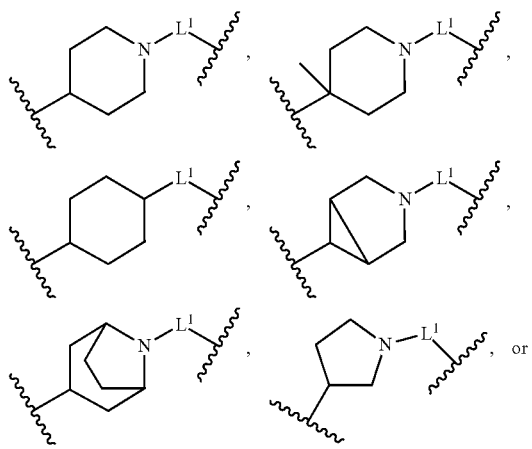

In any one of the preceding embodiments of Formula (I), Formula (Ia), or Formula (Ib), Z is phenyl or 5- to 10-membered heteroaryl, wherein the phenyl and heteroaryl are independently substituted with 0 to 5 $R^8$, wherein $R^8$ is the same as defined above.

In any one of the preceding embodiments of Formula (I), Formula (Ia), or Formula (Ib), $L^1$ is a covalent bond.

In any one of the preceding embodiments of Formula (I), Formula (Ia), or Formula (Ib), —Z—$R^x$ is selected from

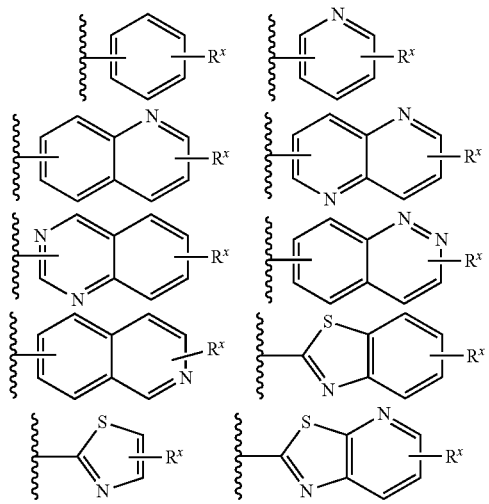

-continued

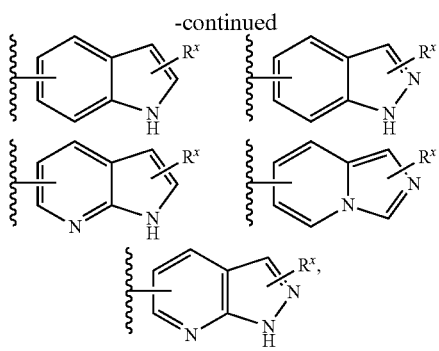

wherein the Z moiety is further substituted with 0 to 3 $R^8$, and $R^8$ is the same as defined above.

In any one of the preceding embodiments of Formula (I), Formula (Ia), or Formula (Ib), Y is N.

In any one of the preceding embodiments of Formula (I), Formula (Ia), or Formula (Ib), Y is CH; and $L^1$ is a covalent bond, O, S, or NH.

In any one of the preceding embodiments of Formula (I), Formula (Ia), or Formula (Ib), $R^2$ is phenyl or 6-membered heteroaryl, wherein the phenyl and heteroaryl are substituted with 0 to 3 $R^{10}$.

In any one of the preceding embodiments of Formula (I), Formula (Ia), or Formula (Ib), $L^2$ is a covalent bond.

In any one of the preceding embodiments of Formula (I), Formula (Ia), or Formula (Ib), $R^3$ and $R^4$ are each independently hydrogen or $C_{1-6}$ alkyl.

In one embodiment of Formula (I), the compound is represented by Formula (II):

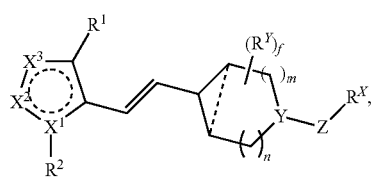

(II)

$X^1$ is C or N;

$X^2$ and $X^3$ are each independently CH, N, O, or S;

Z is phenyl or a 5- to 10-membered heteroaryl, wherein the phenyl and heteroaryl are independently substituted with 0 to 3 $R^8$;

m and n are each independently an integer of 0 or 1; provided that when m and n are both 0, then the optional covalent bond of the dashed line is absent;

$R^X$ is —C(O)O$R^{13}$;

each $R^Y$ is independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

f is an integer of 0, 1, or 2;

$R^1$ is $C_{1-6}$ alkyl or $C_{3-5}$ cycloalkyl, wherein the alkyl and cycloalkyl are independently substituted with 0 to 3 $R^9$;

$R^2$ is phenyl or 6-membered heteroaryl, wherein the phenyl and heteroaryl are independently substituted with 0 to 3 $R^{10}$; and $R^8$, $R^9$, $R^{10}$, and $R^{13}$ are the same as defined above.

In one embodiment of Formula (II), the

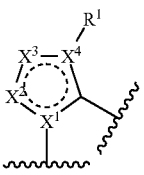

moiety is or

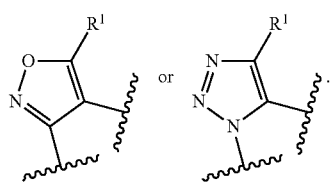

In any one of the preceding embodiments of Formula (II), $R^2$ is phenyl or pyridinyl, each of which is independently substituted with 0 to 3 $R^{10}$.

In any one of the preceding embodiments of Formula (II), wherein m and n are both 1.

In any one of the preceding embodiments of Formula (II), f is 0.

In any one of the preceding embodiments of Formula (II), Z is a 5- or 6-membered monocyclic heteroaryl or 8- to 10-membered bicyclic heteroaryl, wherein each of the heteroaryls is independently substituted with 0 to 3 $R^8$.

In any one of the preceding embodiments of Formula (II), $R^X$ is —C(O)OH.

In one embodiment of Formula (I), Formula (Ia), Formula (Ib), or Formula (II), $X^1$ is C.

In one embodiment of Formula (I), Formula (Ia), Formula (Ib), or Formula (II), $X^2$ is N.

In one embodiment of Formula (I), Formula (Ia), Formula (Ib), or Formula (II), $X^3$ is O.

In one embodiment of Formula (I), Formula (Ia), or Formula (Ib), $X^4$ is C.

In one embodiment of Formula (I), Formula (Ia), or Formula (Ib), $X^1$ is C and $X^4$ is C.

In one embodiment of Formula (I) Formula (Ia), Formula (Ib), or Formula (II), one of $X^2$ and $X^3$ is N and the other of $X^2$ and $X^3$ is O.

In one embodiment of Formula (I), Formula (Ia), Formula (Ib), or Formula (II), $X^2$ is N and $X^3$ is O.

In one embodiment of Formula (I), Formula (Ia), Formula (Ib), or Formula (II), $X^2$ is O and $X^3$ is N.

In one embodiment of Formula (I), Formula (Ia), Formula (Ib), or Formula (II), $X^1$ is C; $X^2$ is N; and $X^3$ is O.

In one embodiment of Formula (I), Formula (Ia), or Formula (Ib), $X^1$ is C; one of $X^2$ and $X^3$ is N and the other of $X^2$ and $X^3$ is O; and $X^4$ is C.

In one embodiment of Formula (I), Formula (Ia), or Formula (Ib), $X^1$ is C; $X^2$ is N; $X^3$ is O; and $X^4$ is C.

In one embodiment of Formula (I), Formula (Ia), or Formula (Ib), $X^1$ is C; $X^2$ is O; $X^3$ is N; and $X^4$ is C.

In one embodiment of Formula (I), Formula (Ia), Formula (Ib), or Formula (II), $X^1$ is N; $X^2$ is N; and $X^3$ is N.

In one embodiment of Formula (I), Formula (Ia), or Formula (Ib), the

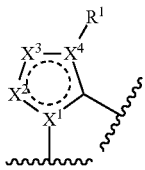

moiety is

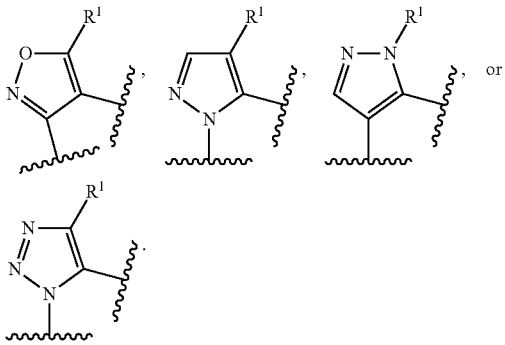

In one embodiment of Formula (II), the

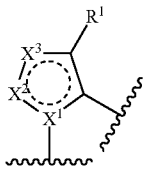

moiety is

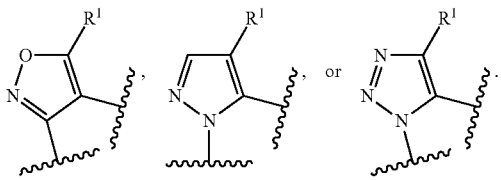

In one embodiment of Formula (I), Formula (Ia), Formula (Ib), or Formula (II), the

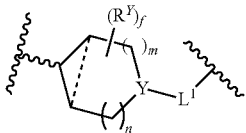

moiety is:

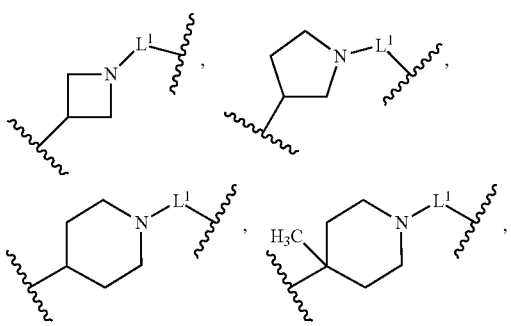

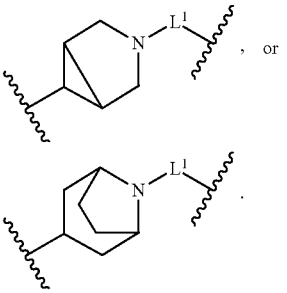

In one embodiment of Formula (I), Formula (Ia), Formula (Ib), or Formula (II), $L^1$ is a covalent bond, $C_{1-2}$ alkylene, $C_{1-2}$ heteroalkylene, $C_{2-4}$ alkenylene, $C_{2-4}$ alkynylene, phenyl, or a 5- to 6-membered heteroaryl containing 1 to 3 heteroatoms independently selected from N, O, and S; wherein the alkylene, phenyl, heteroalkylene, and heteroaryl are each independently substituted with 0 to 3 $R^{11}$.

In one embodiment of Formula (I), Formula (Ia), Formula (Ib), or Formula (II), $L^1$ is a covalent bond, —CH$_2$—, —CH$_2$CH$_2$—, —CH$_2$O—, —OCH$_2$—, —CH=CH—, phenyl, or a 5- to 6-membered heteroaryl containing 1 to 3 heteroatoms independently selected from N, O, and S; wherein the phenyl and heteroaryl are each independently substituted with 0 to 2 $R^{11}$.

In one embodiment of Formula (I), Formula (Ia), Formula (Ib), or Formula (II), $L^1$ is a covalent bond, phenyl, thiazolyl, oxadiazolyl, thiadiazolyl, or pyridinyl.

In one embodiment of Formula (I), Formula (Ia), Formula (Ib), or Formula (II), Z is 6- to 10-membered aryl or 5- to 10-membered heteroaryl, wherein the aryl and heteroaryl are independently substituted with 0 to 3 $R^8$.

In one embodiment of Formula (I), Formula (Ia), Formula (Ib), or Formula (II), Z is 1,5-naphthyridinyl, benzo[d]imidazolyl, benzo[d]isothiazolyl, benzo[d]oxazolyl, benzo[d]thiazolyl, cinnolinyl, imidazo[3,4-a]pyridinyl, indazolyl, indolyl, isoquinolinyl, phenyl, pyrazinyl, pyrazolo[1,5-a]pyridinyl, pyrazolo[4,3-b]pyridinyl, pyrazolyl, pyridazinyl, pyridinyl, pyrimidinyl, pyrrolo[2,1-f]triazinyl, pyrrolo[2,3-b]pyridinyl, pyrrolo[2,3-d]pyrimidinyl, pyrrolo[3,2-b]pyridinyl, quinolinonyl, quinolinyl, quinoxalinyl, thiazolo[5,4-b]pyridinyl, or thiazolyl, each independently substituted with 0 to 2 $R^8$.

In one embodiment of Formula (I), Formula (Ia), Formula (Ib), or Formula (II), $L^1$ is a covalent bond, phenyl, thiazolyl, oxadiazolyl, thiadiazolyl, or pyridinyl; and Z is 6- to 10-membered aryl or 5- to 10-membered heteroaryl, wherein the aryl and heteroaryl are independently substituted with 0 to 3 $R^8$.

In one embodiment of Formula (I), Formula (Ia), Formula (Ib), or Formula (II), $L^1$ is a covalent bond, phenyl, thiazolyl, oxadiazolyl, thiadiazolyl, or pyridinyl; and Z is 1,5-naphthyridinyl, benzo[d]imidazolyl, benzo[d]isothiazolyl, benzo[d]oxazolyl, benzo[d]thiazolyl, cinnolinyl, imidazo[3,4-a]pyridinyl, indazolyl, indolyl, isoquinolinyl, phenyl, pyrazinyl, pyrazolo[1,5-a]pyridinyl, pyrazolo[4,3-b]pyridinyl, pyrazolyl, pyridazinyl, pyridinyl, pyrimidinyl, pyrrolo[2,1-f]triazinyl, pyrrolo[2,3-b]pyridinyl, pyrrolo[2,3-d]pyrimidinyl, pyrrolo[3,2-b]pyridinyl, quinolinonyl, quinolinyl, quinoxalinyl, thiazolo[5,4-b]pyridinyl, or thiazolyl, each independently substituted with 0 to 2 $R^8$.

In one embodiment of Formula (I), Formula (Ia), Formula (Ib), or Formula (II), $R^X$ is -$L^3$-R;
$L^3$ is a covalent bond or $C_{1-2}$ alkylene; wherein the $C_{1-2}$ alkylene is substituted with 0 to 2 $R^{15}$;
$R^Z$ is —CN, —C(O)OR$^{13}$, —C(O)NR$^{14a}$R$^{14b}$,

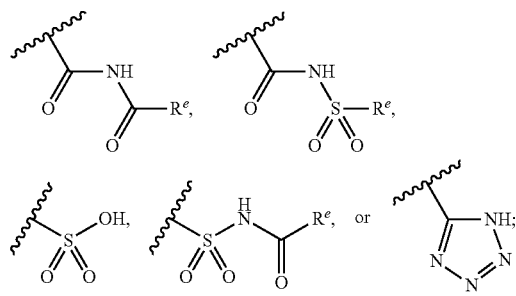

and
$R^{15}$ are each independently F, $C_1$, or —CH$_3$; or alternatively, two $R^{15}$, taken together with the atom(s) to which they are attached, form $C_{3-6}$ cycloalkyl.

In one embodiment of Formula (I) or Formula (II), $R^X$ is -$L^3$-$R^Z$;
$L^3$ is a covalent bond or $C_{1-2}$ alkylene; wherein the $C_{1-2}$ alkylene is substituted with 0 to 2 $R^{15}$;
$R^Z$ is —CN, —C(O)OH, —C(O)NH$_2$,

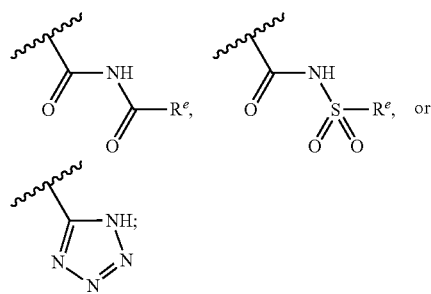

and
$R^{15}$ are each independently F, $C_1$, or —CH$_3$; or alternatively, two $R^{15}$, taken together with the atom(s) to which they are attached, form cyclopropyl.

In one embodiment of Formula (I), Formula (Ia), Formula (Ib), or Formula (II), $R^X$ is —CN, —C(O)OH, —CH$_2$C(O)OH, —C(O)NH$_2$, —C(O)NHS(O)$_2$CH$_3$

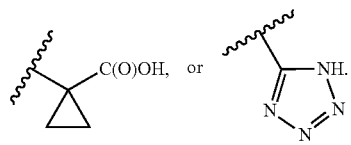

In one embodiment of Formula (I), Formula (Ia), Formula (Ib), or Formula (II), $R^1$ is $C_{1-6}$ alkyl or $C_{3-5}$ cycloalkyl, wherein the alkyl and cycloalkyl are independently substituted with 0 to 3 $R^9$.

In one embodiment of Formula (I), Formula (Ia), Formula (Ib), or Formula (II), $R^1$ is $C_{1-3}$ alkyl or $C_{3-5}$ cycloalkyl, wherein the alkyl and cycloalkyl are independently substituted with 0 to 3 $R^9$.

In one embodiment of Formula (I), Formula (Ia), Formula (Ib), or Formula (II), $R^1$ is $C_{3-4}$ cycloalkyl substituted with 0 to 3 $R^9$.

In one embodiment of Formula (I), Formula (Ia), Formula (Ib), or Formula (II), $R^1$ is cyclopropyl.

In one embodiment of Formula (I), Formula (Ia), Formula (Ib), or Formula (II), $L^2$ is a covalent bond or $C_{1-2}$ alkylene, wherein the alkylene is independently substituted with 0 to 3 $R^{16}$.

In one embodiment of Formula (I), Formula (Ia), Formula (Ib), or Formula (II), $L^2$ is a covalent bond.

In one embodiment of Formula (I), Formula (Ia), Formula (Ib), or Formula (II), $R^2$ is phenyl or pyridinyl, each independently substituted with 1 to 2 $R^{10}$.

In one embodiment of Formula (I), Formula (Ia), Formula (Ib), or Formula (II), $L^2$ is a covalent bond or $C_{1-2}$ alkylene, wherein the alkylene is independently substituted with 0 to 3 $R^{16}$; and $R^2$ is phenyl or pyridinyl, each independently substituted with 1 to 2 $R^{10}$.

In one embodiment of Formula (I), Formula (Ia), Formula (Ib), or Formula (II), $L^2$ is a covalent bond; and $R^2$ is phenyl or pyridinyl, each independently substituted with 1 to 2 $R^{10}$.

One embodiment provides a compound of Formula (I), Formula (Ia), Formula (Ib), or Formula (II), or a stereoisomer, a tautomer, or a pharmaceutically acceptable salt or solvate thereof; wherein:
the

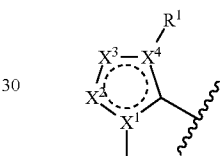

moiety is

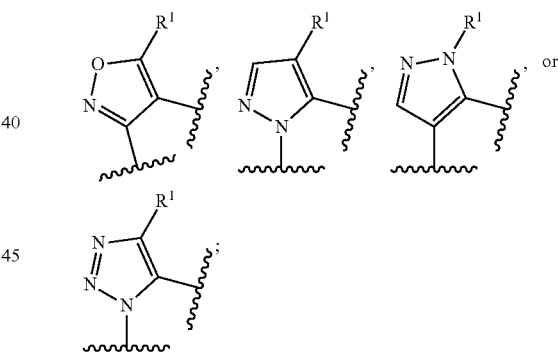

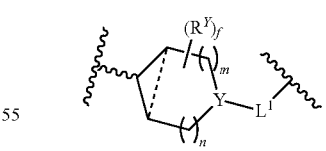

the

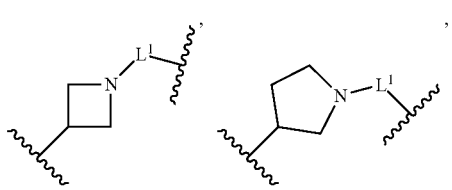

moiety is:

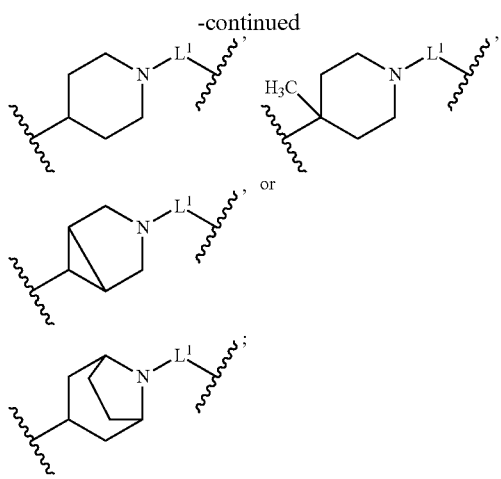

L¹ is a covalent bond, phenyl, thiazolyl, oxadiazolyl, thiadiazolyl, or pyridinyl;

Z is 1,5-naphthyridinyl, benzo[d]imidazolyl, benzo[d]isothiazolyl, benzo[d]oxazolyl, benzo[d]thiazolyl, cinnolinyl, imidazo[3,4-a]pyridinyl, indazolyl, indolyl, isoquinolinyl, phenyl, pyrazinyl, pyrazolo[1,5-a]pyridinyl, pyrazolo[4,3-b]pyridinyl, pyrazolyl, pyridazinyl, pyridinyl, pyrimidinyl, pyrrolo[2,1-f]triazinyl, pyrrolo[2,3-b] pyridinyl, pyrrolo[2,3-d] pyrimidinyl, pyrrolo[3,2-b]pyridinyl, quinolinonyl, quinolinyl, quinoxalinyl, thiazolo[5,4-b] pyridinyl, or thiazolyl, each independently substituted with 0 to 2 R⁸;

R$^X$ is —CN, —C(O)OH, —CH₂C(O)OH, —C(O)NH₂, —C(O)NHS(O)₂CH₃,

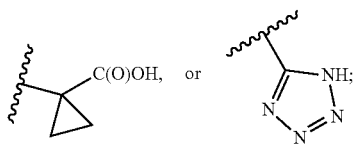

R¹ is cyclopropyl;
R² is phenyl or pyridinyl, each independently substituted with 1 to 2 R¹⁰;
R³ is hydrogen;
R⁴ is hydrogen or —CH₃;
R⁸ is each independently F, C₁, —CH₃, —CH₂CH₃, —CH₂OCH₃, —CF₃, —OCH₃, —OCD₃, —OCH₂CH₃, —CH(CH₃)₂, —OCH₂CH₂OCH₃, —OCHF₂, —OCH₂CHF₂, —CH₂(cyclopropyl), —O(cyclopropyl), —O(cyclobutyl), —O(difluorocyclobutyl), —O(fluorocyclobutyl), —O(oxetanyl), —O(tetrahydrofuranyl), or —OCH₂(methoxyphenyl);
L² is a covalent bond; and
R¹⁰ is each independently C₁, —CF₃, or —OCF₃.

In one embodiment, the present invention provides, inter alia, compounds selected from any one of the Examples as described in the specification, or a stereoisomer, a tautomer, or a pharmaceutically acceptable salt or solvate thereof.

II. Pharmaceutical Compositions, Therapeutic Utilities, and Combinations

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e. g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, comeal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3 S)-tetrahydro-3-furanyl]-8-[(2,4,6-trifluorophenyl)amino]-9H-purin-2-yl] amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrastemal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and nonaqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 0.1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention. As used herein, "a compound of the invention" or "compounds of the invention" means one or more compounds encompassed by any one of Formula (I), (IIa), and (IIb), or stereoisomers, tautomers, or pharmaceutically acceptable salts or solvates thereof.

As used herein, the term "alkyl" or "alkylene" is intended to include both branched and straight-chain saturated aliphatic hydrocarbon groups having the specified number of carbon atoms. While "alkyl" denotes a monovalent saturated aliphatic radical (such as ethyl), "alkylene" denotes a bivalent saturated aliphatic radical (such as ethylene). For example, "$C_1$ to $C_{10}$ alkyl" or "$C_{1-10}$ alkyl" is intended to include $C_1$, $C_2$, $C_3$, $C_4$, $C_5$, $C_6$ $C_7$, $C_8$, $C_9$, and $C_{10}$ alkyl groups. "$C_1$ to $C_{10}$ alkylene" or "$C_{1-10}$ alkylene", is intended to include $C_1$, $C_2$, $C_3$, $C_4$, $C_5$, $C_6$, $C_7$, $C_8$, $C_9$, and $C_{10}$ alkylene groups. Additionally, for example, "$C_1$ to $C_6$ alkyl" or "$C_{1-6}$ alkyl" denotes alkyl having 1 to 6 carbon atoms; and "$C_1$ to $C_6$ alkylene" or "$C_{1-6}$ alkylene" denotes alkylene having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —$OCH_3$, etc.), an alkylamino (e.g., —$NHCH_3$, —$N(CH_3)_2$, etc.), or a thioalkyl group (e.g., —$SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —$CH_2CH_2$—O—$CH_3$, etc.), an alkylaminoalkyl (e.g., —$CH_2NHCH_3$, —$CH_2N(CH_3)_2$, etc.), or a thioalkyl ether (e.g., —$CH_2$—S—$CH_3$). If a terminal carbon atom of the alkyl group is replaced with a heteroatom (e.g., O, N, or S), the resulting heteroalkyl groups are, respectively, a hydroxyalkyl group (e.g., —$CH_2CH_2$—OH), an aminoalkyl group (e.g., —$CH_2NH_2$), or an alkyl thiol group (e.g., —$CH_2CH_2$—SH). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. While "alkenyl" denotes a monovalent radical, "alkenylene" denotes a bivalent radical. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. While "alkynyl" denotes a monovalent radical, "alkynylene" denotes a bivalent radical. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

As used herein, "arylalkyl" (a.k.a. aralkyl), "heteroarylalkyl" "carbocyclylalkyl" or "heterocyclylalkyl" refers to an acyclic alkyl radical in which one of the hydrogen atoms bonded to a carbon atom, typically a terminal or $sp^3$ carbon atom, is replaced with an aryl, heteroaryl, carbocyclyl, or heterocyclyl radical, respectively. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl, heteroarylalkyl, carbocyclylalkyl, or heterocyclylalkyl group can comprise 4 to 20 carbon atoms and 0 to 5 heteroatoms, e.g., the alkyl moiety may contain 1 to 6 carbon atoms.

The term "benzyl", as used herein, refers to a methyl group on which one of the hydrogen atoms is replaced by a phenyl group, wherein said phenyl group may optionally be substituted with 1 to 5 groups, preferably 1 to 3 groups, —OH, —OCH$_3$, C$_1$, F, Br, I, —CN, —NO$_2$, —NH$_2$, —NH (CH$_3$), —N(CH$_3$)$_2$, —CF$_3$, —OCF$_3$, —C(=O)CH$_3$, —SCH$_3$, —S(=O)CH$_3$, —S(=O)$_2$CH$_3$, —CH$_3$, —CH$_2$CH$_3$, —CO$_2$H, and —CO$_2$CH$_3$. "Benzyl" can also be represented by formula "Bn".

The term "lower alkoxy", "alkoxy" or "alkyloxy", "aryloxy" or "aralkoxy" refers to any of the above alkyl, aralkyl or aryl groups linked to an oxygen atom. "C$_1$ to C$_6$ alkoxy" or "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "lower alkylthio", "alkylthio", "thioalkoxy", "arylthio", or "aralkylthio" represents an alkyl, aryl, or aralkyl group as defined above with the indicated number of carbon atoms attached through a sulfur bridge; for example methyl-S— and ethyl-S—.

The term "alkanoyl" or "alkylcarbonyl" as used herein alone or as part of another group refers to alkyl linked to a carbonyl group. For example, alkylcarbonyl may be represented by alkyl-C(O)—. "C$_1$ to C$_6$ alkylcarbonyl" (or alkylcarbonyl), is intended to include C$_1$, C$_2$, C$_3$, C$_4$, C$_5$, and C$_6$ alkyl-C(O)— groups.

The term "alkylsulfonyl" or "sulfonamide" as used herein alone or as part of another group refers to alkyl or amino linked to a sulfonyl group. For example, alkylsulfonyl may be represented by —S(O)$_2$R', while sulfonamide may be represented by —S(O)$_2$NR$^c$R$^d$. R' is C$_1$ to C$_6$ alkyl; and R$^c$ and R$^d$ are the same as defined below for "amino".

The term "carbamate" as used herein alone or as part of another group refers to oxygen linked to an amido group. For example, carbamate may be represented by N(R$^c$R$^d$)—C(O)—O—, and R$^c$ and R$^d$ are the same as defined below for "amino".

The term "amido" as used herein alone or as part of another group refers to amino linked to a carbonyl group. For example, amido may be represented by N(R$^c$R$^d$)—C(O)—, and R$^c$ and R$^d$ are the same as defined below for "amino".

The term "amino" is defined as —NR$^{c1}$R$^{c2}$, wherein R$^{c1}$ and R$^{c2}$ are independently H or C$_{1-6}$ alkyl; or alternatively, R$^{c1}$ and R$^{c2}$, taken together with the atoms to which they are attached, form a 3- to 8-membered heterocyclic ring which is optionally substituted with one or more group selected from halo, cyano, hydroxyl, amino, oxo, C$_{1-6}$ alkyl, alkoxy, and aminoalkyl. When R$^{c1}$ or R$^{c2}$ (or both of them) is C$_{1-6}$ alkyl, the amino group can also be referred to as alkylamino. Examples of alkylamino group include, without limitation, —NH$_2$, methylamino, ethylamino, propylamino, isopropylamino and the like.

The term "aminoalkyl" refers to an alkyl group on which one of the hydrogen atoms is replaced by an amino group. For example, aminoalkyl may be represented by N(R$^{c1}$R$^{c2}$)-alkylene-. "C$_1$ to C$_6$" or "C$_{1-6}$" aminoalkyl" (or aminoalkyl), is intended to include C$_1$, C$_2$, C$_3$, C$_4$, C$_5$, and C$_6$ aminoalkyl groups.

The term "halogen" or "halo" as used herein alone or as part of another group refers to chlorine, bromine, fluorine, and iodine, with chlorine or fluorine being preferred.

"Haloalkyl" is intended to include both branched and straight-chain saturated aliphatic hydrocarbon groups having the specified number of carbon atoms, substituted with one or more halogens. "C$_1$ to C$_6$ haloalkyl" or "C$_{1-6}$ haloalkyl" (or haloalkyl), is intended to include C$_1$, C$_2$, C$_3$, C$_4$, C$_5$, and C$_6$ haloalkyl groups. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms. The term "polyhaloalkyl" as used herein refers to an "alkyl" group as defined above which includes from 2 to 9, preferably from 2 to 5, halo substituents, such as F or C$_1$, preferably F, such as polyfluoroalkyl, for example, CF$_3$CH$_2$, CF$_3$ or CF$_3$CF$_2$CH$_2$.

"Haloalkoxy" or "haloalkyloxy" represents a haloalkyl group as defined above with the indicated number of carbon atoms attached through an oxygen bridge. For example, "C$_1$ to C$_6$ haloalkoxy" or "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy. Other examples of haloalkoxy also include "fluoroalkoxy" which represents a fluoroalkyl group as defined above with the indicated number of carbon atoms attached through an oxygen bridge. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—. The term "polyhaloalkyloxy" as used herein refers to an "alkoxy" or "alkyloxy" group as defined above which includes from 2 to 9, preferably from 2 to 5, halo substituents, such as F or C$_1$, preferably F, such as polyfluoroalkoxy, for example, —OCH$_2$CF$_3$, —OCF$_3$, or —OCH$_2$CF$_2$CF$_3$.

"Hydroxyalkyl" is intended to include both branched and straight-chain saturated aliphatic hydrocarbon groups having the specified number of carbon atoms, substituted with 1 or more hydroxyl (OH). "C$_1$ to C$_6$ hydroxyalkyl" (or hydroxyalkyl), is intended to include C$_1$, C$_2$, C$_3$, C$_4$, C$_5$, and C$_6$ hydroxyalkyl groups.

The term "cycloalkyl" refers to cyclized alkyl groups, including mono-, bi- or poly-cyclic ring systems. "C$_3$ to C$_7$ cycloalkyl" or "C$_{3-7}$ cycloalkyl" is intended to include C$_3$, C$_4$, C$_5$, C$_6$, and C$_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

The term "cycloheteroalkyl" refers to cyclized heteroalkyl groups, including mono-, bi- or poly-cyclic ring systems. "C$_3$ to C$_7$ cycloheteroalkyl" or "C$_{3-7}$ cycloheteroalkyl" is intended to include C$_3$, C$_4$, C$_5$, C$_6$, and C$_7$ cycloheteroalkyl groups. Example cycloheteroalkyl groups include, but are not limited to, oxetanyl, tetrahydrofuranyl, tetrahydropyranyl, azetidinyl, pyrrolidinyl, piperidinyl, morpholinyl, and piperazinyl. Branched cycloheteroalkyl groups, such as piperidinylmethyl, piperazinylmethyl, morpholinylmethyl, pyridinylmethyl, pyridizylmethyl, pyrimidylmethyl, and pyrazinylmethyl, are included in the definition of "cycloheteroalkyl".

As used herein, the term "azacyclyl" refers to a cycloheteroalkyl containing one or more nitrogen atoms in the ring. Example azacyclyl groups include, but are not limited to, pyrrolidinyl, piperidinyl, morpholinyl, and piperazinyl.

As used herein, "carbocycle", "carbocyclyl", or "carbocyclic" is intended to mean any stable 3-, 4-, 5-, 6-, 7-, or 8-membered monocyclic or 5-, 6-, 7-, 8-, 9-, 10-, 11-, 12-, or 13-membered polycyclic (including bicyclic or tricyclic) hydrocarbon ring, any of which may be saturated or partially unsaturated. That is, the term "carbocycle", "carbocyclyl", or "carbocyclic" includes, without limitation, cycloalkyl and cycloalkenyl. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, indanyl, adamantyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, indanyl, and tetrahydronaphthyl. A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

Furthermore, the term "carbocyclyl", including "cycloalkyl" and "cycloalkenyl", as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons or 3 to 6 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

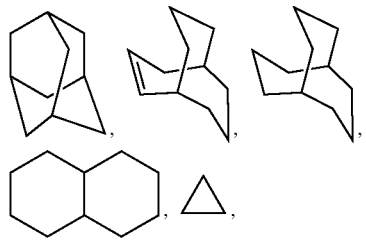

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated or partially unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, 1,2-dihydronaphthyl, 1,2,3,4-tetrahydronaphthyl, and indanyl.

As used herein, the term "aryl", as employed herein alone or as part of another group, refers to monocyclic or polycyclic (including bicyclic and tricyclic) aromatic hydrocarbons, including, for example, phenyl, naphthyl, anthracenyl, and phenanthranyl. Aryl moieties are well known and described, for example, in Lewis, R. J., ed., *Hawley's Condensed Chemical Dictionary*, 13th Edition, John Wiley & Sons, Inc., New York (1997). In one embodiment, the term "aryl" denotes monocyclic and bicyclic aromatic groups containing 6 to 10 carbons in the ring portion (such as phenyl or naphthyl including 1-naphthyl and 2-naphthyl). For example, "$C_6$ or $C_{10}$ aryl" or "$C_{6-10}$ aryl" refers to phenyl and naphthyl. Unless otherwise specified, "aryl", "$C_6$ or $C_{10}$ aryl", "$C_{6-10}$ aryl", or "aromatic residue" may be unsubstituted or substituted with 1 to 5 groups, preferably 1 to 3 groups, selected from —OH, —OCH$_3$, F, C$_1$, Br, I, —CN, —NO$_2$, —NH$_2$, —NH(CH$_3$), —N(CH$_3$)$_2$, —CF$_3$, —OCF$_3$, —C(O)CH$_3$, —SCH$_3$, —S(O)CH$_3$, —S(O)$_2$CH$_3$, —CH$_3$, —CH$_2$CH$_3$, —CO$_2$H, and —CO$_2$CH$_3$.

As used herein, the term "heterocycle", "heterocyclyl", or "heterocyclic group" is intended to mean a stable 3-, 4-, 5-, 6-, or 7-membered monocyclic or 5-, 6-, 7-, 8-, 9-, 10-, 11-, 12-, 13-, or 14-membered polycyclic (including bicyclic and tricyclic) heterocyclic ring that is saturated, or partially unsaturated, and that contains carbon atoms and 1, 2, 3 or 4 heteroatoms independently selected from the group consisting of N, O and S; and including any polycyclic group in which any of the above-defined heterocyclic rings is fused to a carbocyclic or an aryl (e.g., benzene) ring. That is, the term "heterocycle", "heterocyclyl", or "heterocyclic group" includes non-aromatic ring systems, such as heterocycloalkyl and heterocycloalkenyl. The nitrogen and sulfur heteroatoms may optionally be oxidized (i.e., N—O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Examples of hetercyclyl include, without limitation, azetidinyl, piperazinyl, piperidinyl, piperidonyl, piperonyl, pyranyl, morpholinyl, tetrahydrofuranyl, tetrahydroisoquinolinyl, tetrahydroquinolinyl, morpholinyl, and dihydrofuro[2,3-b]tetrahydrofuran.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1. Examples of a bicyclic heterocyclic group are, but not limited to, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl, and 1,2,3,4-tetrahydro-quinazolinyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

As used herein, the term "heteroaryl" is intended to mean stable monocyclic and polycyclic (including bicyclic and tricyclic) aromatic hydrocarbons that include at least one heteroatom ring member such as sulfur, oxygen, or nitrogen. Heteroaryl groups include, without limitation, pyridinyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of heteroaryl include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, furanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathianyl, phenoxazinyl, phthalazinyl, pteridinyl, purinyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Examples of 5- to 10-membered heteroaryl include, but are not limited to, pyridinyl, furanyl, thienyl, pyrazolyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl. Examples of 5- to 6-membered heterocycles include, but are not limited to, pyridinyl, furanyl, thienyl, pyrrolyl, pyrazolyl, pyrazinyl, imidazolyl, imidazolidinyl, indolyl, tetrazolyl, isoxazolyl, oxazolyl, oxadiazolyl, oxazolidinyl, thiadiazinyl, thiadiazolyl, thiazolyl, triazinyl, and triazolyl.

Unless otherwise indicated, "carbocyclyl" or "heterocyclyl" includes one to three additional rings fused to the carbocyclic ring or the heterocyclic ring (such as aryl, cycloalkyl, heteroaryl or cycloheteroalkyl rings, for example,

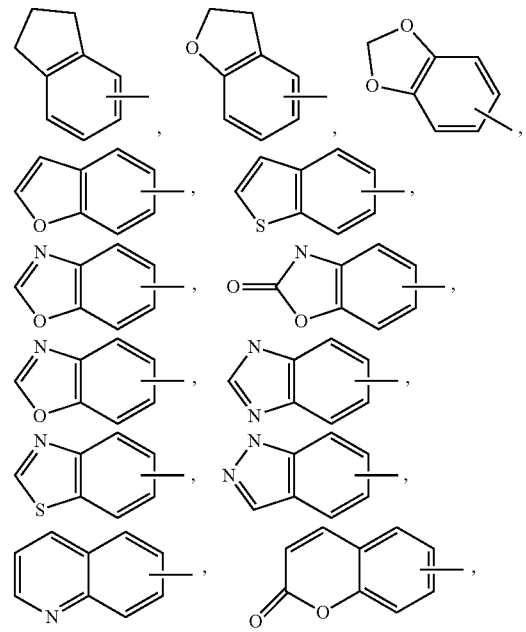

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl and/or any of the alkyl substituents set out herein.

When any of the terms alkyl, alkenyl, alkynyl, cycloalkyl, carbocyclyl, heterocyclyl, aryl, and heteroaryl are used as part of another group, the number of carbon atoms and ring members are the same as those defined in the terms by themselves. For example, alkoxy, haloalkoxy, alkylamino, haloalkyl, hydroxyalkyl, aminoalkyl, haloalkoxy, alkoxyalkoxy, haloalkylamino, alkoxyalkylamino, haloalkoxyalkylamino, alkylthio, and the like each independently contains the number of carbon atoms which are the same as defined for the term "alkyl", such as 1 to 4 carbon atoms, 1 to 6 carbon atoms, 1 to 10 carbon atoms, etc. Similarly, cycloalkoxy, heterocyclyloxy, cycloalkylamino, heterocyclylamino, aralkylamino, arylamino, aryloxy, aralkyloxy, heteroaryloxy, heteroarylalkyloxy, and the like each independently contains ring members which are the same as defined for the terms "cycloalkyl", "heterocyclyl", "aryl", and "heteroaryl", such as 3 to 6-membered, 4 to 7-membered, 6 to 10-membered, 5 to 10-membered, 5 or 6-membered, etc.

In accordance with a convention used in the art, a bond pointing to a bold line, such as

as used in structural formulas herein, depicts the bond that is the point of attachment of the moiety or substituent to the core or backbone structure.

In accordance with a convention used in the art, a wavy or squiggly bond in a structural formula, such as

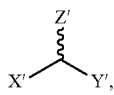

is used to depict a stereogenic center of the carbon atom to which X', Y', and Z' are attached and is intended to represent both enantiomers in a single FIGURE. That is, a structural formula with such as wavy bond denotes each of the enantiomers individually, such as

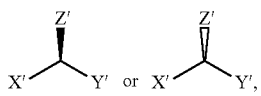

as well as a racemic mixture thereof. When a wavy or squiggly bond is attached to a double bond (such as C=C or C=N) moiety, it include cis- or trans- (or E- and Z-) geometric isomers or a mixture thereof.

It is understood herein that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the terms "pyridinyl" and "pyridyl" mean 2-, 3- or 4-pyridinyl, the term "thienyl" means 2- or 3-thienyl, and so forth.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

One skilled in the art will recognize that substituents and other moieties of the compounds of the present invention should be selected in order to provide a compound which is sufficiently stable to provide a pharmaceutically useful compound which can be formulated into an acceptably stable pharmaceutical composition. Compounds of the present invention which have such stability are contemplated as falling within the scope of the present invention.

The term "counter ion" is used to represent a negatively charged species such as chloride, bromide, hydroxide, acetate, and sulfate. The term "metal ion" refers to alkali metal ions such as sodium, potassium or lithium and alkaline earth metal ions such as magnesium and calcium, as well as zinc and aluminum.

As referred to herein, the term "substituted" means that at least one hydrogen atom (attached to carbon atom or heteroatom) is replaced with a non-hydrogen group, provided that normal valencies are maintained and that the substitution results in a stable compound. When a substituent is oxo (i.e., =O), then 2 hydrogens on the atom are replaced. Oxo substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N). The term "substituted" in reference to alkyl, cycloalkyl, heteroalkyl, cycloheteroalkyl, alkylene, aryl, arylalkyl, heteroaryl, heteroarylalkyl, carbocyclyl, and heterocyclyl, means alkyl, cycloalkyl, heteroalkyl, cycloheteroalkyl, alkylene, aryl, arylalkyl, heteroaryl, heteroarylalkyl, carbocyclyl, and heterocyclyl, respectively, in which one or more hydrogen atoms, which are attached to either carbon or heteroatom, are each independently replaced with one or more non-hydrogen substituent(s).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0, 1, 2, or 3 R groups, then said group be unsubstituted when it is substituted with 0 R group, or be substituted with up to three R groups, and at each occurrence R is selected independently from the definition of R.

Also, combinations of substituents and/or variables are permissible only if such combinations result in stable compounds.

As used herein, the term "tautomer" refers to each of two or more isomers of a compound that exist together in equilibrium, and are readily interchanged by migration of an atom or group within the molecule. For example, one skilled in the art would readily understand that a 1,2,3-triazole exists in two tautomeric forms as defined above:

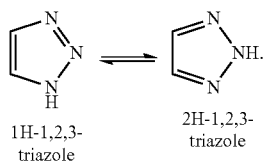

1H-1,2,3-triazole          2H-1,2,3-triazole

Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

The compounds of the present invention can be present as salts, which are also within the scope of this invention. Pharmaceutically acceptable salts are preferred. As used herein, "pharmaceutically acceptable salts" refer to derivatives of the disclosed compounds wherein the parent compound is modified by making acid or base salts thereof. The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula (I) or their pharmaceutically acceptable salts, are also included.

Preferred salts of the compounds of Formula (I) which contain a basic group include monohydrochloride, hydrogensulfate, methanesulfonate, phosphate, nitrate or acetate.

Preferred salts of the compounds of Formula (I) which contain an acid group include sodium, potassium and magnesium salts and pharmaceutically acceptable organic amines.

In addition, the compounds of the present invention may have prodrug forms. Any compound that will be converted in vivo to provide the bioactive agent is a prodrug within the scope and spirit of the invention. The term "prodrug" as used herein encompasses both the prodrugs based on the carboxylic acid residue, i.e., "prodrug esters", and the prodrugs based on the arginine mimetics moiety, i.e., "prodrugs of arginine mimetics". Such prodrugs are preferably administered orally since hydrolysis in many instances occurs principally under the influence of the digestive enzymes. Parenteral administration may be used where the ester per se is active, or in those instances where hydrolysis occurs in the blood.

The compounds of the present invention contain a carboxy group which can form physiologically hydrolyzable esters that serve as prodrugs, i.e., "prodrug esters", by being hydrolyzed in the body to yield the compounds of the present invention per se. Examples of physiologically hydrolyzable esters of compounds of the present invention include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. The "prodrug esters" can be formed by reacting the carboxylic acid moiety of the compounds of the present invention with either alkyl or aryl alcohol, halide, or sulfonate employing procedures known to those skilled in the art. Furthermore, various forms of prodrugs are well known in the art. For examples of such prodrug derivatives, see:

Bundgaard, H., ed., *Design of Prodrugs*, Elsevier (1985), and Widder, K. et al., eds., *Methods in Enzymology*, 112: 309-396, Academic Press (1985);

Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

Bundgaard, H., *Adv. Drug Deliv. Rev.*, 8:1-38 (1992);

Bundgaard, H. et al., *J. Pharm. Sci.*, 77:285 (1988); and

Kakeya, N. et al., *Chem. Pharm. Bull.*, 32:692 (1984).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydro-* lysis in Drug and Prodrug Metabolism. Chemistry, Biochemistry and Enzymology, VCHA and Wiley-VCH, Zurich, Switzerland (2003); Wermuth, C. G., ed., *The Practice of Medicinal Chemistry*, Academic Press, San Diego, Calif. (1999); Rautio, J. et al., *Nature Review Drug Discovery*, 17, 559-587, (2018).

The present invention is intended to include all isotopes of atoms occurring in the present compounds. Isotopes include those atoms having the same atomic number but different mass numbers. By way of general example and without limitation, isotopes of hydrogen include deuterium (symbol D or $^2$H) and tritium (symbol T or $^3$H). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

The term "glycosyl" means a monovalent free radical or substituent moiety obtained by removing the hemiacetal hydroxyl group from the cyclic form of a monosaccharide and, by extension, of a lower oligosaccharide. In one embodiment, the glycosyl group has the following structure:

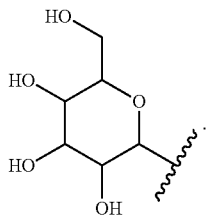

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Abbreviations

Furthermore, the following abbreviations are employed in the Schemes, Examples and elsewhere herein:
Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
ACN acetonitrile
AcOH or HOAc acetic acid
AlCl$_3$ aluminum chloride
AIBN azobisisobutyronitrile
BBr$_3$ boron tribromide
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz carbobenzyloxy
DCM or CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
DBU 1,8-diazabicyclo[5.4.0]undec-7-ene
DCE 1,2 dichloroethane
DEA diethylamine
DMP or Dess-Martin 1,1,1-tris(acetyloxy)-1,1-dihydro-1,2-beniziodoxol-3-(1H)-one Periodinane
DIC or DIPCDI diisopropylcarbodiimide
DIEA, DIPEA or diisopropylethylamine
Hunig's base
DMAP 4-dimethylaminopyridine
DME 1,2-dimethoxyethane
DMF dimethyl formamide
DMSO dimethyl sulfoxide
cDNA complimentary DNA Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et$_3$N or TEA triethylamine
EtOAc ethyl acetate
Et$_2$O diethyl ether
EtOH ethanol
GMF glass microfiber filter
Grubbs II (1,3-bis(2,4,6-trimethylphenyl)-2-imidazolidinylidene)dichloro phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperaxine-1-ethanesulfonic acid
Hex hexanes
HOBt or HOBT 1-hydroxybenzotriazole
H$_2$O$_2$ hydrogen peroxide
IBX 2-iodoxybenzoic acid
H2SO$_4$ sulfuric acid
Jones reagent CrO$_3$ in aqueous H$_2$SO$_4$, 2 M
K$_2$CO$_3$ potassium carbonate
K$_2$HPO$_4$ potassium phosphate dibasic
KOAc potassium acetate
K$_3$PO$_4$ potassium phosphate
LAH lithium aluminum hydride
LG leaving group
LiOH lithium hydroxide
MeOH methanol
MgSO$_4$ magnesium sulfate
MsCl methanesulfonyl chloride
MsOH or MSA methylsulfonic acid
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NH$_4$COOH ammonium formate
NMM N-methylmorpholine
OTf triflate or trifluoromethanesulfonate
Pd$_2$(dba)$_3$ tris(dibenzylideneacetone)dipalladium(0)
Pd(OAc)$_2$ palladium(II) acetate
Pd/C palladium on carbon
Pd(dppf)Cl$_1$ [1,1'-bis(diphenylphosphino)-ferrocene]dichloropalladium(II)
Ph$_3$PCl$_2$ triphenylphosphine dichloride
PG protecting group
POCl$_3$ phosphorus oxychloride
PPTS pyridinium p-toluenesulfonate
i-PrOH or IPA isopropanol
PS Polystyrene
PtO$_2$ platinum oxide
rt room temperature
RuPhos-Pd-G2 chloro(2-dicyclohexylphosphino-2',6'-diisopropoxy-1,1'-biphenyl)[2-(2'-amino-1,1'-biphenyl)]palladium(II)
SEM-Cl 2-(trimethysilyl)ethoxymethyl chloride
SiO$_2$ silica oxide
SnCl$_2$ tin(II) chloride
TBAI tetra-n-butylammonium iodide
TFA trifluoroacetic acid
THF tetrahydrofuran
TMSCHN$_2$ trimethylsilyldiazomethane
T3P propane phosphonic acid anhydride
TRIS tris (hydroxymethyl) aminomethane
pTsOH p-toluenesulfonic acid
TsCl p-tolunesulfonyl chloride IV. Methods of Preparation The compounds of the present invention can be prepared in a number of ways well known to one skilled in the art of organic synthesis using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds described in this invention. A particularly useful compendium of synthetic methods which may be applicable to the preparation of compounds of the present invention may be found in Larock, R. C., *Comprehensive Organic Transformations*, VCH, New York (1989).

The compounds of the present invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula (I) falling into a given class may be compatible with some of the reaction conditions required in some of the methods described. Such restrictions to the substituents, which are compatible with the reaction conditions, will be readily apparent to one skilled in the art and alternate methods must be used. A particularly useful compendium of synthetic methods which may be applicable to the preparation of compounds of the present invention may be found in Larock, R. C., *Comprehensive Organic Transformations*, VCH, New York (1989).

Generic Schemes

Compounds of the present invention, represented by Formula (I), Formula (II), or any subgenera or species thereof, can be prepared according to the general routes shown in SCHEMES 1 to 5 below.

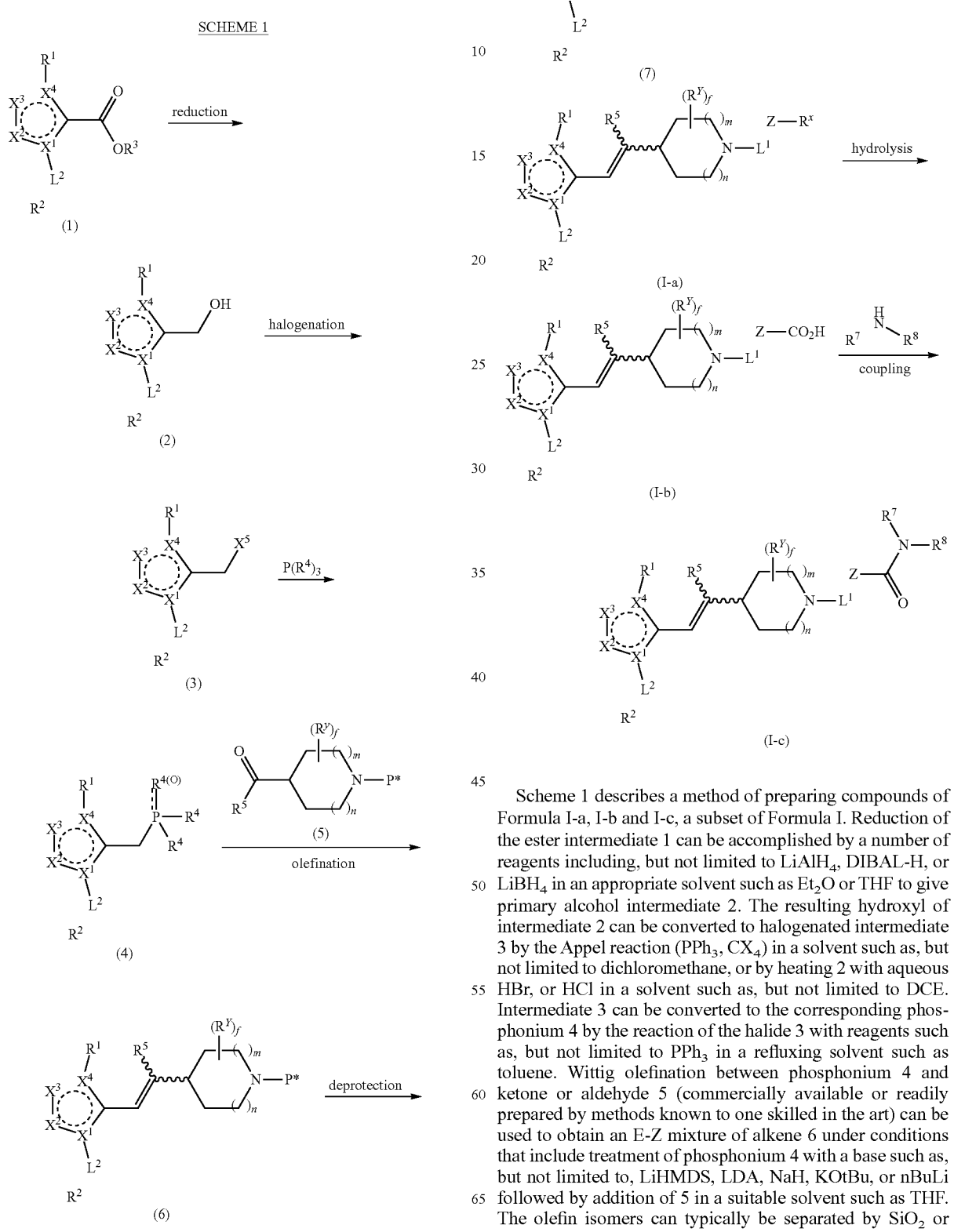

Scheme 1 describes a method of preparing compounds of Formula I-a, I-b and I-c, a subset of Formula I. Reduction of the ester intermediate 1 can be accomplished by a number of reagents including, but not limited to LiAlH$_4$, DIBAL-H, or LiBH$_4$ in an appropriate solvent such as Et$_2$O or THF to give primary alcohol intermediate 2. The resulting hydroxyl of intermediate 2 can be converted to halogenated intermediate 3 by the Appel reaction (PPh$_3$, CX$_4$) in a solvent such as, but not limited to dichloromethane, or by heating 2 with aqueous HBr, or HCl in a solvent such as, but not limited to DCE. Intermediate 3 can be converted to the corresponding phosphonium 4 by the reaction of the halide 3 with reagents such as, but not limited to PPh$_3$ in a refluxing solvent such as toluene. Wittig olefination between phosphonium 4 and ketone or aldehyde 5 (commercially available or readily prepared by methods known to one skilled in the art) can be used to obtain an E-Z mixture of alkene 6 under conditions that include treatment of phosphonium 4 with a base such as, but not limited to, LiHMDS, LDA, NaH, KOtBu, or nBuLi followed by addition of 5 in a suitable solvent such as THF. The olefin isomers can typically be separated by SiO$_2$ or C-18 reverse phase chromatography. Alternatively, heating 3 neat in a trialkoxy phosphite such as, but not limited to, triethoxy phosphite can yield the corresponding phosphonate 4. Horner-Wadsworth-Emmons (HWE) olefination can be employed to couple 4 and 5 under conditions similar to those described for Witting olefination. The alkene 6 obtained under HWE olefination conditions typically favors formation of the E isomer and if a mixture of E-Z isomers is obtained they can likewise be separated by $SiO_2$ or C-18 reverse phase chromatography. Removal of the protecting group P* can be accomplished by a variety of conditions that will vary depending on the nature of P* and on compatibility with other functional groups present in 6. In most examples P*=Boc, and appropriately acidic conditions (i.e. TFA, HCl) can be used to facilitate removal of the protecting group to give intermediate 7. However, if alternative protecting groups are required for functional group compatibility, then they can be removed by methods known to one skilled in the art. Additional methods for protecting group removal may be found in Greene, T. and Wuts, P. G. M., *Protecting Groups in Organic Synthesis*, John Wiley & Sons, Inc., New York, N.Y., 2006 and references therein. Intermediate 7 can be converted to products I-a through coupling with $X^6$-$L^1$-Z—$R^x$ (commercially available or readily prepared by methods known to one skilled in the art, where $X^6$ represents a halide, triflate or equivalent) under conditions that are well-known to one skilled in the art. The products I-a can be obtained through a variety of C—N bond forming reactions between intermediate 1 and a suitable aryl halide, triflate or equivalent. Some examples include, but are not limited to, Pd-catalyzed Buchwald-Hartwig reaction, Cu-mediated Ullmann coupling, Ni-mediated amination, or nucleophilic aromatic substitution (SNAr). Alternatively, the Cu-catalyzed Chan-Evans-Lam coupling can be employed if $X^6$ represents a boronic acid or ester which can be commercially available or obtained by borylation of the corresponding aryl halide. In each case, optimization of variables for the coupling reaction such as catalyst, ligand, solvent, base, additives and temperature may be required. If I-a contains an ester or nitrile it can be hydrolyzed to the corresponding carboxylic acid I-b under conditions such as but not limited to treatment with NaOH or LiOH in solvents consisting of MeOH, THF, and water at a temperature suitable to enable the hydrolysis. Acid-mediated hydrolysis of particular esters, such as a tert-butyl ester, may be required in some cases to obtain I-b. Examples I-c can be obtained by the coupling of I-b with $R^7$—N—$R^8$ (commercially available or readily prepared by methods known to one skilled in the art) utilizing coupling reagents such as but not limited to, T3P, EDC, DCC or CDI in the presence of a suitable base, for example triethylamine, Hunig's base, or pyridine with or without additives such as HOBT or DMAP in an appropriate solvent such as dichloromethane, ethyl acetate, DMF or THF. In each case the specific conditions utilized to obtain I-c, including temperature and concentration, may require optimization.

SCHEME 2

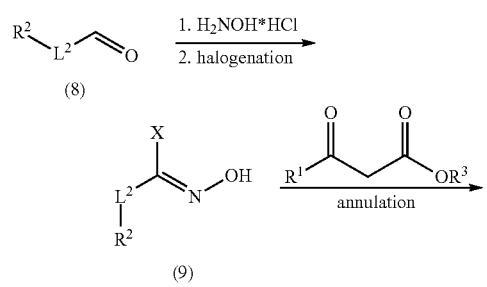

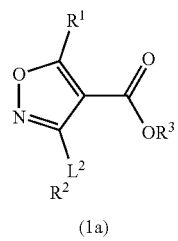

(1a)

Scheme 2 describes a method for preparing intermediate 1a, a subset of intermediate 1. Aldehydes 8 (commercially available or readily prepared by methods known to one skilled in the art) can be condensed with hydroxylamine hydrochloride under a variety of conditions including, but not limited to, stirring both reactants in pyridine at room temperature, or gently heating the reactants in the presence of a base like sodium hydroxide or sodium acetate in a suitable solvent such as ethanol. The resultant oximes can be converted to the corresponding hydroximoyl halides 9 through halogenation by reagents such as but not limited to NCS or NBS in a suitable solvent such as DMF. Hydroximoyl halides 9 can be reacted with β-ketoesters (commercially available or readily prepared by methods known to one skilled in the art) in the presence of triethyl amine or another suitable base in a solvent such as, but not limited to, dichloromethane to give 3,4,5-substituted isoxalole ester intermediate 1a.

SCHEME 3

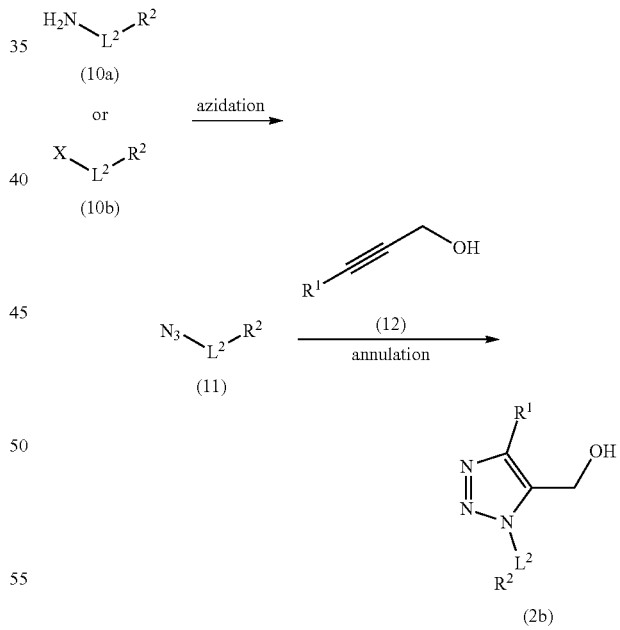

Scheme 3 describes a method for preparing intermediate 2b, a subset of intermediate 2. The synthesis can commence with azidation of amine 10a (commercially available or readily prepared by methods known to one skilled in the art) under conditions such as, but not limited to, treatment with sodium nitrite in acidic media ($H_2O$/TFA) followed by addition of sodium azide in an appropriate solvent, such as water at a suitable temperature to give azide 11. Alternatively, azide 11 can be obtained by the heating of halide 10b (commercially available or readily prepared by methods known to one skilled in the art) with an azide salt, such as sodium azide, in a mixture of DMSO/water at an appropriate temperature. The resultant azide 11 can undergo cyclization with an alkyne 12 by heating the reactants in a solvent such as toluene to give 1b. Alkynes 12 are commercially available, or can be obtained by a variety of methods including, but not limited to, the deprotonation of the corresponding terminal alkyne and trapping the resulting anion with formaldehyde or a formaldehyde equivalent.

SCHEME 4

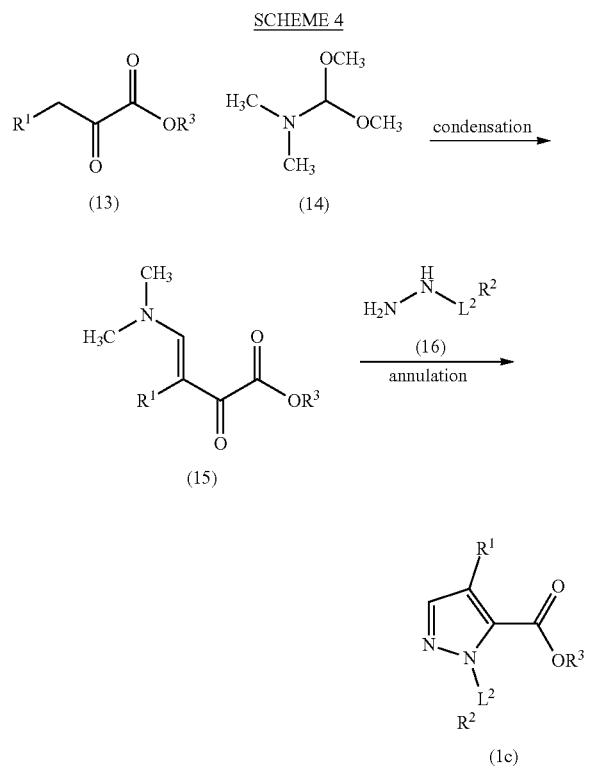

Scheme 4 describes a method for preparing intermediate 1c, a subset of intermediate 1. α-Ketoesters 13 (commercially available or readily prepared by methods known to one skilled in the art) can be condensed with N,N-dimethylformamide dimethyl acetal 14 by heating in a suitable solvent such as EtOH or MeOH to give intermediate 15. Hydrazines 16 can undergo annulation with intermediates 15 to give intermediates 1c by heating the two reactants in an appropriate solvent such as EtOH or MeOH. Hydrazines 16 are commercially available or can be prepared by the treatment of the corresponding amine with a reagent such as, but not limited to sodium nitrite in acidic media, or the coupling of the corresponding aryl halide with hydrazine.

SCHEME 5

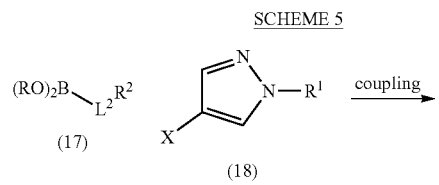

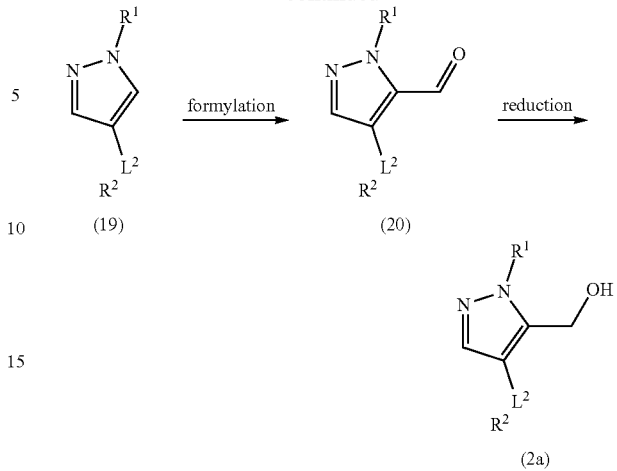

Scheme 5 describes a method for preparing intermediate 2a, a subset of intermediate 2. An appropriately substituted boronic acid or ester 17 (commercially available or readily prepared by methods known to one skilled in the art) and a pyrazole 18 bearing a suitably reactive halogen or equivalent X, (commercially available or readily prepared by methods known to one skilled in the art) can be coupled through the Pd-catalyzed Suzuki reaction to give intermediate 19. Typical conditions for the Suzuki coupling include, but are not limited to, heating the reactants 17 and 18 together with a palladium catalyst, ligand and base at a suitable temperature in a deoxygenated solvent or solvent mixture. Specific conditions include, but are not limited to $PdCl_2(dppf)_2$, $Na_2CO_3$ in THF/water at 120° C. In each case the specific conditions utilized to obtain 19, including stoichiometry, palladium source, ligand, base, solvent, temperature, and concentration may require independent optimization. The coupling partners 17 and 18, are either commercially available or can be readily prepared by methods known to one skilled in the art. Intermediate 19 can be deprotonated at the 5-position of the pyrazole by a sufficiently strong base such as, but not limited to, n-BuLi, or LDA in a suitable solvent such as THF or $Et_2O$. The resulting anion from deprotonation of 19 can be trapped in situ with a formyl equivalent such as DMF to yield aldehyde intermediate 20. Reduction of the aldehyde 20 can be accomplished by a number of reagents including, but not limited to $LiAlH_4$, DIBAL-H, or $LiBH_4$ in an appropriate solvent such as, but not limited to, THF or $Et_2O$ to give intermediate 2a.

EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

As appropriate, reactions were conducted under an atmosphere of dry nitrogen (or argon). For anhydrous reactions, DRISOLV® solvents from EM were employed. For other reactions, reagent grade or HPLC grade solvents were utilized. Unless otherwise stated, all commercially obtained reagents were used as received.

HPLC/MS and Preparatory/Analytical HPLC Methods Employed in Characterization or Purification of Examples NMR (nuclear magnetic resonance) spectra were typically obtained on Bruker or JEOL 400 MHz and 500 MHz instruments in the indicated solvents. All chemical shifts are reported in ppm from tetramethylsilane with the solvent resonance as the internal standard. $^1$HNMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

The term HPLC refers to a Shimadzu high performance liquid chromatography instrument with one of following methods:

General Method A

Example 1

(E)-6-(4-(2-(5-Cyclopropyl-3-(2,6-dichlorophenyl)isoxazol-4-yl)vinyl)piperidin-1-yl) nicotinic acid

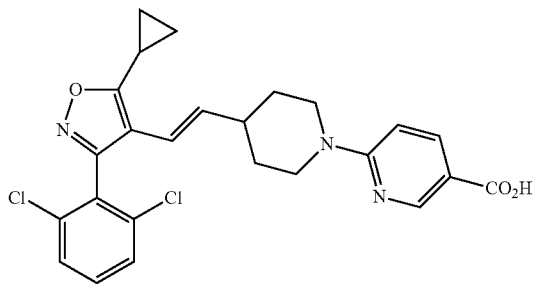

(1)

Step 1. 2,6-Dichlorobenzaldehyde oxime

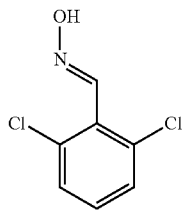 [SMILES: O/N=C/c1c(Cl)cccc1Cl]

Hydroxylamine hydrochloride (6.6 g, 95 mmol) was added to a room temperature solution of 2,6-dichlorobenzaldehyde (11.1 g, 63.4 mmol) in pyridine (31.7 mL) giving a mild exotherm. After 10 minutes the excess pyridine was removed in vacuo and the residue was partitioned between Et$_2$O and water. The organic layer was sequentially washed with saturated aqueous NH$_4$Cl, brine and the combined aqueous layers were back extracted with several small portions of Et$_2$O. The combined organic extracts were dried over Na$_2$SO$_4$, filtered and concentrated in vacuo to give 2,6-dichlorobenzaldehyde oxime (12.4 g, 65.3 mmol, 100% yield) as a white solid. The product was carried on to the next step without further purification. $^1$H NMR (400 MHz, CDCl$_3$) δ 8.39 (s, 1H), 7.92 (s, 1H), 7.40-7.36 (m, 2H), 7.27-7.22 (m, 1H).

Step 2. 2,6-Dichloro-N-hydroxybenzimidoyl chloride

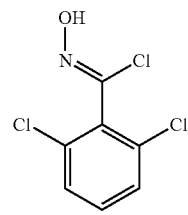 [SMILES: O/N=C(\Cl)c1c(Cl)cccc1Cl]

2,6-Dichlorobenzaldehyde oxime (12.0 g, 63.1 mmol) was dissolved in DMF (45.9 mL) and heated to 40° C. NCS (10.1 g, 76.0 mmol) dissolved in DMF (38.3 mL) was added to the warm solution over the space of approximately 3 minutes. After stirring overnight the reaction mixture was cooled to room temperature, poured into ice, and extracted with Et$_2$O. The organic layer was collected and washed with brine. The combined aqueous layers were back extracted with Et$_2$O. The combined organic layers were dried over Na$_2$SO$_4$, filtered and concentrated to dryness in vacuo. The residue was purified by flash chromatography on SiO$_2$ (0-50% EtOAc/hexanes, Isco 120 g column) to give 2,6-dichloro-N-hydroxybenzimidoyl chloride (13.3 g, 59.3 mmol, 94% yield) as a waxy white solid. $^1$H NMR (500 MHz, CDCl$_3$) δ 8.02 (s, 1H), 7.43-7.37 (m, 2H), 7.37-7.30 (m, 1H).

Step 3. Methyl 5-cyclopropyl-3-(2,6-dichlorophenyl)isoxazole-4-carboxylate

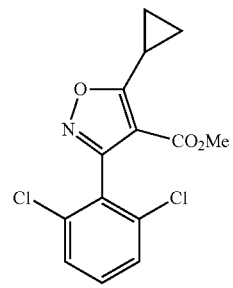 [SMILES: COC(=O)c1c(-c2c(Cl)cccc2Cl)noc1C1CC1]

To a 50 mL round bottom flask containing methyl 3-cyclopropyl-3-oxopropanoate (1.3 g, 8.9 mmol) was added triethylamine (2.5 mL, 17.8 mmol). The resulting clear solution was stirred at room temperature for 15 minutes and was cooled in an ice water bath. To the stirring solution was added a solution of 2,6-dichloro-N-hydroxybenzimidoyl chloride (2.0 g, 8.9 mmol) in EtOH (4 mL) over the space of 10 minutes giving a white suspension. After stirring at room temperature overnight, the reaction mixture was concentrated in vacuo and the residue was purified by flash chromatography on SiO$_2$ (0-10% EtOAc/hexanes, Isco 80 g column) to give methyl 5-cyclopropyl-3-(2,6-dichlorophenyl)isoxazole-4-carboxylate (2.4 g, 7.7 mmol, 87% yield) as a white solid. $^1$H NMR (500 MHz, CDCl$_3$) δ 7.45-7.39 (m, 2H), 7.39-7.33 (m, 1H), 3.71 (s, 3H), 2.93 (tt, J=8.5, 5.2 Hz, 1H), 1.47-1.40 (m, 2H), 1.34-1.27 (m, 2H).

Step 4. (5-Cyclopropyl-3-(2,6-dichlorophenyl)isoxazol-4-yl)methanol

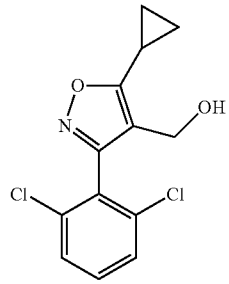 [SMILES: OCc1c(-c2c(Cl)cccc2Cl)noc1C1CC1]

To a solution of methyl 5-cyclopropyl-3-(2,6-dichlorophenyl)isoxazole-4-carboxylate (3.0 g, 9.6 mmol) in THF (11.1 mL) at 0° C. was added 1 M diisobutyl aluminum hydride (20.2 mL, 20.2 mmol) in toluene. The reaction mixture was warmed to room temperature and stirred for 2 h. The reaction was cooled to 0° C. and quenched by the addition of MeOH (2 mL) and 1 M aq. HCl (~75 mL). The mixture was then extracted with EtOAc, and the organic layer was washed with brine. The organic layer was dried over MgSO$_4$ and concentrated to give (5-cyclopropyl-3-(2,6-dichlorophenyl)isoxazol-4-yl)methanol (2.5 g, 8.9 mmol, 92% yield) as a white solid, which was used without further purification. $^1$H NMR (500 MHz, CDCl$_3$) δ 7.46 (d, J=1.1 Hz, 1H), 7.45 (s, 1H), 7.41-7.36 (m, 1H), 4.44 (s, 2H), 2.22 (tt, J=8.5, 5.2 Hz, 1H), 1.42 (br s, 1H), 1.35-1.25 (m, 2H), 1.23-1.11 (m, 2H).

Step 5. 5-Cyclopropyl-3-(2,6-dichlorophenyl)isoxazole-4-carbaldehyde

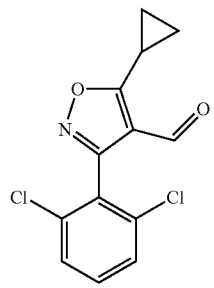 [SMILES: O=Cc1c(-c2c(Cl)cccc2Cl)noc1C1CC1]

To a solution of (5-cyclopropyl-3-(2,6-dichlorophenyl)isoxazol-4-yl)methanol (2.1 g, 7.4 mmol) in dichloromethane (37.0 mL) was added a mixture of pyridinium chlorochromate (6.4 g, 29.6 mmol) and finely ground 3 Å molecular sieves (6.1 g). The resulting mixture was stirred at room temperature for 30 min and then filtered through a pad of Celite. The pad was washed with MeOH/DCM. The filtrate was evaporated and the residue was purified by flash chromatography on SiO$_2$ (0-100% EtOAc/hexanes, Isco 80 g column) to give 5-cyclopropyl-3-(2,6-dichlorophenyl)isoxazole-4-carbaldehyde (1.9 g, 6.8 mmol, 93% yield) as a white solid. $^1$H NMR (500 MHz, CDCl$_3$) δ 9.67 (s, 1H), 7.49-7.44 (m, 2H), 7.43-7.37 (m, 1H), 2.82 (tt, J=8.3, 5.2 Hz, 1H), 1.52-1.45 (m, 2H), 1.40-1.33 (m, 2H).

Step 6. 4-(bromomethyl)-5-cyclopropyl-3-(2,6-dichlorophenyl)isoxazole

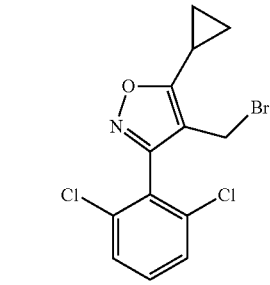 [SMILES: Clc1cccc(Cl)c1-c1noc(C2CC2)c1CBr]

Tetrabromomethane (3.8 g, 11.4 mmol) dissolved in dichloromethane (5.1 mL) was added to a 0° C. solution of (5-cyclopropyl-3-(2,6-dichlorophenyl)isoxazol-4-yl)methanol (2.2 g, 7.6 mmol) and triphenylphosphine (3.0 g, 11.4 mmol) in dichloromethane (25.2 mL). The reaction mixture was allowed to warm to room temperature and stirred for 2 h. The reaction mixture was diluted with dichloromethane and washed with H$_2$O. The dichloromethane layer was concentrated in vacuo to dryness. The resulting residue was purified by flash chromatography on SiO$_2$ (0-20% EtOAc/hexanes, Isco 120 g column) to give 4-(bromomethyl)-5-cyclopropyl-3-(2,6-dichlorophenyl)isoxazole (2.3 g, 6.7 mmol, 89% yield) as a white solid. $^1$H NMR (500 MHz, CDCl$_3$) δ 7.49-7.42 (m, 2H), 7.42-7.36 (m, 1H), 4.23 (s, 2H), 2.14 (tt, J=8.4, 5.1 Hz, 1H), 1.33-1.29 (m, 2H), 1.23-1.17 (m, 2H).

Step 7. Diethyl ((5-cyclopropyl-3-(2,6-dichlorophenyl)isoxazol-4-yl)methyl)phosphonate

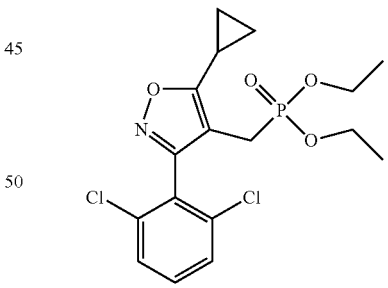

Triethyl phosphite (1.1 mL, 6.2 mmol) was added to a solution of 4-(bromomethyl)-5-cyclopropyl-3-(2,6-dichlorophenyl)isoxazole (1.2 g, 3.5 mmol) in dioxane (1.7 mL). The reaction mixture was stirred at 120° C. overnight. The reaction mixture was loaded onto SiO$_2$ and purified by flash chromatography on SiO$_2$ (0-100% EtOAc/hexanes, Isco 40 g column) to give diethyl ((5-cyclopropyl-3-(2,6-dichlorophenyl)isoxazol-4-yl)methyl)phosphonate (1.4 g, 3.4 mmol, 98% yield) as a white solid. $^1$H NMR (500 MHz, CDCl$_3$) δ 7.46-7.40 (m, 2H), 7.38-7.31 (m, 1H), 4.08-3.86 (m, 4H), 2.97-2.79 (m, 2H), 2.28-2.17 (m, 1H), 1.25 (dd, J=5.0, 2.2 Hz, 2H), 1.22 (t, J=7.0 Hz, 6H), 1.16-1.09 (m, 2H).

Step 8. tert-Butyl (E)-4-(2-(5-cyclopropyl-3-(2,6-dichlorophenyl)isoxazol-4-yl)vinyl) piperidine-1-carboxylate

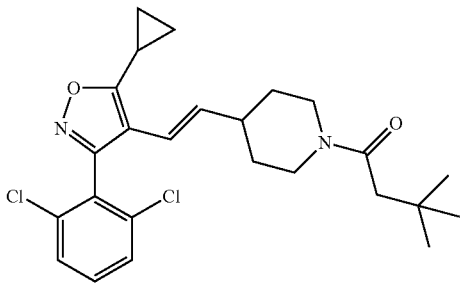 [SMILES: CC(C)(C)CC(=O)N1CCC(/C=C/c2c(-c3c(Cl)cccc3Cl)noc2C2CC2)CC1]

To a solution of diethyl ((5-cyclopropyl-3-(2,6-dichlorophenyl)isoxazol-4-yl) methyl)phosphonate (0.56 g, 1.4 mmol) in THF (11.0 mL) at −78° C. under nitrogen atmosphere, was added LiHMDS (1.0 M in THF) (2.7 mL, 2.7 mmol) dropwise. The mixture was stirred for 30 minutes and a solution of tert-butyl 4-formylpiperidine-1-carboxylate (0.29 g, 1.4 mmol) in THF (2.0 mL) was added. The reaction mixture was allowed to warm up to room temperature and stirred for 5 h. The reaction was quenched with 0.2 mL of MeOH, filtered through a pad of $SiO_2$ gel and concentrated to dryness in vacuo. The residue was purified by flash chromatography on $SiO_2$ (0-100% EtOAc/hexanes) to give tert-butyl (E)-4-(2-(5-cyclopropyl-3-(2,6-dichlorophenyl)isoxazol-4-yl)vinyl)piperidine-1-carboxylate (339 mg, 0.73 mmol, 54% yield) as a soft solid. $^1$H NMR (400 MHz, $CDCl_3$) δ 7.44-7.41 (m, 2H), 7.39-7.33 (m, 1H), 6.04 (dd, J=16.2, 1.2 Hz, 1H), 5.41 (dd, J=16.3, 7.0 Hz, 1H), 4.00 (br d, J=10.6 Hz, 2H), 2.72 (br t, J=12.1 Hz, 2H), 2.17-2.03 (m, 2H), 1.61 (br s, 1H), 1.57 (s, 2H), 1.45 (s, 9H), 1.32-1.21 (m, 2H), 1.17-1.06 (m, 3H).

9. (E)-5-Cyclopropyl-3-(2,6-dichlorophenyl)-4-(2-(piperidin-4-yl)vinyl)isoxazole

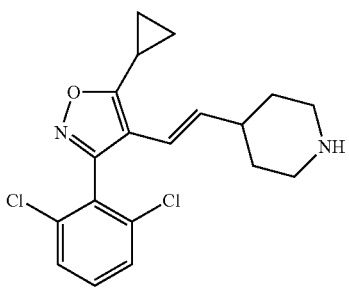 [SMILES: Clc1cccc(Cl)c1-c1noc(C2CC2)c1/C=C/C1CCNCC1]

To a solution of (E)-tert-butyl 4-(2-(5-cyclopropyl-3-(2,6-dichlorophenyl)isoxazol-4-yl)vinyl)piperidine-1-carboxylate (0.16 g, 0.35 mmol) in dichloromethane (0.6 mL) at 0° C. was added TFA (0.14 mL, 1.75 mmol) dropwise. The mixture was stirred at 0° C. for 30 minutes and at room temperature overnight. The excess TFA was removed in vacuo, the residue cooled to 0° C., basified with 1 N NaOH and extracted with three small portions of EtOAc. The extracts were washed with brine, dried over $MgSO_4$, filtered and concentrated in vacuo to give (E)-5-cyclopropyl-3-(2,6-dichlorophenyl)-4-(2-(piperidin-4-yl)vinyl)isoxazole (0.11 g, 0.29 mmol, 83% yield) as a light-yellow sticky solid. The product was used without further purification.

General Method for $S_NAR$: Method A1

Example 1. (E)-6-(4-(2-(5-Cyclopropyl-3-(2,6-dichlorophenyl)isoxazol-4-yl)vinyl)piperidin-1-yl) nicotinic acid A mixture of (E)-5-cyclopropyl-3-(2,6-dichlorophenyl)-4-(2-(piperidin-4-yl)vinyl) isoxazole (18.2 mg, 0.050 mmol), methyl 6-fluoronicotinate (15.5 mg, 0.10 mmol) and cesium carbonate (49.0 mg, 0.15 mmol) in DMA (0.5 mL) was heated at 60° C. After heating for 2 h, the mixture was cooled to room temperature and purified by flash chromatography on $SiO_2$ (0-100% EtOAc/hexanes, Isco 12 g column). The desired fractions were combined and evaporated in vacuo to give (E)-methyl 6-(4-(2-(5-cyclopropyl-3-(2,6-dichlorophenyl)isoxazol-4-yl)vinyl)piperidin-1-yl)nicotinate (20 mg, 0.040 mmol, 80% yield) as an off-white solid. $^1$H NMR (500 MHz, $CDCl_3$) δ 8.77 (d, J=2.2 Hz, 1H), 7.98 (dd, J=9.1, 2.5 Hz, 1H), 7.45-7.38 (m, 2H), 7.37-7.30 (m, 1H), 6.56 (d, J=9.1 Hz, 1H), 6.07 (d, J=16.2 Hz, 1H), 5.43 (dd, J=16.2, 6.9 Hz, 1H), 4.37 (br d, J=13.2 Hz, 2H), 3.86 (s, 3H), 3.02-2.90 (m, 2H), 2.29 (dtd, J=10.9, 7.2, 3.6 Hz, 1H), 2.15-2.05 (m, 1H), 1.80-1.69 (m, 2H), 1.36-1.20 (m, 4H), 1.18-1.07 (m, 2H).

A mixture of (E)-methyl 6-(4-(2-(5-cyclopropyl-3-(2,6-dichlorophenyl)isoxazol-4-yl)vinyl)piperidin-1-yl)nicotinate (20 mg, 0.040 mmol) and 1M aqueous lithium hydroxide, (140 μL, 0.14 mmol) in THF (268 μL) and MeOH (134 μL) was stirred at room temperature. After stirring at room temperature overnight, the mixture was concentrated in vacuo to remove the solvents, cooled to 0° C. and acidified with 1N HCl. The mixture was evaporated in vacuo, dissolved in 1:1 DMF/DMSO (2 mL) and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-80% B over 19 minutes, then a 5-minute hold at 100% B; Flow: 20 mL/min. Fractions containing the desired product were combined and dried via centrifugal evaporation to give (E)-6-(4-(2-(5-cyclopropyl-3-(2,6-dichlorophenyl)isoxazol-4-yl)vinyl)piperidin-1-yl)nicotinic acid (13.9 mg, 0.028 mmol, 69% yield). MS (ESI) m/z: 484.3 [M+H]+; $^1$H NMR (500 MHz, DMSO-$d_6$) δ 8.57 (d, J=2.3 Hz, 1H), 7.88 (dd, J=2.4, 9.1 Hz, 1H), 7.64 (d, J=8.0 Hz, 2H), 7.57 (dd, J=7.0, 9.0 Hz, 1H), 6.79 (d, J=9.2 Hz, 1H), 6.15 (d, J=16.3 Hz, 1H), 5.30 (dd, J=7.0, 16.2 Hz, 1H), 4.28 (d, J=13.3 Hz, 2H), 2.93 (t, J=12.4 Hz, 2H), 2.33 (dq, J=4.3, 5.0, 8.5 Hz, 1H), 1.60 (d, J=12.9 Hz, 2H), 1.23-0.99 (m, 6H); HLE GAL-FXR $EC_{50}$=14 nM.

General Method for Pd-Catalyzed C—N Coupling: Method A2

Example 2

(E)-6-(4-(2-(5-Cyclopropyl-3-(2,6-dichlorophenyl) isoxazol-4-yl)vinyl)piperidin-1-yl)-1-methyl-1H-indole-3-carboxylic acid

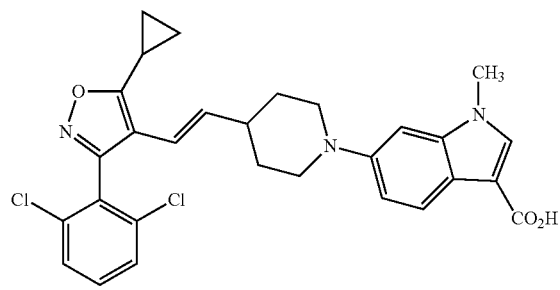
(2)

A slurry of (E)-5-cyclopropyl-3-(2,6-dichlorophenyl)-4-(2-(piperidin-4-yl)vinyl) isoxazole (16.2 mg, 0.045 mmol), methyl 6-bromo-1-methyl-1H-indole-3-carboxylate (14.4 mg, 0.054 mmol) and $Cs_2CO_3$ (29.1 mg, 0.089 mmol) in dioxane (446 µL) was degassed by bubbling nitrogen through the mixture for 5 minutes. Chloro(2-dicyclohexylphosphino-2',6'-diisopropoxy-1,1'-biphenyl)[2-(2'-amino-1,1'-biphenyl)]palladium(II) (RuPhos-Pd-G2) (1.7 mg, 2.2 µmol) was then added and the reaction vessel was sealed and heated to 90° C. After heating for 2 days, the mixture was diluted with MeOH, filtered and concentrated to dryness in vacuo. To the residue was added THF (300 µL), MeOH (150 µL) and 1M aqueous lithium hydroxide (180 µL, 0.18 mmol) and the resulting mixture was stirred at room temperature overnight. The mixture was heated at 50° C. for 10 h, and at 65° C. for 3 h. The mixture was concentrated to remove the solvents, cooled to 0° C. and acidified with 1 N HCl. The mixture was dissolved in DMSO (2 mL), filtered and the crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 45-90% B over 22 minutes, then a 5-minute hold at 100% B; Flow: 20 mL/min. Fractions containing the desired product were combined and dried via centrifugal evaporation to give (E)-6-(4-(2-(5-cyclopropyl-3-(2,6-dichlorophenyl)isoxazol-4-yl)vinyl)piperidin-1-yl)-1-methyl-1H-indole-3-carboxylic acid (5.3 mg, 9.9 µmol, 22% yield). MS (ESI) m/z: 536.1 [M+H]+; $^1$H NMR (500 MHz, DMSO-$d_6$) δ 7.84-7.76 (m, 2H), 7.68 (d, J=8.0 Hz, 2H), 7.60 (dd, J=7.1, 9.1 Hz, 1H), 6.97-6.85 (m, 2H), 6.20 (d, J=16.2 Hz, 1H), 5.37 (dd, J=7.0, 16.2 Hz, 1H), 3.76 (s, 3H), 3.56 (d, J=12.0 Hz, 2H), 2.68 (t, J=11.5 Hz, 2H), 2.37 (q, J=3.4, 5.5 Hz, 1H), 2.15 (br s, 1H), 1.67 (d, J=12.7 Hz, 2H), 1.39-0.97 (m, 6H); HLE GAL-FXR $EC_{50}$=5 nM.

Example 3

(Z)-6-(4-(2-(5-cyclopropyl-3-(2,6-dichlorophenyl) isoxazol-4-yl)vinyl)piperidin-1-yl)nicotinic acid

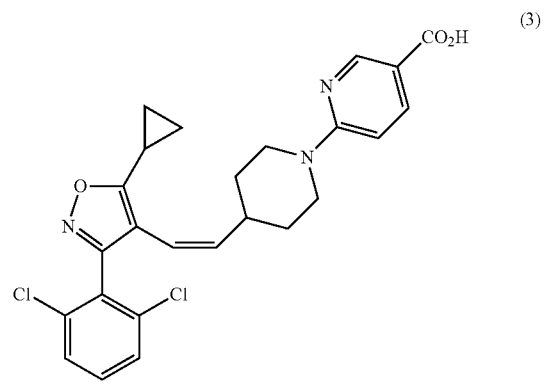 [SMILES: O=C(O)c1ccc(N2CCC(/C=C\c3c(-c4c(Cl)cccc4Cl)noc3C3CC3)CC2)nc1]
(3)

Step 1. (Z)-4-(2-(5-cyclopropyl-3-(2,6-dichlorophenyl)isoxazol-4-yl)vinyl)piperidine-1-carboxylate

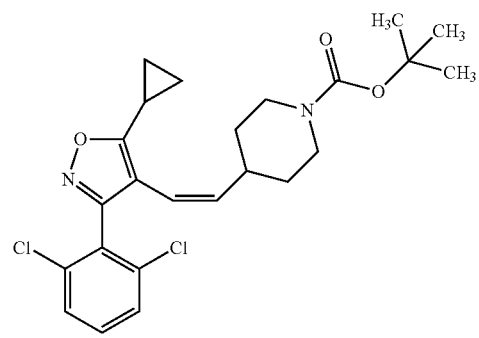 [SMILES: CC(C)(C)OC(=O)N1CCC(/C=C\c2c(-c3c(Cl)cccc3Cl)noc2C2CC2)CC1]

The title compound was obtained as a minor isolate from General Method A, step 8. $^1$H NMR (500 MHz, CDCl$_3$) δ 7.42-7.39 (m, 2H), 7.34-7.30 (m, 1H), 5.89 (d, J=11.3 Hz, 1H), 5.48 (t, J=10.7 Hz, 1H), 4.00 (br s, 2H), 2.36-2.21 (m, 1H), 1.98 (tt, J=8.5, 5.0 Hz, 1H), 1.44 (s, 9H), 1.29-1.23 (m, 3H), 1.21-1.12 (m, 4H), 1.12-1.05 (m, 2H).

Step 2. (Z)-5-Cyclopropyl-3-(2,6-dichlorophenyl)-4-(2-(piperidin-4-yl)vinyl)isoxazole

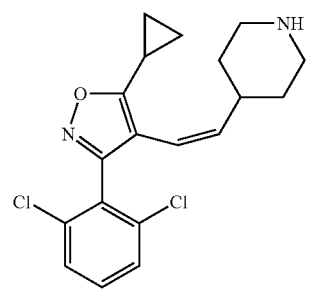 [SMILES: Clc1cccc(Cl)c1-c1noc(C2CC2)c1/C=C\C1CCNCC1]

To a solution of (Z)-tert-butyl 4-(2-(5-cyclopropyl-3-(2,6-dichlorophenyl)isoxazol-4-yl)vinyl)piperidine-1-carboxylate (47 mg, 0.10 mmol) in $CH_2Cl_2$ (0.6 mL) at 0° C. was added TFA (0.04 mL, 0.51 mmol) dropwise. The mixture was stirred at 0° C. for 30 minutes and at room temperature overnight. The mixture was concentrated to dryness in vacuo, cooled to 0° C., basified with 1 N NaOH and then extracted three times with EtOAc. The extracts were washed with brine, dried over MgSO₄ and concentrated in vacuo to give (Z)-5-Cyclopropyl-3-(2,6-dichlorophenyl)-4-(2-(piperidin-4-yl)vinyl)isoxazole (36.8 mg, 1.0 mmol, 100% yield) as an off-white solid. The product was used without further purification. ¹H NMR (400 MHz, CDCl₃) δ 7.42-7.38 (m, 2H), 7.35-7.29 (m, 1H), 5.94 (d, J=11.0 Hz, 1H), 5.50 (t, J=10.7 Hz, 1H), 3.15 (br d, J=12.8 Hz, 2H), 2.63 (td, J=12.5, 2.5 Hz, 2H), 2.40-2.25 (m, 1H), 1.96 (tt, J=8.4, 5.1 Hz, 1H), 1.51-1.36 (m, 2H), 1.33-1.21 (m, 5H), 1.13-1.04 (m, 2H).

Example 3. (Z)-6-(4-(2-(5-Cyclopropyl-3-(2,6-dichlorophenyl)isoxazol-4-yl)vinyl)piperidin-1-yl) nicotinic acid The title compound was prepared as described in General Method A1 for the preparation of Example 1 with the replacement of (E)-5-Cyclopropyl-3-(2,6-dichlorophenyl)-4-(2-(piperidin-4-yl)vinyl)isoxazole with (Z)-5-Cyclopropyl-3-(2,6-dichlorophenyl)-4-(2-(piperidin-4-yl)vinyl) isoxazole in step 10. MS (ESI) m/z: 484.3 [M+H]+; ¹H NMR (500 MHz, DMSO-d₆) δ 8.57 (d, J=2.4 Hz, 1H), 7.88 (dd, J=2.4, 9.2 Hz, 1H), 7.65 (d, J=8.1 Hz, 2H), 7.57 (dd, J=7.3, 9.0 Hz, 1H), 6.80 (d, J=9.2 Hz, 1H), 5.87 (d, J=11.1 Hz, 1H), 5.55 (t, J=10.8 Hz, 1H), 4.34 (d, J=13.3 Hz, 2H), 2.76 (q, J=9.3, 11.8 Hz, 2H), 2.34 (d, J=9.9 Hz, 1H), 2.09 (td, J=5.6, 9.9, 11.2 Hz, 1H), 1.28-1.00 (m, 8H); HLE GAL-FXR EC₅₀=107 nM.

Example 4

(E)-2-(4-(1-(5-Cyclopropyl-3-(2,6-dichlorophenyl) isoxazol-4-yl)prop-1-en-2-yl)piperidin-1-yl)-4-fluorobenzo[d]thiazole-6-carboxylic acid (4)

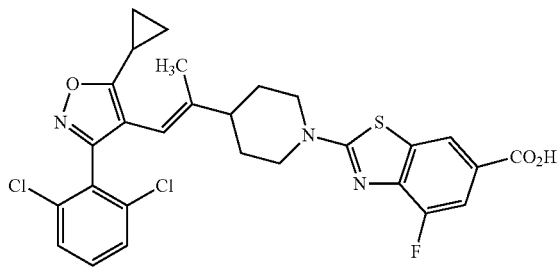

Step 1. tert-Butyl (E)-4-(1-(5-cyclopropyl-3-(2,6-dichlorophenyl)isoxazol-4-yl)prop-1-en-2-yl)piperidine-1-carboxylate

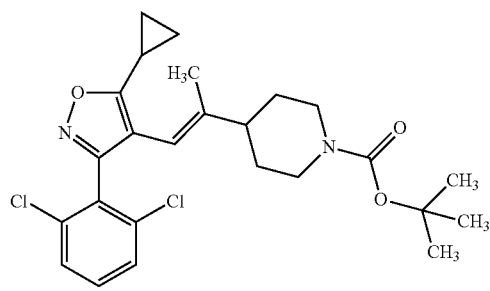 [SMILES: C/C(=C\c1c(-c2c(Cl)cccc2Cl)noc1C1CC1)C1CCN(C(=O)OC(C)(C)C)CC1]

To a solution of diethyl ((5-cyclopropyl-3-(2,6-dichlorophenyl)isoxazol-4-yl) methyl)phosphonate (0.21 g, 0.51 mmol, synthesis described in General Method A) in toluene (1.3 mL), was added tert-butyl 4-acetylpiperidine-1-carboxylate (0.17 g, 0.76 mmol), KOtBu (0.11 g, 1.0 mmol), and 18-crown-6 (0.27 g, 1.0 mmol). The reaction mixture was heated for 2 h at 50° C. and was diluted with H₂O and extracted with EtOAc. The EtOAc layer was concentrated in vacuo to dryness. The resulting residue was purified by flash chromatography on SiO₂ (0-15% EtOAc/hexanes, Isco 40 g column) to give a mixture of E and Z isomers; tert-butyl (E)-4-(2-(5-cyclopropyl-3-(2,6-dichlorophenyl)isoxazol-4-yl)vinyl)-4-methylpiperidine-1-carboxylate and tert-butyl (Z)-4-(2-(5-cyclopropyl-3-(2,6-dichlorophenyl)isoxazol-4-yl)vinyl)-4-methylpiperidine-1-carboxylate (0.10 g) as a white solid. The E and Z isomers were separated by preparative SFC (Column: Chiralpak IC, 4.6×250 mm, 5 μM; Mobile Phase 15% MeOH/85% CO₂, Flow: 2.0 mL/min, 150 Bar, 40° C.) to yield tert-butyl (E)-4-(1-(5-cyclopropyl-3-(2,6-dichlorophenyl)isoxazol-4-yl)prop-1-en-2-yl)piperidine-1-carboxylate (75 mg, 0.16 mmol, 31% yield) upon concentration in vacuo. ¹H NMR (500 MHz, CDCl₃) δ 7.39 (s, 1H), 7.38 (s, 1H), 7.33-7.29 (m, 1H), 5.66 (s, 1H), 4.14 (br d, J=6.6 Hz, 2H), 2.66 (br s, 2H), 2.12-2.02 (m, 1H), 1.88 (tt, J=8.5, 5.2 Hz, 1H), 1.62-1.59 (m, 2H), 1.58 (d, J=1.1 Hz, 3H), 1.46 (s, 9H), 1.41-1.31 (m, 2H), 1.24-1.20 (m, 2H), 1.11-1.05 (m, 2H).

Step 2. (E)-5-Cyclopropyl-3-(2,6-dichlorophenyl)-4-(2-(piperidin-4-yl)prop-1-en-1-yl)isoxazole

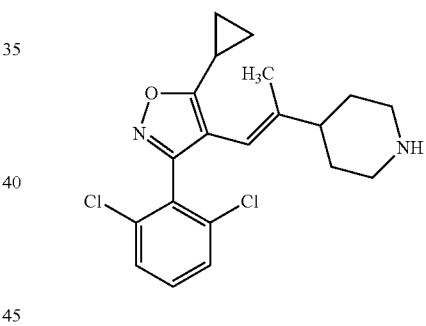

To a 1 dram vial was added tert-butyl (E)-4-(1-(5-cyclopropyl-3-(2,6-dichlorophenyl)isoxazol-4-yl)prop-1-en-2-yl) piperidine-1-carboxylate (0.16 g, 0.34 mmol), dichloromethane (0.34 mL) and TFA (0.13 mL, 1.7 mmol). After 30 minutes the reaction mixture was cooled to 0° C. and basified with 1N NaOH until ~pH 8-9. More dichloromethane was added and the mixture was washed with H₂O. The aqueous layer was extracted three times with dichloromethane, and the combined organic layers where dried over Na₂SO₄, filtered, and concentrated in vacuo to give (E)-5-cyclopropyl-3-(2,6-dichlorophenyl)-4-(2-(piperidin-4-yl) prop-1-en-1-yl)isoxazole (0.13 g, 0.34 mmol, 99% yield) as an off-white foam.

Example 4. (E)-2-(4-(1-(5-cyclopropyl-3-(2,6-dichlorophenyl)isoxazol-4-yl)prop-1-en-2-yl)piperidin-1-yl)-4-fluorobenzo[d]thiazole-6-carboxylic acid The title compound was prepared as described in General Method A1 for the preparation of Example 1 with the replacement of (E)-5-cyclopropyl-3-(2,6-dichlorophenyl)-4-(2-(piperidin-4-yl)vinyl)isoxazole and methyl 6-fluoronicotinate with (E)-5-cyclopropyl-3-(2,6-dichlorophenyl)-4-(2-(piperidin-4-yl)prop-1-en-1-yl)isoxazole and ethyl 2-bromo-4-fluorobenzo[d]thiazole-6-carboxylate. MS (ESI) m/z: 572.3 [M+H]+; $^1$H NMR (500 MHz, DMSO-$d_6$) δ 8.24-8.06 (m, 1H), 7.61-7.59 (m, 1H), 7.59-7.56 (m, 2H), 7.55-7.50 (m, 1H), 5.67 (s, 1H), 4.08 (br d, J=10.6 Hz, 2H), 3.23 (br s, 2H), 2.35-2.26 (m, 1H), 2.04-1.95 (m, 1H), 1.70 (br d, J=12.6 Hz, 2H), 1.54 (s, 3H), 1.51-1.41 (m, 2H), 1.15-1.09 (m, 2H), 1.07-1.02 (m, 2H); HLE GAL-FXR $EC_{50}$=2055 nM.

Example 5

(E)-6-(4-(1-(5-Cyclopropyl-3-(2,6-dichlorophenyl)isoxazol-4-yl)prop-1-en-2-yl)piperidin-1-yl)quinoline-2-carboxylic acid (5)

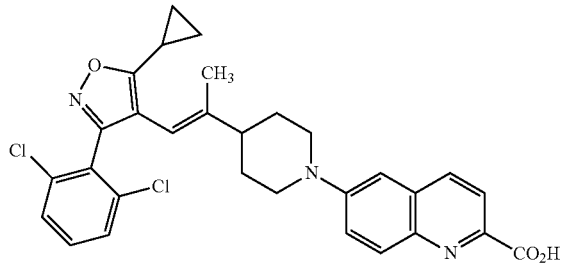

The title compound was prepared as described in General Method A2 for the preparation of Example 2 with the replacement of (E)-5-cyclopropyl-3-(2,6-dichlorophenyl)-4-(2-(piperidin-4-yl)vinyl)isoxazole and methyl 6-bromo-1-methyl-1H-indole-3-carboxylate with (E)-5-cyclopropyl-3-(2,6-dichlorophenyl)-4-(2-(piperidin-4-yl)prop-1-en-1-yl)isoxazole and methyl 6-bromoquinoline-2-carboxylate. MS (ESI) m/z: 548.4 [M+H]+; $^1$H NMR (500 MHz, DMSO-$d_6$) δ 7.66-7.48 (m, 5H), 7.25-6.93 (m, 3H), 5.62-5.58 (m, 1H), 4.36-4.14 (m, 2H), 4.03-3.85 (m, 2H), 2.56 (br s, 2H), 2.19-2.11 (m, 1H), 2.00-1.96 (m, 1H), 1.59-1.54 (m, 2H), 1.50 (br s, 3H), 1.11 (br d, J=5.5 Hz, 2H), 1.03 (br d, J=1.3 Hz, 2H); HLE GAL-FXR $EC_{50}$=1250 nM.

Example 6

(E)-2-(4-(2-(5-Cyclopropyl-3-(2,6-dichlorophenyl)isoxazol-4-yl)vinyl)-4-methylpiperidin-1-yl)-4-fluorobenzo[d]thiazole-6-carboxylic acid (6)

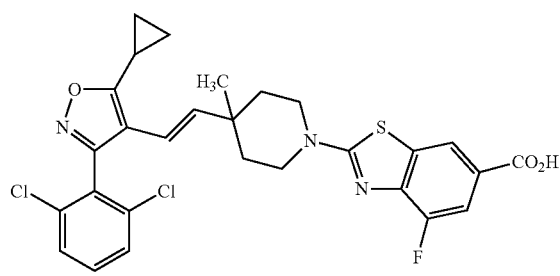

Step 1. tert-Butyl (E)-4-(2-(5-cyclopropyl-3-(2,6-dichlorophenyl)isoxazol-4-yl)vinyl)-4-methylpiperidine-1-carboxylate

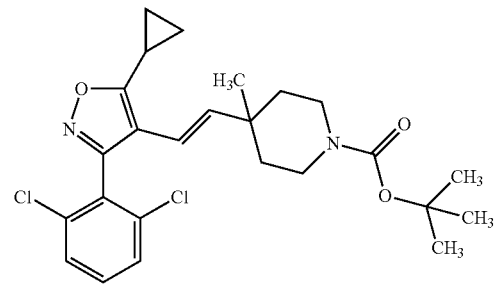 [SMILES: CC1(/C=C/c2c(-c3c(Cl)cccc3Cl)noc2C2CC2)CCN(C(=O)OC(C)(C)C)CC1]

The title compound was prepared as described for the preparation of tert-butyl (E)-4-(2-(5-cyclopropyl-3-(2,6-dichlorophenyl)isoxazol-4-yl)vinyl)piperidine-1-carboxylate (General Method A, step 8) with replacement of tert-butyl 4-formylpiperidine-1-carboxylate with tert-butyl 4-formyl-4-methylpiperidine-1-carboxylate. $^1$H NMR (500 MHz, $CDCl_3$) δ 7.48-7.42 (m, 2H), 7.40-7.35 (m, 1H), 6.05 (d, J=16.8 Hz, 1H), 5.44 (d, J=16.5 Hz, 1H), 3.76-3.60 (m, 1H), 3.49 (br d, J=11.6 Hz, 2H), 3.22-3.10 (m, 1H), 3.10-2.99 (m, 2H), 2.17-2.06 (m, 1H), 1.99-1.87 (m, 1H), 1.47 (s, 9H), 1.42 (br d, J=4.1 Hz, 2H), 1.37-1.30 (m, 3H), 1.30-1.24 (m, 2H), 1.21-1.13 (m, 2H).

Step 2. (E)-5-Cyclopropyl-3-(2,6-dichlorophenyl)-4-(2-(4-methylpiperidin-4-yl)vinyl) isoxazole

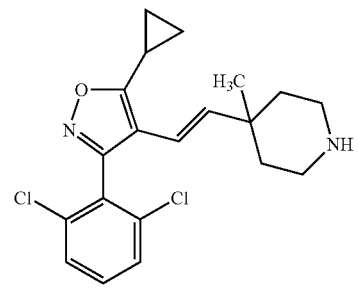 [SMILES: CC1(/C=C/c2c(-c3c(Cl)cccc3Cl)noc2C2CC2)CCNCC1]

To a 10 mL flask was added (E)-tert-butyl 4-(2-(5-cyclopropyl-3-(2,6-dichlorophenyl)isoxazol-4-yl)vinyl)-4-methylpiperidine-1-carboxylate (0.13 g, 0.27 mmol), dichloromethane (0.27 mL) and TFA (0.10 mL, 1.3 mmol). The reaction mixture was stirred at room temperature for 30 minutes and then more TFA (0.10 mL, 1.3 mmol) was added. After 20 minutes 1.0 M NaOH added until pH>7. The mixture was diluted with dichloromethane and washed with $H_2O$. The dichloromethane layer was washed with brine, dried over $Na_2SO_4$, filtered, and concentrated in vacuo to give (E)-5-cyclopropyl-3-(2,6-dichlorophenyl)-4-(2-(4-methylpiperidin-4-yl)vinyl)isoxazole (0.10 g, 0.26 mmol, 98% yield) as a colorless oil. The product was used in subsequent steps without further purification or characterization.

Example 6. (E)-2-(4-(2-(5-Cyclopropyl-3-(2,6-dichlorophenyl)isoxazol-4-yl)vinyl)-4-methylpiperidin-1-yl)-4-fluorobenzo[d]thiazole-6-carboxylic acid The title compound was prepared as described in General Method A1 for the preparation of Example 1 with the replacement of (E)-5-cyclopropyl-3-(2,6-dichlorophenyl)-4-(2-(piperidin-4-yl)vinyl)isoxazole and methyl 6-fluoronicotinate with (E)-5-cyclopropyl-3-(2,6-dichlorophenyl)-4-(2-(4-methylpiperidin-4-yl)vinyl)isoxazole and ethyl 2-bromo-4-fluorobenzo[d]thiazole-6-carboxylate. MS (ESI) m/z: 572.0 [M+H]+; $^1$H NMR (500 MHz, DMSO-$d_6$) δ 8.19 (br s, 1H), 7.65 (s, 1H), 7.64 (s, 1H), 7.61-7.52 (m, 2H), 6.27 (d, J=16.8 Hz, 1H), 5.32 (d, J=16.8 Hz, 1H), 3.74-3.56 (m, 1H), 3.29-3.20 (m, 1H), 3.16 (s, 1H), 2.45-2.35 (m, 1H), 1.56-1.50 (m, 2H), 1.49-1.41 (m, 2H), 1.22 (s, 1H), 1.19-1.14 (m, 2H), 1.09 (br d, J=3.1 Hz, 2H), 0.97 (s, 3H); HLE GAL-FXR $EC_{50}$=536 nM.

Example 7

(E)-6-(4-(2-(5-cyclopropyl-3-(2,6-dichlorophenyl)isoxazol-4-yl)vinyl)-4-methylpiperidin-1-yl)quinoline-2-carboxylic acid

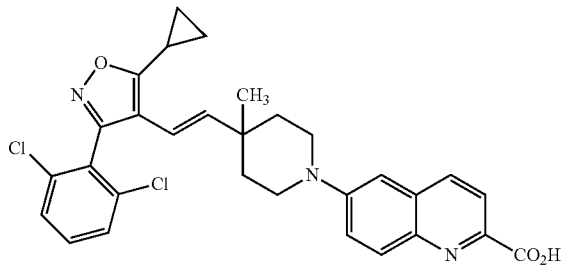

(7)

The title compound was prepared as described in General Method A2 for the preparation of Example 2 with the replacement of (E)-5-cyclopropyl-3-(2,6-dichlorophenyl)-4-(2-(piperidin-4-yl)vinyl)isoxazole and methyl 6-bromo-1-methyl-1H-indole-3-carboxylate with (E)-5-cyclopropyl-3-(2,6-dichlorophenyl)-4-(2-(4-methylpiperidin-4-yl)vinyl)isoxazole and methyl 6-bromoquinoline-2-carboxylate. MS (ESI) m/z: 548.0 [M+H]+; $^1$H NMR (500 MHz, DMSO-$d_6$) δ 8.24 (br d, J=8.5 Hz, 1H), 7.97 (d, J=8.5 Hz, 1H), 7.93 (br d, J=9.5 Hz, 1H), 7.65 (br d, J=7.3 Hz, 1H), 7.61 (s, 1H), 7.59 (s, 1H), 7.53-7.45 (m, 1H), 7.15 (br d, J=2.1 Hz, 1H), 6.30-6.29 (m, 1H), 6.26 (d, J=16.5 Hz, 1H), 5.38 (d, J=16.8 Hz, 1H), 2.94 (br t, J=8.9 Hz, 2H), 2.44-2.34 (m, 1H), 1.58-1.41 (m, 4H), 1.23 (s, 2H), 1.16 (br d, J=7.9 Hz, 2H), 1.09 (br d, J=2.4 Hz, 2H), 0.99 (s, 3H); HLE GAL-FXR $EC_{50}$=227 nM.

Example 8

(E)-2-(6-(2-(5-Cyclopropyl-3-(2,6-dichlorophenyl)isoxazol-4-yl)vinyl)-3-azabicyclo[3.1.0]hexan-3-yl)-4-fluorobenzo[d]thiazole-6-carboxylic acid (8)

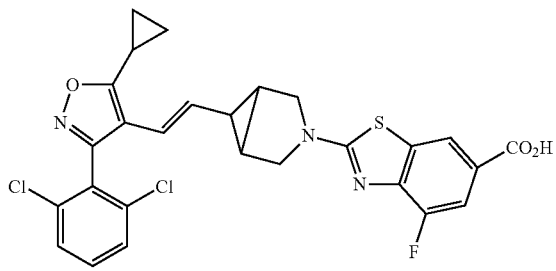

Step 1. tert-Butyl (E)-6-(2-(5-cyclopropyl-3-(2,6-dichlorophenyl)isoxazol-4-yl)vinyl)-3-azabicyclo[3.1.0]hexane-3-carboxylate

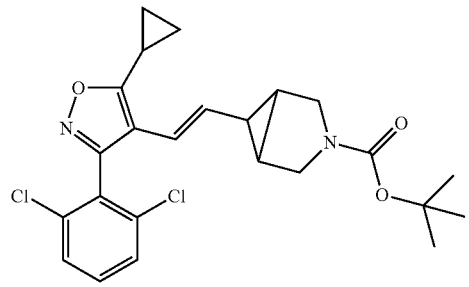 [SMILES: CC(C)(C)OC(=O)N1CC2C(/C=C/c3c(-c4c(Cl)cccc4Cl)noc3C3CC3)C2C1]

To a solution of diethyl ((5-cyclopropyl-3-(2,6-dichlorophenyl)isoxazol-4-yl)methyl)phosphonate (0.46 g, 1.14 mmol, synthesis described in General Method A) and tert-butyl 6-formyl-3-azabicyclo[3.1.0]hexane-3-carboxylate (0.29 g, 1.4 mmol) in THF (7 mL) at 40° C., was added KOtBu (1.0 M in THF, 1.4 mL, 1.4 mmol). The reaction mixture was quenched with 2 mL of saturated aqueous NH$_4$Cl, and extracted with EtOAc (2×20 mL). The combined EtOAc layers were concentrated in vacuo giving a yellow oil. The residue was purified by preparative HPLC (Phenomenex Axia Luna C18 5µ30×100 mm column, 10 minute gradient from 5 to 100% B in A, A=10:90:0.1 MeCN:H$_2$O:TFA, B=90:10:0.1 MeCN:H$_2$O:TFA). The product containing fractions were combined, and concentrated in vacuo to give tert-butyl (E)-6-(2-(5-cyclopropyl-3-(2,6-dichlorophenyl)isoxazol-4-yl)vinyl)-3-azabicyclo[3.1.0]hexane-3-carboxylate (0.40 g, 0.88 mmol, 77% yield) as a foam. $^1$H NMR (400 MHz, CDCl$_3$) δ 7.46-7.39 (m, 2H), 7.39-7.32 (m, 1H), 6.04 (d, J=16.1 Hz, 1H), 5.12 (dd, J=16.0, 8.7 Hz, 1H), 3.70-3.48 (m, 2H), 3.44-3.26 (m, 2H), 2.08 (tt, J=8.4, 5.1 Hz, 1H), 1.43 (s, 11H), 1.31-1.20 (m, 3H), 1.17-1.05 (m, 2H).

Step 2. (E)-4-(2-(3-Azabicyclo[3.1.0]hexan-6-yl)vinyl)-5-cyclopropyl-3-(2,6-dichlorophenyl)isoxazole

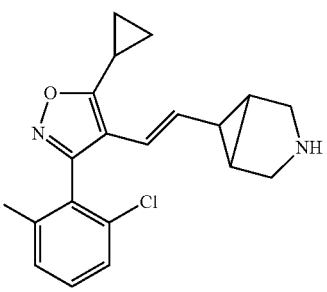

To a 1 dram vial was added tert-butyl (E)-6-(2-(5-cyclopropyl-3-(2,6-dichlorophenyl)isoxazol-4-yl)vinyl)-3-azabicyclo[3.1.0]hexane-3-carboxylate (85.1 mg, 0.18 mmol), dichloromethane (184 µL) and TFA (355 µL, 4.6 mmol), and the mixture was stirred for 30 minutes. The reaction mixture was neutralized with 1.0 N NaOH, diluted with dichloromethane and washed with H$_2$O. The dichloromethane layer was dried over Na$_2$SO$_4$, filtered, and concentrated in vacuo giving (E)-4-(2-(3-azabicyclo[3.1.0]hexan-6-yl)vinyl)-5-cyclopropyl-3-(2,6-dichlorophenyl)isoxazole (66.5 mg, 0.18 mmol, 100% yield) as a white foam. The product was used without further purification or characterization. MS (ESI) m/z: 361.0 [M+H]+.

Example 8. (E)-2-(6-(2-(5-Cyclopropyl-3-(2,6-dichlorophenyl)isoxazol-4-yl)vinyl)-3-azabicyclo[3.1.0]hexan-3-yl)-4-fluorobenzo[d]thiazole-6-carboxylic acid The title compound was prepared as described in General Method A1 for the preparation of Example 1 with the replacement of (E)-5-cyclopropyl-3-(2,6-dichlorophenyl)-4-(2-(piperidin-4-yl)vinyl)isoxazole and methyl 6-fluoronicotinate with (E)-4-(2-(3-azabicyclo[3.1.0]hexan-6-yl)vinyl)-5-cyclopropyl-3-(2,6-dichlorophenyl)isoxazole and ethyl 2-bromo-4-fluorobenzo[d]thiazole-6-carboxylate. MS (ESI) m/z: 556.2 [M+H]+; $^1$H NMR (500 MHz, DMSO-$d_6$) δ 8.21 (d, J=1.4 Hz, 1H), 7.66 (d, J=1.4 Hz, 1H), 7.65 (s, 1H), 7.60 (d, J=6.9 Hz, 1H), 7.58 (d, J=7.2 Hz, 1H), 6.13 (d, J=16.0 Hz, 1H), 5.19 (dd, J=16.2, 8.8 Hz, 1H), 3.80-3.63 (m, 4H), 2.38-2.30 (m, 1H), 1.75 (br s, 2H), 1.47-1.37 (m, 1H), 1.20-1.12 (m, 2H), 1.11-1.03 (m, 2H); HLE GAL-FXR $EC_{50}$=120 nM.

Example 9

(E)-6-(6-(2-(5-cyclopropyl-3-(2,6-dichlorophenyl)isoxazol-4-yl)vinyl)-3-azabicyclo[3.1.0]hexan-3-yl)quinoline-2-carboxylic acid (9)

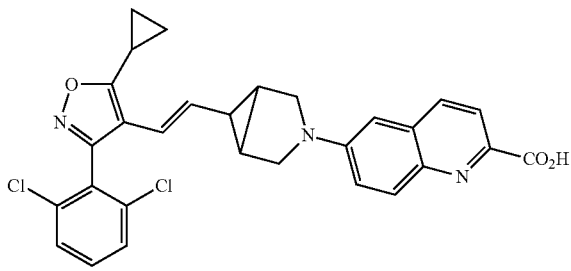

The title compound was prepared as described in General Method A2 for the preparation of Example 2 with the replacement of (E)-5-cyclopropyl-3-(2,6-dichlorophenyl)-4-(2-(piperidin-4-yl)vinyl)isoxazole and methyl 6-bromo-1-methyl-1H-indole-3-carboxylate with (E)-4-(2-(3-azabicyclo[3.1.0]hexan-6-yl)vinyl)-5-cyclopropyl-3-(2,6-dichlorophenyl)isoxazole and methyl 6-bromoquinoline-2-carboxylate. MS (ESI) m/z: 531.9 [M+H]+; $^1$H NMR (500 MHz, DMSO-$d_6$) δ 8.13 (d, J=8.5 Hz, 1H), 7.92 (d, J=3.6 Hz, 1H), 7.90 (d, J=4.1 Hz, 1H), 7.67 (d, J=1.4 Hz, 1H), 7.66 (s, 1H), 7.62-7.57 (m, 1H), 7.32 (dd, J=9.4, 2.5 Hz, 1H), 6.78 (d, J=2.5 Hz, 1H), 6.15 (d, J=16.2 Hz, 1H), 5.16 (dd, J=16.1, 8.9 Hz, 1H), 3.69 (d, J=9.9 Hz, 2H), 3.58-3.53 (m, 2H), 3.16 (br d, J=5.5 Hz, 2H), 2.38-2.32 (m, 1H), 1.47-1.35 (m, 1H), 1.22-1.13 (m, 2H), 1.11-1.05 (m, 2H); HLE GAL-FXR $EC_{50}$=39 nM.

General Method B

Example 10

(E)-2-(4-(2-(4-Cyclopropyl-1-(2,6-dichlorophenyl)-1H-1,2,3-triazol-5-yl)vinyl)piperidin-1-yl)-4-fluorobenzo[d]thiazole-6-carboxylic acid (10)

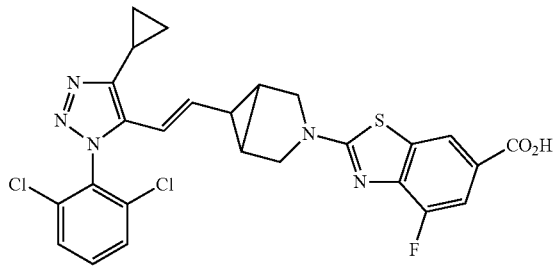

Step 1. 2-Azido-1,3-dichlorobenzene

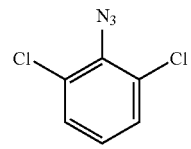 [SMILES: [N-]=[N+]=Nc1c(Cl)cccc1Cl]

To a solution of 2,6-dichloroaniline (0.96 g, 5.9 mmol) in TFA (10 mL) and water (2 mL) at 0° C. was added sodium nitrite (0.41 g, 5.9 mmol) over the space of 30 minutes. Sodium azide (0.98 g, 15.0 mmol) dissolved in minimal water was then added gradually. The reaction mixture was stirred at 0° C. for 10 minutes, and allowed to warm to room temperature. After 2 h, the reaction was quenched with water, and extracted with EtOAc. The organic layer was concentrated in vacuo and the residue was purified by flash chromatography on $SiO_2$ (0-20% EtOAc/hexanes) to afford 2-azido-1,3-dichlorobenzene (1.1 g, 5.7 mmol, 97% yield) as an oil. $^1$H NMR (500 MHz, $CDCl_3$) δ 7.30 (d, J=8.25 Hz, 2H), 7.05 (t, J=8.12 Hz, 1H)

Step 2. (4-Cyclopropyl-1-(2,6-dichlorophenyl)-1H-1,2,3-triazol-5-yl)methanol

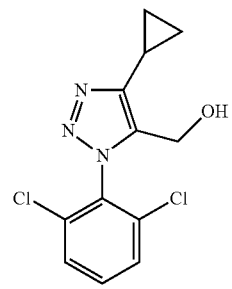 [SMILES: OCc1c(C2CC2)nnn1-c1c(Cl)cccc1Cl]

A mixture of 2-azido-1,3-dichlorobenzene (3.5 g, 18.6 mmol) and 3-cyclopropylprop-2-yn-1-ol (1.8 g, 18.6 mmol)

in toluene (12.4 mL) was sealed and heated at 110° C. over the weekend. The crude reaction mixture was purified by flash chromatography on SiO₂ (0-100% EtOAc/hexanes) to afford (4-cyclopropyl-1-(2,6-dichlorophenyl)-1H-1,2,3-triazol-5-yl)methanol (1.2 g, 4.1 mmol, 22% yield) as a tan solid. $^1$H NMR (500 MHz, CDCl₃) δ 7.49-7.53 (m, 2H), 7.42-7.47 (m, 1H), 4.63 (s, 2H), 1.96-1.99 (m, 1H), 1.10-1.16 (m, 2H), 0.99-1.04 (m, 2H).

Step 3. 5-(Bromomethyl)-4-cyclopropyl-1-(2,6-dichlorophenyl)-1H-1,2,3-triazole

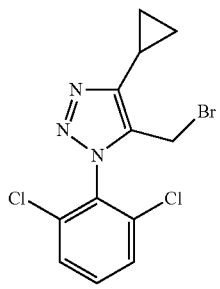 [SMILES: Clc1cccc(Cl)c1-n1nnc(C2CC2)c1CBr]

To a solution of (4-cyclopropyl-1-(2,6-dichlorophenyl)-1H-1,2,3-triazol-5-yl)methanol (0.33 g, 1.2 mmol) in dichloromethane (4.6 mL) was added triphenylphosphine (0.79 g, 3.0 mmol). After 15 minutes, CBr₄ (1.0 g, 3.0 mmol) was added portionwise. The resulting mixture was stirred at room temperature for 1 h and the crude reaction mixture was purified by flash chromatography on SiO₂ (0-20% EtOAc/hexanes) to afford 5-(bromomethyl)-4-cyclopropyl-1-(2,6-dichlorophenyl)-1H-1,2,3-triazole (426 mg, 1.154 mmol, 99% yield) as a tan foam. $^1$H NMR (500 MHz, CDCl₃) δ 7.52-7.58 (m, 2H), 7.47-7.51 (m, 1H), 4.38 (s, 2H), 1.87-1.98 (m, 1H), 1.18 (dd, J=2.06, 4.81 Hz, 2H), 1.02-1.12 (m, 2H).

Step 4. Diethyl ((4-cyclopropyl-1-(2,6-dichlorophenyl)-1H-1,2,3-triazol-5-yl)methyl)phosphonate

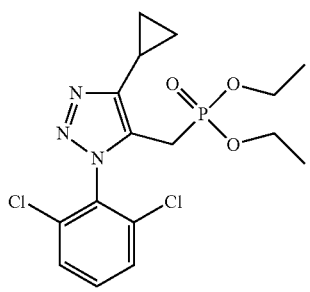 [SMILES: CCOP(=O)(Cc1c(C2CC2)nnn1-c1c(Cl)cccc1Cl)OCC]

A mixture of 5-(bromomethyl)-4-cyclopropyl-1-(2,6-dichlorophenyl)-1H-1,2,3-triazole (1.5 g, 4.3 mmol) and triethyl phosphite (1.3 g, 7.8 mmol) in dioxane (1.4 mL) was heated with stirring in a sealed tube at 120° C. overnight. The reaction mixture was loaded directly onto to a SiO₂ gel column for purification by flash chromatography (0-80% EtOAc/hexanes) to afford diethyl ((4-cyclopropyl-1-(2,6-dichlorophenyl)-1H-1,2,3-triazol-5-yl)methyl)phosphonate (1.81 g, 4.30 mmol, 99% yield) as an off-white solid. $^1$H NMR (400 MHz, CDCl₃) δ 7.46-7.52 (m, 2H), 7.39-7.46 (m, 1H), 3.98 (ddd, J=7.26, 8.47, 14.64 Hz, 4H), 3.10-3.22 (m, 2H), 1.90-1.99 (m, 1H), 1.21 (t, J=7.04 Hz, 6H), 1.07-1.15 (m, 2H), 1.00 (dd, J=2.31, 8.25 Hz, 2H).

Step 5. tert-Butyl (E)-4-(2-(4-cyclopropyl-1-(2,6-dichlorophenyl)-1H-1,2,3-triazol-5-yl)vinyl)piperidine-1-carboxylate

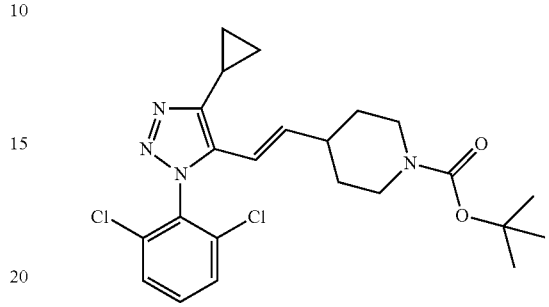

To a solution of diethyl ((4-cyclopropyl-1-(2,6-dichlorophenyl)-1H-1,2,3-triazol-5-yl)methyl)phosphonate (0.66 g, 1.6 mmol) in THF (12.0 mL) at −78° C. under nitrogen atmosphere, LiHMDS (1.0 M in THF) (3.1 mL, 3.1 mmol) was added dropwise. The mixture was stirred for 30 minutes and a solution of tert-butyl 4-formylpiperidine-1-carboxylate (0.33 g, 1.6 mmol) in THF (2.0 mL) was added. The reaction was allowed to warm up to room temperature. After three h the reaction was quenched with 0.3 mL of MeOH, and filtered through a pad of SiO₂ gel and concentrated in vacuo to an oil. The oil was purified by flash chromatography on SiO₂ (0-15% EtOAc/hexanes Isco SiO₂ column) to give tert-butyl (E)-4-(2-(4-cyclopropyl-1-(2,6-dichlorophenyl)-1H-1,2,3-triazol-5-yl)vinyl)piperidine-1-carboxylate (0.35 g, 0.75 mmol, 48% yield) as a solid. $^1$H NMR (400 MHz, CDCl₃) δ 7.44-7.54 (m, 3H), 5.97-6.08 (m, 2H), 4.07 (br d, J=10.34 Hz, 2H), 2.74 (br s, 2H), 2.22 (br d, J=5.94 Hz, 1H), 1.88-1.97 (m, 1H), 1.65 (br dd, J=1.98, 12.98 Hz, 2H), 1.46 (s, 9H), 1.22-1.31 (m, 2H), 1.14 (dd, J=1.76, 5.28 Hz, 2H), 1.04 (dd, J=2.31, 8.25 Hz, 2H).

Step 6. (E)-4-(2-(4-Cyclopropyl-1-(2,6-dichlorophenyl)-1H-1,2,3-triazol-5-yl)vinyl)piperidine

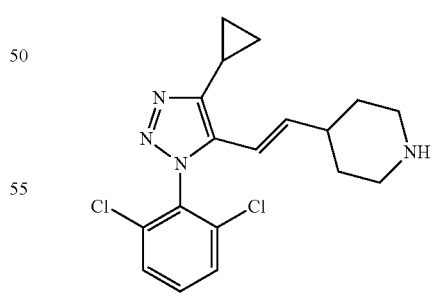

To a solution of (E)-tert-butyl 4-(2-(4-cyclopropyl-1-(2,6-dichlorophenyl)-1H-1,2,3-triazol-5-yl)vinyl)piperidine-1-carboxylate (46 mg, 0.10 mmol) in dichloromethane (0.5 mL) was added HCl (4 M in dioxane, 0.30 mL, 1.2 mmol). The reaction was stirred at 25° C. for 90 minutes and was concentrated in vacuo to afford (E)-4-(2-(4-cyclopropyl-1-(2,6-dichlorophenyl)-1H-1,2,3-triazol-5-yl)vinyl)piperi-

Example 10. (E)-2-(4-(2-(4-Cyclopropyl-1-(2,6-dichlorophenyl)-1H-1,2,3-triazol-5-yl) vinyl)piperidin-1-yl)-4-fluorobenzo[d]thiazole-6-carboxylic acid The title compound was prepared as described in General Method A1 for the preparation of Example 1 with the replacement of (E)-5-cyclopropyl-3-(2,6-dichlorophenyl)-4-(2-(piperidin-4-yl)vinyl)isoxazole and methyl 6-fluoronicotinate with (E)-4-(2-(4-Cyclopropyl-1-(2,6-dichlorophenyl)-1H-1,2,3-triazol-5-yl)vinyl)piperidine and ethyl 2-bromo-4-fluorobenzo[d]thiazole-6-carboxylate. MS (ESI) m/z: 558.2 [M+H]+; $^1$H NMR (500 MHz, DMSO-$d_6$) δ 8.15 (s, 1H), 7.74-7.79 (m, 2H), 7.69 (br d, J=7.63 Hz, 1H), 7.57 (br d, J=11.29 Hz, 1H), 6.12 (d, J=16.17 Hz, 1H), 5.96-6.03 (m, 1H), 4.00 (br d, J=10.07 Hz, 1H), 3.22 (br t, J=11.90 Hz, 2H), 2.04 (br s, 1H), 1.71 (br d, J=11.29 Hz, 2H), 1.24-1.37 (m, 2H), 1.01 (br d, J=5.80 Hz, 2H), 0.86-0.93 (m, 2H); HLE GAL-FXR $EC_{50}$=64 nM.

General Method C

Example 11

(E)-6-(4-(2-(4-Cyclopropyl-1-(2,6-dichlorophenyl)-1H-pyrazol-5-yl)vinyl)piperidin-1-yl) nicotinic acid

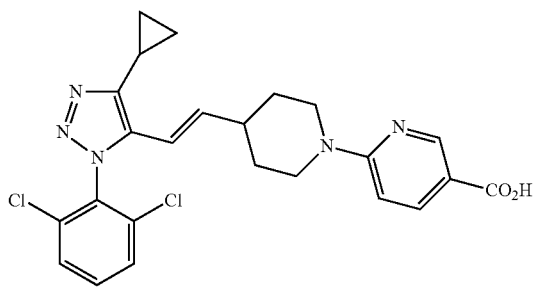

(11)

Step 1. Ethyl 3-cyclopropyl-4-(dimethylamino)-2-oxobut-3-enoate

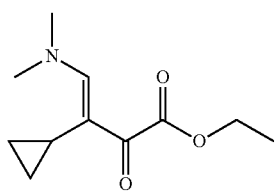

A mixture of ethyl 3-cyclopropyl-2-oxopropanoate (0.50 g, 3.2 mmol) and 1,1-dimethoxy-N,N-dimethylmethanamine (0.68 mL, 5.1 mmol) in THF (1.75 mL) was heated in a sealed tube at 80° C. for 2 h. The reaction mixture was concentrated to dryness in vacuo and the residue was purified by flash chromatography on SiO$_2$ (0-80% EtOAc/hexanes) to afford ethyl 3-cyclopropyl-4-(dimethylamino)-2-oxobut-3-enoate (0.52 g, 2.5 mmol, 77% yield) as an oil. $^1$H NMR (400 MHz, CDCl$_3$) δ 7.21-7.47 (m, 1H), 4.27 (q, J=7.04 Hz, 2H), 3.23 (br s, 6H), 1.48 (br t, J=7.04 Hz, 1H), 1.33 (t, J=7.15 Hz, 3H), 0.79 (q, J=5.80 Hz, 2H), 0.39-0.47 (m, 2H).

Step 2. Ethyl 4-cyclopropyl-1-(2,6-dichlorophenyl)-1H-pyrazole-5-carboxylate

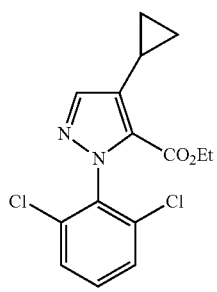 [SMILES: CCOC(=O)c1c(C2CC2)cnn1-c1c(Cl)cccc1Cl]

To a solution of ethyl 3-cyclopropyl-4-(dimethylamino)-2-oxobut-3-enoate (0.40 g, 1.9 mmol) in EtOH (4.0 mL) was added (2,6-dichlorophenyl)hydrazine (0.34 g, 1.9 mmol). The reaction flask was sealed and heated with stirring at 90° C. for 3 h. The reaction mixture was concentrated in vacuo, and the residue was purified by flash chromatography on SiO$_2$ (0-30% EtOAc/hexanes) to afford ethyl 4-cyclopropyl-1-(2,6-dichlorophenyl)-1H-pyrazole-5-carboxylate (0.40 g, 1.2 mmol, 63% yield) as an oil which solidified upon standing. $^1$H NMR (400 MHz, CDCl$_3$) δ 7.20-7.30 (m, 3H), 7.13-7.19 (m, 1H), 4.03 (q, J=7.04 Hz, 2H), 2.25 (tt, J=5.14, 8.50 Hz, 1H), 0.96 (t, J=7.15 Hz, 3H), 0.88 (dd, J=1.87, 8.47 Hz, 2H), 0.57 (dd, J=1.76, 5.28 Hz, 2H).

Step 3. (4-Cyclopropyl-1-(2,6-dichlorophenyl)-1H-pyrazol-5-yl)methanol

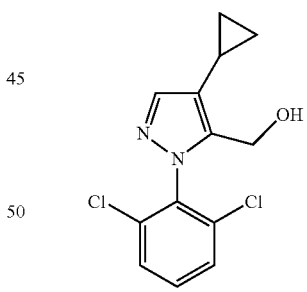

To a solution of ethyl 4-cyclopropyl-1-(2,6-dichlorophenyl)-1H-pyrazole-5-carboxylate (0.32 g, 0.97 mmol) in THF (3.9 mL) at 0° C. was added diisobutyl aluminum hydride (1.0 M in toluene) (3.9 mL, 3.9 mmol) dropwise over 15 minutes. The reaction mixture was then allowed to warm to room temperature. After 1 h the mixture was diluted with EtOAc, washed with 0.1M HCl, brine, dried over MgSO$_4$, filtered, and concentrated in vacuo to afford (4-cyclopropyl-1-(2,6-dichlorophenyl)-1H-pyrazol-5-yl)methanol (243 mg, 0.86 mmol, 88% yield) as a tan solid. The product was used without further purification. $^1$H NMR (500 MHz, CDCl$_3$) δ 7.42-7.49 (m, 3H), 7.35-7.42 (m, 1H), 4.54 (br s, 2H), 0.95 (br d, J=7.98 Hz, 2H), 0.62-0.74 (m, 2H).

Step 4. 5-(Bromomethyl)-4-cyclopropyl-1-(2,6-dichlorophenyl)-1H-pyrazole

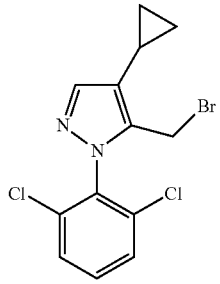 [SMILES: Clc1cccc(Cl)c1-n1ncc(C2CC2)c1CBr]

To a solution of (4-cyclopropyl-1-(2,6-dichlorophenyl)-1H-pyrazol-5-yl)methanol (0.15 g, 0.52 mmol) in dichloromethane (2.1 mL) was added triphenylphosphine (0.34 g, 1.3 mmol). After stirring the mixture for 15 minutes CBr$_4$ (0.43 g, 1.3 mmol) was added portion wise, and the resulting mixture was stirred at room temperature for 90 minutes. The crude reaction mixture was directly purified by flash chromatography on SiO$_2$ (0-20% EtOAc/hexanes) to afford 5-(bromomethyl)-4-cyclopropyl-1-(2,6-dichlorophenyl)-1H-pyrazole (0.15 g, 0.44 mmol, 85% yield) as a tan solid. $^1$H NMR (500 MHz, CDCl$_3$) δ 7.44-7.51 (m, 3H), 7.38-7.43 (m, 1H), 4.37 (s, 2H), 1.75 (tt, J=5.05, 8.42 Hz, 1H), 0.92-1.03 (m, 2H), 0.66-0.76 (m, 2H).

Step 5. Diethyl ((4-cyclopropyl-1-(2,6-dichlorophenyl)-1H-pyrazol-5-yl)methyl)phosphonate

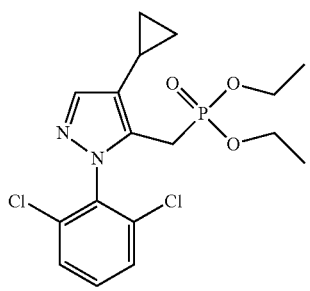 [SMILES: CCOP(=O)(Cc1c(C2CC2)cnn1-c1c(Cl)cccc1Cl)OCC]

A solution of 5-(bromomethyl)-4-cyclopropyl-1-(2,6-dichlorophenyl)-1H-pyrazole (61 mg, 0.18 mmol) and triethyl phosphite (0.06 mL, 0.35 mmol) in dioxane (0.1 mL) was heated with stirring in a sealed tube at 140° C. overnight. The reaction mixture was cooled to room temperature and the crude mixture was directly purified by flash chromatography on SiO$_2$ (0-80% EtOAc/hexanes) to afford diethyl ((4-cyclopropyl-1-(2,6-dichlorophenyl)-1H-pyrazol-5-yl)methyl)phosphonate (64 mg, 0.16 mmol, 90% yield) as a film. $^1$H NMR (400 MHz, CDCl$_3$) δ 7.43-7.38 (m, 2H), 7.33-7.26 (m, 1H), 7.10 (s, 1H), 4.10 (t, J=7.3 Hz, 4H), 3.41 (s, 1H), 3.35 (s, 1H), 1.89 (s, 1H), 1.28 (t, J=7.0 Hz, 6H), 0.94-0.87 (m, 2H), 0.52 (dd, J=5.1, 1.8 Hz, 2H).

Step 6. tert-Butyl (E)-4-(2-(4-cyclopropyl-1-(2,6-dichlorophenyl)-1H-pyrazol-5-yl)vinyl)piperidine-1-carboxylate

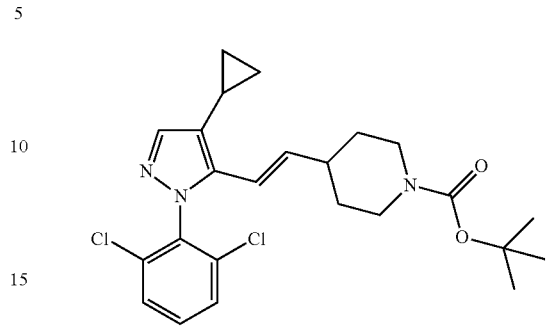

To a solution of diethyl ((4-cyclopropyl-1-(2,6-dichlorophenyl)-1H-pyrazol-5-yl)methyl)phosphonate (0.11 g, 0.26 mmol) in THF (2.5 mL) at −78° C. was added n-butyllithium (2.5 M in hexanes) (0.12 mL, 0.29 mmol) dropwise. The mixture was stirred for 15 minutes and a solution of tert-butyl 4-formylpiperidine-1-carboxylate (62.3 mg, 0.29 mmol) in THF (0.5 mL) was added. The reaction mixture was allowed to warm to room temperature. After 30 minutes, the reaction was diluted with EtOAc, washed with water and brine, dried over Na$_2$SO$_4$, filtered, and concentrated in vacuo. The residue was purified by flash chromatography on SiO$_2$ (0-20% EtOAc/hexanes) to afford tert-butyl (E)-4-(2-(4-cyclopropyl-1-(2,6-dichlorophenyl)-1H-pyrazol-5-yl)vinyl)piperidine-1-carboxylate (56 mg, 0.12 mmol, 46% yield) as an oil containing~25% of tert-butyl (Z)-4-(2-(4-cyclopropyl-1-(2,6-dichlorophenyl)-1H-pyrazol-5-yl)vinyl)piperidine-1-carboxylate. MS (ESI) m/z: 462.2 [M+H]$^+$.

Step 7. (E)-4-(2-(4-Cyclopropyl-1-(2,6-dichlorophenyl)-1H-pyrazol-5-yl)vinyl)piperidine

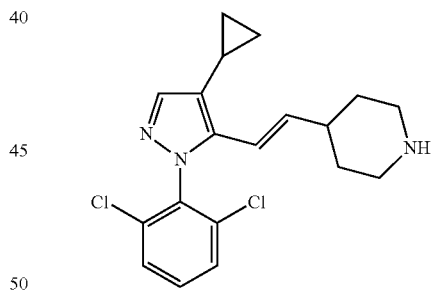

To a solution of tert-butyl (E)-4-(2-(3-cyclopropyl-1-(2,6-dichlorophenyl)-1H-pyrrol-2-yl)vinyl)piperidine-1-carboxylate (56 mg, 0.12 mmol) in dichloromethane (0.36 mL) was added HCl (4 M in dioxane, 0.36 mL, 1.5 mmol). The reaction was stirred at 25° C. for 1 h and was concentrated in vacuo to afford (E)-4-(2-(4-cyclopropyl-1-(2,6-dichlorophenyl)-1H-pyrazol-5-yl)vinyl)piperidine, HCl (50 mg, 0.13 mmol, 100% yield) as a tan solid. The product was used without further purification or characterization. MS (ESI) m/z: 362.1 [M+H]$^+$.

Example 11. (E)-6-(4-(2-(4-Cyclopropyl-1-(2,6-dichlorophenyl)-1H-pyrazol-5-yl)vinyl)piperidin-1-yl)nicotinic acid The title compound was prepared as described in General Method A1 for the preparation of Example 1 with the replacement of (E)-5-cyclopropyl-3-(2,6-dichlorophenyl)-4-(2-(piperidin-4-yl)vinyl)isoxazole with (E)-4-(2-(4-cyclopropyl-1-(2,6-dichlorophenyl)-1H-pyrazol-5-yl)vinyl)piperidine, HCl. MS (ESI) m/z: 482.8 [M+H]+; $^1$H NMR (500 MHz, DMSO-$d_6$) δ 8.50-8.58 (m, 1H), 7.83 (br s, 1H), 7.64 (s, 2H), 7.56 (br d, J=8.24 Hz, 1H), 7.40 (s, 1H), 6.77 (br d, J=9.16 Hz, 1H), 5.94-6.03 (m, 1H), 5.90 (br d, J=7.02 Hz, 1H), 4.30 (br d, J=12.51 Hz, 2H), 4.23 (br d, J=7.02 Hz, 1H), 2.83-2.94 (m, 2H), 1.72 (br s, 1H), 1.59 (br d, J=12.51 Hz, 2H), 1.12 (br d, J=9.46 Hz, 2H), 0.85 (br d, J=6.71 Hz, 2H), 0.54 (br d, J=3.97 Hz, 2H); HLE GAL-FXR $EC_{50}$=148 nM.

General Method D

Example 12

(E)-2-(4-(2-(1-Cyclopropyl-4-(2,6-dichlorphenyl)-1H-pyrazol-5-yl)vinyl)piperidin-1-yl)-4-fluorobenzo[d]thiazole-6-carboxylic acid (12)

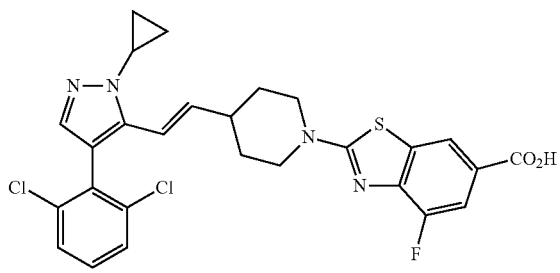

Step 1.
1-Cyclopropyl-4-(2,6-dichlorophenyl)-1H-pyrazole

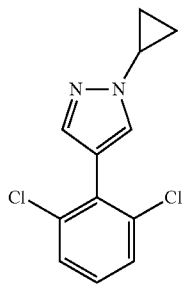 [SMILES: Clc1cccc(Cl)c1-c1cnn(C2CC2)c1]

A mixture of (2,6-dichlorophenyl)boronic acid (1.9 g, 10.1 mmol), 4-bromo-1-cyclopropyl-1H-pyrazole (1.7 g, 9.2 mmol), PdCl$_2$(dppf)-CH$_2$Cl$_2$ adduct (0.30 g, 0.34 mmol) and Na$_2$CO$_3$ (1.9 g, 18.4 mmol) in THF (15 mL) and water (5 mL) was degassed and then heated under microwave irradiation at 100° C. for 3 h. The reaction mixture was diluted with EtOAc, washed with saturated aqueous NH$_4$Cl and brine, dried over MgSO$_4$, filtered, and concentrated in vacuo. The residue was purified by flash chromatography on SiO$_2$ (0-30% EtOAc/hexanes) to afford 1-cyclopropyl-4-(2,6-dichlorophenyl)-1H-pyrazole (1.4 g, 5.5 mmol, 60% yield) as an oil which became solid upon standing. $^1$H NMR (500 MHz, CDCl$_3$) δ 7.63 (s, 2H), 7.35-7.43 (m, 2H), 7.15 (t, J=7.98 Hz, 1H), 3.68 (tt, J=3.78, 7.36 Hz, 1H), 1.21 (dt, J=1.10, 3.03 Hz, 2H), 1.07 (dd, J=1.93, 7.15 Hz, 2H).

Step 2. 1-Cyclopropyl-4-(2,6-dichlorophenyl)-1H-pyrazole-5-carbaldehyde

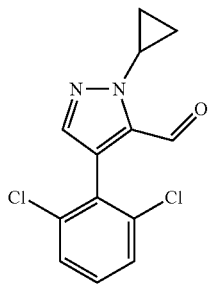 [SMILES: O=Cc1c(-c2c(Cl)cccc2Cl)cnn1C1CC1]

To a −78° C. solution of 1-cyclopropyl-4-(2,6-dichlorophenyl)-1H-pyrazole (0.59 g, 2.3 mmol) in THF (4.6 mL) was added n-butyllithium (2.5 M in hexane, 1.2 mL, 2.9 mmol) dropwise. The reaction mixture was stirred for 60 minutes followed by dropwise addition of N,N-dimethylformamide (0.23 mL, 2.9 mmol) in THF (2.3 mL). The reaction was continued at −78° C. for an additional 60 minutes and was diluted with EtOAc, washed with saturated aqueous NH$_4$Cl and brine, dried over MgSO$_4$, filtered, and concentrated in vacuo. The residue was purified by flash chromatography on SiO$_2$ (0-10% EtOAc/hexanes) to afford 1-cyclopropyl-4-(2,6-dichlorophenyl)-1H-pyrazole-5-carbaldehyde (0.22 g, 0.79 mmol, 34% yield) as an off-white solid. $^1$H NMR (400 MHz, CDCl$_3$) δ 9.70 (s, 1H), 7.40-7.49 (m, 3H), 7.25-7.33 (m, 1H), 4.38 (tt, J=3.82, 7.51 Hz, 1H), 1.27-1.44 (m, 2H), 1.10-1.21 (m, 2H).

Step 3. (1-Cyclopropyl-4-(2,6-dichlorophenyl)-1H-pyrazol-5-yl)methanol

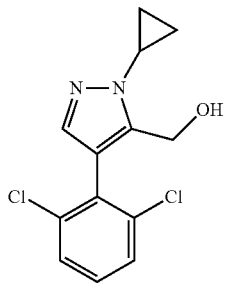 [SMILES: OCc1c(-c2c(Cl)cccc2Cl)cnn1C1CC1]

To a solution of 1-cyclopropyl-4-(2,6-dichlorophenyl)-1H-pyrazole-5-carbaldehyde (0.22 g, 0.77 mmol) in THF (3.1 mL) at 0° C. was added diisobutyl aluminum hydride (1.0 M in toluene, 1.7 mL, 1.7 mmol) dropwise over 15 minutes. The reaction mixture was allowed to warm to room temperature and after 1 h was diluted with EtOAc, washed with 0.1M HCl and brine, dried over MgSO$_4$, filtered and concentrated in vacuo. The residue was purified by flash chromatography on SiO$_2$ (0-30% EtOAc/hexanes) to afford (1-cyclopropyl-4-(2,6-dichlorophenyl)-1H-pyrazol-5-yl)methanol (0.20 g, 0.71 mmol, 90% yield) as a white solid. $^1$H NMR (400 MHz, CDCl$_3$) δ 7.36-7.41 (m, 2H), 7.32 (s, 1H), 7.21 (dd, J=7.59, 8.47 Hz, 1H), 4.60 (s, 2H), 3.70 (tt, J=3.85, 7.37 Hz, 1H), 2.22 (br s, 1H), 1.23-1.38 (m, 2H).

Step 4. 5-(Bromomethyl)-1-cyclopropyl-4-(2,6-dichlorophenyl)-1H-pyrazole

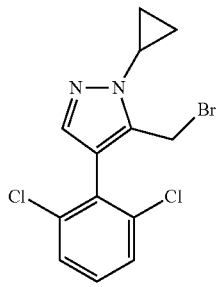 [SMILES: Clc1cccc(Cl)c1-c1cnn(C2CC2)c1CBr]

To a solution of (1-cyclopropyl-4-(2,6-dichlorophenyl)-1H-pyrazol-5-yl)methanol (0.13 g, 0.45 mmol) in dichloromethane (1.8 mL) was added triphenylphosphine (0.30 g, 1.1 mmol). The reaction mixture was stirred for 15 minutes, followed by portion wise addition of CBr$_4$ (0.38 g, 1.1 mmol). The resulting mixture was stirred at room temperature 2 h and was directly purified by flash chromatography on SiO$_2$ (0-20% EtOAc/hexanes) to afford 5-(bromomethyl)-1-cyclopropyl-4-(2,6-dichlorophenyl)-1H-pyrazole (0.12 g, 0.35 mmol, 77% yield) as an oil. $^1$H NMR (400 MHz, CDCl$_3$) δ 7.36-7.43 (m, 3H), 7.22-7.29 (m, 1H), 4.45 (s, 2H), 3.61 (tt, J=3.74, 7.26 Hz, 1H), 1.26-1.41 (m, 2H), 1.13-1.22 (m, 2H).

Step 5. Diethyl ((1-cyclopropyl-4-(2,6-dichlorophenyl)-1H-pyrazol-5-yl)methyl)phosphonate

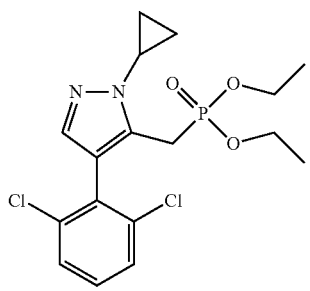 [SMILES: CCOP(=O)(Cc1c(-c2c(Cl)cccc2Cl)cnn1C1CC1)OCC]

A solution of 5-(bromomethyl)-1-cyclopropyl-4-(2,6-dichlorophenyl)-1H-pyrazole (121 mg, 0.35 mmol) and triethyl phosphite (120 µL, 0.70 mmol) in dioxane (120 µL) was heated with stirring in a sealed tube at 120° C. overnight. The reaction was heated at 140° C. for 4 h, cooled to room temperature, and directly purified by flash chromatography on SiO$_2$ (0-80% EtOAc/hexanes) to afford diethyl ((1-cyclopropyl-4-(2,6-dichlorophenyl)-1H-pyrazol-5-yl)methyl)phosphonate (160 mg, 0.35 mmol, 100% yield) as an oil. $^1$H NMR (400 MHz, CDCl$_3$) δ 7.39 (s, 2H), 7.35-7.38 (m, 1H), 7.19 (dd, J=7.70, 8.36 Hz, 1H), 3.77-3.98 (m, 4H), 3.65-3.77 (m, 1H), 3.40 (s, 1H), 3.34 (s, 1H), 1.27 (td, J=1.71, 3.63 Hz, 2H), 1.12-1.20 (m, 6H), 1.10 (dd, J=2.20, 7.26 Hz, 2H).

Step 6. tert-Butyl (E)-4-(2-(1-cyclopropyl-4-(2,6-dichlorophenyl)-1H-pyrazol-5-yl)vinyl)piperidine-1-carboxylate

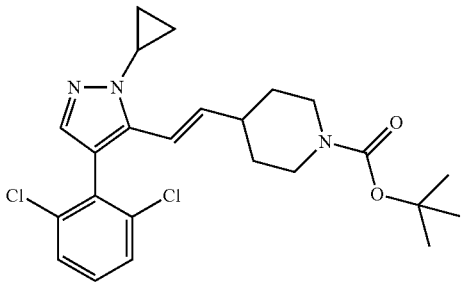 [SMILES: CC(C)(C)OC(=O)N1CCC(/C=C/c2c(-c3c(Cl)cccc3Cl)cnn2C2CC2)CC1]

To a −78° C. solution of diethyl ((1-cyclopropyl-4-(2,6-dichlorophenyl)-1H-pyrazol-5-yl)methyl)phosphonate (51 mg, 0.13 mmol) in THF (1.5 mL) under nitrogen atmosphere, LiHMDS (1.0 M in THF, 0.25 mL, 0.25 mmol) was added dropwise. The mixture was stirred for 30 minutes and a solution of tert-butyl 4-formylpiperidine-1-carboxylate (27.0 mg, 0.13 mmol) in THF (0.5 mL) was added. The reaction mixture was allowed to warm up to room temperature and after 30 minutes was diluted with EtOAc, washed with saturated aqueous NH$_4$Cl and brine, dried over MgSO$_4$, and concentrated in vacuo. The residue was purified by flash chromatography on SiO$_2$ (0-20% EtOAc/hexanes) to afford tert-butyl (E)-4-(2-(1-cyclopropyl-4-(2,6-dichlorophenyl)-1H-pyrazol-5-yl)vinyl)piperidine-1-carboxylate (40 mg, 0.09 mmol, 68% yield) as a film. $^1$H NMR (400 MHz, CDCl$_3$) δ 7.33 (d, J=7.9 Hz, 2H), 7.22 (s, 1H), 7.16 (dd, J=8.5, 7.6 Hz, 1H), 6.38 (dd, J=16.3, 0.7 Hz, 1H), 5.48 (dd, J=16.1, 7.0 Hz, 1H), 3.95 (br s, 3H), 3.42 (tt, J=7.3, 3.7 Hz, 1H), 2.95-2.83 (m, 1H), 2.68 (br t, J=12.1 Hz, 2H), 2.12 (dtd, J=10.6, 7.1, 3.5 Hz, 1H), 1.92-1.79 (m, 1H), 1.40 (s, 9H), 1.28-1.18 (m, 3H), 1.08-0.98 (m, 3H).

Step 7. (E)-4-(2-(1-Cyclopropyl-4-(2,6-dichlorophenyl)-1H-pyrazol-5-yl)vinyl)piperidine

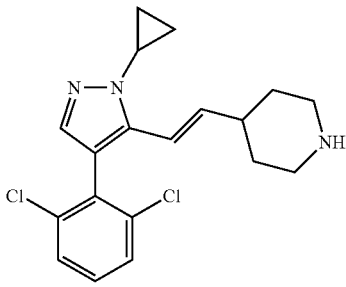 [SMILES: Clc1cccc(Cl)c1-c1cnn(C2CC2)c1/C=C/C1CCNCC1]

To a solution of tert-butyl (E)-4-(2-(1-cyclopropyl-4-(2,6-dichlorophenyl)-1H-pyrazol-5-yl)vinyl)piperidine-1-carboxylate (40 mg, 0.09 mmol) in dichloromethane (0.25 mL) was added HCl (4 M in dioxane, 0.26 mL, 1.0 mmol). The reaction was stirred at room temperature for 2 h and was concentrated in vacuo to give (E)-4-(2-(1-cyclopropyl-4-(2,6-dichlorophenyl)-1H-pyrazol-5-yl)vinyl)piperidine. The product was used without further purification or characterization.

Example 12. (E)-2-(4-(2-(1-Cyclopropyl-4-(2,6-dichlorophenyl)-1H-pyrazol-5-yl)vinyl)piperidin-1-yl)-4-fluorobenzo[d]thiazole-6-carboxylic acid The title compound was prepared as described in General Method A1 for the preparation of Example 1 with the replacement of (E)-5-cyclopropyl-3-(2,6-dichlorophenyl)-4-(2-(piperidin-4-yl)vinyl)isoxazole and methyl 6-fluoronicotinate with (E)-4-(2-(1-cyclopropyl-4-(2,6-dichlorophenyl)-1H-pyrazol-5-yl)vinyl)piperidine and ethyl 2-bromo-4-fluorobenzo[d]thiazole-6-carboxylate. MS (ESI) m/z: 557.0 [M+H]+; $^1$H NMR (500 MHz, DMSO-$d_6$) δ 8.18 (s, 1H), 7.58 (br d, J=11.60 Hz, 1H), 7.53 (s, 2H), 7.40 (d, J=7.93 Hz, 1H), 7.31 (s, 1H), 6.54 (d, J=16.48 Hz, 1H), 5.51 (dd, J=7.02, 16.17 Hz, 1H), 3.99 (br d, J=10.68 Hz, 2H), 3.63-3.73 (m, 1H), 3.26 (br t, J=11.60 Hz, 2H), 2.41 (br d, J=7.63 Hz, 1H), 1.72 (br d, J=11.60 Hz, 2H), 1.26 (br s, 2H), 1.07 (br s, 2H), 0.99 (d, J=6.41 Hz, 2H); HLE GAL-FXR EC$_{50}$=226 nM.

General Method E

Example 56

(E)-4-(2-(1-(4-(1H-Tetrazol-5-yl)phenyl)piperidin-4-yl)vinyl)-5-cyclopropyl-3-(2,6-dichlorophenyl)isoxazole

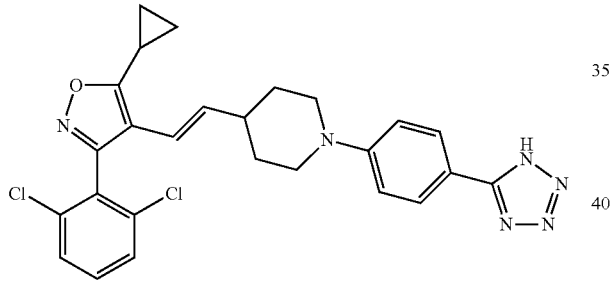

(56)

A mixture of (E)-4-(4-(2-(5-cyclopropyl-3-(2,6-dichlorophenyl)isoxazol-4-yl)vinyl)piperidin-1-yl)benzonitrile (33 mg, 0.071 mmol, Example 50), ammonium acetate (6.6 mg, 0.085 mmol) and sodium azide (5.5 mg, 0.085 mmol) in DMF (0.47 mL) in a sealed tube was heated at 120° C. for 20 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-80% B over 19 minutes, then a 5-minute hold at 100% B; Flow: 20 mL/min. Fractions containing the desired product were combined and dried via centrifugal evaporation to give (E)-4-(2-(1-(4-(1H-tetrazol-5-yl)phenyl)piperidin-4-yl)vinyl)-5-cyclopropyl-3-(2,6-dichlorophenyl)isoxazole (2.7 mg, 0.005 mmol, 7% yield). MS (ESI) m/z: 507.3 [M+H]+; $^1$H NMR (500 MHz, DMSO-$d_6$) δ 7.82 (d, J=8.85 Hz, 2H), 7.62-7.67 (m, 2H), 7.54-7.60 (m, 1H), 7.03 (br d, J=8.85 Hz, 2H), 6.17 (d, J=16.48 Hz, 1H), 5.32 (dd, J=6.87, 16.33 Hz, 1H), 3.74 (br d, J=13.12 Hz, 2H), 2.81 (br t, J=11.44 Hz, 2H), 2.28-2.41 (m, 1H), 2.23 (br s, 1H), 1.62 (br d, J=11.90 Hz, 2H), 1.12-1.24 (m, 4H), 1.03-1.11 (m, 2H); HLE GAL-FXR EC$_{50}$=3 nM.

General Method F

Example 70

(E)-4-(6-(2-(5-Cyclopropyl-3-(2,6-dichlorophenyl)isoxazol-4-yl)vinyl)-3-azabicyclo[3.1.0]hexan-3-yl)benzamide

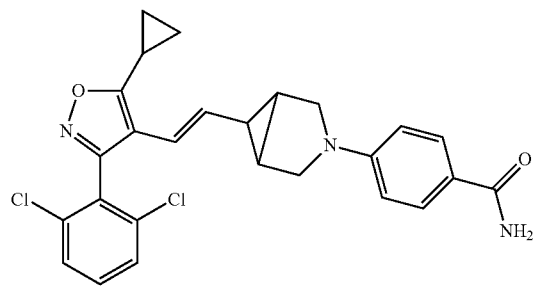

(70)

Step 1. (E)-4-(6-(2-(5-Cyclopropyl-3-(2,6-dichlorophenyl)isoxazol-4-yl)vinyl)-3-azabicyclo[3.1.0]hexan-3-yl)benzonitrile

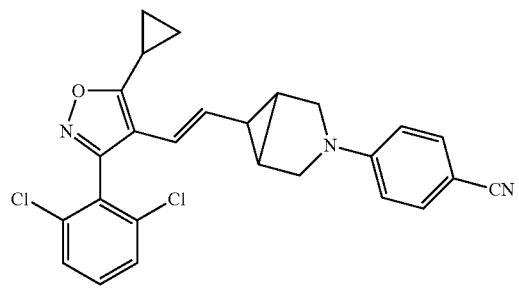 [SMILES: N#Cc1ccc(N2CC3C(/C=C/c4c(-c5c(Cl)cccc5Cl)noc4C4CC4)C3C2)cc1]

A slurry of (E)-4-(2-(3-azabicyclo[3.1.0]hexan-6-yl)vinyl)-5-cyclopropyl-3-(2,6-dichlorophenyl)isoxazole (30 mg, 0.083 mmol), 4-bromobenzonitrile (35 mg, 0.19 mmol) and Cs$_2$CO$_3$ (75 mg, 0.23 mmol) in dioxane (0.9 mL) was degassed by bubbling nitrogen through the mixture for 5 minutes. Chloro(2-dicyclohexylphosphino-2',6'-diisopropoxy-1,1'-biphenyl)[2-(2'-amino-1,1'-biphenyl)]palladium(II) (RuPhos-Pd-G2) (7 mg, 9.0 μmol) was then added and the reaction vessel was sealed and heated to 100° C. for 6 h. The reaction mixture was filtered through a pad of Celite, washed with dichloromethane (3 mL). The filtrate was concentrated in vacuo to dryness and purified by flash chromatography on SiO$_2$ (0-50% EtOAc/hexanes) to afford (E)-4-(6-(2-(5-Cyclopropyl-3-(2,6-dichlorophenyl)isoxazol-4-yl)vinyl)-3-azabicyclo[3.1.0]hexan-3-yl)benzonitrile (30 mg 89% yield) as a foam. MS (ESI) m/z: 461.9 [M+H]+; $^1$H NMR (400 MHz, CDCl$_3$) δ 7.48-7.45 (m, 2H), 7.45-7.42 (m, 2H), 7.37 (dd, J=9.2, 6.8 Hz, 1H), 6.56-6.41 (m, 2H), 6.08 (d, J=16.0 Hz, 1H), 5.17 (dd, J=16.0, 8.7 Hz, 1H), 3.59 (d, J=9.7 Hz, 2H), 3.39 (ddd, J=9.7, 3.0, 1.4 Hz, 2H), 2.15-2.01 (m, 2H), 1.68 (td, J=3.1, 1.3 Hz, 2H), 1.36 (dt, J=8.7, 3.3 Hz, 1H), 1.32-1.04 (m, 4H).

Example 70. (E)-4-(6-(2-(5-Cyclopropyl-3-(2,6-dichlorophenyl)isoxazol-4-yl)vinyl)-3-azabicyclo[3.1.0]hexan-3-yl)benzamide A solution of (E)-4-(6-(2-(5-cyclopropyl-3-(2,6-dichlorophenyl)isoxazol-4-yl)vinyl)-3-azabicyclo[3.1.0]hexan-3-yl) benzonitrile (34 mg, 0.074 mmol), hydroxylamine hydrochloride (6.6 mg, 0.096 mmol) and Na$_2$CO$_3$ (8.0 mg, 0.096 mmol) in ethanol (0.7 mL) and water (0.1 mL) was heated at 80° C. in a sealed vial. After 3 h hydroxylamine hydrochloride (14 mg), Na$_2$CO$_3$ (17 mg) and ethanol (0.3 mL) were added. The reaction mixture was heated at 80° C. for 20 h. The solvent was evaporated, the reaction mixture was diluted with water (2 mL) and, extracted with EtOAc (2×8 mL). The combined organic layers were concentrated in vacuo to dryness and the residue was purified by flash chromatography on SiO$_2$ (0-80% EtOAc/hexanes). The product was further purified via preparative LC/MS with the following conditions: Column: XBridge C18, 19×200 mm, 5-m particles; Mobile Phase A: 5:95 acetonitrile:water with 10-mM ammonium acetate; Mobile Phase B: 95:5 acetonitrile:water with 10-mM ammonium acetate; Gradient: 36-76% B over 20 minutes, then a 5-minute hold at 100% B; Flow: 20 mL/min. Fractions containing the desired product were combined and dried via centrifugal evaporation to give (E)-4-(6-(2-(5-cyclopropyl-3-(2,6-dichlorophenyl)isoxazol-4-yl)vinyl)-3-azabicyclo[3.1.0]hexan-3-yl)benzamide (3.1 mg, 9% yield) as white solid. MS (ESI) m/z: 480.1 [M+H]$^+$; $^1$H NMR (500 MHz, DMSO-d$_6$) δ 7.70 (d, J=8.6 Hz, 2H), 7.67-7.62 (m, 2H), 7.59 (dd, J=9.2, 6.8 Hz, 1H), 6.50 (d, J=8.6 Hz, 2H), 6.12 (d, J=16.1 Hz, 1H), 5.18 (dd, J=16.1, 8.7 Hz, 1H), 3.56 (d, J=9.9 Hz, 2H), 3.20-3.18 (two proton signals were lost due to water suppression), 2.32 (td, J=8.5, 4.3 Hz, 1H), 1.71-1.62 (m, 2H), 1.36 (dt, J=8.8, 3.3 Hz, 1H), 1.23-1.01 (m, 4H); HLE GAL-FXR EC$_{50}$=377 nM.

General Method G

Example 71

(E)-4-(6-(2-(5-Cyclopropyl-3-(2,6-dichlorophenyl)isoxazol-4-yl)vinyl)-3-azabicyclo[3.1.0]hexan-3-yl)-N-(methylsulfonyl)benzamide

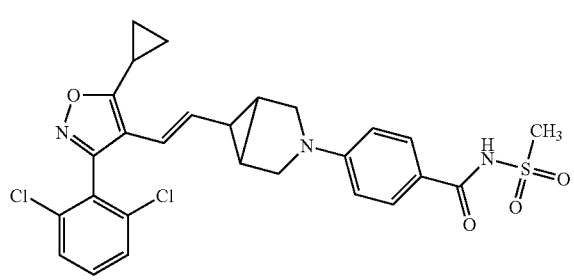

(71)

A mixture of (E)-4-(6-(2-(5-cyclopropyl-3-(2,6-dichlorophenyl)isoxazol-4-yl)vinyl)-3-azabicyclo[3.1.0]hexan-3-yl) benzoic acid (Example 47, 15 mg, 0.031 mmol) and CDI (15.2 mg, 0.093 mmol) in THF (500 μL) was heated at 60° C. in a sealed vial for 1 h. Methanesulfonamide (11.9 mg, 0.12 mmol) and DBU (14.1 μL, 0.093 mmol) were added. The reaction mixture was stirred at 60° C. for 1.5 h. Solvents were evaporated and the product was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 42-82% B over 23 minutes, then a 5-minute hold at 100% B; Flow: 20 mL/min. Fractions containing the desired product were combined and dried via centrifugal evaporation to give (E)-4-(6-(2-(5-cyclopropyl-3-(2,6-dichlorophenyl)isoxazol-4-yl)vinyl)-3-azabicyclo[3.1.0]hexan-3-yl)-N-(methylsulfonyl)benzamide (9.0 mg, 52% yield) as white solid. MS (ESI) m/z: 558.1 [M+H]$^+$; $^1$H NMR (500 MHz, DMSO-d$_6$) δ 7.77 (d, J=8.6 Hz, 2H).7.66 (d, J=8.0 Hz, 2H), 7.60 (dd, J=9.1, 7.0 Hz, 1H), 6.54 (d, J=8.7 Hz, 2H), 6.13 (d, J=16.1 Hz, 1H), 5.14 (dd, J=16.1, 8.9 Hz, 1H), 3.58 (d, J=10.2 Hz, 2H), 3.31 (s, 3H), 3.20-3.18 (two proton signals were lost due to water suppression), 2.44-2.25 (m, 1H), 1.69 (s, 2H), 1.37-1.24 (m, 1H), 1.24-0.99 (m, 4H); HLE GAL-FXR EC$_{50}$=83 nM.

General Method H

Example 116

(E)-4-(3-(6-(2-(5-Cyclopropyl-3-(3,5-dichloropyridin-4-yl)isoxazol-4-yl)vinyl)-3-azabicyclo[3.1.0]hexan-3-yl)-1,2,4-oxadiazol-5-yl)benzoic acid

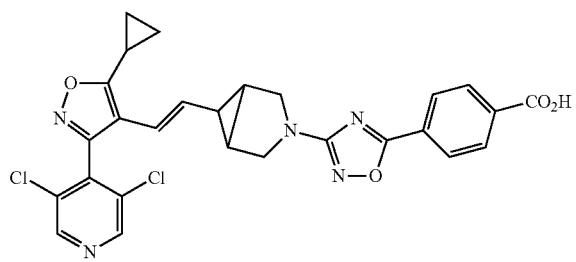

(116)

Step 1. (E)-4-(2-(3-Azabicyclo[3.1.0]hexan-6-yl)vinyl)-5-cyclopropyl-3-(3,5-dichloropyridin-4-yl)isoxazole

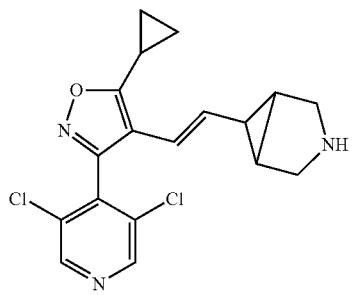 [SMILES: Clc1cncc(Cl)c1-c1noc(C2CC2)c1/C=C/C1C2CNCC12]

The title compound was prepared according to the procedure described for the (E)-4-(2-(3-azabicyclo[3.1.0]hexan-6-yl)vinyl)-5-cyclopropyl-3-(2,6-dichlorophenyl) isoxazole (Step 2 for Example 8) with the replacement of 2,6-dichlorobenzaldehyde with 3,5-dichloroisonicotinaldehyde. MS (ESI) m/z: 362.0 [M+H]$^+$.

Step 2. (E)-6-(2-(5-Cyclopropyl-3-(3,5-dichloropyridin-4-yl)isoxazol-4-yl)vinyl)-3-azabicyclo[3.1.0]hexane-3-carbonitrile

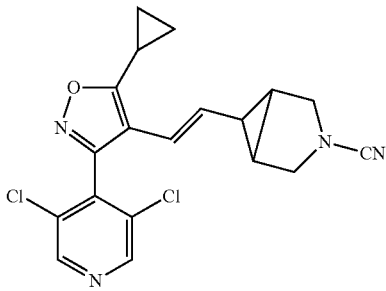 [SMILES: N#CN1CC2C(/C=C/c3c(-c4c(Cl)cncc4Cl)noc3C3CC3)C2C1]

To a mixture of (E)-4-(2-(3-azabicyclo[3.1.0]hexan-6-yl)vinyl)-5-cyclopropyl-3-(3,5-dichloropyridin-4-yl)isoxazole (25.0 mg, 0.069 mmol) and potassium carbonate (28.6 mg, 0.21 mmol) in H$_2$O (0.6 mL) was added a solution of cyanic bromide (8.0 mg, 0.076 mmol) in CH$_2$Cl$_2$ (0.6 mL). The reaction mixture was stirred at room temperature for 2 h. Aqueous hydrochloric acid solution (0.21 mL, 0.21 mmol, 1M) was added, and the mixture was extracted with CH$_2$Cl$_2$ (2×8 mL). The organic layer was dried over MgSO$_4$, filtered and concentrated in vacuo to give (E)-6-(2-(5-cyclopropyl-3-(3,5-dichloropyridin-4-yl)isoxazol-4-yl)vinyl)-3-azabicyclo[3.1.0]hexane-3-carbonitrile the product as light brown foam solid. MS (ESI) m/z: 387.0 [M+H]$^+$; $^1$H NMR (400 MHz, CDCl$_3$) δ 8.63 (s, 2H), 6.06 (dd, J=16.0, 0.7 Hz, 1H), 5.13 (dd, J=16.0, 8.4 Hz, 1H), 3.52 (dt, J=9.7, 1.7 Hz, 2H), 3.47 (d, J=9.8 Hz, 2H), 2.08 (tt, J=8.4, 5.1 Hz, 1H), 1.56-1.48 (m, 2H), 1.45 (dt, J=8.5, 3.5 Hz, 1H), 1.31-1.08 (m, 4H).

Step 3. (E)-6-((E)-2-(5-Cyclopropyl-3-(3,5-dichloropyridin-4-yl)isoxazol-4-yl)vinyl)-N'-hydroxy-3-azabicyclo[3.1.0]hexane-3-carboximidamide

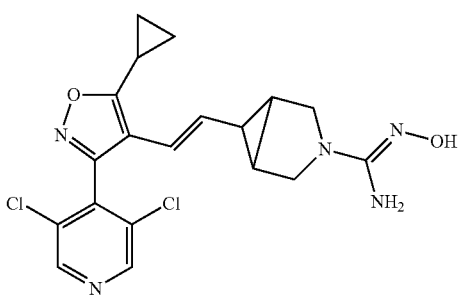 [SMILES: N/C(=N\O)N1CC2C(/C=C/c3c(-c4c(Cl)cncc4Cl)noc3C3CC3)C2C1]

A mixture of (E)-6-(2-(5-cyclopropyl-3-(3,5-dichloropyridin-4-yl)isoxazol-4-yl)vinyl)-3-azabicyclo[3.1.0]hexane-3-carbonitrile (164 mg, 0.42 mmol), hydroxylamine hydrochloride (38.3 mg, 0.55 mmol) and sodium acetate (34.7 mg, 0.42 mmol) in ethanol (6 mL) was heated at 60° C. in a sealed vial for 2 h. The solvent was evaporated, the reaction mixture was diluted with water (8 mL), and filtered. The collected solid was dried under vacuum to give (E)-6-((E)-2-(5-cyclopropyl-3-(3,5-dichloropyridin-4-yl)isoxazol-4-yl)vinyl)-N'-hydroxy-3-azabicyclo[3.1.0]hexane-3-carboximidamide (168 mg, 0.40 mmol, 94% yield) as white powder. MS (ESI) m/z: 420.1 [M+H]$^+$.

Step 4. Methyl (E)-4-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)benzoate

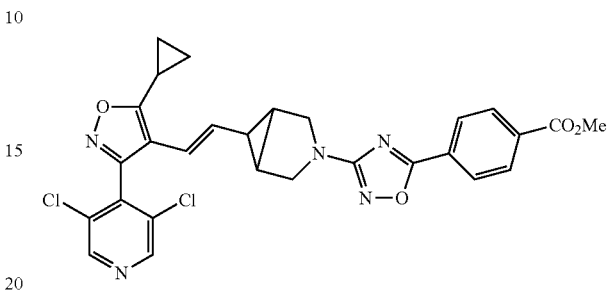

To a mixture of 4-(methoxycarbonyl)benzoic acid (9.0 mg, 0.050 mmol) in CH$_2$Cl$_2$ (1.0 mL) was added HOBT (7.6 mg, 0.050 mmol) and EDC (9.6 mg, 0.050 mmol). The reaction mixture was stirred for 1 h. (E)-6-((E)-2-(5-cyclopropyl-3-(3,5-dichloropyridin-4-yl)isoxazol-4-yl)vinyl)-N'-hydroxy-3-azabicyclo[3.1.0]hexane-3-carboximidamide (20 mg, 0.048 mmol) was added and the mixture was stirred at room temperature for 1.5 h. The solvent was evaporated, the resulting white solid was taken up in EtOH (1.5 mL), and the resulting mixture was heated in a sealed vial at 85° C. for 5 h. The reaction mixture was cooled to room temperature and concentrated to dryness in vacuo. The residue was purified by flash chromatography on SiO$_2$ (0-40% EtOAc/hexanes) to afford methyl (E)-4-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)benzoate (15 mg, 57% yield) as white solid. MS (ESI) m/z: 564.1 [M+H]$^+$; $^1$H NMR (400 MHz, CDCl$_3$) δ 8.63 (s, 2H), 8.32-7.91 (m, 4H), 6.02 (d, J=15.8 Hz, 1H), 5.21 (dd, J=16.0, 8.7 Hz, 1H), 3.96 (s, 3H), 3.79 (d, J=10.2 Hz, 2H), 3.53 (dt, J=10.3, 2.0 Hz, 2H), 2.09 (tt, J=8.4, 5.1 Hz, 1H), 1.67-1.58 (m, 2H), 1.44-1.35 (m, 1H), 1.30-1.07 (m, 4H).

Example 116. (E)-4-(3-(6-(2-(5-Cyclopropyl-3-(3,5-dichloropyridin-4-yl)isoxazol-4-yl)vinyl)-3-azabicyclo[3.1.0]hexan-3-yl)-1,2,4-oxadiazol-5-yl)benzoic acid A solution of methyl (E)-4-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)benzoate (17 mg, 0.030 mmol) in methanol (0.9 mL), THF (0.3 mL) and 1 M aqueous sodium hydroxide (0.12 mL, 0.120 mmol) was heated in a sealed vial at 60° C. for 2 h. The volatiles were removed in vacuo and the residue was purified by preparative HPLC (Column: Sunfire C18 OBD, 30×100 mm, 5-µm particles; Mobile Phase A: 5:95 acetonitrile:water with 0.1% TFA; Mobile Phase B: 95:5 acetonitrile:water with 0.1% TFA; Gradient: 65-100% B over 10 minutes, then a 5-minute hold at 100% B; Flow: 40 mL/min) to afford (E)-4-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)benzoic acid (7.1 mg, 29% yield) as beige solid. MS (ESI) m/z: 550.1 [M+H]$^+$; $^1$H NMR (500 MHz, DMSO-d$_6$) δ 8.86 (s, 2H), 8.13 (s, 4H), 6.16 (d, J=16.0 Hz, 1H), 5.29 (dd, J=16.0, 8.8 Hz, 1H), 3.64 (d, J=10.2 Hz, 2H), 3.48 (d, J=9.7

Hz, 2H), 2.43-2.33 (m, 1H), 1.74 (s, 2H), 1.45-1.38 (m, 1H), 1.28-0.95 (m, 4H); HLE GAL-FXR EC$_{50}$=862 nM.

General Method I

Example 133

(E)-3-(5-(6-(2-(5-Cyclopropyl-3-(3,5-dichloropyridin-4-yl)isoxazol-4-yl)vinyl)-3-azabicyclo[3.1.0]hexan-3-yl)-1,2,4-oxadiazol-3-yl)benzoic acid

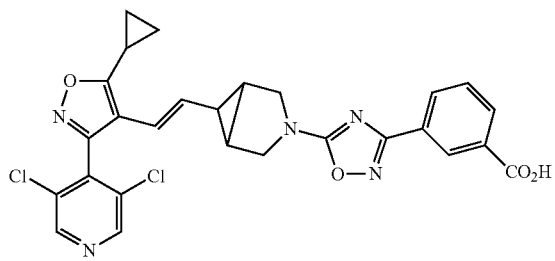

(133)

Step 1. Methyl (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-3-yl)benzoate

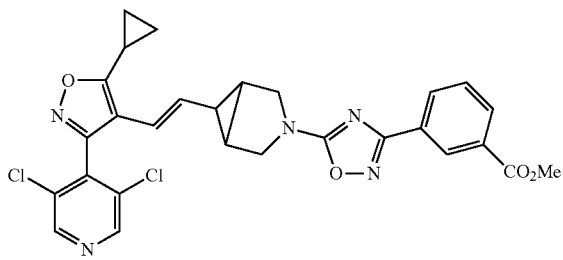 [SMILES: COC(=O)c1cccc(-c2noc(N3CC4C(/C=C/c5c(-c6c(Cl)cncc6Cl)noc5C5CC5)C4C3)n2)c1]

To a mixture of (E)-6-(2-(5-cyclopropyl-3-(3,5-dichloropyridin-4-yl)isoxazol-4-yl)vinyl)-3-azabicyclo[3.1.0]hexane-3-carbonitrile (Step 2 for Example 116, 31 mg, 0.080 mmol), methyl (Z)-3-(N'-hydroxycarbamimidoyl)benzoate (23.3 mg, 0.12 mmol) in ethyl acetate (0.7 mL) was slowly added zinc chloride solution (0.24 mL, 0.12 mmol, 0.5 M in THF). The reaction mixture was stirred at room temperature for 1 h. The solvent was evaporated and the crude product was treated with ether (1.5 mL). The top clear layer was decanted and the remaining material was concentrated in vacuo to give a white solid. The solid was suspended in dioxane (0.88 mL), and hydrochloric acid solution (0.040 mL, 0.16 mmol, 4M in dioxane) was added. The mixture was heated in a sealed vial at 100° C. for 1.5 h. The excess solvent was evaporated and the residue was diluted with CH$_2$Cl$_2$ (5 mL) and washed with saturated NaHCO$_3$ solution (1 mL). The organic layer was separated and concentrated to dryness in vacuo. The residue was purified by flash chromatography on SiO$_2$ (0-50% EtOAc/hexanes) to give methyl (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-3-yl)benzoate (20 mg, 45% yield) as white solid. MS (ESI) m/z: 564.2 [M+H]$^+$; $^1$H NMR (400 MHz, CDCl$_3$) δ 8.64 (t, J=1.8 Hz, 1H), 8.63 (s, 2H), 8.16 (dt, J=7.9, 1.6 Hz, 1H), 8.13 (dt, J=7.9, 1.6 Hz, 1H), 7.52 (t, J=7.8 Hz, 1H), 6.04 (d, J=16.1 Hz, 1H), 5.19 (dd, J=16.0, 8.6 Hz, 1H), 3.94 (s, 3H), 3.91 (d, J=10.7 Hz, 2H), 3.74-3.67 (m, 2H), 2.09 (tt, J=8.4, 5.1 Hz, 1H), 1.70-1.63 (m, 2H), 1.39-1.31 (m, 1H), 1.30-1.06 (m, 4H).

Example 133. (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-3-yl)benzoic acid A solution of methyl (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-3-yl)benzoate (20 mg, 0.036 mmol) in ethanol (0.9 mL), THF (0.3 mL) and 1 M aqueous sodium hydroxide (0.14 mL, 0.14 mmol) was heated in a sealed vial at 60° C. for 2 h. The volatiles were removed in vacuo and the residue was purified by preparative HPLC (Column: Sunfire C18 OBD, 30×100 mm, 5-µm particles; Mobile Phase A: 5:95 acetonitrile:water with 0.1% TFA; Mobile Phase B: 95:5 acetonitrile:water with 0.1% TFA; Gradient: 65-100% B over 10 minutes, then a 5-minute hold at 100% B; Flow: 40 mL/min) to give (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-3-yl)benzoic acid (11.6 mg, 39% yield) as beige solid. MS (ESI) m/z: 550.2 [M+H]$^+$; $^1$H NMR (400 MHz, DMSO-d$_6$) δ 8.86 (s, 2H), 8.44 (t, J=1.8 Hz, 1H), 8.10 (ddt, J=10.9, 7.8, 1.4 Hz, 2H), 7.65 (t, J=7.8 Hz, 1H), 6.14 (d, J=16.0 Hz, 1H), 5.32 (dd, J=16.1, 8.8 Hz, 1H), 3.76 (d, J=10.5 Hz, 2H), 3.70 (dt, J=10.5, 1.8 Hz, 2H), 2.38 (tt, J=8.6, 5.2 Hz, 1H), 1.83-1.78 (m, 2H), 1.46 (dt, J=8.7, 3.4 Hz, 1H), 1.26-1.01 (m, 4H); HLE GAL-FXR EC$_{50}$=1292 nM.

General Method J1

Example 183

(E)-4-Cyclopropoxy-6-(6-(2-(5-cyclopropyl-3-(2-(trifluoromethyl)phenyl)-isoxazol-4-yl)vinyl)-3-azabicyclo[3.1.0]hexan-3-yl)quinoline-2-carboxamide

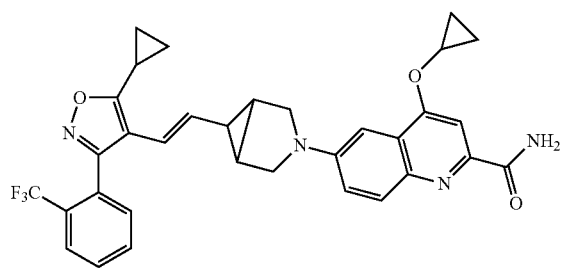

(183)

Step 1. (E)-4-Cyclopropoxy-6-(6-(2-(5-cyclopropyl-3-(2-(trifluoromethyl)phenyl) isoxazol-4-yl)vinyl)-3-azabicyclo[3.1.0]hexan-3-yl)quinoline-2-carbonitrile

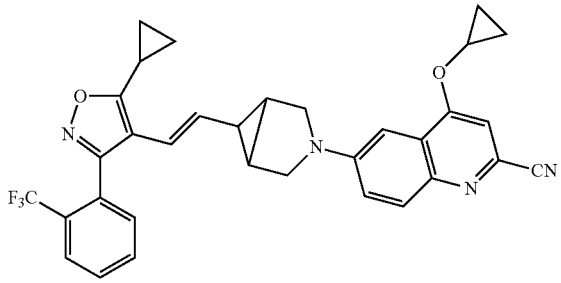 [SMILES: N#Cc1cc(OC2CC2)c2cc(N3CC4C(/C=C/c5c(-c6ccccc6C(F)(F)F)noc5C5CC5)C4C3)ccc2n1]

A slurry of (E)-4-(2-(3-azabicyclo[3.1.0]hexan-6-yl)vinyl)-5-cyclopropyl-3-(2-(trifluoromethyl)phenyl)isoxazole (25 mg, 0.069 mmol), 6-bromo-4-cyclopropoxy quinoline-2-carbonitrile (25 mg, 0.086 mmol) and $Cs_2CO_3$ (90 mg, 0.28 mmol) in dioxane (800 μL) was degassed by bubbling nitrogen through the mixture for 5 minutes. Chloro(2-dicyclohexylphosphino-2',6'-diisopropoxy-1,1'-biphenyl)[2-(2'-amino-1,1'-biphenyl)]palladium(II) (RuPhos-Pd-G2) (8 mg, 10.3 μmol) was then added and the reaction vessel was sealed and heated to 105° C. for 2 h. The reaction was filtered through a pad of Celite and washed with dichloromethane (3 mL). The filtrate was concentrated to give a crude product which was further purified by flash chromatography (silica gel, hexanes:EtOAc, 100:0 to 50:50) to afford (E)-4-cyclopropoxy-6-(6-(2-(5-cyclopropyl-3-(2-(trifluoromethyl)isoxazol-4-yl)vinyl)-3-azabicyclo[3.1.0]hexan-3-yl)quinoline-2-carbonitrile (35 mg, 0.062 mmol, 89% yield) as yellow foam. $^1$H NMR (400 MHz, $CDCl_3$) δ 7.90 (d, J=9.3 Hz, 1H), 7.82 (dd, J=7.6, 1.7 Hz, 1H), 7.69-7.56 (m, 2H), 7.41 (dd, J=7.4, 1.7 Hz, 1H), 7.30 (s, 1H), 7.17 (dd, J=9.3, 2.8 Hz, 1H), 6.80 (d, J=2.7 Hz, 1H), 6.02 (d, J=16.0 Hz, 1H), 5.16 (dd, J=16.1, 8.8 Hz, 1H), 4.04-3.83 (m, 1H), 3.71 (d, J=9.7 Hz, 2H), 3.46 (dt, J=9.9, 1.8 Hz, 2H), 2.13-2.03 (m, 1H), 1.75-1.63 (m, 2H), 1.38 (dt, J=8.9, 3.2 Hz, 1H), 1.26-1.20 (m, 2H), 1.18-1.09 (m, 2H), 1.05-0.89 (m, 4H); MS (ESI): m/z 569.3 [M+H]$^+$.

Example 183. (E)-4-Cyclopropoxy-6-(6-(2-(5-cyclopropyl-3-(2-(trifluoromethyl)-phenyl)isoxazol-4-yl)vinyl)-3-azabicyclo[3.1.0]hexan-3-yl)quinoline-2-carboxamide A mixture of (E)-4-cyclopropoxy-6-(6-(2-(5-cyclopropyl-3-(2-(trifluoromethyl)phenyl)isoxazol-4-yl)vinyl)-3-azabicyclo[3.1.0]hexan-3-yl)quinoline-2-carbonitrile (35 mg, 0.062 mmol) in MeOH (1.5 mL) and 6M aqueous potassium hydroxide solution (0.10 mL, 0.62 mmol) was heated at 120° C. under microwave condition for 40 min. The pH of the mixture was brought to 4 by adding aqueous conc. HCl. The solvent was evaporated to give the crude product. The crude material was purified via preparative LC/MS with the following conditions (Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 50% B, 50-90% B over 20 minutes, then a 4-minute hold at 100% B; Flow Rate: 20 mL/min; Column Temperature: 25° C.) to afford the (E)-4-cyclopropoxy-6-(6-(2-(5-cyclopropyl-3-(2-(trifluoromethyl)phenyl)isoxazol-4-yl)vinyl)-3-azabicyclo[3.1.0]hexan-3-yl)quinoline-2-carboxamide (6.0 mg, 35% yield) as an orange powder. $^1$H NMR (500 MHz, DMSO-$d_6$) δ 8.00 (bs, 1H), 7.91 (d, J=7.8 Hz, 1H), 7.87-7.62 (m, 4H), 7.48 (d, J=7.5 Hz, 1H), 7.34 (bs, 1H), 7.24 (dd, J=9.3, 2.7 Hz, 1H), 6.75 (d, J=2.7 Hz, 1H), 6.04 (d, J=16.1 Hz, 1H), 5.19 (dd, J=16.1, 8.8 Hz, 1H), 4.27-3.97 (m, 1H), 3.62 (d, J=9.8 Hz, 2H), 3.41-3.27 (m, 2H), 2.26 (td, J=8.5, 4.3 Hz, 1H), 1.73-1.64 (m, 2H), 1.36-1.31 (m, 1H), 1.15-1.11 (m, 2H), 1.07-1.01 (m, 2H), 0.97-0.90 (m, 2H), 0.84-0.77 (m, 2H); MS (ESI) m/z: 587.2 [M+H]$^+$. HLE GAL-FXR $EC_{50}$=908 nM.

General Method J2

Example 184

(E)-4-Cyclopropoxy-6-(6-(2-(5-cyclopropyl-3-(2-(trifluoromethyl)phenyl)-isoxazol-4-yl)vinyl)-3-azabicyclo[3.1.0]hexan-3-yl)quinoline-2-carboxylic acid

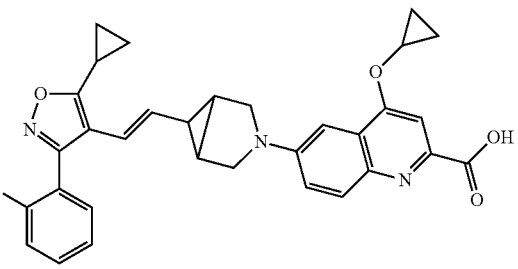

(184)

A mixture of (E)-4-cyclopropoxy-6-(6-(2-(5-cyclopropyl-3-(2-(trifluoromethyl) phenyl)isoxazol-4-yl)vinyl)-3-azabicyclo[3.1.0]hexan-3-yl)quinoline-2-carboxamide (7 mg, 0.012 mmol) in MeOH (1.1 mL) and aqueous 6M potassium hydroxide solution (110 μL, 0.660 mmol) was heated at 130° C. under microwave condition for 1 h. Solvent was evaporated. The reaction mixture was diluted with $CH_2Cl_2$ (3 mL) and 4 drops of TFA was added. Solvent was evaporated to give a crude product which was purified by preparative HPLC (Column: Sunfire C18 OBD, 30×100 mm, 5-μm particles; Mobile Phase A: 5:95 acetonitrile:water with 0.1% TFA; Mobile Phase B: 95:5 acetonitrile:water with 0.1% TFA; Gradient: 65-100% B over 10 minutes, then a 5-minute hold at 100% B; Flow: 40 mL/min) to afford (E)-4-cyclopropoxy-6-(6-(2-(5-cyclopropyl-3-(2-(trifluoromethyl)phenyl)isoxazol-4-yl)vinyl)-3-azabicyclo[3.1.0]hexan-3-yl)quinoline-2-carboxylic acid (6.24 mg, 70.8% yield) as orange solid: MS (ESI) m/z: 588.3 [M+H]$^+$; $^1$H NMR (400 MHz, Methanol-$d_4$) δ 8.16 (d, J=9.1 Hz, 1H), 8.06 (s, 1H), 7.98-7.83 (m, 1H), 7.83-7.66 (m, 2H), 7.58 (d, J=8.8 Hz, 1H), 7.46 (d, J=7.2 Hz, 1H), 7.03-6.80 (m, 1H), 6.11 (d, J=16.1 Hz, 1H), 5.22 (dd, J=16.0, 8.7 Hz, 1H), 4.47-4.40 (m, 1H), 3.74 (d, J=9.9 Hz, 2H), 3.52 (d, J=10.1 Hz, 2H), 2.24 (tt, J=8.0, 5.2 Hz, 1H), 1.82-1.67 (m, 2H), 1.49-1.25 (m, 1H), 1.28-0.79 (m, 8H); HLE GAL-FXR $EC_{50}$=50 nM.

General Method K

Example 208

(E)-3-(2-(6-(2-(5-Cyclopropyl-3-(3,5-dichloropyridin-4-yl)isoxazol-4-yl)vinyl)-3-azabicyclo[3.1.0]hexan-3-yl)thiazol-4-yl)-5-methoxybenzoic acid

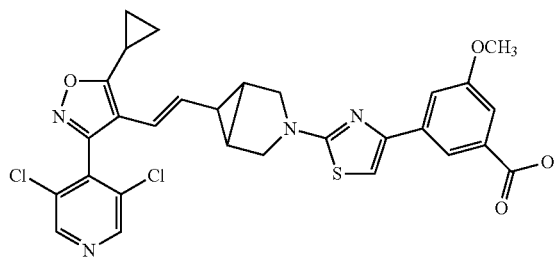

(208)

Step 1. (E)-4-(2-(3-(4-Bromothiazol-2-yl)-3-azabicyclo[3.1.0]hexan-6-yl)vinyl)-5-cyclopropyl-3-(3,5-dichloropyridin-4-yl)isoxazole

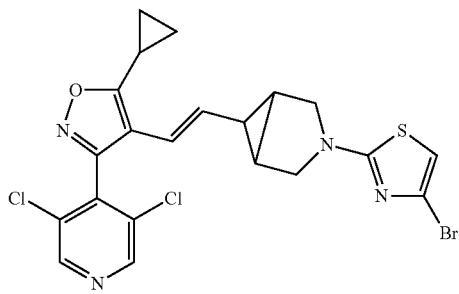 [SMILES: Clc1cncc(Cl)c1-c1noc(C2CC2)c1/C=C/C1C2CN(c3nc(Br)cs3)CC12]

A solution of (E)-4-(2-(3-azabicyclo[3.1.0]hexan-6-yl)vinyl)-5-cyclopropyl-3-(3,5-dichloropyridin-4-yl)isoxazole (23 mg, 0.063 mmol), 2,4-dibromothiazole (18 mg, 0.074 mmol) and Et$_3$N (0.027 mL, 0.190 mmol) in DMF (0.1 mL) was heated at 100° C. in a sealed vial for 2 h. The reaction mixture was filtered through a pad of Celite. The pad was washed with a small amount of dichloromethane. The filtrate was collected and concentrated to give a crude product which was purified by flash chromatography (silica gel, hexanes:EtOAc, 100:0 to 50:50) to afford (E)-4-(2-(3-(4-bromothiazol-2-yl)-3-azabicyclo[3.1.0]hexan-6-yl)vinyl)-5-cyclopropyl-3-(3,5-dichloropyridin-4-yl)isoxazole (25 mg, 0.048 mmol, 75% yield) as yellow foam solid. $^1$H NMR (400 MHz, CDCl$_3$) δ 8.62 (s, 2H), 6.33 (s, 1H), 6.02 (dd, J=15.9, 0.7 Hz, 1H), 5.17 (dd, J=16.0, 8.6 Hz, 1H), 3.66 (d, J=10.2 Hz, 2H), 3.53 (ddd, J=10.2, 2.7, 1.5 Hz, 2H), 2.09 (tt, J=8.4, 5.1 Hz, 1H), 1.70-1.61 (m, 2H), 1.34 (dt, J=8.7, 3.3 Hz, 1H), 1.27-1.22 (m, 2H), 1.20-1.05 (m, 2H); MS (ESI): m/z 523.0 [M+H]$^+$.

Step 2. tert-Butyl (E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-4-yl)-5-methoxybenzoate

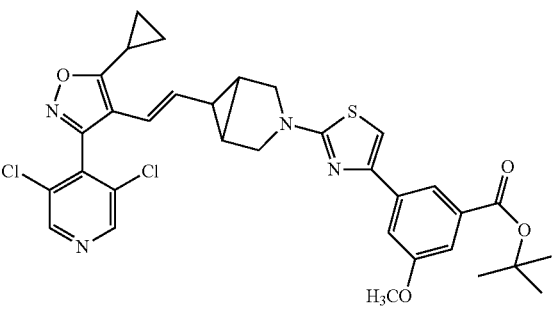 [SMILES: COc1cc(C(=O)OC(C)(C)C)cc(-c2csc(N3CC4C(/C=C/c5c(-c6c(Cl)cncc6Cl)noc5C5CC5)C4C3)n2)c1]

A mixture of (E)-4-(2-(3-(4-bromothiazol-2-yl)-3-azabicyclo[3.1.0]hexan-6-yl)vinyl)-5-cyclopropyl-3-(3,5-dichloropyridin-4-yl)isoxazole (25 mg, 0.048 mmol), tert-butyl 3-methoxy-5-(4,4,5,5-tetramethyl-1,3,2-dioxaborolan-2-yl) benzoate (19.13 mg, 0.057 mmol), PdCl$_2$(dppf)-CH$_2$Cl$_2$ adduct (2.337 mg, 2.86 µmol), and 2M aqueous potassium triphosphate solution (0.072 mL, 0.143 mmol) in Dioxane (0.8 mL) was heated at 100° C. for 1 h. The mixture was diluted with ethyl acetate (5 mL) and filtered through Celite. The filtrate was concentrated under vacuum to dryness. The residue was diluted with water (3 mL) and extracted with CH$_2$Cl$_2$ (2×10 mL). The combined extract was dried over anhydrous MgSO$_4$ and evaporated to dryness to afford a crude product. The crude product was purified by flash chromatography (silica gel, hexanes:EtOAc, 100:0 to 0:100) to afford tert-butyl (E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-4-yl)-5-methoxybenzoate (25 mg, 0.038 mmol, 80% yield) as a white solid: $^1$H NMR (400 MHz, Chloroform-d) δ 8.63 (s, 2H), 7.98 (t, J=1.5 Hz, 1H), 7.59 (dd, J=2.7, 1.5 Hz, 1H), 7.45-7.40 (m, 1H), 6.74 (s, 1H), 6.02 (d, J=16.1 Hz, 1H), 5.20 (dd, J=16.0, 8.7 Hz, 1H), 3.88 (s, 3H), 3.76 (d, J=10.2 Hz, 2H), 3.64-3.38 (m, 2H), 2.09 (tt, J=8.4, 5.1 Hz, 1H), 1.70-1.63 (m, 2H), 1.60 (s, 9H), 1.41 (dt, J=8.8, 3.3 Hz, 1H), 1.31-1.22 (m, 2H), 1.21-1.06 (m, 2H); MS (ESI): m/z 651.2[M+H]$^+$.

Example 208. (E)-3-(2-(6-(2-(5-Cyclopropyl-3-(3,5-dichloropyridin-4-yl)isoxazol-4-yl)vinyl)-3-azabicyclo[3.1.0]hexan-3-yl)thiazol-4-yl)-5-methoxybenzoic acid A mixture of tert-butyl (E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-4-yl)-5-methoxybenzoate (25 mg, 0.038 mmol) in dichloromethane (0.4 mL) and TFA (0.4 mL) was stirred at rt for 1 h. Solvent was evaporated to give a crude product which was purified by preparative HPLC (Column: Sunfire C18 OBD, 30×100 mm, 5-µm particles; Mobile Phase A: 5:95 acetonitrile:water with 0.1% TFA; Mobile Phase B: 95:5 acetonitrile:water with 0.1% TFA; Gradient:30-100% B over 10 minutes, then a 5-minute hold at 100% B; Flow: 40 mL/min) to afford (E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-4-yl)-5-methoxybenzoic acid (17.11 mg, 0.023 mmol, 59.7% yield) as white solid. MS (ESI) m/z: 595.1 [M+H]$^+$; $^1$H NMR (400

MHz, Methanol-d$_4$) δ 8.73 (s, 2H), 7.98 (t, J=1.5 Hz, 1H), 7.60 (dd, J=2.6, 1.4 Hz, 1H), 7.53 (dd, J=2.5, 1.6 Hz, 1H), 7.10 (s, 1H), 6.19 (d, J=16.0 Hz, 1H), 5.30 (dd, J=16.0, 8.5 Hz, 1H), 3.91 (s, 3H), 3.80 (d, J=10.5 Hz, 2H), 3.76 (dt, J=10.5, 1.8 Hz, 2H), 2.28 (tt, J=8.2, 5.3 Hz, 1H), 1.90-1.81 (m, 2H), 1.47 (dt, J=8.6, 3.5 Hz, 1H), 1.29-1.05 (m, 4H); HLE GAL-FXR EC$_{50}$=247 nM.

General Method L

Example 210

(E)-3-(3-(6-(2-(5-Cyclopropyl-3-(3,5-dichloropyridin-4-yl)isoxazol-4-yl)vinyl)-3-azabicyclo[3.1.0]hexan-3-yl)-1,2,4-thiadiazol-5-yl)-5-methoxybenzoic acid (210)

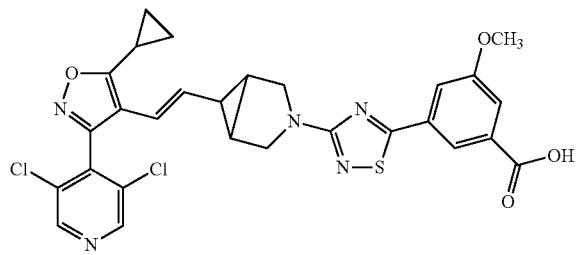

Step 1. tert-Butyl (E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-5-yl)-5-methoxybenzoate

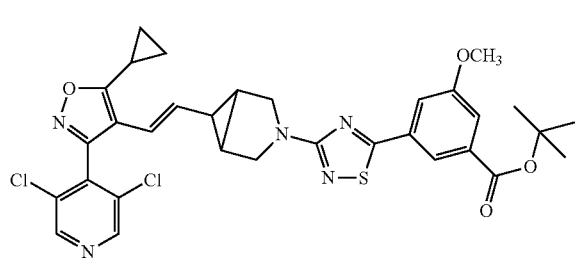 [SMILES: COc1cc(C(=O)OC(C)(C)C)cc(-c2nc(N3CC4C(/C=C/c5c(-c6c(Cl)cncc6Cl)noc5C5CC5)C4C3)ns2)c1]

A mixture of (E)-4-(2-(3-azabicyclo[3.1.0]hexan-6-yl)vinyl)-5-cyclopropyl-3-(3,5-dichloropyridin-4-yl)isoxazole (15 mg, 0.041 mmol), tert-butyl 3-(3-chloro-1,2,4-thiadiazol-5-yl)-5-methoxybenzoate (17.59 mg, 0.054 mmol) and Et$_3$N (0.017 mL, 0.124 mmol) in DMF (0.1 mL) was heated at 105° C. for 6 h. Solvent was evaporated to give the crude product which was purified by flash chromatography (silica gel, hexanes:EtOAc, 100:0 to 30: 70) to afford tert-butyl (E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-5-yl)-5-methoxybenzoate (17 mg, 0.026 mmol, 63% yield) as a foam solid. $^1$H NMR (400 MHz, CDCl$_3$) δ 8.63 (s, 2H), 8.01 (t, J=1.4 Hz, 1H), 7.62 (dd, J=2.6, 1.4 Hz, 1H), 7.58 (dd, J=2.6, 1.5 Hz, 1H), 6.01 (d, J=16.1 Hz, 1H), 5.22 (dd, J=16.0, 8.7 Hz, 1H), 4.01 (d, J=10.5 Hz, 2H), 3.91 (s, 3H), 3.65 (dt, J=10.5, 1.8 Hz, 2H), 2.10 (tt, J=8.4, 5.1 Hz, 1H), 1.61 (s, 11H), 1.47-1.37 (m, 1H), 1.27-1.21 (m, 2H), 1.18-1.11 (m, 2H). MS (ESI): m/z 652.2[M+H]$^+$.

Example 210. (E)-3-(3-(6-(2-(5-Cyclopropyl-3-(3,5-dichloropyridin-4-yl)isoxazol-4-yl)vinyl)-3-azabicyclo[3.1.0]hexan-3-yl)-1,2,4-thiadiazol-5-yl)-5-methoxybenzoic acid A mixture of tert-butyl (E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-5-yl)-5-methoxybenzoate (15 mg, 0.023 mmol) in dichloromethane (0.4 mL) and TFA (0.4 mL) was stirred at rt for 1 h. Solvent was evaporated to give a crude product which was purified by preparative HPLC (Column: Sunfire C18 OBD, 30×100 mm, 5-µm particles; Mobile Phase A: 5:95 acetonitrile:water with 0.1% TFA; Mobile Phase B: 95:5 acetonitrile:water with 0.1% TFA; Gradient:45-100% B over 10 minutes, then a 5-minute hold at 100% B; Flow: 40 mL/min) to afford (E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-5-yl)-5-methoxybenzoic acid (8.65 mg, 0.012 mmol, 50.3% yield) as white solid: MS (ESI) m/z: 596.1 [M+H]$^+$; $^1$H NMR (400 MHz, Methanol-d$_4$) δ 8.74 (s, 2H), 8.10 (t, J=1.5 Hz, 1H), 7.73 (dd, J=2.6, 1.4 Hz, 1H), 7.68 (dd, J=2.6, 1.5 Hz, 1H), 6.16 (d, J=16.1 Hz, 1H), 5.27 (dd, J=16.0, 8.7 Hz, 1H), 3.97 (d, J=10.6 Hz, 2H), 3.94 (s, 3H), 3.66 (dt, J=10.6, 2.0 Hz, 2H), 2.28 (tt, J=8.2, 5.2 Hz, 1H), 1.76-1.60 (m, 2H), 1.50-1.36 (m, 1H), 1.27-1.09 (m, 4H). HLE GAL-FXR EC$_{50}$=670 nM.

General Method M

Example 214

(E)-3-(5-(6-(2-(5-Cyclopropyl-3-(3,5-dichloropyridin-4-yl)isoxazol-4-yl)vinyl)-3-azabicyclo[3.1.0]hexan-3-yl)-1,2,4-thiadiazol-3-yl)-5-methoxybenzoic acid (214)

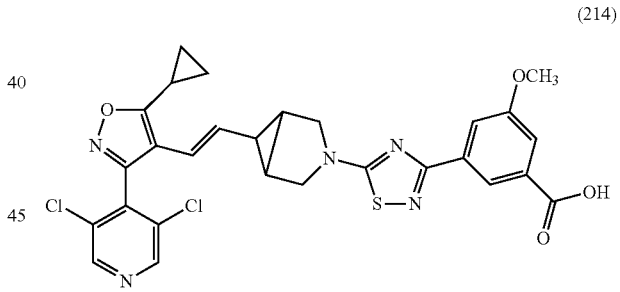

Step 1. (E)-4-(2-(3-(3-Bromo-1,2,4-thiadiazol-5-yl)-3-azabicyclo[3.1.0]hexan-6-yl)vinyl)-5-cyclopropyl-3-(3,5-dichloropyridin-4-yl)isoxazole

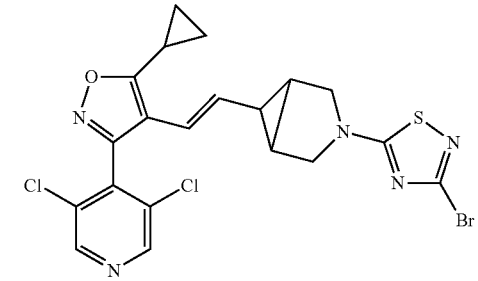 [SMILES: Clc1cncc(Cl)c1-c1noc(C2CC2)c1/C=C/C1C2CN(c3nc(Br)ns3)CC12]

A mixture of (E)-4-(2-(3-azabicyclo[3.1.0]hexan-6-yl)vinyl)-5-cyclopropyl-3-(3,5-dichloropyridin-4-yl)isoxazole (15 mg, 0.041 mmol), 3-bromo-5-chloro-1,2,4-thiadiazole (9 mg, 0.045 mmol) and Et$_3$N (8.66 µL, 0.062 mmol) in THF (0.5 mL) was stirred at rt for 2 h. Solvent was evaporated to give the crude product which was purified by flash chromatography (silica gel, hexanes:EtOAc, 100:0 to 30: 70) to afford (E)-4-(2-(3-(3-bromo-1,2,4-thiadiazol-5-yl)-3-azabicyclo[3.1.0]hexan-6-yl)vinyl)-5-cyclopropyl-3-(3,5-dichloropyridin-4-yl)isoxazole (17 mg, 0.032 mmol, 78% yield) as yellow foam solid: MS (ESI): m/z 524.0[M+H].

Step 2. tert-Butyl (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-3-yl)-5-methoxybenzoate

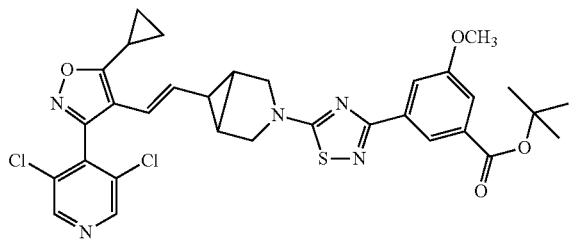 [SMILES: COc1cc(C(=O)OC(C)(C)C)cc(-c2nsc(N3CC4C(/C=C/c5c(-c6c(Cl)cncc6Cl)noc5C5CC5)C4C3)n2)c1]

A mixture of (E)-4-(2-(3-(3-bromo-1,2,4-thiadiazol-5-yl)-3-azabicyclo[3.1.0]hexan-6-yl)vinyl)-5-cyclopropyl-3-(3,5-dichloropyridin-4-yl)isoxazole (17 mg, 0.032 mmol), tert-butyl 3-methoxy-5-(4,4,5,5-tetramethyl-1,3,2-dioxaborolan-2-yl)benzoate (12.98 mg, 0.039 mmol), PdCl$_2$(dppf)-CH$_2$Cl$_2$ adduct (1.586 mg, 1.942 µmol), and 2M aqueous potassium triphosphate solution (0.049 mL, 0.097 mmol) in dioxane (0.8 mL) was heated at 100° C. for 1 h. The mixture was diluted with ethyl acetate (5 mL) and filtered through Celite. The filtrate was concentrated under vacuum to dryness. The residue was diluted with water (3 mL) and extracted with CH$_2$Cl$_2$ (3×5 mL). The combined extract was dried over anhydrous MgSO$_4$ and evaporated to dryness to afford a crude product. The crude product was purified by flash chromatography (silica gel, hexanes:EtOAc, 100:0 to 10:90) to afford tert-butyl (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-3-yl)-5-methoxybenzoate (17 mg, 0.026 mmol, 80% yield) as a white solid. $^1$H NMR (400 MHz, CDCl$_3$) δ 8.63 (d, J=0.7 Hz, 3H), 8.37 (t, J=1.4 Hz, 1H), 7.89 (dd, J=2.7, 1.4 Hz, 1H), 7.57 (dd, J=2.7, 1.5 Hz, 1H), 6.04 (d, J=16.0 Hz, 2H), 5.20 (dd, J=16.0, 8.6 Hz, 1H), 3.90 (s, 3H), 3.81-3.58 (m, 4H), 2.16-2.05 (m, 1H), 1.73-1.68 (m, 2H), 1.61 (s, 9H), 1.43-1.35 (m, 1H), 1.25-1.21 (m, 2H), 1.21-1.12 (m, 2H).

Example 214. (E)-3-(5-(6-(2-(5-Cyclopropyl-3-(3,5-dichloropyridin-4-yl)isoxazol-4-yl)vinyl)-3-azabicyclo[3.1.0]hexan-3-yl)-1,2,4-thiadiazol-3-yl)-5-methoxybenzoic acid A mixture of tert-butyl (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-3-yl)-5-methoxybenzoate (17 mg, 0.026 mmol) in dichloromethane (0.4 mL) and TFA (0.4 mL) was stirred at rt for 1 h. Solvent was evaporated to give a crude product which was purified by preparative HPLC (Column: Sun fire C18 OBD, 30×100 mm, 5-µm particles; Mobile Phase A: 5:95 acetonitrile:water with 0.1% TFA; Mobile Phase B: 95:5 acetonitrile:water with 0.1% TFA; Gradient:45-100% B over 10 minutes, then a 5-minute hold at 100% B; Flow: 40 mL/min) to afford (E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-3-yl)-5-methoxybenzoic acid (5.4 mg, 7.2 µmol, 29% yield) as a white solid. MS (ESI) m/z: 596.1 [M+H]$^+$; $^1$H NMR (400 MHz, DMSO-d$_6$) δ 8.86 (s, 2H), 8.25 (t, J=1.5 Hz, 1H), 7.81 (dd, J=2.6, 1.4 Hz, 1H), 7.52 (dd, J=2.6, 1.5 Hz, 1H), 6.15 (d, J=16.0 Hz, 1H), 5.33 (dd, J=16.1, 8.8 Hz, 1H), 3.87 (s, 3H), 3.81-3.51 (m, 4H), 2.46-2.28 (m, 1H), 1.87-1.77 (m, 2H), 1.44 (dt, J=8.9, 3.4 Hz, 1H), 1.23-1.02 (m, 4H); HLE GAL-FXR EC$_{50}$=107 nM.

General Method N

Example 216

(E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-5-yl)-5-methoxybenzoic acid (216)

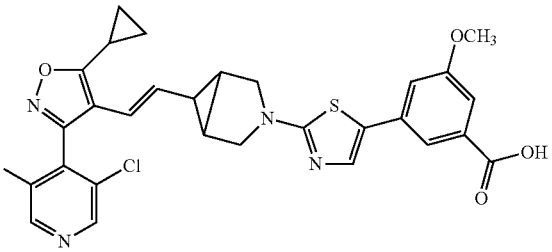

Step 1. (E)-4-(2-(3-(5-bromothiazol-2-yl)-3-azabicyclo[3.1.0]hexan-6-yl)vinyl)-5-cyclopropyl-3-(3,5-dichloropyridin-4-yl)isoxazole

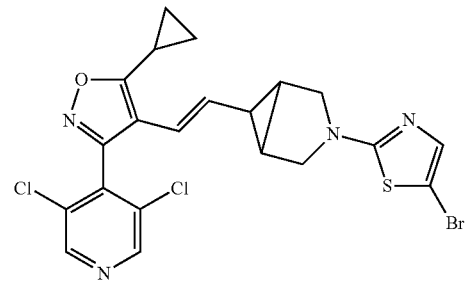 [SMILES: Clc1cncc(Cl)c1-c1noc(C2CC2)c1/C=C/C1C2CN(c3ncc(Br)s3)CC12]

A solution of (E)-4-(2-(3-azabicyclo[3.1.0]hexan-6-yl)vinyl)-5-cyclopropyl-3-(3,5-dichloropyridin-4-yl)isoxazole (23 mg, 0.063 mmol), 2,5-dibromothiazole (18 mg, 0.074 mmol) and Et$_3$N (0.027 mL, 0.19 mmol) in DMF (0.1 mL) was heated at 100° C. in a sealed vial for 2 h. Solvent was evaporated to give a crude product which was purified by flash chromatography (silica gel, hexanes:EtOAc, 100:0 to 50:50) to afford (E)-4-(2-(3-(5-bromothiazol-2-yl)-3-azabicyclo[3.1.0]hexan-6-yl)vinyl)-5-cyclopropyl-3-(3,5-dichloropyridin-4-yl)isoxazole (23 mg, 0.044 mmol, 69% yield) as yellow foam solid. ¹H NMR (400 MHz, CDCl₃) δ 8.62 (s, 2H), 7.03 (s, 1H), 6.02 (dd, J=16.0, 1.4 Hz, 1H), 5.18 (dd, J=16.0, 8.6 Hz, 1H), 3.61 (d, J=10.1 Hz, 2H), 3.50 (ddd, J=10.1, 2.7, 1.4 Hz, 2H), 2.08 (tt, J=8.4, 5.1 Hz, 1H), 1.71-1.62 (m, 2H), 1.36 (dt, J=8.8, 3.4 Hz, 1H), 1.30-1.22 (m, 2H), 1.19-1.07 (m, 2H); MS (ESI): m/z 523.0 [M+H]⁺.

Step 2. tert-Butyl (E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-5-yl)-5-methoxybenzoate

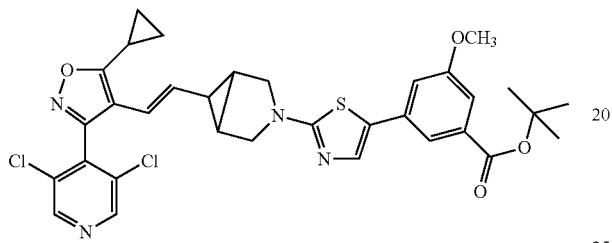

A mixture of (E)-4-(2-(3-(5-bromothiazol-2-yl)-3-azabicyclo[3.1.0]hexan-6-yl)vinyl)-5-cyclopropyl-3-(3,5-dichloropyridin-4-yl)isoxazole (23 mg, 0.044 mmol), tert-butyl 3-methoxy-5-(4,4,5,5-tetramethyl-1,3,2-dioxaborolan-2-yl) benzoate (17.60 mg, 0.053 mmol), PdCl₂(dppf)-CH₂Cl₂ adduct (2.150 mg, 2.63 μmol), and 2M aqueous potassium triphosphate solution (0.061 mL, 0.122 mmol) in Dioxane (0.8 mL) was heated at 100° C. for 0.5 h. The mixture was diluted with ethyl acetate (5 mL) and filtered through Celite. The filtrate was concentrated under vacuum to dryness. The residue was diluted with water (3 mL) and extracted with CH₂Cl₂ (3×5 mL). The combined extract was dried over anhydrous MgSO₄ and evaporated to dryness to afford a crude product. The crude product was purified by flash chromatography (silica gel, hexanes:EtOAc, 100:0 to 20:80) to afford tert-butyl (E)-3-(2-(6-(2-(5-cyclopropyl-3-(3,5-dichloropyridin-4-yl)isoxazol-4-yl)vinyl)-3-azabicyclo[3.1.0] hexan-3-yl)thiazol-5-yl)-5-methoxybenzoate (25 mg, 0.038 mmol, 87% yield) as a white solid. ¹H NMR (400 MHz, Chloroform-d) δ 8.63 (s, 2H), 7.61 (t, J=1.5 Hz, 1H), 7.42 (s, 1H), 7.34 (dd, J=2.6, 1.3 Hz, 1H), 7.07 (dd, J=2.5, 1.6 Hz, 1H), 6.04 (d, J=15.9 Hz, 1H), 5.20 (dd, J=16.0, 8.6 Hz, 1H), 3.86 (s, 3H), 3.72 (d, J=10.2 Hz, 2H), 3.61-3.55 (m, 2H), 2.09 (tt, J=8.4, 5.1 Hz, 1H), 1.71-1.65 (m, 2H), 1.60 (s, 9H), 1.44-1.36 (m, 1H), 1.30-1.21 (m, 2H), 1.15-1.11 (m, 2H); MS (ESI): m/z 651.2[M+H]⁺.

Example 216. (E)-3-(2-(6-(2-(5-Cyclopropyl-3-(3,5-dichloropyridin-4-yl)isoxazol-4-yl)vinyl)-3-azabicyclo[3.1.0]hexan-3-yl)thiazol-5-yl)-5-methoxybenzoic acid A mixture of tert-butyl (E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-5-yl)-5-methoxybenzoate (25 mg, 0.038 mmol) in dichloromethane (0.4 mL) and TFA (0.4 mL) was stirred at rt for 1 h. Solvent was evaporated to give a crude product which was purified by preparative HPLC (Column: Sunfire C18 OBD, 30×100 mm, 5-μm particles; Mobile Phase A: 5:95 acetonitrile:water with 0.1% TFA; Mobile Phase B: 95:5 acetonitrile:water with 0.1% TFA; Gradient:20-100% B over 10 minutes, then a 5-minute hold at 100% B; Flow: 40 mL/min) to afford (E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-5-yl)-5-methoxybenzoic acid (7.0 mg, 9.4 μmol, 25% yield) as a white solid. MS (ESI) m/z: 595.1 [M+H]⁺; ¹H NMR (400 MHz, Methanol-d₄) δ 8.62 (s, 2H), 7.65 (s, 1H), 7.60 (t, J=1.5 Hz, 1H), 7.45-7.41 (m, 1H), 7.20 (t, J=2.1 Hz, 1H), 6.08 (d, J=16.0 Hz, 1H), 5.20 (dd, J=16.0, 8.5 Hz, 1H), 3.79 (s, 3H), 3.69 (d, J=11.5 Hz, 2H), 3.65 (d, J=10.5 Hz, 2H), 2.16 (tt, J=8.2, 5.3 Hz, 1H), 1.82-1.76 (m, 2H), 1.38 (dt, J=8.8, 3.5 Hz, 1H), 1.17-0.87 (m, 4H); HLE GAL-FXR EC₅₀=202 nM.

Intermediates

Methyl 6-bromo-4-(cyclopentyloxy)quinoline-2-carboxylate

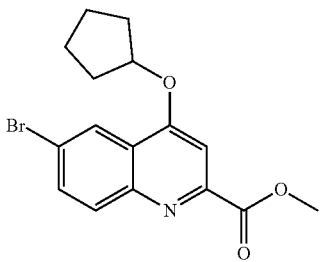 [SMILES: COC(=O)c1cc(OC2CCCC2)c2cc(Br)ccc2n1]

Methyl 6-bromo-4-hydroxyquinoline-2-carboxylate (200 mg, 0.71 mmol), iodocyclopentane (0.25 mL, 2.13 mmol) and potassium carbonate (300 mg, 2.13 mmol) in acetonitrile (15 mL) were heated to 80° C. After 16 h, the reaction mixture was diluted with water (25 mL) and, extracted with ethyl acetate (2×25 mL). The organic layer was dried over Na₂SO₄, filtered, concentrated in vacuo, and purified by flash chromatography on SiO₂ to provide methyl 6-bromo-4-(cyclopentyloxy)quinoline-2-carboxylate (211 mg, 85% yield). MS (ESI) m/z: 352.0 [M+H]+; ¹H NMR (500 MHz, CDCl₃) δ 8.37 (d, J=2.2 Hz, 1H), 8.10 (d, J=9.1 Hz, 1H), 7.83 (dd, J=8.8, 2.2 Hz, 1H), 7.59 (s, 1H), 5.15 (dt, J=5.6, 3.0 Hz, 1H), 4.10 (s, 3H), 2.18-2.09 (m, 2H), 2.08-2.01 (m, 2H), 1.97-1.88 (m, 2H), 1.81-1.65 (m, 2H).

Methyl 6-bromo-4-(2,2-difluoroethoxy)quinoline-2-carboxylate

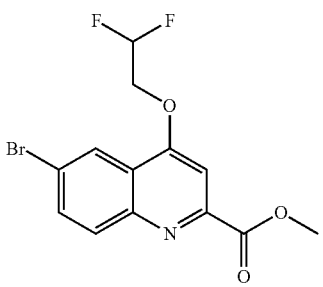 [SMILES: COC(=O)c1cc(OCC(F)F)c2cc(Br)ccc2n1]

Methyl 6-bromo-4-(2,2-difluoroethoxy)quinoline-2-carboxylate was prepared following the procedure described for the preparation of methyl 6-bromo-4-(cyclopentyloxy)quinoline-2-carboxylate with replacement of iodocyclopentane with 1,1-difluoro-2-iodoethane (60% yield). MS (ESI) m/z: 345.9 [M+H]+; 1H NMR (400 MHz, CDCl3) δ 8.22-8.36 (m, 1H), 8.03 (d, J=9.02 Hz, 1H), 7.78 (dd, J=2.20, 9.02 Hz, 1H), 7.50 (s, 1H), 6.00-6.48 (m, 1H), 4.43 (dt, J=3.96, 12.76 Hz, 2H), 4.01 (s, 3H).

Methyl 6-bromo-4-(2-methoxyethoxy)quinoline-2-carboxylate

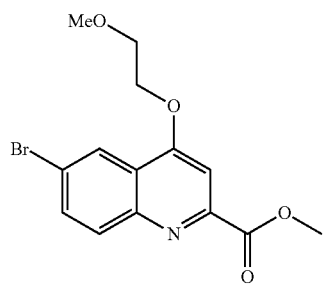 [SMILES: COCCOc1cc(C(=O)OC)nc2ccc(Br)cc12]

Methyl 6-bromo-4-(2-methoxyethoxy)quinoline-2-carboxylate was prepared following the procedure described for the preparation of methyl 6-bromo-4-(cyclopentyloxy)quinoline-2-carboxylate with replacement of iodocyclopentane with 1-bromo-2-methoxyethane (79% yield). MS (ESI) m/z: 340.08 [M+H]+; 1H NMR (500 MHz, CDCl3) δ 8.46 (d, J=1.9 Hz, 1H), 8.11 (d, J=9.1 Hz, 1H), 7.85 (dd, J=9.1, 2.2 Hz, 1H), 7.63 (s, 1H), 4.51-4.42 (m, 2H), 4.10 (s, 3H), 3.98-3.91 (m, 2H), 3.54 (s, 3H).

Methyl 6-bromo-4-(2-hydroxyethoxy)quinoline-2-carboxylate

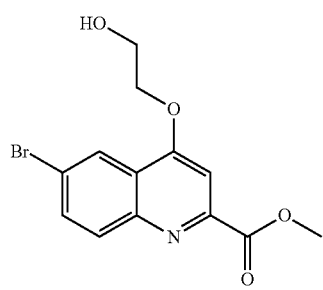 [SMILES: COC(=O)c1cc(OCCO)c2cc(Br)ccc2n1]

Methyl 6-bromo-4-(2-hydroxyethoxy)quinoline-2-carboxylate was prepared following the procedure described for the preparation of methyl 6-bromo-4-(cyclopentyloxy)quinoline-2-carboxylate with replacement of iodocyclopentane with 2-bromoethan-1-ol (88% yield). MS (ESI) m/z: 326.08 [M+H]+; 1H NMR (400 MHz, DMSO-d6) δ 8.52 (d, J=2.2 Hz, 1H), 8.09-8.01 (m, 1H), 8.00-7.94 (m, 1H), 7.60-7.56 (m, 1H), 4.36 (t, J=4.5 Hz, 2H), 3.95 (s, 3H), 3.92-3.84 (m, 2H).

Methyl 6-bromo-4-cyclobutoxyquinoline-2-carboxylate

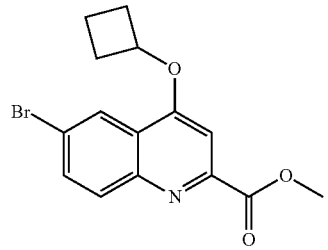 [SMILES: COC(=O)c1cc(OC2CCC2)c2cc(Br)ccc2n1]

Methyl 6-bromo-4-cyclobutoxyquinoline-2-carboxylate was prepared following the procedure described for the preparation of methyl 6-bromo-4-(cyclopentyloxy)quinoline-2-carboxylate with replacement of iodocyclopentane with bromocyclobutane (54% yield). MS (ESI) m/z: 336.08 [M+H]+; MS (ESI) m/z: 336.08 [M+H]+; 1H NMR (500 MHz, CDCl3) δ 8.43 (d, J=1.9 Hz, 1H), 8.10 (d, J=9.1 Hz, 1H), 7.84 (dd, J=8.8, 2.2 Hz, 1H), 7.45 (s, 1H), 5.05-4.96 (m, 1H), 4.09 (s, 3H), 2.73-2.59 (m, 2H), 2.44 (br d, J=9.1 Hz, 2H), 2.07-1.95 (m, 1H), 1.92-1.77 (m, 1H).

Methyl (R)-6-bromo-4-((tetrahydrofuran-3-yl)oxy)quinoline-2-carboxylate

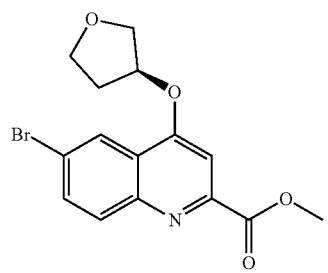

Step 1. (S)-Tetrahydrofuran-3-yl 4-methylbenzenesulfonate

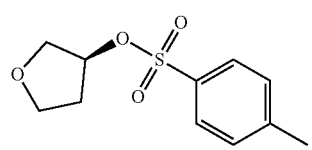 [SMILES: Cc1ccc(S(=O)(=O)O[C@H]2CCOC2)cc1]

To a mixture of (S)-tetrahydrofuran-3-ol (1 g, 11.35 mmol) and pyridine (1.8 mL, 22.7 mmol) in CH2Cl2 (20 mL) was added p-toluenesulfonyl chloride (3.3 g, 17.3 mmol) at room temperature. The reaction mixture was stirred at this temperature for 2 h. After evaporation of the solvents, the crude product was diluted with EtOAc (50 mL), washed with water, then 1 N HCl. The organic layer was dried over MgSO4, filtered and concentrated in vacuo. The residue was purified by flash chromatography on SiO2 (0-50% EtOAc/ hexanes) to afford (S)-tetrahydrofuran-3-yl 4-methylbenzenesulfonate (1.9 g, 69% yield) as a colorless oil. MS (ESI): m/z 243.1 [M+H]+; 1H NMR (400 MHz, CDCl3) δ 7.81 (d, J=8.1 Hz, 2H), 7.37 (d, J=8.1 Hz, 2H), 5.14 (tt, J=4.8, 2.5 Hz, 1H), 3.99-3.75 (m, 4H), 2.48 (s, 3H), 2.17-2.05 (m, 2H).

Step 2. Methyl (R)-6-bromo-4-((tetrahydrofuran-3-yl)oxy)quinoline-2-carboxylate

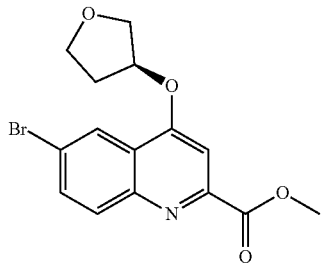 [SMILES: COC(=O)c1cc(O[C@H]2CCOC2)c2cc(Br)ccc2n1]

The title compound was prepared following the procedure described for the preparation of methyl 6-bromo-4-(cyclopentyloxy)quinoline-2-carboxylate with replacement of iodocyclopentane with (S)-tetrahydrofuran-3-yl 4-methylbenzenesulfonate (190 mg, 73% yield) as white solid. MS (ESI) m/z: 352.0 [M+H]+; 1H NMR (400 MHz, CDCl3) δ 8.38 (d, J=2.3 Hz, 1H), 8.09 (d, J=9.0 Hz, 1H), 7.84 (dd, J=9.0, 2.2 Hz, 1H), 7.52 (s, 1H), 5.34-5.25 (m, 1H), 4.20-4.14 (m, 2H), 4.14-3.95 (m, 2H), 4.08 (s, 3H), 2.56-2.17 (m, 2H).

Methyl (S)-6-bromo-4-((tetrahydrofuran-3-yl)oxy)quinoline-2-carboxylate

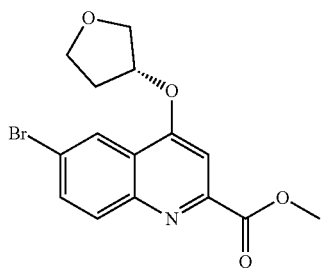

The title compound was prepared following the procedure described for the preparation of methyl (R)-6-bromo-4-((tetrahydrofuran-3-yl)oxy)quinoline-2-carboxylate with replacement of (S)-tetrahydrofuran-3-ol with (R)-tetrahydrofuran-3-ol. MS (ESI) m/z: 352.0 [M+H]+; 1H NMR (400 MHz, CDCl3) δ 8.38 (d, J=2.2 Hz, 1H), 8.09 (d, J=9.0 Hz, 1H), 7.84 (dd, J=9.0, 2.2 Hz, 1H), 7.52 (s, 1H), 5.32-5.25 (m, 1H), 4.19-4.14 (m, 2H), 4.13-3.93 (m, 2H), 4.08 (s, 3H), 2.52-2.22 (m, 2H).

(±) Methyl-6-bromo-4-((tetrahydrofuran-3-yl)oxy)quinoline-2-carboxylate

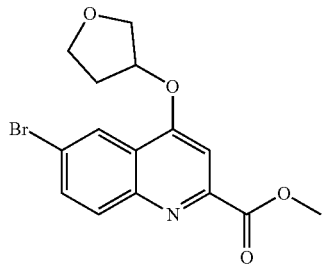 [SMILES: COC(=O)c1cc(OC2CCOC2)c2cc(Br)ccc2n1]

The title compound was prepared following the procedure described for the preparation of methyl (R)-6-bromo-4-((tetrahydrofuran-3-yl)oxy)quinoline-2-carboxylate with replacement of (S)-tetrahydrofuran-3-ol with (+)-tetrahydrofuran-3-ol. MS (ESI) m/z: 352.0 [M+H]+; 1H NMR (400 MHz, CDCl3) δ 8.38 (d, J=2.2 Hz, 1H), 8.10 (d, J=9.0 Hz, 1H), 7.85 (dd, J=9.0, 2.3 Hz, 1H), 7.53 (s, 1H), 5.31-5.26 (m, 1H), 4.20-4.14 (m, 2H), 4.13-3.96 (m, 2H), 4.09 (s, 3H), 2.52-2.25 (m, 2H).

Methyl 6-bromo-4-(oxetan-3-yloxy)quinoline-2-carboxylate

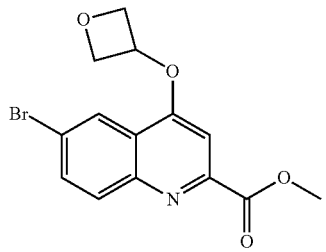

A mixture of methyl 6-bromo-4-hydroxyquinoline-2-carboxylate (0.44 g, 1.6 mmol), 3-iodooxetane (0.53 g, 2.9 mmol) and K2CO3 (0.64 g, 4.7 mmol) in DMF (8 mL) was heated at 85° C. in a sealed vial for 6 h. Another portion of 3-iodooxetane (0.20 g, 1.1 mmol) and K2CO3 (0.1 g, 0.72 mmol) was added. The reaction mixture was heated at 85° C. in a sealed vial for another 16 h. The reaction mixture was cooled to room temperature, diluted with CH2Cl2 (20 mL) and filtered. The filtrate was concentrated in vacuo and the residue was purified by flash chromatography on SiO2 (0-80% EtOAc/hexanes) to afford methyl 6-bromo-4-(oxetan-3-yloxy)quinoline-2-carboxylate (0.29 g, 54% yield) as white solid. MS (ESI) m/z: 340.0 [M+H]+; 1H NMR (400 MHz, CDCl3) δ 8.45 (d, J=2.2 Hz, 1H), 8.11 (d, J=9.0 Hz, 1H), 7.87 (dd, J=9.0, 2.3 Hz, 1H), 7.16 (s, 1H), 5.54 (tt, J=6.0, 4.9 Hz, 1H), 5.15 (ddd, J=7.2, 6.0, 1.0 Hz, 2H), 4.90 (ddd, J=7.6, 5.0, 1.0 Hz, 2H), 4.07 (s, 3H).

Methyl 6-bromo-4-(3,3-difluorocyclobutoxy)quinoline-2-carboxylate

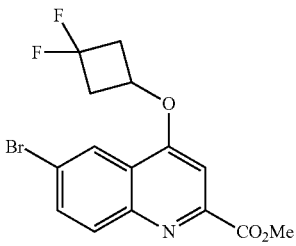 [SMILES: COC(=O)c1cc(OC2CC(F)(F)C2)c2cc(Br)ccc2n1]

A mixture of methyl 6-bromo-4-hydroxyquinoline-2-carboxylate (0.30 g, 1.1 mmol), 3-bromo-1,1-difluorocyclobutane (0.25 g, 1.4 mmol), and potassium carbonate (0.37 g, 2.7 mmol) in DMF (10 mL) was heated at 80° C. for 20 h. The reaction mixture was diluted with ethyl acetate (20 mL) and filtered through Celite. The filtrate was diluted with ethyl acetate (80 mL) and subsequently washed with water (3×25 mL) and brine (25 mL). The organic layer was dried over MgSO$_4$, filtered and concentrated to dryness in vacuo. The residue was loaded onto an Isco solid load cartridge and purified by flash chromatography on SiO$_2$ (20-60% EtOAc/hexanes) to give methyl 6-bromo-4-(3,3-difluorocyclobutoxy)quinoline-2-carboxylate (40 mg, 0.11 mmol, 10% yield) as a white solid. MS (ESI) m/z: 372.1 [M+H]$^+$.

Methyl 6-bromo-4-(difluoromethoxy)quinoline-2-carboxylate

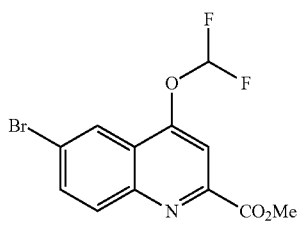 [SMILES: COC(=O)c1cc(OC(F)F)c2cc(Br)ccc2n1]

To a stirred suspension of Cs$_2$CO$_3$ (0.98 g, 3.0 mmol) in DMF (5 mL) at 0° C. was added methyl 6-bromo-4-hydroxyquinoline-2-carboxylate (0.28 g, 1.0 mmol) and sodium chlorodifluoroacetate (0.46 g, 3.0 mmol). The reaction mixture was stirred with heating at 80° C. for 30 minutes. After cooling the reaction mixture to room temperature, water (25 mL) was added, and the resulting suspension was stirred for 1 h. The solid was collected by suction filtration and washed with water (2×5 mL). After drying under vacuum overnight, methyl 6-bromo-4-(difluoromethoxy)quinoline-2-carboxylate (0.28 g, 0.81 mmol, 81% yield) was obtained as a white solid. MS (ESI) m/z: 333.9 [M+H]$^+$; $^1$H NMR (400 MHz, CDCl$_3$) δ 8.38 (d, J=2.20 Hz, 1H), 8.16 (d, J=9.02 Hz, 1H), 7.91 (dd, J=2.20, 9.24 Hz, 1H), 7.85 (t, J=1.10 Hz, 1H), 6.61-7.17 (m, 1H), 4.09 (s, 3H).

Methyl 7-chloro-1-methylisoquinoline-3-carboxylate

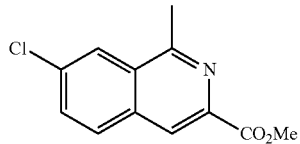 [SMILES: COC(=O)c1cc2ccc(Cl)cc2c(C)n1]

Step 1. Methyl (R)-7-chloro-1-methyl-3,4-dihydroisoquinoline-3-carboxylate

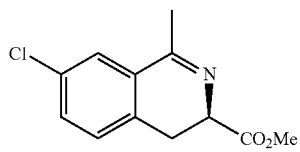 [SMILES: COC(=O)[C@H]1Cc2ccc(Cl)cc2C(C)=N1]

To a solution of methyl (R)-2-acetamido-3-(4-chlorophenyl)propanoate (0.61 g, 2.37 mmol) in dichloromethane (15.8 mL) at 0° C. was added oxalyl dichloride (1.42 mL, 2.8 mmol) dropwise. The mixture was stirred at 0° C. for 1 h and room temperature for 1 h. The reaction was cooled to 0° C., and iron (III) chloride (0.46 g, 2.8 mmol) was added portionwise. The mixture was allowed to warm to room temperature, stirred at for 1.5 h, filtered through a pad of SiO$_2$, and concentrated in vacuo. The oily residue was purified by flash chromatography on SiO$_2$ (0-60% EtOAc/hexanes) to give methyl (R)-7-chloro-1-methyl-3,4-dihydroisoquinoline-3-carboxylate (0.62 g, 2.0 mmol, 84% yield) as an oil. MS (ESI) m/z: 238.0 (M+H)$^+$.

Step 2. Methyl 7-chloro-1-methylisoquinoline-3-carboxylate

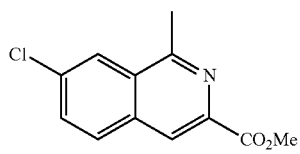 [SMILES: COC(=O)c1cc2ccc(Cl)cc2c(C)n1]

A mixture of methyl (R)-7-chloro-1-methyl-3,4-dihydroisoquinoline-3-carboxylate (0.60 g, 1.9 mmol) and 10% Pd—C (0.62 g, 0.58 mmol) in DCE (4.9 mL) in a sealed tube was heated at 110° C. for 4 h. The reaction mixture was loaded onto a SiO$_2$ solid cartridge and purified by flash chromatography on SiO$_2$ (0-50% EtOAc/hexanes) to give methyl 7-chloro-1-methylisoquinoline-3-carboxylate (110 mg, 0.47 mmol, 24% yield) as a tan solid. MS (ESI) m/z: 236.0 (M+H)+; 1H NMR (400 MHz, CDCl3) δ 8.44 (s, 1H), 8.16-8.19 (m, 1H), 7.92 (d, J=8.58 Hz, 1H), 7.72 (dd, J=1.98, 8.80 Hz, 1H), 4.06 (s, 3H), 3.03 (s, 3H).

Ethyl 7-bromo-1-methoxyisoquinoline-3-carboxylate

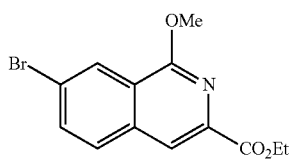

Step 1. 7-Bromo-3-(ethoxycarbonyl)isoquinoline 2-oxide

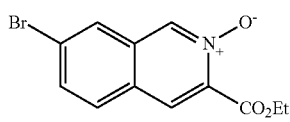

To a solution of ethyl 7-bromoisoquinoline-3-carboxylate (0.46 g, 1.6 mmol) in dichloromethane (10 mL) at 0° C. was added 3-chlorobenzoperoxoic acid (0.55 g, 2.4 mmol) in one portion. The resulting solution was stirred at room temperature for 22 h, quenched with saturated aqueous NaHCO3 (20 mL) and extracted with dichloromethane (3×40 mL). The combined extracts were dried over Na2SO4, filtered and concentrated in vacuo to dryness. The residue was loaded onto an Isco solid load cartridge and purified by flash chromatography on SiO2 (60-95% EtOAc/hexanes) to give 7-bromo-3-(ethoxycarbonyl)isoquinoline 2-oxide (0.34 g, 1.1 mmol, 70% yield) as a white solid. MS (ESI) m/z: 297.9 (M+H)+.

Step 2. Ethyl 7-bromo-1-chloroisoquinoline-3-carboxylate

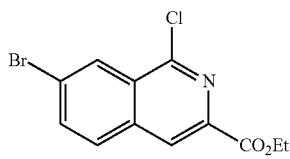 [SMILES: CCOC(=O)c1cc2ccc(Br)cc2c(Cl)n1]

A mixture of 7-bromo-3-(ethoxycarbonyl)isoquinoline 2-oxide (0.19 g, 0.64 mmol) and phosphoryl trichloride (4.0 mL, 42.9 mmol) was heated at 100° C. for 3 h. The reaction mixture was cooled to room temperature and concentrated under vacuum to dryness. The residue was dissolved in acetonitrile and purified by preparative HPLC (Column: Phenomenex Luna Axia 5u C18 21.2×100. Solvent A: 90% H2O-10% ACN-0.1% TFA; Solvent B: 10% ACN-90% H2O 0.1% TFA. 16 minute linear gradient from 32-100% B in A). The product containing fractions were combined, neutralized with saturated aqueous NaHCO3, concentrated under vacuum, and extracted with dichloromethane (3×30 mL). The combined extracts were dried over Na2SO4, filtered and concentrated in vacuo to give ethyl 7-bromo-4-chloroisoquinoline-3-carboxylate (61 mg, 0.19 mmol, 30% yield) as a white solid. MS (ESI) m/z: 313.9 [M+H]+; 1H NMR (500 MHz, DMSO-d6) δ 8.75 (s, 1H), 8.52 (s, 1H), 8.33 (d, J=8.8 Hz, 1H), 8.19 (dd, J=8.8, 1.9 Hz, 1H), 4.42 (q, J=7.1 Hz, 2H), 1.39 (t, J=7.2 Hz, 3H).

Step 3. Ethyl 7-bromo-1-methoxyisoquinoline-3-carboxylate

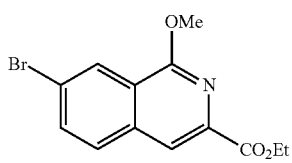 [SMILES: CCOC(=O)c1cc2ccc(Br)cc2c(OC)n1]

To a suspension of ethyl 7-bromo-1-chloroisoquinoline-3-carboxylate (0.13 g, 0.43 mmol) in MeOH (5 mL) at 0° C. was added sodium methoxide in MeOH (0.32 mL, 1.7 mmol) dropwise. The resulting mixture was stirred at room temperature for 3 h. Additional sodium methoxide in MeOH (0.32 mL, 1.7 mmol) was added and the mixture was stirred for another 2 h. The reaction mixture was cooled to 0° C., quenched with saturated aqueous NH4Cl (10 mL) and the resulting mixture was extracted with dichloromethane (4×30 mL). The combined organic extracts were dried over MgSO4, filtered and concentrated in vacuo. The residue was loaded onto an Isco solid load cartridge and purified by flash chromatography on SiO2 (8-25% EtOAc/hexanes) to give methyl 7-bromo-1-methoxyisoquinoline-3-carboxylate (80 mg, 0.27 mmol, 63% yield) as a white solid. MS (ESI) m/z: 295.9 [M+H]+.

Methyl 2-bromo-7-methylthiazolo[5,4-b]pyridine-5-carboxylate

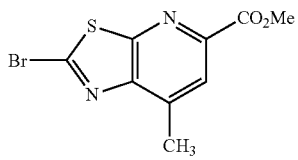

Step 1. 5-Chloro-7-methylthiazolo[5,4-b]pyridin-2-amine

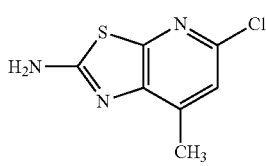

To a mixture of 2,6-dichloro-4-methylpyridin-3-amine (0.50 g, 2.8 mmol) and potassium thiocyanate (0.82 g, 8.5 mmol) in ethanol (7.5 mL) at room temperature was added concentrated hydrochloric acid (10.0 mL, 330 mmol) dropwise. The mixture was heated at 100° C. for 44 h. Additional potassium thiocyanate (0.82 g, 8.5 mmol) was added, and the mixture was heated at 100° C. for additional 31 h. The reaction mixture was cooled to room temperature and concentrated under vacuum to dryness. To the residue was added 1 N aqueous NaOH (10 mL) followed by solid $K_2CO_3$ until the mixture became basic (pH=9-10). The mixture was extracted with dichloromethane (4×40 mL). The combined organic extracts were dried over anhydrous $Na_2SO_4$, filtered and concentrated to dryness in vacuo. The residue was loaded onto an Isco solid load cartridge and purified by flash chromatography on $SiO_2$ (0-6% MeOH/DCM) to give 5-chloro-7-methylthiazolo[5,4-b]pyridin-2-amine (0.33 g, 1.7 mmol, 59% yield) as a tan solid. MS (ESI) m/z: 199.9 $[M+H]^+$; $^1H$ NMR (500 MHz, DMSO-$d_6$) δ 7.90 (s, 2H), 7.22 (s, 1H), 2.41 (s, 3H).

Step 2. tert-Butyl (5-chloro-7-methylthiazolo[5,4-b]pyridin-2-yl)carbamate

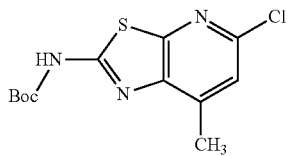 [SMILES: Cc1cc(Cl)nc2sc(NC(=O)OC(C)(C)C)nc12]

To a suspension of 5-chloro-7-methylthiazolo[5,4-b]pyridin-2-amine (0.33 g, 1.65 mmol) in dichloromethane (8 mL) at 0° C. was added di-tert-butyl dicarbonate (0.54 g, 2.5 mmol) in dichloromethane (2 mL), followed by DMAP (0.030 g, 0.25 mmol). The heterogeneous mixture was stirred at room temperature for 1 h giving a homogeneous solution. The solution was diluted with dichloromethane (120 mL), washed with water (2×25 mL) and brine (25 mL). The organic layer was dried over anhydrous $MgSO_4$, filtered and concentrated to dryness in vacuo. The residue was loaded onto an Isco solid load cartridge and purified by flash chromatography on $SiO_2$ (5-35% EtOAc/hexanes) to give tert-butyl (5-chloro-7-methylthiazolo[5,4-b]pyridin-2-yl)carbamate (0.40 g, 1.3 mmol, 82% yield) as a beige solid.

Step 3. Methyl 2-((tert-butoxycarbonyl)amino)-7-methylthiazolo[5,4-b]pyridine-5-carboxylate

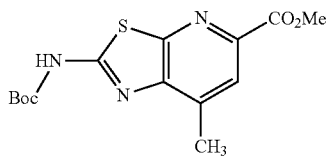 [SMILES: COC(=O)c1cc(C)c2nc(NC(=O)OC(C)(C)C)sc2n1]

A mixture of tert-butyl (5-chloro-7-methylthiazolo[5,4-b]pyridin-2-yl)carbamate (0.40 g, 1.3 mmol), methanol (15 mL, 1.3 mmol), 1,3-bis(diphenylphosphanyl)propane (0.067 g, 0.16 mmol), palladium(II) acetate (0.036 g, 0.16 mmol), and potassium carbonate (0.30 g, 2.2 mmol) was heated under CO (50 psi) in a pressure bottle at 90° C. for 16 h. The reaction mixture was cooled to room temperature, diluted with ethyl acetate (40 mL) and filtered through Celite. The filtrate was concentrated under vacuum to dryness. To the residue was added water (15 mL), and the resulting beige solid was collected by suction filtration. The solid was loaded onto an Isco solid load cartridge and purified by flash chromatography on $SiO_2$ (10-50% EtOAc/hexanes) to give methyl 2-((tert-butoxycarbonyl)amino)-7-methylthiazolo[5,4-b]pyridine-5-carboxylate (0.28 g, 0.86 mmol, 64% yield) as a beige solid. MS (ESI) m/z: 324.0 $[M+H]^+$.

Step 4. Methyl 2-amino-7-methylthiazolo[5,4-b]pyridine-5-carboxylate

To a suspension of methyl 2-((tert-butoxycarbonyl)amino)-7-methylthiazolo[5,4-b]pyridine-5-carboxylate (0.28 g, 0.86 mmol) in dichloromethane (6 mL) at 0° C. was added TFA (6 mL, 78 mmol) over 2 min. The resulting solution was stirred at room temperature for 1.5 h and concentrated under vacuum to dryness. To the residue was added saturated aqueous $NaHCO_3$ (10 mL) and the resulting precipitate was collected and dried under vacuum to give methyl 2-amino-7-methylthiazolo[5,4-b]pyridine-5-carboxylate (0.16 g, 0.73 mmol, 85% yield) as a beige solid. MS (ESI) m/z: 223.9 $[M+H]^+$; $^1H$ NMR (500 MHz, DMSO-$d_6$) δ 8.22 (s, 2H), 7.84 (s, 1H), 3.85 (s, 3H), 2.47 (s, 3H).

Step 5. Methyl 2-bromo-7-methylthiazolo[5,4-b]pyridine-5-carboxylate

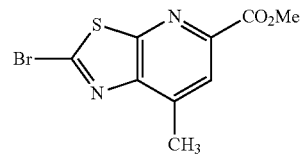

To a mixture of copper(II) bromide (0.20 g, 0.90 mmol) in acetonitrile (7 mL) at 0° C. was added tert-butyl nitrite (0.15 mL, 1.3 mmol) dropwise, followed by methyl 2-amino-7-methylthiazolo[5,4-b]pyridine-5-carboxylate (0.16 g, 0.72 mmol) portionwise. The reaction mixture was stirred at room temperature for 6 h, diluted with ethyl acetate (15 mL) and filtered through Celite. The filtrate was concentrated under vacuum. The residue was loaded onto an Isco solid load cartridge and purified by flash chromatography on $SiO_2$ (20-80% EtOAc/hexanes, Isco 40 g column)

to give methyl 2-bromo-7-methylthiazolo[5,4-b]pyridine-5-carboxylate (74 mg, 0.26 mmol, 36% yield) as a tan solid. (ESI) m/z: 286.8 [M+H]$^+$.

Methyl 2-bromo-7-methoxythiazolo[5,4-b]pyridine-5-carboxylate

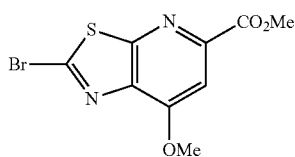 [SMILES: COC(=O)c1cc(OC)c2nc(Br)sc2n1]

Step 1. 5-Chloro-7-methoxythiazolo[5,4-b]pyridin-2-amine

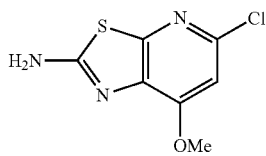 [SMILES: COc1cc(Cl)nc2sc(N)nc12]

To a mixture of 6-chloro-4-methoxypyridin-3-amine (0.50 g, 3.1 mmol) and potassium isothiocyanate (0.61 g, 6.3 mmol) in acetic acid (5 mL) at room temperature was added bromine (0.18 mL, 3.4 mmol) in acetic acid (2 mL) over 30 min. The mixture was stirred at room temperature for 16 h before additional potassium isothiocyanate (0.61 g, 6.3 mmol) and acetic acid (1 mL) were added. The mixture was stirred at room temperature for 24 h. To the mixture was added water (100 mL) and the mixture was stirred for 2 h. The insoluble material was collected by suction filtration and the filter cake was suspended in water (100 mL) and stirred for 2 h. The solid was collected by suction filtration and dried under vacuum at 50° C. to give 5-chloro-7-methoxythiazolo[5,4-b]pyridin-2-amine (0.70 g, 3.1 mmol, 100% yield) as a tan solid. MS (ESI) m/z: 215.9 [M+H]$^+$; 1H NMR (500 MHz, DMSO-d$_6$) δ 7.74 (br s, 2H), 7.02 (s, 1H), 3.94 (s, 3H).

Step 2. 5-Chloro-2-bis(Boc)amino-7-methoxythiazolo[5,4-b]pyridine

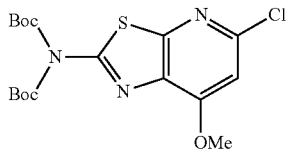 [SMILES: COc1cc(Cl)nc2sc(N(C(=O)OC(C)(C)C)C(=O)OC(C)(C)C)nc12]

To a suspension of 5-chloro-7-methoxythiazolo[5,4-b]pyridin-2-amine (0.70 g, 3.1 mmol) in dichloromethane (15 mL) at 0° C. was added di-tert-butyl dicarbonate (2.0 g, 9.4 mmol) in dichloromethane (5 mL), followed by DMAP (0.076 g, 0.62 mmol). The heterogeneous mixture was heated at reflux for 2 h. The mixture was diluted with dichloromethane (250 mL) and washed with water (40 mL). The aqueous layer was extracted with dichloromethane (2×30 mL). The combined organic phase was dried over anhydrous Na$_2$SO$_4$, filtered and concentrated to dryness in vacuo. The residue was loaded onto an Isco solid load cartridge and purified by flash chromatography on SiO$_2$ (10-30% EtOAc/hexanes, Isco 40 g column) to give 5-chloro-2-bis(Boc)amino-7-methoxythiazolo[5,4-b]pyridine (0.54 g, 1.3 mmol, 42% yield) as a white solid. MS (ESI) m/z: 416.1 [M+H]$^+$; $^1$H NMR (500 MHz, DMSO-d$_6$) δ 7.27 (s, 1H), 4.05 (s, 3H), 1.55 (s, 18H).

Step 3. Methyl 2-((tert-butoxycarbonyl)amino)-7-methoxythiazolo[5,4-b]pyridine-5-carboxylate

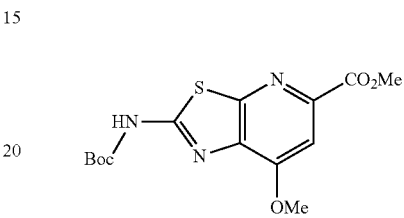

A mixture of 5-chloro-2-bis(Boc)amino-7-methoxythiazolo[5,4-b]pyridine (0.54 g, 1.3 mmol), methanol (11 mL, 1.3 mmol), 1,3-bis(diphenylphosphanyl)propane (0.080 g, 0.20 mmol), palladium(II) acetate (0.044 g, 0.20 mmol), and potassium carbonate (0.32 g, 2.3 mmol) in DMF (3.5 mL) was heated under CO (50 psi) in a pressure bottle at 90° C. for 7 h. The mixture was diluted with ethyl acetate (30 mL), filtered through Celite and concentrated under vacuum to dryness. To the residue was added water (20 mL), and the mixture was extracted with dichloromethane (4×40 mL). The combined extracts were washed with water (3×25 mL), dried over anhydrous Na$_2$SO$_4$, filtered and concentrated to dryness in vacuo. The residue was loaded onto an Isco solid load cartridge and purified by flash chromatography on SiO$_2$ (30-80% EtOAc/hexanes, Isco 40 g column) to give methyl 2-((tert-butoxycarbonyl)amino)-7-methoxythiazolo[5,4-b]pyridine-5-carboxylate (0.20 g, 0.58 mmol, 44% yield). MS (ESI) m/z: 340.0 [M+H]$^+$; $^1$H NMR (500 MHz, DMSO-d$_6$) δ 12.16 (s, 1H), 7.68 (s, 1H), 4.06 (s, 3H), 3.91 (s, 3H), 1.53 (s, 9H).

Step 4. Methyl 2-amino-7-methoxythiazolo[5,4-b]pyridine-5-carboxylate

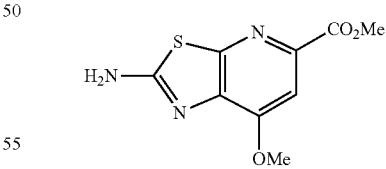

To a suspension of methyl 2-((tert-butoxycarbonyl)amino)-7-methoxythiazolo[5,4-b]pyridine-5-carboxylate (0.26 g, 0.76 mmol) in dichloromethane (5 mL) at 0° C. was added TFA (5 mL, 65 mmol) over 2 min. The resulting solution was stirred for 1.5 h and then concentrated under vacuum to dryness. To the residue was added saturated NaHCO$_3$ solution (10 mL). The resulting solid was collected and dried at 50° C. under vacuum to give methyl 2-amino-7-methoxythiazolo[5,4-b]pyridine-5-carboxylate (0.160 g, 0.669 mmol, 88% yield) as a beige solid. MS (ESI) m/z:

240.0 [M+H]⁺; ¹H NMR (500 MHz, DMSO-d₆) δ 8.05 (s, 2H), 7.57 (s, 1H), 3.98 (s, 3H), 3.86 (s, 3H).

Step 5. Methyl 2-bromo-7-methoxythiazolo[5,4-b]pyridine-5-carboxylate

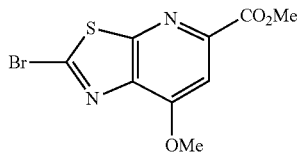 [SMILES: COC(=O)c1cc(OC)c2nc(Br)sc2n1]

To a mixture of copper(II) bromide (0.18 g, 0.82 mmol) in acetonitrile (6 mL) at 0° C. was added tert-butyl nitrite (0.16 mL, 1.3 mmol) dropwise, followed by methyl 2-amino-7-methoxythiazolo[5,4-b]pyridine-5-carboxylate (0.16 g, 0.66 mmol) portionwise. The mixture was stirred at 0° C. for 1 h and then at room temperature for 4 h. The yellow insoluble material was collected as the first crop of product (0.17 g) by suction filtration. The filtrate was diluted with dichloromethane (50 mL), washed with water (2×15 mL), dried over anhydrous Na₂SO₄, filtered and concentrated under vacuum. The residue was loaded onto an Isco solid load cartridge and purified by flash chromatography on SiO₂ (10-40% EtOAc/hexanes, Isco 40 g column) give a second crop of methyl 2-bromo-7-methoxythiazolo[5,4-b]pyridine-5-carboxylate (67 mg) as a pale solid. MS (ESI) m/z: 302.9 [M+H]⁺; ¹H NMR (500 MHz, DMSO-d₆) δ 7.78 (br s, 1H), 4.13 (s, 3H), 3.93 (s, 3H).

Methyl 2-bromothiazolo[5,4-b]pyridine-5-carboxylate

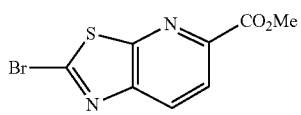 [SMILES: COC(=O)c1ccc2nc(Br)sc2n1]

Step 1. tert-Butyl (5-chlorothiazolo[5,4-b]pyridin-2-yl)carbamate

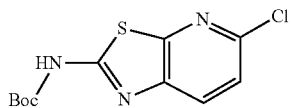 [SMILES: CC(C)(C)OC(=O)Nc1nc2ccc(Cl)nc2s1]

To a suspension of 5-chlorothiazolo[5,4-b]pyridin-2-amine (0.53 g, 2.8 mmol) in dichloromethane (10 mL) at 0° C. was added di-tert-butyl dicarbonate (0.93 g, 4.3 mmol) followed by DMAP (0.069 g, 0.57 mmol). The heterogeneous mixture was stirred at room temperature for 3.5 h and then concentrated under vacuum to dryness. To the residue was added hexane (10 mL) and the resulting solid was collected by suction filtration to give, tert-butyl (5-chlorothiazolo[5,4-b]pyridin-2-yl)carbamate (0.58 g, 2.0 mmol, 71% yield), as a white solid.

Step 2. Methyl 2-((tert-butoxycarbonyl)amino)thiazolo[5,4-b]pyridine-5-carboxylate

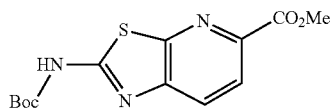 [SMILES: COC(=O)c1ccc2nc(NC(=O)OC(C)(C)C)sc2n1]

A mixture of tert-butyl (5-chlorothiazolo[5,4-b]pyridin-2-yl)carbamate (0.30 g, 1.0 mmol), 1,3-bis(diphenylphosphanyl)propane (0.052 g, 0.13 mmol), palladium(II) acetate (0.028 g, 0.13 mmol), and potassium carbonate (0.23 g, 1.7 mmol) in methanol (5 mL) and DMF (2.5 mL) was heated under CO (48 psi) in a pressure bottle at 85° C. for 7.5 h. The mixture was diluted with ethyl acetate (30 mL) and filtered through Celite. The filtrate was concentrated under vacuum to dryness. The residue was dissolved in ethyl acetate (100 mL) and washed with water (20 mL). The aqueous layer was separated and the desired product crystallized from the aqueous layer. The solid was collected by suction filtration to give a first crop of methyl 2-((tert-butoxycarbonyl)amino)thiazolo[5,4-b]pyridine-5-carboxylate (126 mg, 39%) as a white solid. The organic layer was dried over anhydrous Na₂SO₄, filtered, and concentrated under vacuum. The residue was purified by flash chromatograph on SiO₂ (20-80% ethyl EtOAc/hexanes, Isco 40 g column) to give a second crop of methyl 2-((tert-butoxycarbonyl)amino)thiazolo[5,4-b]pyridine-5-carboxylate (0.090 g, 28%). MS (ESI) m/z: 310.0 [M+H]⁺; ¹H NMR (500 MHz, DMSO-d₆) δ 12.25 (br s, 1H), 8.29-8.00 (m, 2H), 3.91 (s, 3H), 1.54 (s, 9H).

Step 3. Methyl 2-aminothiazolo[5,4-b]pyridine-5-carboxylate

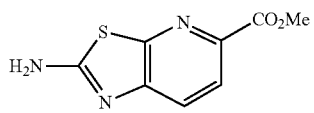 [SMILES: COC(=O)c1ccc2nc(N)sc2n1]

To a suspension of methyl 2-((tert-butoxycarbonyl)amino)thiazolo[5,4-b]pyridine-5-carboxylate (0.212 g, 0.685 mmol) in dichloromethane (5 mL) at 0° C. was added TFA (5 mL, 64.9 mmol) over 2 min. The resulting solution was stirred at room temperature for 1 h and then concentrated under vacuum to dryness. To the residue was added saturated NaHCO₃ solution (7 mL) and the resulting solid was collected by suction filtration and dried in vacuo at 50° C. to give methyl 2-aminothiazolo[5,4-b]pyridine-5-carboxylate (0.128 g, 0.612 mmol, 89% yield), as a white solid. MS (ESI) m/z: 209.9 [M+H]⁺.

Step 4. Methyl 2-bromothiazolo[5,4-b]pyridine-5-carboxylate

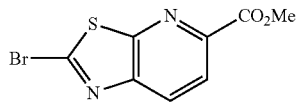 [SMILES: COC(=O)c1ccc2nc(Br)sc2n1]

To copper(II) bromide (0.17 g, 0.76 mmol) in acetonitrile (6 mL) at 0° C. was added tert-butyl nitrite (0.13 mL, 1.1 mmol) followed by methyl 2-aminothiazolo[5,4-b]pyridine-5-carboxylate (128 mg, 0.61 mmol). The mixture was stirred at room temperature for 18 h. Additional copper (II) bromide (0.17 g, 0.76 mmol) and tert-butyl nitrite (0.13 mL, 1.1 mmol) were added, and the mixture was stirred at room temperature for 4 h. A third portion of tert-butyl nitrite (0.065 mL, 0.55 mmol) was added and the mixture was stirred at room temperature for 4 h. Another portion of tert-butyl nitrite (0.060 mL, 0.54 mmol) was added and the mixture was stirred at room temperature for 2 h. The mixture was diluted with ethyl acetate (25 mL) and filtered through Celite. The filtrate was concentrated under vacuum and the residue was purified by flash chromatograph on SiO$_2$ (20-80% EtOAc/hexanes, Isco 40 g column) to give methyl 2-bromothiazolo[5,4-b]pyridine-5-carboxylate (90 mg, 0.33 mmol, 54% yield) as a beige solid. MS (ESI) m/z: 272.8 [M+H]$^+$; $^1$H NMR (500 MHz, DMSO-d$_6$) δ 8.59 (d, J=8.5 Hz, 1H), 8.25 (d, J=8.5 Hz, 1H), 3.94 (s, 3H).

Methyl 6-bromo-4-cyclopropoxyquinoline-2-carboxylate

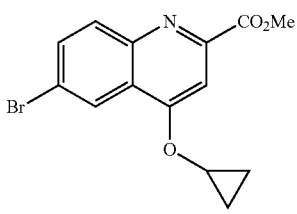 [SMILES: COC(=O)c1cc(OC2CC2)c2cc(Br)ccc2n1]

Step 1. 6-Bromo-4-cyclopropoxyquinoline

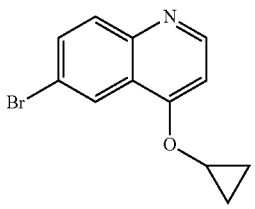 [SMILES: Brc1ccc2nccc(OC3CC3)c2c1]

To 6-bromoquinolin-4-ol (0.63 g, 2.8 mmol), KI (0.23 g, 1.4 mmol) and Cs$_2$CO$_3$ (1.6 g, 5.0 mmol) in DMF (7.0 mL) was added bromocyclopropane (0.42 mL, 5.6 mmol), the reaction flask was sealed and heated under microwave irradiation at 180° C. for 5 h. The reaction mixture was diluted with water, extracted with ethyl acetate (3×60 mL), the extracts were combined and concentrated to dryness in vacuo. The residue was purified by flash chromatography (40 g silica gel column, solid loading, 0-60% EtOAc/hexanes) to give 6-bromo-4-cyclopropoxyquinoline (0.31 g, 1.2 mmol, 42% yield) as an tan solid. MS (ESI) m/z: 264.0 [M+H]$^+$; $^1$H NMR (400 MHz, CDCl$_3$) δ 8.76 (d, J=5.06 Hz, 1H), 8.27 (d, J=2.20 Hz, 1H), 7.89 (d, J=9.02 Hz, 1H), 7.74 (dd, J=2.31, 8.91 Hz, 1H), 7.12 (d, J=5.06 Hz, 1H), 3.94-3.99 (m, 1H), 0.91-0.97 (m, 4H).

Step 2. 6-Bromo-4-cyclopropoxyquinoline 1-oxide

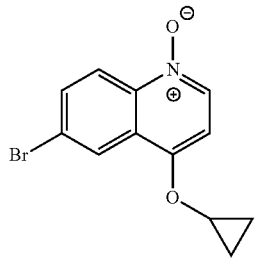 [SMILES: [O-][n+]1ccc(OC2CC2)c2cc(Br)ccc21]

To 6-bromo-4-cyclopropoxyquinoline (0.31 g, 1.2 mmol) in CH$_2$Cl$_2$ (8 mL) was added 3-chloroperoxybenzoic acid (0.47 g, 2.1 mmol), the resulting solution was stirred at room temperature overnight. The solid was removed via suction filtration and the filtrate was concentrated to dryness in vacuo. The residue was purified by flash chromatography (24 g silica gel column, 0-10% MeOH/CH$_2$Cl$_2$) to give 6-bromo-4-cyclopropoxyquinoline 1-oxide (0.32 g, 1.2 mmol, 98% yield) as an off-white solid. MS (ESI) m/z: 280.0 [M+H]$^+$; $^1$H NMR (400 MHz, CDCl$_3$) δ 8.57-8.64 (m, 1H), 8.41-8.50 (m, 1H), 8.28 (d, J=1.98 Hz, 1H), 7.85 (dd, J=2.20, 9.24 Hz, 1H), 7.01-7.06 (m, 1H), 3.93-3.99 (m, 1H), 0.92-0.99 (m, 4H).

Step 3. 6-Bromo-4-cyclopropoxyquinoline-2-carbonitrile

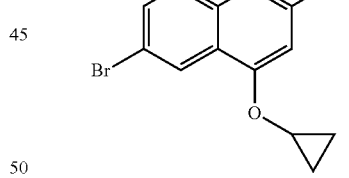

A solution of 6-bromo-4-cyclopropoxyquinoline 1-oxide (0.32 g, 1.2 mmol) in acetonitrile (2.2 mL) was added to a solution of KCN (0.15 g, 2.3 mmol) in MeOH (1.1 mL), stirred for 15 min, followed by dropwise addition of benzoyl chloride (0.27 mL, 2.3 mmol). The resulting mixture was stirred at room temperature overnight. The reaction mixture was concentrated to dryness in vacuo, and the crude solid was purified by flash chromatography (40 g silica gel column, solid loading, 0-20% EtOAc/hexanes) to give 6-bromo-4-cyclopropoxyquinoline-2-carbonitrile (0.27 g, 0.93 mmol, 80% yield) as an off white solid. MS (ESI) m/z: 289.1 [M+H]$^+$; $^1$H NMR (500 MHz, Chloroform-d) δ 8.29 (d, J=1.93 Hz, 1H), 7.93 (d, J=9.08 Hz, 1H), 7.85 (dd, J=2.20, 9.08 Hz, 1H), 7.43 (s, 1H), 4.00-4.05 (m, 1H), 1.01-1.05 (m, 2H), 0.98 (dd, J=1.79, 3.16 Hz, 2H).

Step 4.
6-Bromo-4-cyclopropoxyquinoline-2-carboxylic acid

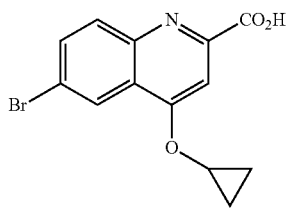 [SMILES: O=C(O)c1cc(OC2CC2)c2cc(Br)ccc2n1]

To 6-bromo-4-cyclopropoxyquinoline-2-carbonitrile (0.3 g, 1.0 mmol) in 2-propanol (10 mL) was added KOH (6M) (0.85 m, 5.1 mmol). The reaction mixture was heated at 80° C. overnight. The reaction mixture was cooled to room temperature and water (20 mL) and ethyl acetate (50 mL) were added. The precipitating product, 6-bromo-4-cyclopropoxyquinoline-2-carboxylic acid (0.26 g, 0.83 mmol, 81% yield) was collected as a white solid. MS (ESI) m/z: 308.0 [M+H]$^+$; $^1$H NMR (500 MHz, Methanol-d$_4$) δ 8.19-8.23 (m, 1H), 7.98 (d, J=9.08 Hz, 1H), 7.90 (s, 1H), 7.79 (dd, J=2.06, 8.94 Hz, 1H), 4.12-4.17 (m, 1H), 0.99 (br d, J=6.05 Hz, 2H), 0.91 (br s, 2H).

Step 5. Methyl 6-bromo-4-cyclopropoxyquinoline-2-carboxylate

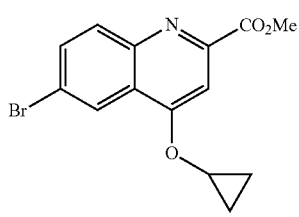 [SMILES: COC(=O)c1cc(OC2CC2)c2cc(Br)ccc2n1]

To 6-bromo-4-cyclopropoxyquinoline-2-carboxylic acid (0.36 g, 1.2 mmol) and K$_2$CO$_3$ (0.32 g, 2.3 mmol) in DMF (7 mL) was added iodomethane (1.8 mL, 3.5 mmol). The reaction mixture was stirred at room temperature for 15 min. The reaction mixture was diluted with ethyl acetate, and washed with saturated aqueous NH$_4$Cl and brine solution. The organic layer was dried over anhydrous MgSO$_4$ and concentrated under vacuum. The residue was purified by flash chromatography (40 g silica gel column, 0-30% EtOAc/hexanes) to afford methyl 6-bromo-4-cyclopropoxyquinoline-2-carboxylate (252 mg, 0.782 mmol, 67.0% yield) as an off-white solid. MS (ESI) m/z: 322.0 [M+H]$^+$; $^1$H NMR (500 MHz, CDCl$_3$) δ 8.27 (d, J=2.20 Hz, 1H), 8.05 (d, J=9.08 Hz, 1H), 7.90 (s, 1H), 7.79 (dd, J=2.20, 9.08 Hz, 1H), 4.07 (s, 3H), 4.02-4.06 (m, 1H), 0.98 (s, 2H), 0.94 (br s, 2H).

Methyl 6-bromo-4-(methoxymethyl)quinoline-2-carboxylate

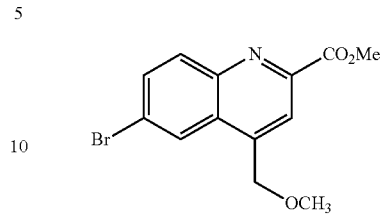

Step 1. Methyl 6-bromo-4-cyclopropoxyquinoline-2-carboxylate

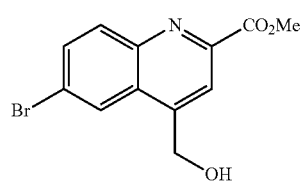 [SMILES: COC(=O)c1cc(CO)c2cc(Br)ccc2n1]

To a mixture of methyl 6-bromoquinoline-2-carboxylate (0.52 g, 2.0 mmol), iron(II) sulfate heptahydrate (0.16 g, 0.59 mmol) and iron (0.11 g, 2.0 mmol) in MeOH (3 mL) and H$_2$O (2 mL) at 0° C. was added H2SO$_4$ (0.10 mL, 2.0 mmol), followed by dropwise addition of H$_2$O$_2$ (50%) (0.40 mL, 11.7 mmol). The reaction mixture was allowed to warm to room temperature and stirred for 4 h. The mixture was diluted with water, basified with NH$_4$OH, and extracted with EtOAc (2×100 mL). The combined extracts were washed with brine, dried over anhydrous MgSO$_4$ and concentrated in vacuo. The residue was purified by flash chromatography (40 g silica gel column, 0-100% EtOAc/hexanes) to afford methyl 6-bromo-4-(hydroxymethyl)quinoline-2-carboxylate (0.29 g, 0.97 mmol, 49% yield) as a tan solid. MS (ESI) m/z: 296.0 [M+H]$^+$; $^1$H NMR (400 MHz, CDCl$_3$) δ 8.30-8.35 (m, 1H), 8.19 (dd, J=3.19, 5.39 Hz, 2H), 7.86 (dd, J=2.09, 9.13 Hz, 1H), 5.22 (s, 2H), 4.09 (s, 3H).

Step 2. Methyl 6-bromo-4-cyclopropoxyquinoline-2-carboxylate

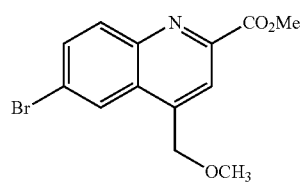 [SMILES: COCc1cc(C(=O)OC)nc2ccc(Br)cc12]

To methyl 6-bromo-4-(hydroxymethyl)quinoline-2-carboxylate (0.29 g, 0.97 mmol) in DMF (6.4 mL) was added NaH (60% in mineral oil) (0.08 g, 1.9 mmol) portionwise.

The reaction mixture was stirred at room temperature for 30 min, followed by addition of iodomethane (0.18 mL, 2.9 mmol). The reaction mixture was stirred at room temperature for 5 h and then diluted with ethyl acetate (50 mL), washed with water and brine, dried over anhydrous MgSO₄, filtered and concentrated under vacuum. The residue was purified by flash chromatography (24 g silica gel, 0-30% EtOAc/hexanes) to give methyl 6-bromo-4-(methoxymethyl)quinoline-2-carboxylate (71 mg, 0.23 mmol, 24% yield) as a light yellow solid. MS (ESI) m/z: 310.0 [M+H]⁺; ¹H NMR (400 MHz, CDCl₃) δ 8.25-8.27 (m, 1H), 8.17-8.22 (m, 2H), 7.86 (dd, J=2.20, 9.02 Hz, 1H), 4.92 (d, J=0.88 Hz, 2H), 4.09 (s, 3H), 3.54 (s, 3H).

Methyl 3-(6-chloropyridin-3-yl)-5-(trifluoromethyl)benzoate

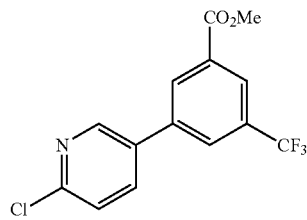 [SMILES: COC(=O)c1cc(-c2ccc(Cl)nc2)cc(C(F)(F)F)c1]

A mixture of (6-chloropyridin-3-yl)boronic acid (0.14 g, 0.89 mmol), methyl 3-bromo-5-(trifluoromethyl)benzoate (0.24 g, 0.85 mmol) and potassium phosphate tribasic (2M aqueous solution) (0.85 mL, 1.7 mmol) in dioxane (3.5 mL) was added PdCl₂(dppf)-CH₂Cl₂ adduct (41.5 mg, 0.051 mmol), the reaction was degassed and heated at 75° C. overnight. The organic layer was separated and concentrated. The residue was purified by flash chromatography (12 g silica gel, 0-30% ethyl acetate/hexanes) to afford methyl 3-(6-chloropyridin-3-yl)-5-(trifluoromethyl)benzoate (0.22 g, 0.70 mmol, 82% yield) as a white solid. MS (ESI) m/z: 316.0 [M+H]⁺; ¹H NMR (500 MHz, CDCl₃) δ 8.65 (d, J=2.75 Hz, 1H), 8.41 (s, 1H), 8.34 (s, 1H), 7.97 (s, 1H), 7.91 (dd, J=2.48, 8.25 Hz, 1H), 7.47 (d, J=8.25 Hz, 1H), 4.00 (s, 3H).

Methyl 3-(6-chloropyridin-3-yl)-5-fluorobenzoate

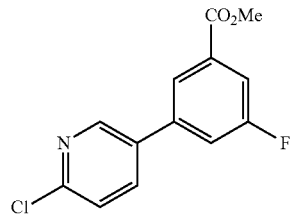 [SMILES: COC(=O)c1cc(F)cc(-c2ccc(Cl)nc2)c1]

Methyl 3-(6-chloropyridin-3-yl)-5-fluorobenzoate was prepared following the procedure described for the preparation of methyl 3-(6-chloropyridin-3-yl)-5-(trifluoromethyl)benzoate with replacement of methyl 3-bromo-5-(trifluoromethyl)benzoate with methyl 3-bromo-5-fluorobenzoate (76% yield). MS (ESI) m/z: 265.9 [M+H]⁺; ¹H NMR (400 MHz, CDCl₃) δ 8.65-8.61 (m, 1H), 8.04 (t, J=1.4 Hz, 1H), 7.87 (dd, J=8.3, 2.5 Hz, 1H), 7.82-7.73 (m, 1H), 7.49-7.42 (m, 2H), 3.98 (s, 3H).

Methyl 3-(5-chloropyridin-2-yl)-5-(trifluoromethyl)benzoate

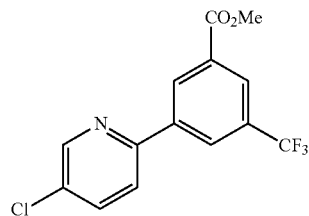

Methyl 3-(5-chloropyridin-2-yl)-5-(trifluoromethyl)benzoate was prepared following the procedure described for the preparation of methyl 3-(6-chloropyridin-3-yl)-5-(trifluoromethyl)benzoate with replacement of (6-chloropyridin-3-yl)boronic acid with (5-chloropyridin-2-yl)boronic acid (11% yield). MS (ESI) m/z: 315.9 [M+H]⁺; ¹H NMR (500 MHz, Chloroform-d) δ 8.79 (s, 1H), 8.69 (t, J=1.5 Hz, 1H), 8.51 (s, 1H), 8.35 (s, 1H), 7.80 (d, J=1.7 Hz, 2H), 4.03-3.99 (m, 3H).

TABLE 1

| Ex. No. | Structure | LCMS, FXR EC₅₀ (nM) & NMR | Method |
|---|---|---|---|
| 1 | 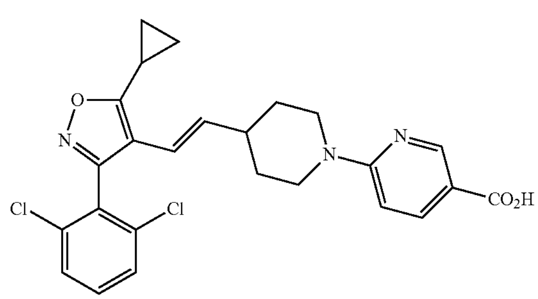 | MS (ESI) m/z: 484.3 [M + H]⁺; EC₅₀ = 14; ¹H NMR (500 MHz, DMSO-d₆) δ 8.57 (d, J = 2.3 Hz, 1H), 7.88 (dd, J = 2.4, 9.1 Hz, 1H), 7.64 (d, J = 8.0 Hz, 2H), 7.57 (dd, J = 7.0, 9.0 Hz, 1H), 6.79 (d, J = 9.2 Hz, 1H), 6.15 (d, J = 16.3 Hz, 1H), 5.30 (dd, J = 7.0, 16.2 Hz, 1H), 4.28 (d, J = 13.3 Hz, 2H), 2.93 (t, J = 12.4 Hz, 2H), 2.33 (dq, J = 4.3, 5.0, 8.5 Hz, 1H), 1.60 (d, J = 12.9 Hz, 2H), 1.23-0.99 (m, 6H). | A1 |

TABLE 1-continued

| Ex. No. | Structure | LCMS, FXR EC$_{50}$ (nM) & NMR | Method |
|---|---|---|---|
| 2 | 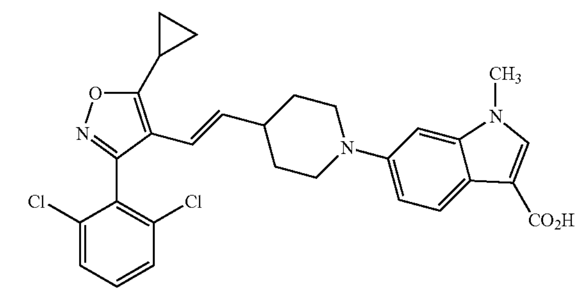 [SMILES: Cn1cc(C(=O)O)c2ccc(N3CCC(/C=C/c4c(-c5c(Cl)cccc5Cl)noc4C4CC4)CC3)cc21] | MS (ESI) m/z: 536.1 [M + H]$^+$; EC$_{50}$ = 5; $^1$H NMR (500 MHz, DMSO-d$_6$) δ 7.84-7.76 (m, 2H), 7.68 (d, J = 8.0 Hz, 2H), 7.60 (dd, J = 7.1, 9.1 Hz, 1H), 6.97-6.85 (m, 2H), 6.20 (d, J = 16.2 Hz, 1H), 5.37 (dd, J = 7.0, 16.2 Hz, 1H), 3.76 (s, 3H), 3.56 (d, J = 12.0 Hz, 2H), 2.68 (t, J = 11.5 Hz, 2H), 2.37 (q, J = 3.4, 5.5 Hz, 1H), 2.15 (br s, 1H), 1.67 (d, J = 12.7 Hz, 2H), 1.39-0.97 (m, 6H). | A2 |
| 3 | 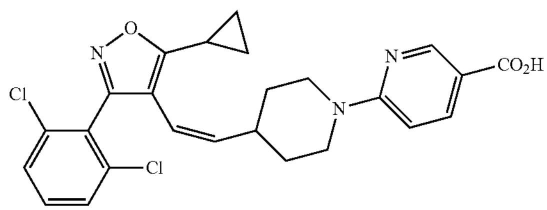 [SMILES: O=C(O)c1ccc(N2CCC(/C=C\c3c(-c4c(Cl)cccc4Cl)noc3C3CC3)CC2)nc1] | MS (ESI) m/z: 484.3 [M + H]$^+$; EC$_{50}$ = 107; $^1$H NMR (500 MHz, DMSO-d6) δ 8.57 (d, J = 2.4 Hz, 1H), 7.88 (dd, J = 2.4, 9.2 Hz, 1H), 7.65 (d, J = 8.1 Hz, 2H), 7.57 (dd, J = 7.3, 9.0 Hz, 1H), 6.80 (d, J = 9.2 Hz, 1H), 5.87 (d, J = 11.1 Hz, 1H), 5.55 (t, J = 10.8 Hz, 1H), 4.34 (d, J = 13.3 Hz, 2H), 2.76 (q, J = 9.3, 11.8 Hz, 2H), 2.34 (d, J = 9.9 Hz, 1H), 2.09 (td, J = 5.6, 9.9, 11.2 Hz, 1H), 1.28-1.00 (m, 8H). | A1 |
| 4 | 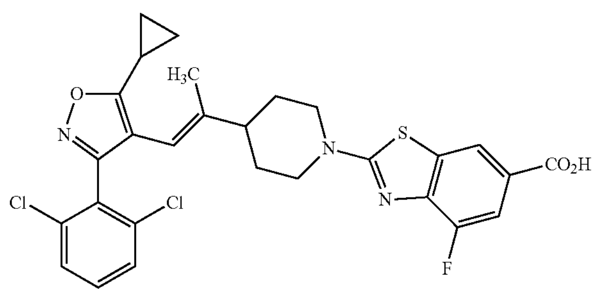 [SMILES: C/C(=C\c1c(-c2c(Cl)cccc2Cl)noc1C1CC1)C1CCN(c2nc3c(F)cc(C(=O)O)cc3s2)CC1] | MS (ESI) m/z: 572.3 [M + H]$^+$; EC$_{50}$ = 2055; $^1$H NMR (500 MHz, DMSO-d$_6$) δ 8.24-8.06 (m, 1H), 7.61-7.59 (m, 1H), 7.59-7.56 (m, 2H), 7.55-7.50 (m, 1H), 5.67 (s, 1H), 4.08 (br d, J = 10.6 Hz, 2H), 3.23 (br s, 2H), 2.35-2.26 (m, 1H), 2.04-1.95 (m, 1H), 1.70 (br d, J = 12.6 Hz, 2H), 1.54 (s, 3H), 1.51-1.41 (m, 2H), 1.15-1.09 (m, 2H), 1.07-1.02 (m, 2H). | A1 |
| 5 | 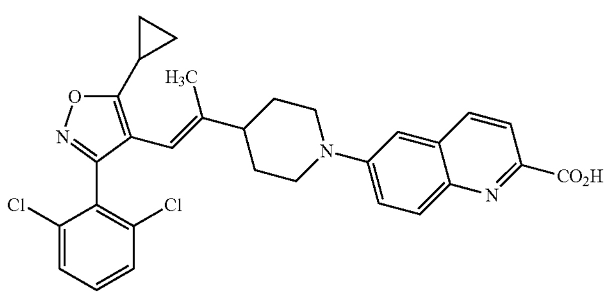 [SMILES: C/C(=C\c1c(-c2c(Cl)cccc2Cl)noc1C1CC1)C1CCN(c2ccc3nc(C(=O)O)ccc3c2)CC1] | MS (ESI) m/z: 548.4 [M + H]$^+$; EC$_{50}$ = 1250; $^1$H NMR (500 MHz, DMSO-d$_6$) δ 7.66-7.48 (m, 5H), 7.25-6.93 (m, 3H), 5.62-5.58 (m, 1H), 4.36-4.14 (m, 2H), 4.03-3.85 (m, 2H), 2.56 (br s, 2H), 2.19-2.11 (m, 1H), 2.00-1.96 (m, 1H), 1.59-1.54 (m, 2H), 1.50 (br s, 3H), 1.11 (br d, J = 5.5 Hz, 2H), 1.03 (br d, J = 1.3 Hz, 2H). | A2 |
| 6 | 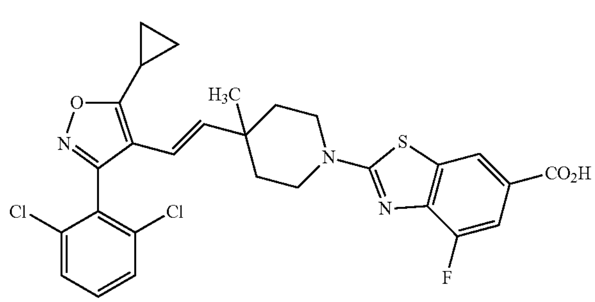 [SMILES: CC1(/C=C/c2c(-c3c(Cl)cccc3Cl)noc2C2CC2)CCN(c2nc3c(F)cc(C(=O)O)cc3s2)CC1] | MS (ESI) m/z: 572.0 [M + H]$^+$; EC$_{50}$ = 536; $^1$H NMR (500 MHz, DMSO-d$_6$) δ 8.19 (br s, 1H), 7.65 (s, 1H), 7.64 (s, 1H), 7.61-7.52 (m, 2H), 6.27 (d, J = 16.8 Hz, 1H), 5.32 (d, J = 16.8 Hz, 1H), 3.74-3.56 (m, 1H), 3.29-3.20 (m, 1H), 3.16 (s, 1H), 2.45-2.35 (m, 1H), 1.56-1.50 (m, 2H), 1.49-1.41 (m, 2H), 1.22 (s, 1H), 1.19-1.14 (m, 2H), 1.09 (br d, J = 3.1 Hz, 2H), 0.97 (s, 3H). | A1 |

TABLE 1-continued

| Ex. No. | Structure | LCMS, FXR EC$_{50}$ (nM) & NMR | Method |
|---|---|---|---|
| 7 | 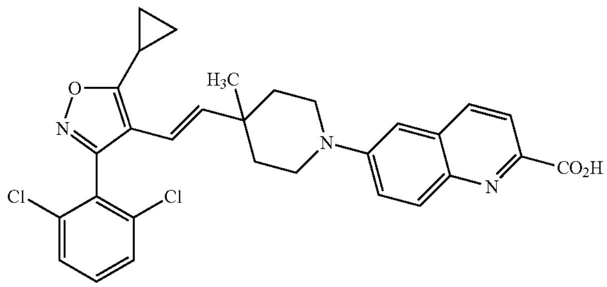 [SMILES: CC1(/C=C/c2c(-c3c(Cl)cccc3Cl)noc2C2CC2)CCN(c2ccc3nc(C(=O)O)ccc3c2)CC1] | MS (ESI) m/z: 548.0 [M + H]$^+$; EC$_{50}$ = 227; $^1$H NMR (500 MHz, DMSO-d$_6$) δ 8.24 (br d, J = 8.5 Hz, 1H), 7.97 (d, J = 8.5 Hz, 1H), 7.93 (br d, J = 9.5 Hz, 1H), 7.65 (br d, J = 7.3 Hz, 1H), 7.61 (s, 1H), 7.59 (s, 1H), 7.53-7.45 (m, 1H), 7.15 (br d, J = 2.1 Hz, 1H), 6.30-6.29 (m, 1H), 6.26 (d, J = 16.5 Hz, 1H), 5.38 (d, J = 16.8 Hz, 1H), 2.94 (br t, J = 8.9 Hz, 2H), 2.44-2.34 (m, 1H), 1.58-1.41 (m, 4H), 1.23 (s, 2H), 1.16 (br d, J = 7.9 Hz, 2H), 1.09 (br d, J = 2.4 Hz, 2H), 0.99 (s, 3H). | A2 |
| 8 | 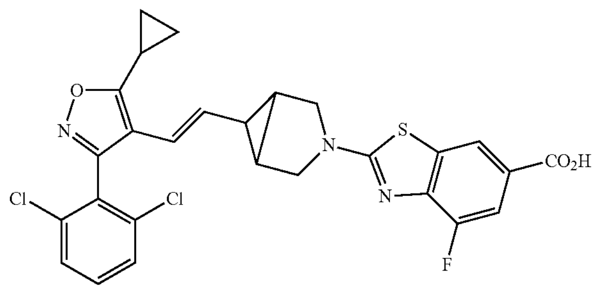 [SMILES: O=C(O)c1cc(F)c2nc(N3CC4C(/C=C/c5c(-c6c(Cl)cccc6Cl)noc5C5CC5)C4C3)sc2c1] | MS (ESI) m/z: 556.2 [M + H]$^+$; EC$_{50}$ = 120; $^1$H NMR (500 MHz, DMSO-d$_6$) δ 8.21 (d, J = 1.4 Hz, 1H), 7.66 (d, J = 1.4 Hz, 1H), 7.65 (s, 1H), 7.60 (d, J = 6.9 Hz, 1H), 7.58 (d, J = 7.2 Hz, 1H), 6.13 (d, J = 16.0 Hz, 1H), 5.19 (dd, J = 16.2, 8.8 Hz, 1H), 3.80-3.63 (m, 4H), 2.38-2.30 (m, 1H), 1.75 (br s, 2H), 1.47-1.37 (m, 1H), 1.20-1.12 (m, 2H), 1.11-1.03 (m, 2H). | A1 |
| 9 | 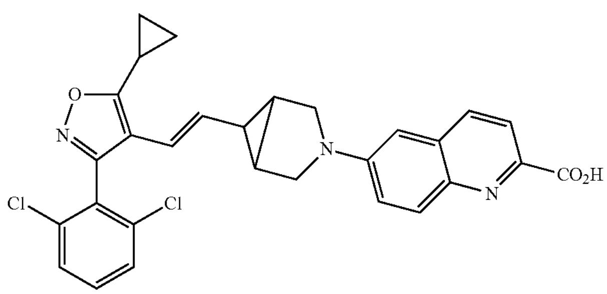 [SMILES: O=C(O)c1ccc2cc(N3CC4C(/C=C/c5c(-c6c(Cl)cccc6Cl)noc5C5CC5)C4C3)ccc2n1] | MS (ESI) m/z: 531.9 [M + H]$^+$; EC$_{50}$ = 39; $^1$H NMR (500 MHz, DMSO-d$_6$) δ 8.13 (d, J = 8.5 Hz, 1H), 7.92 (d, J = 3.6 Hz, 1H), 7.90 (d, J = 4.1 Hz, 1H), 7.67 (d, J = 1.4 Hz, 1H), 7.66 (s, 1H), 7.62-7.57 (m, 1H), 7.32 (dd, J = 9.4, 2.5 Hz, 1H), 6.78 (d, J = 2.5 Hz, 1H), 6.15 (d, J = 16.2 Hz, 1H), 5.16 (dd, J = 16.1, 8.9 Hz, 1H), 3.69 (d, J = 9.9 Hz, 2H), 3.58-3.53 (m, 2H), 3.16 (br d, J = 5.5 Hz, 2H), 2.38-2.32 (m, 1H), 1.47-1.35 (m, 1H), 1.22-1.13 (m, 2H), 1.11-1.05 (m, 2H). | A2 |
| 10 | 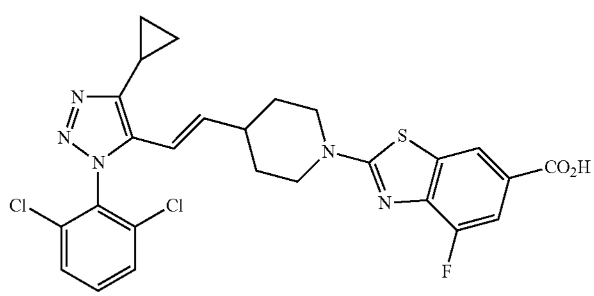 [SMILES: O=C(O)c1cc(F)c2nc(N3CCC(/C=C/c4c(C5CC5)nnn4-c4c(Cl)cccc4Cl)CC3)sc2c1] | MS (ESI) m/z: 558.2 [M + H]$^+$; EC$_{50}$ = 64; $^1$H NMR (500 MHz, DMSO-d6) δ 8.15 (s, 1H), 7.74-7.79 (m, 2H), 7.69 (br d, J = 7.63 Hz, 1H), 7.57 (br d, J = 11.29 Hz, 1H), 6.12 (d, J = 16.17 Hz, 1H), 5.96-6.03 (m, 1H), 4.00 (br d, J = 10.07 Hz, 1H), 3.22 (br t, J = 11.90 Hz, 2H), 2.04 (br s, 2H), 1.71 (br d, J = 11.29 Hz, 2H), 1.24-1.37 (m, 2H), 1.01 (br d, J = 5.80 Hz, 2H), 0.86-0.93 (m, 2H) additional signals were lost due to water suppression. | A1 |
| 11 | 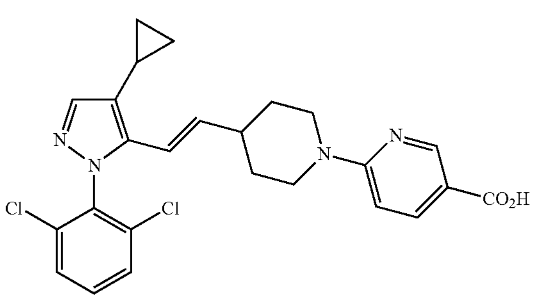 [SMILES: O=C(O)c1ccc(N2CCC(/C=C/c3c(C4CC4)cnn3-c3c(Cl)cccc3Cl)CC2)nc1] | MS (ESI) m/z: 482.8 [M + H]$^+$; EC$_{50}$ = 148; $^1$H NMR (500 MHz, DMSO-d$_6$) δ 8.50-8.58 (m, 1H), 7.83 (br s, 1H), 7.64 (s, 2H), 7.56 (br d, J = 8.24 Hz, 1H), 7.40 (s, 1H), 6.77 (br d, J = 9.16 Hz, 1H), 5.94-6.03 (m, 1H), 5.90 (br d, J = 7.02 Hz, 1H), 4.30 (br d, J = 12.51 Hz, 2H), 4.23 (br d, J = 7.02 Hz, 1H), 2.83-2.94 (m, 2H), 1.72 (br s, 1H), 1.59 (br d, J = 12.51 Hz, 2H), 1.12 (br d, J = 9.46 Hz, 2H), 0.85 (br d, J = 6.71 Hz, 2H), 0.54 (br d, J = 3.97 Hz, 2H). | A1 |

TABLE 1-continued

| Ex. No. | Structure | LCMS, FXR EC$_{50}$ (nM) & NMR | Method |
|---|---|---|---|
| 12 | 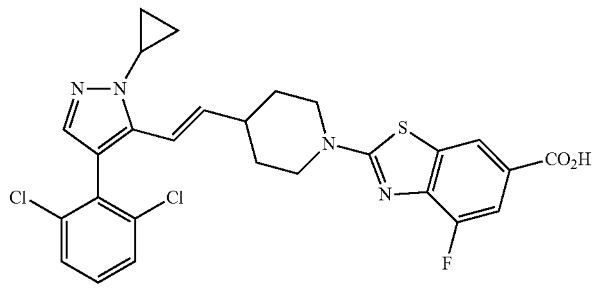 [SMILES: O=C(O)c1cc(F)c2nc(N3CCC(/C=C/c4c(-c5c(Cl)cccc5Cl)cnn4C4CC4)CC3)sc2c1] | MS (ESI) m/z: 557.2 [M + H]$^+$; EC$_{50}$ = 226; $^1$H NMR (500 MHz, DMSO-d$_6$) δ 8.18 (s, 1H), 7.58 (br d, J = 11.60 Hz, 1H), 7.53 (s, 2H), 7.40 (d, J = 7.93 Hz, 1H), 7.31 (s, 1H), 6.54 (d, J = 16.48 Hz, 1H), 5.51 (dd, J = 7.02, 16.17 Hz, 1H), 3.99 (br d, J = 10.68 Hz, 2H), 3.63-3.73 (m, 1H), 3.26 (br t, J = 11.60 Hz, 2H), 2.41 (br d, J = 7.63 Hz, 1H), 1.72 (br d, J = 11.60 Hz, 2H), 1.26 (br s, 2H), 1.07 (br s, 2H), 0.99 (d, J = 6.41 Hz, 2H). | A1 |
| 13 | 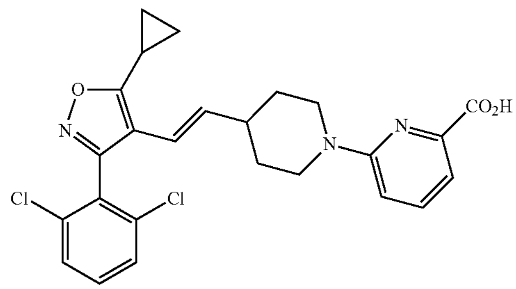 [SMILES: O=C(O)c1cccc(N2CCC(/C=C/c3c(-c4c(Cl)cccc4Cl)noc3C3CC3)CC2)n1] | MS (ESI) m/z: 484.3 [M + H]$^+$; EC$_{50}$ = 206; $^1$H NMR (500 MHz, DMSO-d$_6$) δ 7.74-7.51 (m, 4H), 7.23 (d, J = 7.3 Hz, 1H), 6.99 (d, J = 8.5 Hz, 1H), 6.16 (d, J = 16.2 Hz, 1H), 5.33 (dd, J = 7.0, 16.4 Hz, 1H), 4.26 (d, J = 13.2 Hz, 2H), 2.84 (t, J = 12.3 Hz, 2H), 2.40-2.31 (m, 1H), 2.26 (br s, 1H), 1.60 (d, J = 12.8 Hz, 2H), 1.24-1.00 (m, 6H). | A1 |
| 14 | 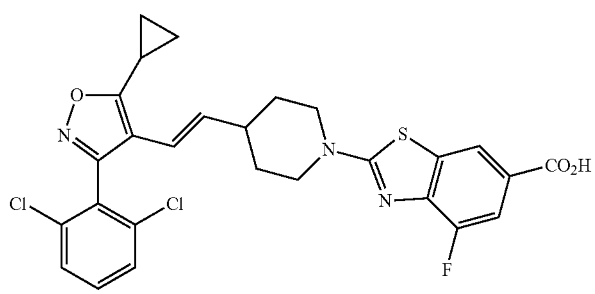 [SMILES: O=C(O)c1cc(F)c2nc(N3CCC(/C=C/c4c(-c5c(Cl)cccc5Cl)noc4C4CC4)CC3)sc2c1] | MS (ESI) m/z: 558.3 [M + H]$^+$; EC$_{50}$ = 11; Mouse in vivo (30 mg/kg, @ 6 h): Cyp7a1 = −96%, FgF15 =+ 10x; $^1$H NMR (500 MHz, DMSO-d$_6$) δ 8.20 (s, 1H), 7.66 (d, J = 7.9 Hz, 2H), 7.62-7.56 (m, 2H), 6.19 (d, J = 16.2 Hz, 1H), 5.35 (dd, J = 6.9, 16.3 Hz, 1H), 3.97 (br s, 2H), 3.24 (t, J = 12.6 Hz, 2H), 2.36 (td, J = 4.4, 8.6 Hz, 2H), 1.70 (d, J = 12.9 Hz, 2H), 1.35-1.01 (m, 6H). | A1 |
| 15 | 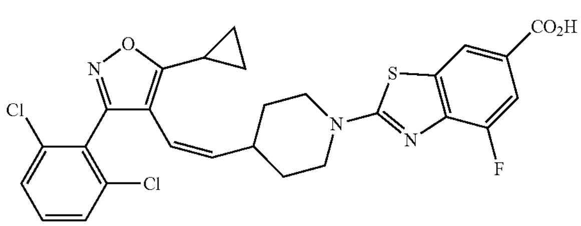 [SMILES: O=C(O)c1cc(F)c2nc(N3CCC(/C=C\c4c(-c5c(Cl)cccc5Cl)noc4C4CC4)CC3)sc2c1] | MS (ESI) m/z: 558.1 [M + H]$^+$; EC$_{50}$ = 130; $^1$H NMR (500 MHz, DMSO-d$_6$) δ 8.19 (s, 1H), 7.67 (d, J = 8.1 Hz, 2H), 7.62-7.55 (m, 2H), 5.89 (d, J = 11.1 Hz, 1H), 5.59 (t, J = 10.8 Hz, 1H), 4.01 (br s, 2H), 3.10 (t, J = 12.4 Hz, 2H), 2.44-2.33 (m, 1H), 2.14-2.06 (m, 1H), 1.42-1.21 (m, 4H), 1.22-1.08 (m, 4H). | A1 |
| 16 | 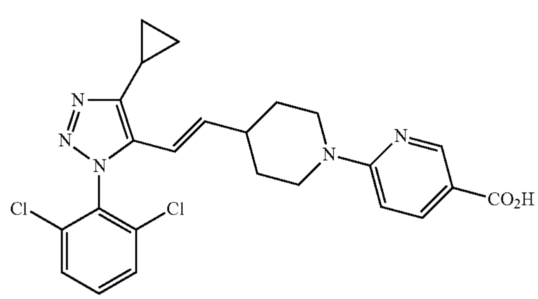 [SMILES: O=C(O)c1ccc(N2CCC(/C=C/c3c(C4CC4)nnn3-c3c(Cl)cccc3Cl)CC2)nc1] | MS (ESI) m/z: 484.1 [M + H]$^+$; EC$_{50}$ = 109; $^1$H NMR (500 MHz, DMSO-d$_6$) δ 8.55 (s, 1H), 7.87 (br d, J = 8.54 Hz, 1H), 7.72-7.79 (m, 2H), 7.67 (br t, J = 8.09 Hz, 1H), 6.79 (br d, J = 9.16 Hz, 1H), 6.09 (br d, J = 16.48 Hz, 1H), 5.94 (br dd, J = 6.87, 16.02 Hz, 1H), 4.30 (br d, J = 12.51 Hz, 2H), 2.92 (br t, J = 12.21 Hz, 2H), 2.02 (br d, J = 3.97 Hz, 1H), 1.63 (br d, J = 12.21 Hz, 2H), 1.14 (br d, J = 10.38 Hz, 2H), 0.96-1.04 (m, 3H), 0.88 (br d, J = 2.75 Hz, 2H). | A1 |

TABLE 1-continued

| Ex. No. | Structure | LCMS, FXR EC$_{50}$ (nM) & NMR | Method |
|---|---|---|---|
| 17 | 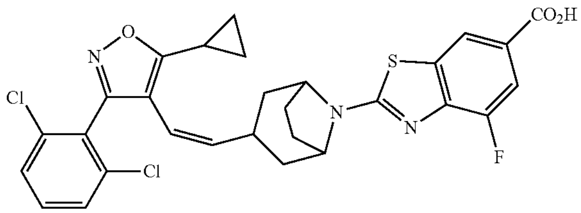 [SMILES: O=C(O)c1cc(F)c2nc(N3C4CCC3CC(/C=C\c3c(-c5c(Cl)cccc5Cl)noc3C3CC3)C4)sc2c1] | MS (ESI) m/z: 584.1 [M + H]$^+$; EC$_{50}$ = 243; $^1$H NMR (500 MHz, DMSO-d$_6$) δ 8.20 (d, J = 1.5 Hz, 1H), 7.64 (d, J = 8.0 Hz, 2H), 7.61-7.54 (m, 2H), 5.72 (d, J = 11.0 Hz, 1H), 5.50 (t, J = 10.4 Hz, 1H), 4.34 (br s, 1H), 2.87-2.75 (m, 1H), 2.12-2.02 (m, 3H), 1.72 (d, J = 7.9 Hz, 1H), 1.61 (t, J = 12.3 Hz, 1H), 1.41 (d, J = 13.1 Hz, 1H), 1.28-1.10 (m, 4H), additional signals missing due to water signal suppression. | A1 |
| 18 | 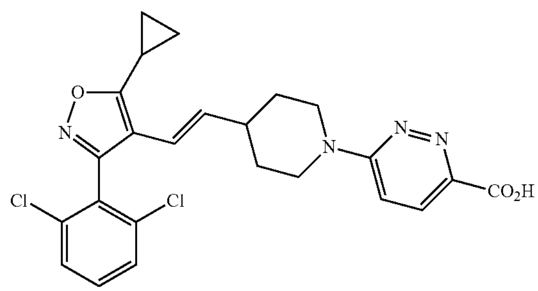 [SMILES: O=C(O)c1ccc(N2CCC(/C=C/c3c(-c4c(Cl)cccc4Cl)noc3C3CC3)CC2)nn1] | MS (ESI) m/z: 485.2 [M + H]$^+$; EC$_{50}$ = 447; $^1$H NMR (500 MHz, DMSO-d$_6$) δ 7.79 (d, J = 9.6 Hz, 1H), 7.65 (d, J = 8.0 Hz, 2H), 7.58 (dd, J = 7.0, 9.0 Hz, 1H), 7.25 (d, J = 9.6 Hz, 1H), 6.18 (d, J = 16.2 Hz, 1H), 5.33 (dd, J = 6.9, 16.3 Hz, 1H), 4.39 (d, J = 13.2 Hz, 2H), 3.05 (t, J = 12.5 Hz, 2H), 2.42-2.25 (m, 2H), 1.66 (d, J = 13.0 Hz, 2H), 1.31-0.94 (m, 6H). | A1 |
| 19 | 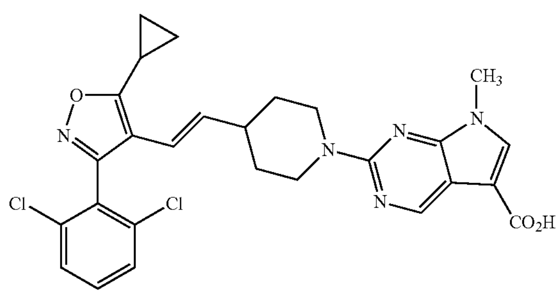 [SMILES: Cn1cc(C(=O)O)c2cnc(N3CCC(/C=C/c4c(-c5c(Cl)cccc5Cl)noc4C4CC4)CC3)nc21] | MS (ESI) m/z: 538.1 [M + H]$^+$; EC$_{50}$ = 194; $^1$H NMR (500 MHz, DMSO-d$_6$) δ 8.79 (s, 1H), 7.83 (s, 1H), 7.66 (d, J = 8.2 Hz, 2H), 7.58 (dd, J = 7.1, 9.0 Hz, 1H), 6.18 (d, J = 16.3 Hz, 1H), 5.34 (dd, J = 6.9, 16.2 Hz, 1H), 4.60 (d, J = 13.1 Hz, 2H), 3.66 (s, 3H), 2.93 (t, J = 12.4 Hz, 2H), 2.42-2.22 (m, 2H), 1.62 (d, J = 12.8 Hz, 2H), 1.21-0.97 (m, 6H). | A1 |
| 20 | 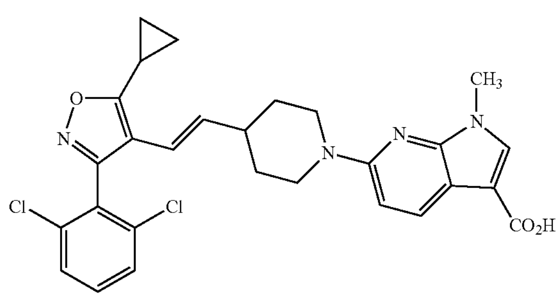 [SMILES: Cn1cc(C(=O)O)c2ccc(N3CCC(/C=C/c4c(-c5c(Cl)cccc5Cl)noc4C4CC4)CC3)nc21] | MS (ESI) m/z: 537.1 [M + H]$^+$; EC$_{50}$ = 21; $^1$H NMR (500 MHz, DMSO-d$_6$) δ 8.02 (d, J = 8.8 Hz, 1H), 7.79 (s, 1H), 7.66 (d, J = 8.0 Hz, 2H), 7.58 (t, J = 8.1 Hz, 1H), 6.77 (d, J = 8.7 Hz, 1H), 6.18 (d, J = 16.2 Hz, 1H), 5.35 (dd, J = 6.9, 16.2 Hz, 1H), 4.23 (d, J = 13.0 Hz, 2H), 3.70 (s, 3H), 2.86 (t, J = 12.2 Hz, 2H), 2.36 (br d, J = 5.5 Hz, 1H), 2.26 (br s, 1H), 1.63 (d, J = 12.7 Hz, 2H), 1.21-0.94 (m, 6H). | A2 |
| 21 | 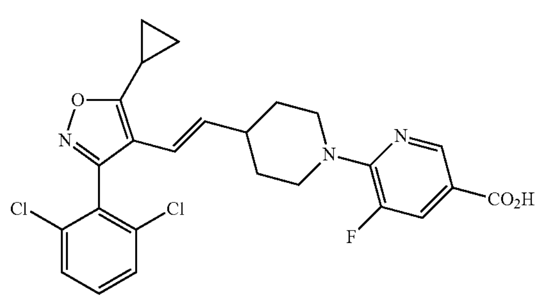 [SMILES: O=C(O)c1cnc(N2CCC(/C=C/c3c(-c4c(Cl)cccc4Cl)noc3C3CC3)CC2)c(F)c1] | MS (ESI) m/z: 502.0 [M + H]$^+$; EC$_{50}$ = 20; $^1$H NMR (500 MHz, DMSO-d$_6$) δ 8.48 (s, 1H), 7.87-7.47 (m, 4H), 6.15 (d, J = 16.2 Hz, 1H), 5.39 (dd, J = 6.8, 16.3 Hz, 1H), 4.16 (d, J = 13.2 Hz, 2H), 3.02 (dd, J = 10.6, 23.1 Hz, 2H), 2.41-2.23 (m, 2H), 1.66 (d, J = 13.2 Hz, 2H), 1.33-1.0 (m, 6H). | A1 |

TABLE 1-continued

| Ex. No. | Structure | LCMS, FXR EC$_{50}$ (nM) & NMR | Method |
|---|---|---|---|
| 22 | 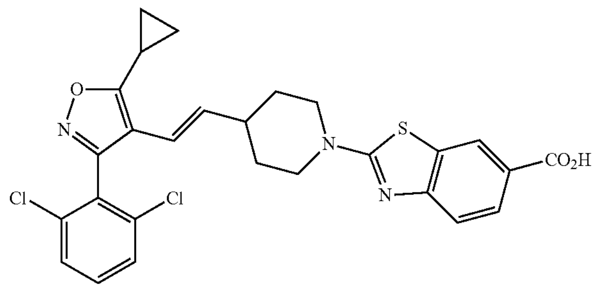 [SMILES: O=C(O)c1ccc2nc(N3CCC(/C=C/c4c(-c5c(Cl)cccc5Cl)noc4C4CC4)CC3)sc2c1] | MS (ESI) m/z: 540.0 [M + H]$^+$; EC$_{50}$ = 12; $^1$H NMR (500 MHz, DMSO-d$_6$) δ 8.32 (s, 1H), 7.86 (s, 1H), 7.65 (d, J = 8.6 Hz, 2H), 7.62-7.56 (m, 1H), 7.45 (s, 1H), 6.18 (d, J = 16.3 Hz, 1H), 5.41 (dd, J = 6.8, 16.3 Hz, 1H), 3.98 (d, J = 13.2 Hz, 2H), 2.44-2.28 (m, 2H), 1.72 (d, J = 13.2 Hz, 2H), 1.32-1.03 (m, 6H), additional signals missing due to water signal suppression. | A1 |
| 23 | 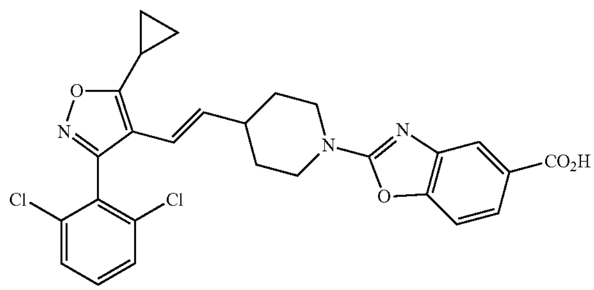 [SMILES: O=C(O)c1ccc2oc(N3CCC(/C=C/c4c(-c5c(Cl)cccc5Cl)noc4C4CC4)CC3)nc2c1] | MS (ESI) m/z: 524.3 [M + H]$^+$; EC$_{50}$ = 156; $^1$H NMR (500 MHz, DMSO-d$_6$) δ 7.77 (s, 1H), 7.71-7.62 (m, 3H), 7.58 (dd, J = 6.9, 9.1 Hz, 1H), 7.44 (d, J = 8.3 Hz, 1H), 6.17 (d, J = 16.2 Hz, 1H), 5.41 (dd, J = 6.8, 16.3 Hz, 1H), 4.06 (d, J = 13.0 Hz, 2H), 2.41-2.25 (m, 2H), 1.69 (d, J = 13.1 Hz, 2H), 1.32-1.21 (m, 2H), 1.17 (dt, J = 3.2, 8.2 Hz, 2H), 1.09 (dt, J = 3.2, 5.5 Hz, 2H), additional signals missing due to water signal suppression. | A1 |
| 24 | 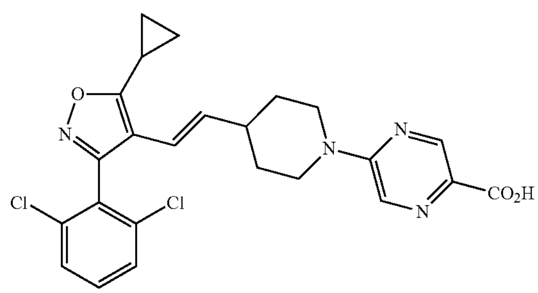 [SMILES: O=C(O)c1cnc(N2CCC(/C=C/c3c(-c4c(Cl)cccc4Cl)noc3C3CC3)CC2)cn1] | MS (ESI) m/z: 485.1 [M + H]$^+$; EC$_{50}$ = 127; $^1$H NMR (500 MHz, DMSO-d$_6$) δ 8.61 (s, 1H), 8.31 (s, 1H), 7.66 (d, J = 8.0 Hz, 2H), 7.59 (dd, J = 7.1, 9.0 Hz, 1H), 6.18 (d, J = 16.3 Hz, 1H), 5.33 (dd, J = 6.9, 16.3 Hz, 1H), 4.37 (d, J = 13.4 Hz, 2H), 3.01 (t, J = 12.5 Hz, 2H), 2.41-2.30 (m, 2H), 1.65 (d, J = 13.0 Hz, 2H), 1.21-1.03 (m, 6H). | A1 |
| 25 | 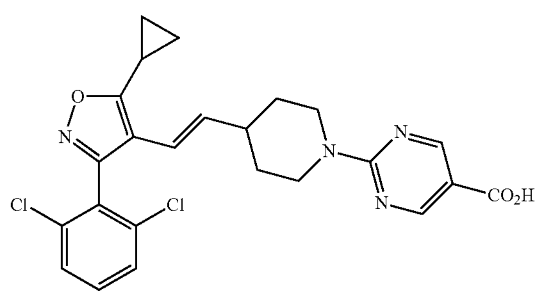 [SMILES: O=C(O)c1cnc(N2CCC(/C=C/c3c(-c4c(Cl)cccc4Cl)noc3C3CC3)CC2)nc1] | MS (ESI) m/z: 485.2 [M + H]$^+$; EC$_{50}$ = 83; $^1$H NMR (500 MHz, DMSO-d$_6$) δ 8.73 (s, 2H), 7.66 (d, J = 8.0 Hz, 2H), 7.59 (dd, J = 7.1, 9.0 Hz, 1H), 6.18 (d, J = 16.2 Hz, 1H), 5.33 (dd, J = 6.9, 16.2 Hz, 1H), 4.61 (d, J = 13.3 Hz, 2H), 3.02 (t, J = 12.4 Hz, 2H), 2.41-2.30 (m, 2H), 1.64 (d, J = 13.0 Hz, 2H), 1.21-1.02 (m, 6H). | A1 |
| 26 | 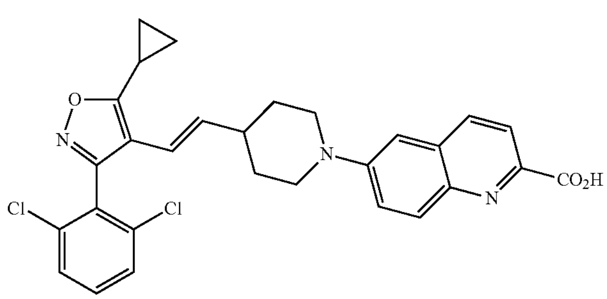 [SMILES: O=C(O)c1ccc2cc(N3CCC(/C=C/c4c(-c5c(Cl)cccc5Cl)noc4C4CC4)CC3)ccc2n1] | MS (ESI) m/z: 534.1 [M + H]$^+$; EC$_{50}$ = 6; $^1$H NMR (500 MHz, DMSO-d$_6$) δ 8.21 (d, J = 8.6 Hz, 1H), 7.95 (dd, J = 8.9, 17.0 Hz, 2H), 7.67 (d, J = 8.1 Hz, 3H), 7.59 (dd, J = 7.2, 9.0 Hz, 1H), 7.19 (d, J = 2.8 Hz, 1H), 6.20 (d, J = 16.2 Hz, 1H), 5.36 (dd, J = 6.9, 16.3 Hz, 1H), 3.86 (d, J = 12.7 Hz, 2H), 2.89 (t, J = 12.1 Hz, 2H), 2.42-2.32 (m, 1H), 2.26 (br. s, 1H), 1.68 (d, J = 12.9 Hz, 2H), 1.34-1.02 (m, 6H). | A2 |

TABLE 1-continued

| Ex. No. | Structure | LCMS, FXR EC$_{50}$ (nM) & NMR | Method |
|---|---|---|---|
| 27 | 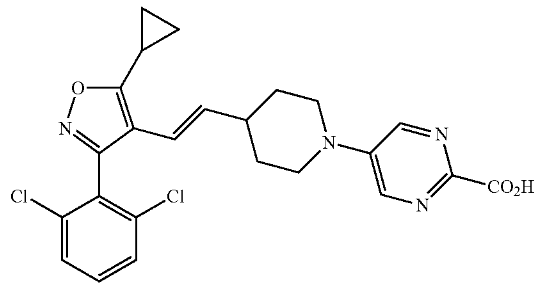 [SMILES: O=C(O)c1ncc(N2CCC(/C=C/c3c(-c4c(Cl)cccc4Cl)noc3C3CC3)CC2)cn1] | MS (ESI) m/z: 485.0 [M + H]$^+$; EC$_{50}$ = 2326; $^1$H NMR (500 MHz, DMSO-d$_6$) δ 8.48 (s, 2H), 7.65 (d, J = 8.1 Hz, 2H), 7.58 (t, J = 8.2 Hz, 1H), 6.18 (d, J = 16.4 Hz, 1H), 5.34 (dd, J = 6.8, 16.2 Hz, 1H), 3.89 (d, J = 12.5 Hz, 2H), 2.92 (t, J = 12.3 Hz, 2H), 2.35 (br s, 1H), 2.28 (br s, 1H), 1.64 (d, J = 13.1 Hz, 2H), 1.31-1.05 (m, 6H). | A2 |
| 28 | 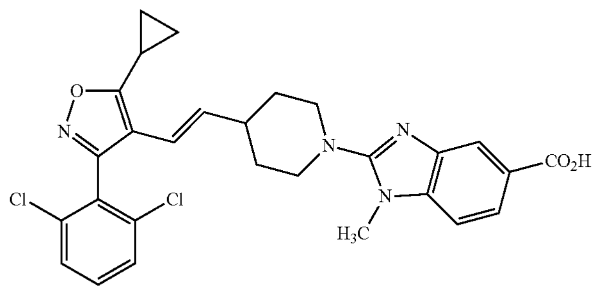 [SMILES: Cn1c(N2CCC(/C=C/c3c(-c4c(Cl)cccc4Cl)noc3C3CC3)CC2)nc2cc(C(=O)O)ccc21] | MS (ESI) m/z: 537.0 [M + H]$^+$; EC$_{50}$ = 500; $^1$H NMR (500 MHz, DMSO-d$_6$) δ 7.94 (s, 1H), 7.74 (d, J = 8.3 Hz, 1H), 7.68 (d, J = 8.1 Hz, 2H), 7.61 (dd, J = 7.1, 9.0 Hz, 1H), 7.37 (d, J = 8.4 Hz, 1H), 6.22 (d, J = 16.2 Hz, 1H), 5.39 (dd, J = 6.8, 16.2 Hz, 1H), 3.59 (s, 3H), 3.53 (d, J = 12.4 Hz, 2H), 2.92 (t, J = 12.1 Hz, 2H), 2.42-2.33 (m, 1H), 2.24 (br s, 1H), 1.67 (d, J = 12.9 Hz, 2H), 1.45-1.30 (m, 2H), 1.22-1.04 (m, 4H). | A1 |
| 29 | 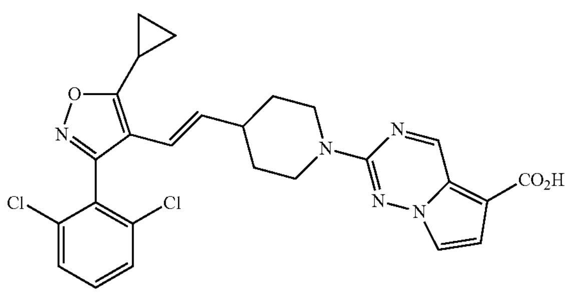 [SMILES: O=C(O)c1ccn2nc(N3CCC(/C=C/c4c(-c5c(Cl)cccc5Cl)noc4C4CC4)CC3)ncc12] | MS (ESI) m/z: 524.2 [M + H]$^+$; EC$_{50}$ = 60; $^1$H NMR (500 MHz, DMSO-d$_6$) δ 9.17 (s, 1H), 7.67-7.63 (m, 3H), 7.58 (dd, J = 7.0, 9.0 Hz, 1H), 7.08 (d, J = 2.7 Hz, 1H), 6.16 (d, J = 16.1 Hz, 1H), 5.34 (dd, J = 6.9, 16.2 Hz, 1H), 4.33 (d, J = 13.2 Hz, 2H), 2.94 (t, J = 12.3 Hz, 2H), 2.40-2.24 (m, 2H), 1.62 (d, J = 12.8 Hz, 2H), 1.22-1.03 (m, 6H). | A1 |
| 30 | 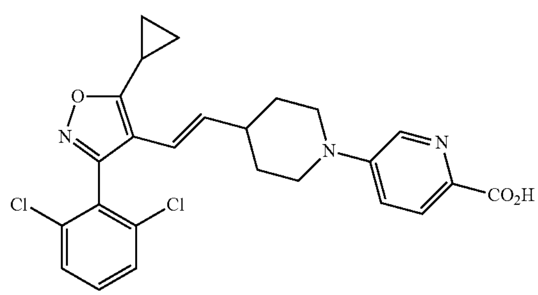 [SMILES: O=C(O)c1ccc(N2CCC(/C=C/c3c(-c4c(Cl)cccc4Cl)noc3C3CC3)CC2)cn1] | MS (ESI) m/z: 484.1 [M + H]$^+$; EC$_{50}$ = 78; $^1$H NMR (500 MHz, DMSO-d$_6$) δ 8.31 (d, J = 3.0 Hz, 1H), 7.83 (d, J = 8.9 Hz, 1H), 7.66 (d, J = 8.0 Hz, 2H), 7.59 (dd, J = 7.0, 9.0 Hz, 1H), 7.30 (dd, J = 3.0, 9.2 Hz, 1H), 6.18 (d, J = 16.3 Hz, 1H), 5.34 (dd, J = 7.0, 16.2 Hz, 1H), 3.84 (d, J = 13.0 Hz, 2H), 2.89 (t, J = 12.3 Hz, 2H), 2.40-2.33 (m, 1H), 2.27 (br s, 1H), 1.64 (d, J = 13.4 Hz, 2H), 1.29-1.03 (m, 6H). | A2 |
| 31 | 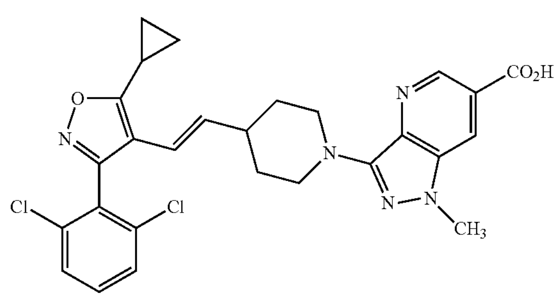 [SMILES: Cn1nc(N2CCC(/C=C/c3c(-c4c(Cl)cccc4Cl)noc3C3CC3)CC2)c2ncc(C(=O)O)cc21] | MS (ESI) m/z: 538.2 [M + H]$^+$; EC$_{50}$ = 414; $^1$H NMR (500 MHz, DMSO-d$_6$) δ 8.78 (d, J = 1.7 Hz, 1H), 8.37 (d, J = 1.8 Hz, 1H), 7.67 (d, J = 7.7 Hz, 2H), 7.60 (dd, J = 7.2, 8.9 Hz, 1H), 6.19 (d, J = 16.1 Hz, 1H), 5.36 (dd, J = 6.9, 16.2 Hz, 1H), 4.35 (d, J = 12.4 Hz, 2H), 3.88 (s, 3H), 2.88 (t, J = 12.1 Hz, 2H), 2.41-2.31 (m, 1H), 2.22 (br s, 1H), 1.65 (d, J = 12.8 Hz, 2H), 1.36-1.02 (m, 6H). | A2 |

TABLE 1-continued

| Ex. No. | Structure | LCMS, FXR EC$_{50}$ (nM) & NMR | Method |
|---|---|---|---|
| 32 | 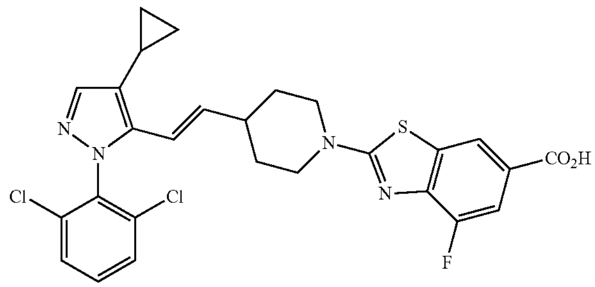 [SMILES: O=C(O)c1cc(F)c2nc(N3CCC(/C=C/c4c(C5CC5)cnn4-c4c(Cl)cccc4Cl)CC3)sc2c1] | MS (ESI) m/z: 557.1 [M + H]$^+$; EC$_{50}$ = 47; $^1$H NMR (500 MHz, DMSO-d$_6$) δ 8.09-8.16 (m, 1H), 7.66 (d, J = 7.99 Hz, 2H), 7.53-7.60 (m, 2H), 7.43 (s, 1H), 6.02 (d, J = 16.24 Hz, 1H), 5.88-5.97 (m, 1H), 3.78 (br s, 3H), 3.17-3.26 (m, 2H), 1.72-1.78 (m, 1H), 1.65-1.71 (m, 2H), 1.26 (br d, J = 9.34 Hz, 2H), 0.84-0.92 (m, 2H), 0.55 (br d, J = 4.46 Hz, 2H). | A1 |
| 33 | 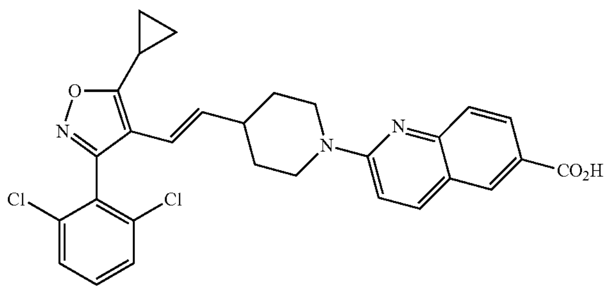 [SMILES: O=C(O)c1ccc2nc(N3CCC(/C=C/c4c(-c5c(Cl)cccc5Cl)noc4C4CC4)CC3)ccc2c1] | MS (ESI) m/z: 534.3 [M + H]$^+$; EC$_{50}$ = 15; $^1$H NMR (500 MHz, DMSO-d$_6$) δ 8.33 (d, J = 2.0 Hz, 1H), 8.12 (d, J = 9.3 Hz, 1H), 7.98 (dd, J = 2.0, 8.7 Hz, 1H), 7.66 (d, J = 8.6 Hz, 2H), 7.58 (dd, J = 7.2, 9.0 Hz, 1H), 7.52 (d, J = 8.8 Hz, 1H), 7.27 (d, J = 9.3 Hz, 1H), 6.19 (d, J = 16.3 Hz, 1H), 5.34 (dd, J = 6.9, 16.3 Hz, 1H), 4.49 (d, J = 13.3 Hz, 2H), 3.07-2.95 (m, 2H), 2.41-2.29 (m, 2H), 1.66 (d, J = 11.9 Hz, 2H), 1.21-1.03 (m, 6H). | A2 |
| 34 | 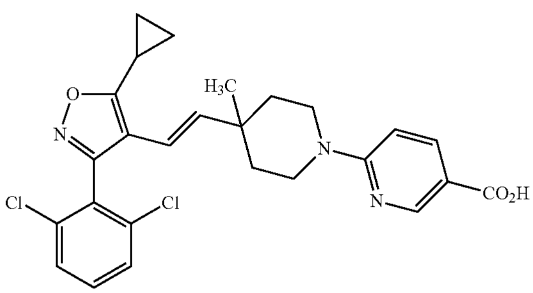 [SMILES: CC1(/C=C/c2c(-c3c(Cl)cccc3Cl)noc2C2CC2)CCN(c2ccc(C(=O)O)cn2)CC1] | MS (ESI) m/z: 498.2 [M + H]$^+$; EC$_{50}$ = 403.3; $^1$H NMR (500 MHz, DMSO-d$_6$) δ 8.58 (br s, 1H), 7.88 (br d, J = 8.8 Hz, 1H), 7.63 (d, J = 8.1 Hz, 2H), 7.58-7.51 (m, 1H), 6.77 (br d, J = 8.9 Hz, 1H), 6.24 (d, J = 16.7 Hz, 1H), 5.34 (d, J = 16.7 Hz, 1H), 3.76 (br d, J = 13.1 Hz, 1H), 3.12 (br t, J = 10.0 Hz, 2H), 2.46-2.32 (m, 1H), 1.47-1.37 (m, 2H), 1.36-1.27 (m, 2H), 1.22 (s, 1H), 1.20-1.14 (m, 2H), 1.10-1.05 (m, 2H), 0.95 (s, 3H). | A1 |
| 35 | 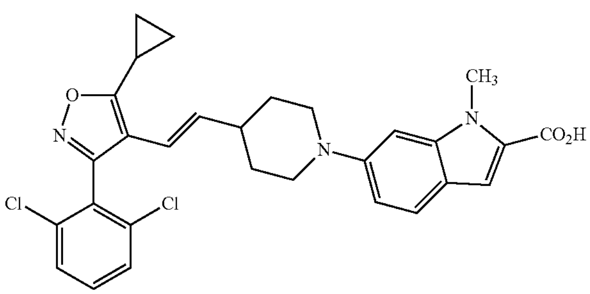 [SMILES: Cn1c(C(=O)O)cc2ccc(N3CCC(/C=C/c4c(-c5c(Cl)cccc5Cl)noc4C4CC4)CC3)cc21] | MS (ESI) m/z: 536.2 [M + H]$^+$; EC$_{50}$ = 25; $^1$H NMR (500 MHz, DMSO-d$_6$) δ 7.69-7.63 (m, 2H), 7.59 (dd, J = 7.1, 9.2 Hz, 1H), 7.45 (d, J = 8.8 Hz, 1H), 7.06 (s, 1H), 6.86 (dd, J = 2.1, 8.8 Hz, 1H), 6.80 (s, 1H), 6.18 (d, J = 16.0 Hz, 1H), 5.42 (dd, J = 6.9, 16.3 Hz, 1H), 3.94 (s, 3H), 3.63 (d, J = 12.1 Hz, 2H), 2.76 (t, J = 11.8 Hz, 2H), 2.41-2.29 (m, 1H), 2.19 (br s, 1H), 1.68 (d, J = 12.2 Hz, 2H), 1.32 (q, J = 12.0, 12.8 Hz, 2H), 1.18 (dq, J = 3.6, 4.1, 6.7 Hz, 2H), 1.09 (dd, J = 2.6, 5.2 Hz, 2H). | A2 |
| 36 | 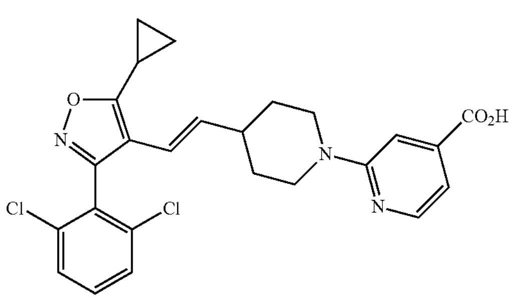 [SMILES: O=C(O)c1ccnc(N2CCC(/C=C/c3c(-c4c(Cl)cccc4Cl)noc3C3CC3)CC2)c1] | MS (ESI) m/z: 484.2 [M + H]$^+$; EC$_{50}$ = 144; $^1$H NMR (500 MHz, CDCl$_3$) δ 8.26 (d, J = 5.0 Hz, 1H), 7.43 (d, J = 1.1 Hz, 1H), 7.41 (s, 1H), 7.36-7.32 (m, 1H), 7.21 (s, 1H), 7.09-7.05 (m, 1H), 6.07 (dd, J = 16.1, 1.0 Hz, 1H), 5.45 (dd, J = 16.0, 7.2 Hz, 1H), 4.34-4.22 (m, 2H), 3.92 (s, 3H), 2.91 (td, J = 12.7, 2.3 Hz, 2H), 2.30-2.21 (m, 1H), 2.11 (tt, J = 8.4, 5.0 Hz, 1H), 1.73 (br dd, J = 13.2, 1.9 Hz, 2H), 1.16-1.11 (m, 2H), 0.91-0.80 (m, 4H). | A1 |

TABLE 1-continued

| Ex. No. | Structure | LCMS, FXR EC$_{50}$ (nM) & NMR | Method |
|---|---|---|---|
| 37 | 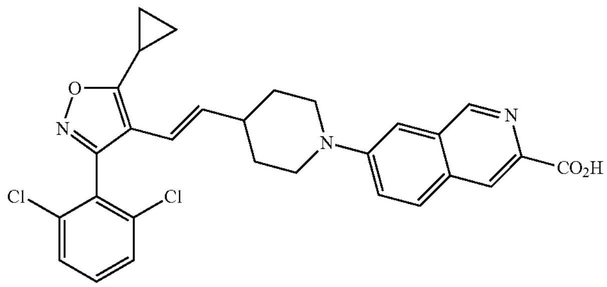 [SMILES: O=C(O)c1cc2ccc(N3CCC(/C=C/c4c(-c5c(Cl)cccc5Cl)noc4C4CC4)CC3)cc2cn1] | MS (ESI) m/z: 534.1 [M + H]$^+$; EC$_{50}$ = 17; $^1$H NMR (500 MHz, DMSO-d$_6$) δ 9.08 (s, 1H), 8.38 (s, 1H), 7.93 (s, 1H), 7.64 (d, J = 8.0 Hz, 3H), 7.58 (q, J = 8.3, 9.4 Hz, 1H), 7.36 (s, 1H), 6.18 (d, J = 16.2 Hz, 1H), 5.34 (dd, J = 6.9, 16.2 Hz, 1H), 3.86 (d, J = 12.8 Hz, 2H), 2.90 (t, J = 12.2 Hz, 2H), 2.42-2.22 (m, 2H), 1.67 (d, J = 12.6 Hz, 2H), 1.33-1.06 (m, 6H). | A2 |
| 38 | 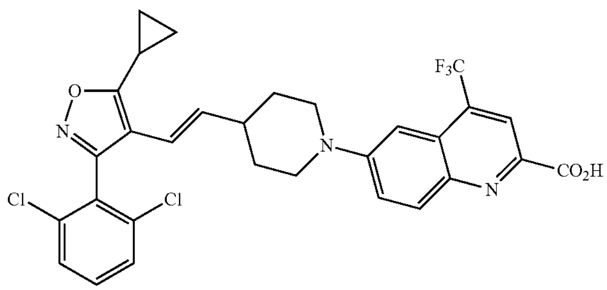 [SMILES: O=C(O)c1cc(C(F)(F)F)c2cc(N3CCC(/C=C/c4c(-c5c(Cl)cccc5Cl)noc4C4CC4)CC3)ccc2n1] | MS (ESI) m/z: 601.9 [M + H]$^+$; EC$_{50}$ = 5; $^1$H NMR (500 MHz, DMSO-d$_6$) δ 8.20 (s, 1H), 8.07 (d, J = 9.4 Hz, 1H), 7.83 (dd, J = 9.6, 1.9 Hz, 1H), 7.65 (s, 1H), 7.63 (s, 1H), 7.59-7.54 (m, 1H), 7.04 (br s, 1H), 6.18 (d, J = 15.7 Hz, 1H), 5.36 (dd, J = 16.2, 6.9 Hz, 1H), 3.89 (br d, J = 13.2 Hz, 2H), 3.03-2.98 (m, 2H), 2.40-2.33 (m, 1H), 2.33-2.27 (m, 1H), 1.71 (br d, J = 11.0 Hz, 2H), 1.31-1.21 (m, 2H), 1.19-1.13 (m, 2H), 1.10-1.06 (m, 2H). | A2 |
| 39 | 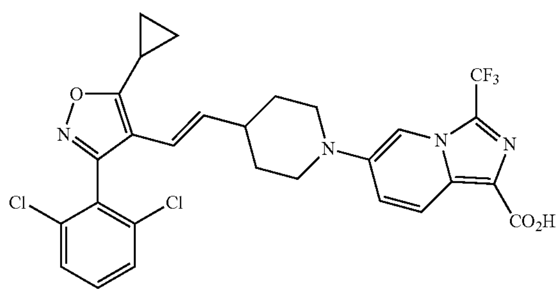 [SMILES: O=C(O)c1nc(C(F)(F)F)n2cc(N3CCC(/C=C/c4c(-c5c(Cl)cccc5Cl)noc4C4CC4)CC3)ccc12] | MS (ESI) m/z: 591.1 [M + H]$^+$; EC$_{50}$ = 5; $^1$H NMR (500 MHz, DMSO-d$_6$) δ 8.05 (d, J = 10.0 Hz, 1H), 7.67 (d, J = 7.9 Hz, 2H), 7.60 (dd, J = 7.1, 9.0 Hz, 1H), 7.55-7.50 (m, 1H), 7.48 (s, 1H), 6.21 (d, J = 16.2 Hz, 1H), 5.38 (dd, J = 7.0, 16.2 Hz, 1H), 3.54 (d, J = 12.1 Hz, 2H), 2.73 (t, J = 11.5 Hz, 2H), 2.42-2.33 (m, 1H), 2.20 (br s, 1H), 1.70 (d, J = 12.8 Hz, 2H), 1.30 (q, J = 10.7 Hz, 2H), 1.18 (dt, J = 3.2, 8.3 Hz, 2H), 1.11 (dt, J = 3.2, 5.5 Hz, 2H). | A2 |
| 40 | 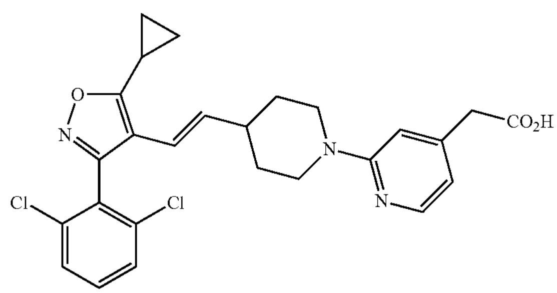 [SMILES: O=C(O)Cc1ccnc(N2CCC(/C=C/c3c(-c4c(Cl)cccc4Cl)noc3C3CC3)CC2)c1] | MS (ESI) m/z: 498.4 [M + H]$^+$; EC$_{50}$ = 947; $^1$H NMR (500 MHz, DMSO-d$_6$) δ 7.97 (d, J = 5.0 Hz, 1H), 7.65 (d, J = 0.8 Hz, 1H), 7.64 (s, 1H), 7.60-7.54 (m, 1H), 6.66 (s, 1H), 6.49 (d, J = 5.0 Hz, 1H), 6.15 (d, J = 17.1 Hz, 1H), 5.32 (dd, J = 16.4, 7.0 Hz, 1H), 4.15-4.08 (m, 2H), 2.80 (br t, J = 11.3 Hz, 2H), 2.37-2.30 (m, 1H), 2.28-2.18 (m, 1H), 1.91 (s, 2H), 1.58 (br dd, J = 12.9, 1.9 Hz, 2H), 1.19-1.13 (m, 2H), 1.11-1.03 (m, 4H). | A1 |
| 41 | 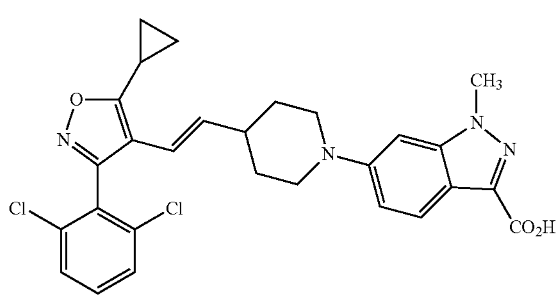 [SMILES: Cn1nc(C(=O)O)c2ccc(N3CCC(/C=C/c4c(-c5c(Cl)cccc5Cl)noc4C4CC4)CC3)cc21] | MS (ESI) m/z: 537.3 [M + H]$^+$; EC$_{50}$ = 236; $^1$H NMR (500 MHz, DMSO-d$_6$) δ 7.68 (dd, J = 4.1, 8.1 Hz, 2H), 7.64-7.53 (m, 2H), 7.39 (s, 1H), 7.25 (d, J = 9.1 Hz, 1H), 6.21 (d, J =16.6 Hz, 1H), 5.37 (dd, J = 6.7, 16.2 Hz, 1H), 4.06 (s, 3H), 2.67 (t, J = 11.7 Hz, 2H), 2.41-2.32 (m, 1H), 2.17 (br s, 1H), 1.69 (br d, J = 12.7 Hz, 2H), 1.32 (br d, J = 12.1 Hz, 2H), 1.18 (br d, J = 8.6 Hz, 2H), 1.10 (br s, 2H), additional signals missing due to water signal suppression. | A2 |

TABLE 1-continued

| Ex. No. | Structure | LCMS, FXR EC$_{50}$ (nM) & NMR | Method |
|---|---|---|---|
| 42 | 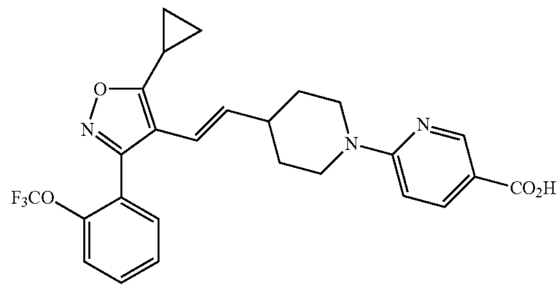 [SMILES: O=C(O)c1ccc(N2CCC(/C=C/c3c(-c4ccccc4OC(F)(F)F)noc3C3CC3)CC2)nc1] | MS (ESI) m/z: 500.3 [M + H]$^+$; EC$_{50}$ = 512; $^1$H NMR (500 MHz, DMSO-d$_6$) δ 8.58 (d, J = 2.14 Hz, 1H), 7.83-7.91 (m, 1H), 7.67 (br s, 1H), 7.54 (br s, 3H), 6.83 (d, J = 9.16 Hz, 1H), 6.09 (d, J = 16.17 Hz, 1H), 5.58 (dd, J = 7.02, 16.17 Hz, 1H), 4.31-4.41 (m, 2H), 2.94 (br s, 2H), 2.30 (br s, 2H), 1.61-1.70 (m, 2H), 1.10-1.21 (m, 4H), 1.02-1.07 (m, 2H). | A1 |
| 43 | 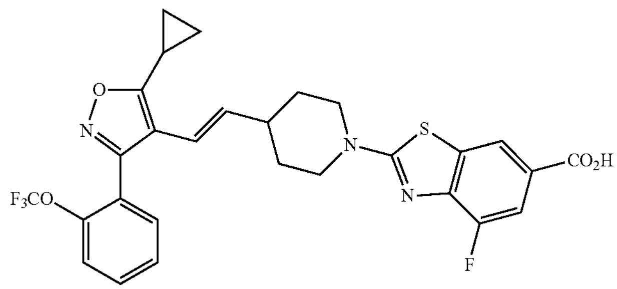 [SMILES: O=C(O)c1cc(F)c2nc(N3CCC(/C=C/c4c(-c5ccccc5OC(F)(F)F)noc4C4CC4)CC3)sc2c1] | MS (ESI) m/z: 574.1 [M + H]$^+$; EC$_{50}$ = 42; $^1$H NMR (500 MHz, DMSO-d$_6$) δ 8.15 (s, 1H), 7.67 (br d, J = 2.14 1H), 7.51-7.60 (m, 4H), 6.07-6.15 (m, 1H), 5.62 (br d, J = 7.02 Hz, 1H), 4.01 (br d, J = 11.90 Hz, 2H), 3.24 (br s, 2H), 2.30 (br s, 2H), 1.73 (br d, J = 12.51 Hz, 2H), 1.24-1.36 (m, 2H), 1.13 (br d, J = 8.24 Hz, 2H), 1.02-1.07 (m, 2H). | A1 |
| 44 | 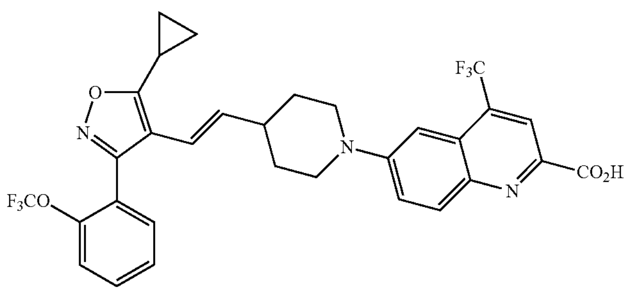 [SMILES: O=C(O)c1cc(C(F)(F)F)c2cc(N3CCC(/C=C/c4c(-c5ccccc5OC(F)(F)F)noc4C4CC4)CC3)ccc2n1] | MS (ESI) m/z: 574.1 [M + H]$^+$; EC$_{50}$ = 31; $^1$H NMR (500 MHz, DMSO-d$_6$) δ 8.15 (s, 1H), 7.67 (br d, J = 2.14 Hz, 1H), 7.51-7.60 (m, 4H), 6.07-6.15 (m, 1H), 5.62 (br d, J = 7.02 Hz, 1H), 4.01 (br d, J = 11.90 Hz, 2H), 3.24 (br s, 2H), 2.30 (br s, 2H), 1.73 (br d, J = 12.51 Hz, 2H), 1.24-1.46 (m, 2H), 1.13 (br d, J = 8.24 Hz, 2H), 1.02-1.07 (m, 2H). | A2 |
| 45 | 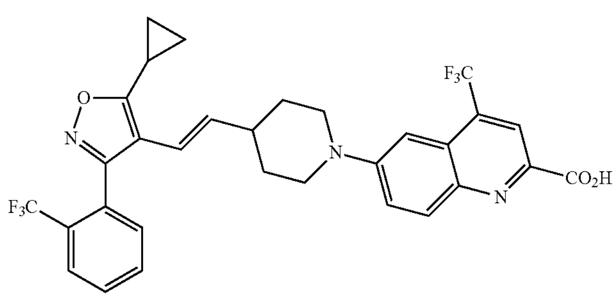 [SMILES: O=C(O)c1cc(C(F)(F)F)c2cc(N3CCC(/C=C/c4c(-c5ccccc5C(F)(F)F)noc4C4CC4)CC3)ccc2n1] | MS (ESI) m/z: 602.3 [M + H]$^+$; EC$_{50}$ = 12; $^1$H NMR (500 MHz, DMSO-d$_6$) δ 8.23 (s, 1H), 8.03-8.10 (m, 1H), 7.93 (br d, J = 7.63 Hz, 1H), 7.74-7.85 (m, 3H), 7.47-7.59 (m, 1H), 7.05 (br s, 1H), 6.11 (d, J = 16.17 Hz, 1H), 5.40 (dd, J = 6.87, 16.33 Hz, 2H), 3.82-3.93 (m, 2H), 2.95 (br t, J = 11.44 Hz, 2H), 2.33 (br t, J = 5.04 Hz, 2H), 1.69 (br d, J = 12.51 Hz, 2H), 1.27 (br d, J = 9.77 Hz, 2H), 1.14-1.20 (m, 2H), 1.07 (br d, J = 3.05 Hz, 2H). | A2 |
| 46 | 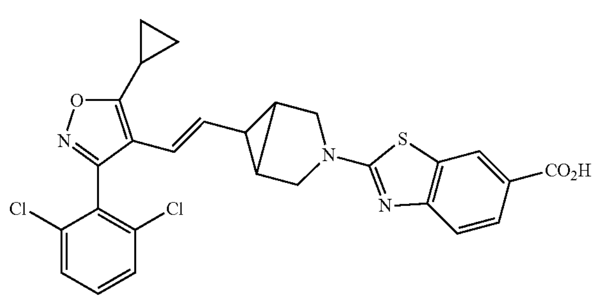 [SMILES: O=C(O)c1ccc2nc(N3CC4C(/C=C/c5c(-c6c(Cl)cccc6Cl)noc5C5CC5)C4C3)sc2c1] | MS (ESI) m/z: 537.9 [M + H]$^+$; EC$_{50}$ = 117; $^1$H NMR (500 MHz, DMSO-d6) δ 8.36 (d, J = 1.8 Hz, 1H), 7.85 (dd, J = 8.5, 1.8 Hz, 1H), 7.67 (d, J = 8.0 Hz, 2H), 7.61 (dd, J = 9.0, 7.0 Hz, 1H), 7.47 (d, J = 8.5 Hz, 1H), 6.16 (d, J = 16.1 Hz, 1H), 5.19 (dd, J = 16.1, 8.8 Hz, 1H), 3.81-3.71 (two proton signals were lost due to water suppression), 3.66 (d, J = 10.0 Hz, 2H), 2.35 (tt, J = 8.5, 5.1 Hz, 1H), 1.75 (s, 2H), 1.43 (dd, J = 8.8, 3.9 Hz, 1H), 1.27-1.04 (m, 4H). | A1 |

TABLE 1-continued

| Ex. No. | Structure | LCMS, FXR EC$_{50}$ (nM) & NMR | Method |
|---|---|---|---|
| 47 | 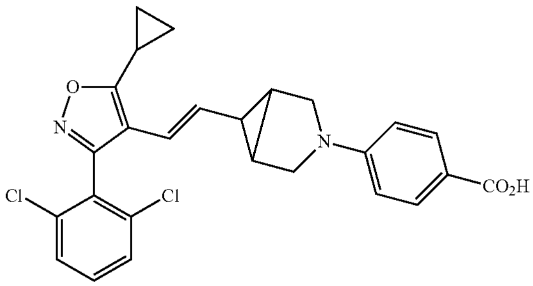 [SMILES: O=C(O)c1ccc(N2CC3C(/C=C/c4c(-c5c(Cl)cccc5Cl)noc4C4CC4)C3C2)cc1] | MS (ESI) m/z: 481.2 [M + H]$^+$; EC$_{50}$ = 40; $^1$H NMR (500 MHz, DMSO-d6) δ 7.72 (d, J = 8.7 Hz, 2H), 7.67 (d, J = 7.4 Hz, 2H), 7.60 (dd, J = 9.1, 7.1 Hz, 1H), 6.53 (d, J = 8.6 Hz, 2H), 6.14 (d, J = 16.1 Hz, 1H), 5.14 (dd, J = 16.0, 9.0 Hz, 1H), 3.56 (d, J = 10.1 Hz, 1H, one proton signal was lost due to water suppression), 3.39-3.19 (m, 2H), 2.34 (td, J = 8.5, 4.3 Hz, 1H), 1.71-1.65 (m, 2H), 1.38-1.30 (m, 1H), 1.21-0.98 (m, 4H). | A2 |
| 48 | 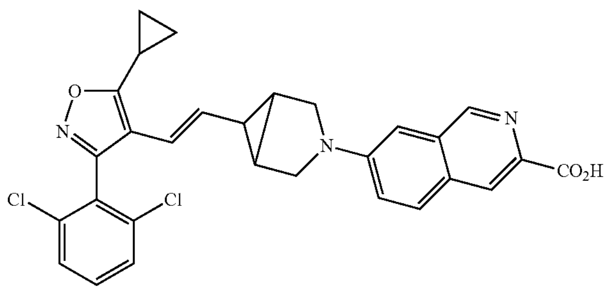 [SMILES: O=C(O)c1cc2ccc(N3CC4C(/C=C/c5c(-c6c(Cl)cccc6Cl)noc5C5CC5)C4C3)cc2cn1] | MS (ESI) m/z: 532.0 [M + H]$^+$; EC$_{50}$ = 468; $^1$H NMR (500 MHz, DMSO-d6) δ 9.14 (s, 1H), 8.49 (s, 1H), 8.03 (d, J = 9.0 Hz, 1H), 7.68 (d, J = 7.9 Hz, 2H), 7.61 (dd, J = 9.0, 7.0 Hz, 1H), 7.40 (d, J = 9.0 Hz, 1H), 7.09 (s, 1H), 6.16 (d, J = 16.2 Hz, 1H), 5.18 9dd, J = 16.1, 8.9 Hz, 1H), 3.72 (d, J = 10.1 Hz, 2H), 3.44 (d, J = 9.5 Hz, 1H, one proton signal was lost due to water suppression), 2.45-2.23 (m, 1H), 1.80-1.72 (m, 2H), 1.45-1.38 (m, 1H), 1.24-0.98 (m, 4H). | A2 |
| 49 | 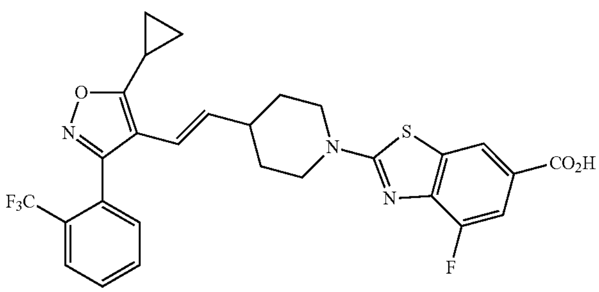 [SMILES: O=C(O)c1cc(F)c2nc(N3CCC(/C=C/c4c(-c5ccccc5C(F)(F)F)noc4C4CC4)CC3)sc2c1] | MS (ESI) m/z: 558.1 [M + H]$^+$; EC$_{50}$ = 23; $^1$H NMR (500 MHz, DMSO-d$_6$) δ 8.21 (br s, 1H), 7.94 (br d, J = 7.32 Hz, 1H), 7.74-7.86 (m, 2H), 7.55-7.66 (m, 1H), 7.52 (br d, J = 7.32 Hz, 1H), 6.11 (br d, J = 16.17 Hz, 1H), 5.40 (br dd, J = 6.71, 16.17 Hz, 1H), 3.99 (br d, J = 9.16 Hz, 2H), 3.16-3.28 (m, 1H), 2.26-2.40 (m, 3H), 1.69 (br d, J = 12.21 Hz, 2H), 1.25 (br d, J = 10.07 Hz, 2H), 1.13-1.19 (m, 2H), 1.08 (br d, J = 2.75 Hz, 2H). | A1 |
| 50 | 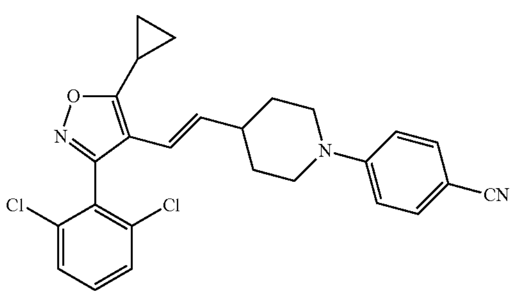 [SMILES: N#Cc1ccc(N2CCC(/C=C/c3c(-c4c(Cl)cccc4Cl)noc3C3CC3)CC2)cc1] | MS (ESI) m/z: 464.1 [M + H]$^+$; EC$_{50}$ = 671; $^1$H NMR (400 MHz, CDCl$_3$) δ 7.39-7.50 (m, 4H), 7.31-7.38 (m, 1H), 6.83 (d, J = 9.02 Hz, 2H), 6.08 (dd, J = 1.21, 16.18 Hz, 1H), 5.44 (dd, J = 7.04, 16.07 Hz, 1H), 3.72-3.80 (m, 2H), 2.81-2.94 (m, 2H), 2.18-2.28 (m, 1H), 2.07-2.14 (m, 1H), 1.74 (br d, J = 10.56 Hz, 2H), 1.29-1.43 (m, 2H), 1.22-1.29 (m, 2H), 1.10-1.18 (m, 2H). | A2 |
| 51 | 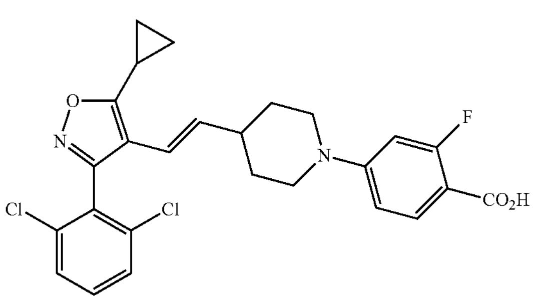 [SMILES: O=C(O)c1ccc(N2CCC(/C=C/c3c(-c4c(Cl)cccc4Cl)noc3C3CC3)CC2)cc1F] | MS (ESI) m/z: 464.1 [M + H]$^+$; EC$_{50}$ = 11; $^1$H NMR (400 MHz, CDCl$_3$) δ 7.39-7.50 (m, 4H), 7.31-7.38 (m, 1H), 6.83 (d, J = 9.02 Hz, 2H), 6.08 (dd, J = 1.21, 16.18 Hz, 1H), 5.44 (dd, J = 7.04, 16.07 Hz, 1H), 3.72-3.80 (m, 2H), 2.81-2.94 (m, 2H), 2.18-2.28 (m, 1H), 2.07-2.14 (m, 1H), 1.74 (br d, J = 10.56 Hz, 2H), 1.29-1.43 (m, 2H), 1.22-1.29 (m, 2H), 1.10-1.18 (m, 2H). | A2 |

TABLE 1-continued

| Ex. No. | Structure | LCMS, FXR EC$_{50}$ (nM) & NMR | Method |
|---|---|---|---|
| 52 | 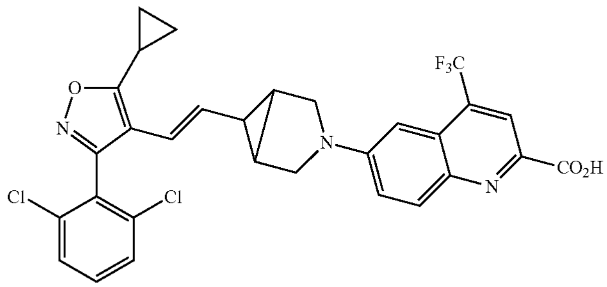 [SMILES: O=C(O)c1cc(C(F)(F)F)c2cc(N3CC4C(/C=C/c5c(-c6c(Cl)cccc6Cl)noc5C5CC5)C4C3)ccc2n1] | MS (ESI) m/z: 600.1 [M + H]$^+$; EC$_{50}$ = 77; $^1$H NMR (400 MHz, DMSO-d$_6$) δ 8.20-8.15 (m, 1H), 8.06 (d, J = 9.5 Hz, 1H), 7.68 (d, J = 1.8 Hz, 1H), 7.66 (s, 1H), 7.62-7.59 (m, 1H), 7.48-7.43 (m, 1H), 6.69 (br s, 1H), 6.13 (d, J = 16.0 Hz, 1H), 5.20 (dd, J = 16.1, 8.9 Hz, 1H), 3.72 (br d, J = 10.1 Hz, 2H), 3.49 (br d, J = 8.9 Hz, 2H), 2.34-2.31 (m, 1H), 1.78 (br s, 2H), 1.45-1.38 (m, 1H), 1.18-1.13 (m, 2H), 1.12-1.03 (m, 2H). | A2 |
| 53 | 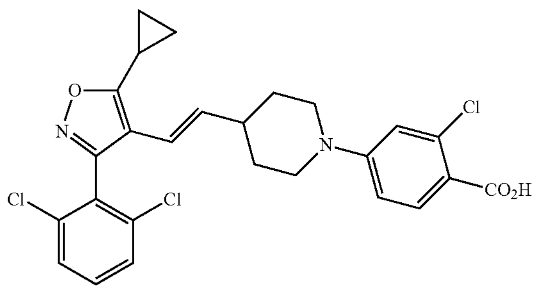 [SMILES: O=C(O)c1ccc(N2CCC(/C=C/c3c(-c4c(Cl)cccc4Cl)noc3C3CC3)CC2)cc1Cl] | MS (ESI) m/z: 516.9 [M + H]$^+$; EC$_{50}$ = 23; $^1$H NMR (500 MHz, DMSO-d$_6$) δ 7.63-7.71 (m, 3H), 7.59 (br d, J = 7.32 Hz, 1H), 6.81-6.89 (m, 2H), 6.15 (d, J = 16.48 Hz, 1H), 5.32 (dd, J = 6.87, 16.33 Hz, 1H), 3.75 (br d, J = 13.12 Hz, 2H), 2.83 (br s, 2H), 2.34 (br s, 1H), 2.24 (br s, 1H), 1.59 (br d, J = 12.82 Hz, 2H), 1.15 (br d, J = 8.54 Hz, 4H), 1.07 (br d, J = 2.7 Hz, 2H). | A2 |
| 54 | 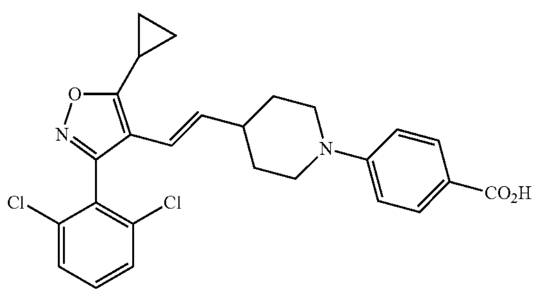 [SMILES: O=C(O)c1ccc(N2CCC(/C=C/c3c(-c4c(Cl)cccc4Cl)noc3C3CC3)CC2)cc1] | MS (ESI) m/z: 516.9 [M + H]$^+$; EC$_{50}$ = 15; $^1$H NMR (500 MHz, DMSO-d$_6$) δ 7.63-7.71 (m, 3H), 7.59 (br d, J = 7.32 Hz, 1H), 6.81-6.89 (m, 2H), 6.15 (d, J = 16.48 Hz, 1H), 5.32 (dd, J = 6.87, 16.33 Hz, 1H), 3.75 (br d, J = 13.12 Hz, 2H), 2.83 (br s, 2H), 2.34 (br s, 1H), 2.24 (br s, 1H), 1.59 (br d, J = 12.82 Hz, 2H), 1.15 (br d, J = 8.54 Hz, 4H), 1.07 (br d, J = 2.75 Hz, 2H). | A2 |
| 55 | 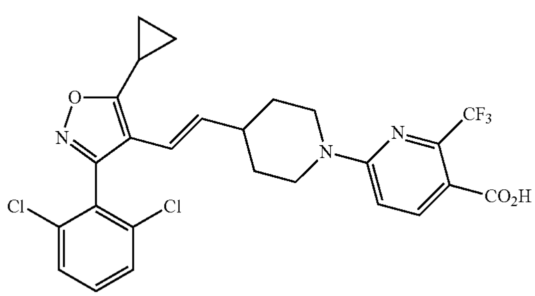 [SMILES: O=C(O)c1ccc(N2CCC(/C=C/c3c(-c4c(Cl)cccc4Cl)noc3C3CC3)CC2)nc1C(F)(F)F] | MS (ESI) m/z: 516.9 [M + H]$^+$; EC$_{50}$ = 90; $^1$H NMR (500 MHz, DMSO-d$_6$) δ 7.63-7.71 (m, 3H), 7.59 (br d, J = 7.32 Hz, 1H), 6.81-6.89 (m, 2H), 6.15 (d, J = 16.48 Hz, 1H), 5.32 (dd, J = 6.87, 16.33 Hz, 1H), 3.75 (br d, J = 13.12 Hz, 2H), 2.83 (br s, 2H), 2.34 (br s, 1H), 2.24 (br s, 1H), 1.59 (br d, J = 12.82 Hz, 2H), 1.15 (br d, J = 8.54 Hz, 4H), 1.07 (br d, J = 2.75 Hz, 2H). | A2 |
| 56 | 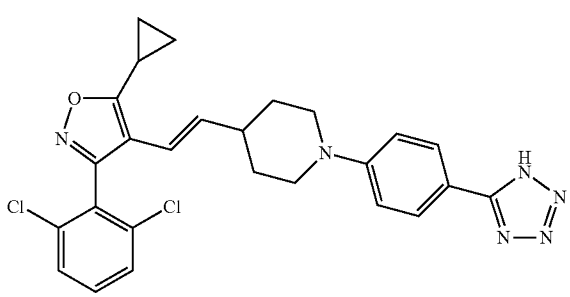 [SMILES: Clc1cccc(Cl)c1-c1noc(C2CC2)c1/C=C/C1CCN(c2ccc(-c3nnn[nH]3)cc2)CC1] | MS (ESI) m/z: 507.3 [M + H]$^+$; EC$_{50}$ = 3; $^1$H NMR (500 MHz, DMSO-d$_6$) δ 7.82 (d, J = 8.85 Hz, 2H), 7.62-7.67 (m, 2H), 7.54-7.60 (m, 1H), 7.03 (br d, J = 8.85 Hz, 2H), 6.17 (d, J = 16.48 Hz, 1H), 5.32 (dd, J = 6.87, 16.33 Hz, 1H), 3.74 (br d, J = 13.12 Hz, 2H), 2.81 (br t, J = 11.44 Hz, 2H), 2.28-2.41 (m, 1H), 2.23 (br s, 1H), 1.62 (br d, J = 11.90 Hz, 2H), 1.12-1.24 (m, 4H), 1.03-1.11 (m, 2H). | E |

TABLE 1-continued

| Ex. No. | Structure | LCMS, FXR EC$_{50}$ (nM) & NMR | Method |
|---|---|---|---|
| 57 | 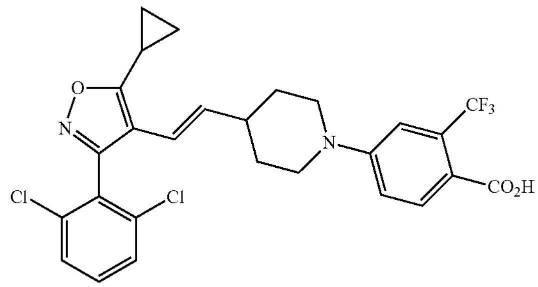 [SMILES: O=C(O)c1ccc(N2CCC(/C=C/c3c(-c4c(Cl)cccc4Cl)noc3C3CC3)CC2)cc1C(F)(F)F] | MS (ESI) m/z: 516.9 [M + H]$^+$; EC$_{50}$ = 45; $^1$H NMR (500 MHz, DMSO-d$_6$) δ 7.63-7.71 (m, 3H), 7.59 (br d, J = 7.32 Hz, 1H), 6.81-6.89 (m, 2H), 6.15 (d, J = 16.48 Hz, 1H), 5.32 (dd, J = 6.87, 16.33 Hz, 1H), 3.75 (br d, J = 13.12 Hz, 2H), 2.83 (br s, 2H), 2.34 (br s, 1H), 2.24 (br s, 1H), 1.59 (br d, J = 12.82 Hz, 2H), 1.15 (br d, J = 8.54 Hz, 4H), 1.07 (br d, J = 2.75 Hz, 2H). | A2 |
| 58 | 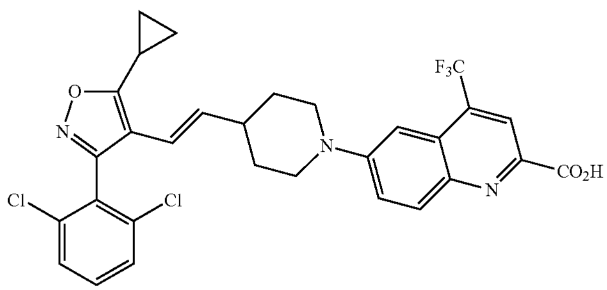 [SMILES: O=C(O)c1cc(C(F)(F)F)c2cc(N3CCC(/C=C/c4c(-c5c(Cl)cccc5Cl)noc4C4CC4)CC3)ccc2n1] | MS (ESI) m/z: 602.1 [M + H]$^+$; EC$_{50}$ = 24; $^1$H NMR (500 MHz, DMSO-d$_6$) δ 8.21 (s, 1H), 8.08 (d, J = 9.51 Hz, 1H), 7.86 (br dd, J = 1.98, 9.55 Hz, 1H), 7.81 (d, J = 8.25 Hz, 2H), 7.68-7.76 (m, 1H), 7.01-7.08 (m, 1H), 6.12-6.21 (m, 1H), 6.06 (d, J = 6.98 Hz, 1H), 3.97 (br d, J = 12.71 Hz, 2H), 3.02 (br t, J = 11.70 Hz, 2H), 2.40-2.48 (m, 1H), 2.08 (s, 1H), 1.76 (br d, J = 11.44 Hz, 2H), 1.38 (br d, J = 10.10 Hz, 2H), 1.03 (br dd, J = 2.27, 8.08 Hz, 2H), 0.91-0.96 (m, 2H). | A2 |
| 59 | 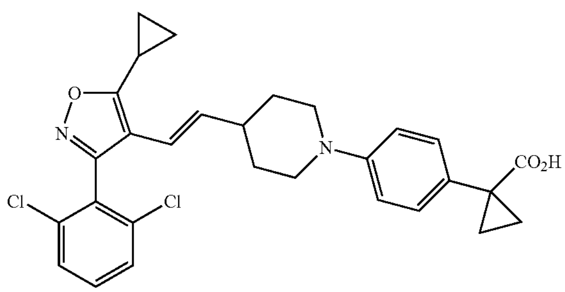 [SMILES: O=C(O)C1(c2ccc(N3CCC(/C=C/c4c(-c5c(Cl)cccc5Cl)noc4C4CC4)CC3)cc2)CC1] | MS (ESI) m/z: 523.2 [M + H]$^+$; EC$_{50}$ = 214; $^1$H NMR (500 MHz, DMSO-d$_6$) δ 7.65 (s, 2H), 7.56-7.62 (m, 1H), 7.10-7.15 (m, 2H), 6.83-6.90 (m, 2H), 6.17 (d, J = 16.17 Hz, 1H), 5.34 (dd, J = 7.02, 16.17 Hz, 1H), 3.53 (br s, 1H), 2.89 (s, 1H), 2.73 (s, 2H), 2.31-2.38 (m, 1H), 2.11-2.20 (m, 1H), 1.60-1.67 (m, 2H), 1.38 (br d, J = 2.44 Hz, 2H), 1.25 (br d, J = 11.90 Hz, 2H), 1.14-1.19 (m, 2H), 1.05-1.11 (m, 2H), 1.04 (br d, J = 2.75 Hz, 2H). | A2 |
| 60 | 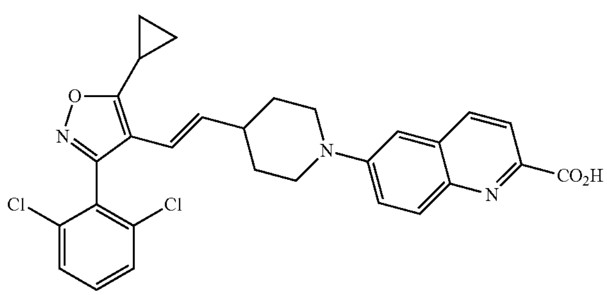 [SMILES: O=C(O)c1ccc2cc(N3CCC(/C=C/c4c(-c5c(Cl)cccc5Cl)noc4C4CC4)CC3)ccc2n1] | MS (ESI) m/z: 523.2 [M + H]$^+$; EC$_{50}$ = 17; $^1$H NMR (500 MHz, DMSO-d$_6$) δ 7.65 (s, 2H), 7.56-7.62 (m, 1H), 7.10-7.15 (m, 2H), 6.83-6.90 (m, 2H), 6.17 (d, J = 16.17 Hz, 1H), 5.34 (dd, J = 7.02, 16.17 Hz, 1H), 3.53 (br s, 1H), 2.89 (s, 1H), 2.73 (s, 2H), 2.31-2.38 (m, 1H), 2.11-2.20 (m, 1H), 1.60-1.67 (m, 2H), 1.38 (br d, J = 2.44 Hz, 2H), 1.25 (br d, J = 11.90 Hz, 2H), 1.14-1.19 (m, 2H), 1.05-1.11 (m, 2H), 1.04 (br d, J = 2.75 Hz, 2H). | A2 |
| 61 | 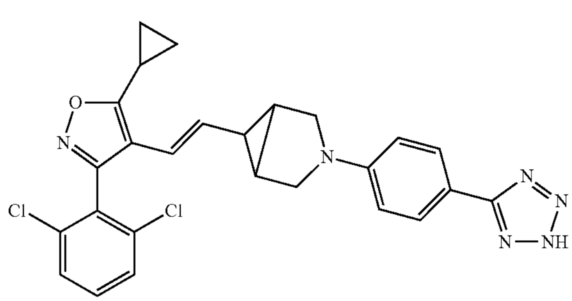 [SMILES: Clc1cccc(Cl)c1-c1noc(C2CC2)c1/C=C/C1C2CN(c3ccc(-c4nn[nH]n4)cc3)CC12] | MS (ESI) m/z: 505.2 [M + H]$^+$; EC$_{50}$ = 41; $^1$H NMR (500 MHz, DMSO-d$_6$) δ 7.79 (br d, J = 8.54 Hz, 2H), 7.63-7.68 (m, 2H), 7.60 (br d, J = 7.02 Hz, 1H), 6.64 (br d, J = 8.54 Hz, 2H), 6.09-6.17 (m, 1H), 5.13 (dd, J = 9.00, 16.02 Hz, 1H), 2.34 (br t, J = 5.04 Hz, 1H), 1.68 (br s, 2H), 1.37 (br d, J = 8.85 Hz, 1H), 1.13-1.18 (m, 2H), 1.07 (br d, J = 2.44 Hz, 2H) additional signals were lost due to water suppression. | A1 |

TABLE 1-continued

| Ex. No. | Structure | LCMS, FXR EC$_{50}$ (nM) & NMR | Method |
|---|---|---|---|
| 62 | 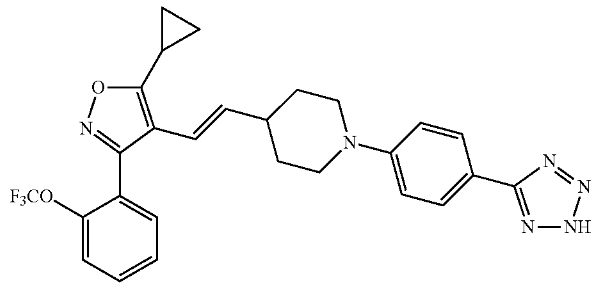 [SMILES: FC(F)(F)Oc1ccccc1-c1noc(C2CC2)c1/C=C/C1CCN(c2ccc(-c3nn[nH]n3)cc2)CC1] | MS (ESI) m/z: 523.2 [M + H]$^+$; EC$_{50}$ = 20; $^1$H NMR (500 MHz, DMSO-d$_6$) δ 7.85 (br d, J = 8.84 Hz, 2H), 7.70 (br s, 1H), 7.52-7.59 (m, 3H), 7.08 (br d, J = 8.85 Hz, 2H), 6.11 (d, J = 16.17 Hz, 1H), 5.62 (dd, J = 6.87, 16.33 Hz, 1H), 3.84 (br d, J = 12.82 Hz, 2H), 2.85 (br t, J = 11.60 Hz, 2H), 2.31 (br dd, J = 5.04, 8.39 Hz, 2H), 1.69 (br d, J = 11.90 Hz, 2H), 1.30 (br d, J = 9.46 Hz, 2H), 1.12-1.20 (m, 2H), 1.04-1.09 (m, 2H). | A1 |
| 63 | 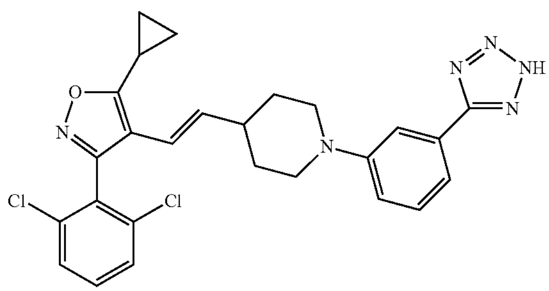 [SMILES: Clc1cccc(Cl)c1-c1noc(C2CC2)c1/C=C/C1CCN(c2cccc(-c3nn[nH]n3)c2)CC1] | MS (ESI) m/z: 507.2 [M + H]$^+$; EC$_{50}$ = 216; $^1$H NMR (500 MHz, DMSO-d$_6$) δ 7.67 (br d, J = 7.93 Hz, 2H), 7.60 (br s, 1H), 7.54 (br s, 1H), 7.39 (br d, J = 7.32 Hz, 1H), 7.20-7.29 (m, 1H), 6.86-6.93 (m, 1H), 6.19 (br d, J = 16.17 Hz, 1H), 5.35 (br dd, J = 6.41, 16.48 Hz, 1H), 3.58-3.65 (m, 1H), 2.74 (br s, 2H), 2.37 (br s, 1H), 2.18 (br s, 1H), 1.92 (s, 2H), 1.65 (br d, J = 12.82 Hz, 2H), 1.27 (br d, J = 10.68 Hz, 2H), 1.17 (br d, J = 5.80 Hz, 2H), 1.09 (br s, 2H). | A1 |
| 64 | 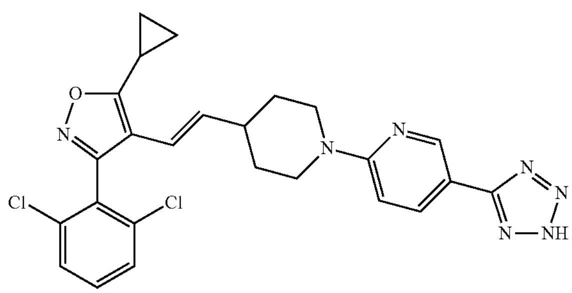 [SMILES: Clc1cccc(Cl)c1-c1noc(C2CC2)c1/C=C/C1CCN(c2ccc(-c3nn[nH]n3)cn2)CC1] | MS (ESI) m/z: 508.2 [M + H]$^+$; EC$_{50}$ = 30; $^1$H NMR (500 MHz, DMSO-d$_6$) δ 7.65 (br d, J = 7.63 Hz, 2H), 7.58 (br d, J = 7.32 Hz, 1H), 6.91-7.04 (m, 1H), 6.10-6.21 (m, 1H), 5.28-5.39 (m, 1H), 4.27 (br d, J = 8.24 Hz, 2H), 2.91 (br s, 2H), 2.34 (br s, 2H), 1.54-1.67 (m, 2H), 1.15 (br d, J = 6.71 Hz, 4H), 1.07 (br s, 2H) additional signals were lost due to water suppression. | E |
| 65 | 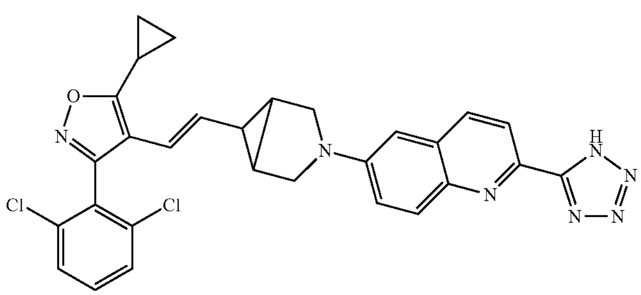 [SMILES: Clc1cccc(Cl)c1-c1noc(C2CC2)c1/C=C/C1C2CN(c3ccc4nc(-c5nnn[nH]5)ccc4c3)CC12] | MS (ESI) m/z: 556.1 [M + H]$^+$; EC$_{50}$ = 189; $^1$H NMR (500 MHz, DMSO-d$_6$) δ 8.14-8.21 (m, 1H), 8.07 (br d, J = 8.55 Hz, 1H), 7.91 (br d, J = 9.16 Hz, 1H), 7.64-7.69 (m, 2H), 7.61 (br d, J = 7.32 Hz, 1H), 7.30 (br d, J = 9.46 Hz, 1H), 6.80 (br s, 1H), 6.09-6.21 (m, 1H), 5.16 (br dd, J = 9.00, 16.02 Hz, 1H), 3.70 (br d, J = 9.77 Hz, 2H), 2.35 (br s, 1H), 1.72 (br s, 2H), 1.39-1.46 (m, 1H), 1.13-1.19 (m, 2H), 1.08 (br d, J = 2.75 Hz, 2H) additional signals were lost due to water suppresiion. | E |
| 66 | 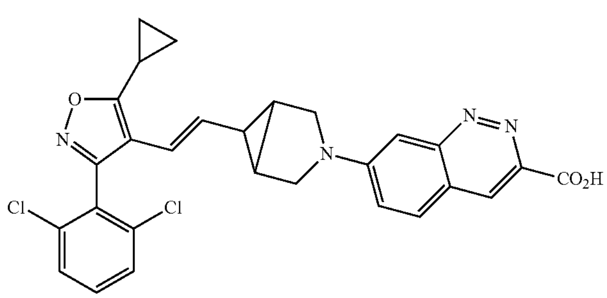 [SMILES: O=C(O)c1cc2ccc(N3CC4C(/C=C/c5c(-c6c(Cl)cccc6Cl)noc5C5CC5)C4C3)cc2nn1] | MS (ESI) m/z 533.1 [M + H]$^+$; EC$_{50}$ = 227. | A2 |

TABLE 1-continued

| Ex. No. | Structure | LCMS, FXR EC$_{50}$ (nM) & NMR | Method |
|---|---|---|---|
| 67 | 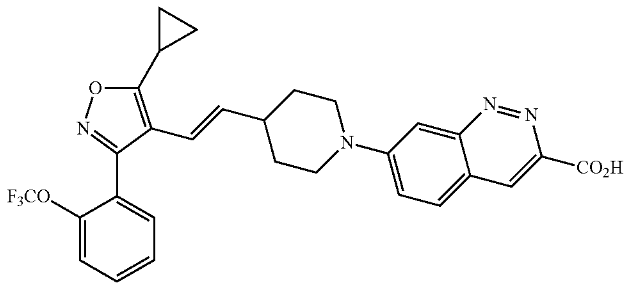 [SMILES: O=C(O)c1cc2ccc(N3CCC(/C=C/c4c(-c5ccccc5OC(F)(F)F)noc4C4CC4)CC3)cc2nn1] | MS (ESI) m/z: 551.2 [M + H]$^+$; EC$_{50}$ = 1212; $^1$H NMR (500 MHz, DMSO-d$_6$) δ 8.47 (br s, 1H), 7.95 (br d, J = 9.16 Hz, 1H), 7.71-7.79 (m, 1H), 7.63 (br s, 1H), 7.45-7.55 (m, 4H), 6.07 (br d, J = 16.17 Hz, 1H), 5.53-5.63 (m, 1H), 4.02 (br d, J = 12.82 Hz, 2H), 2.98 (br s, 2H), 2.21-2.35 (m, 2H), 1.69 (br d, J = 11.90 Hz, 2H), 1.29 (br d, J = 10.07 Hz, 2H), 1.05-1.14 (m, 2H), 0.96-1.04 (m, 2H). | A2 |
| 68 | 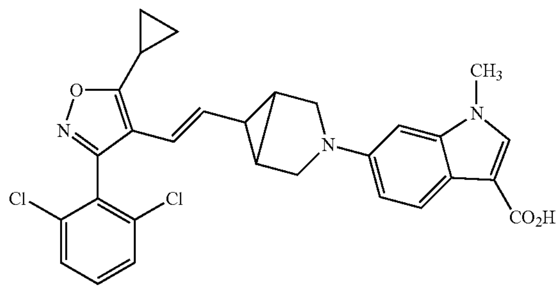 [SMILES: Cn1cc(C(=O)O)c2ccc(N3CC4C(/C=C/c5c(-c6c(Cl)cccc6Cl)noc5C5CC5)C4C3)cc21] | MS (ESI) m/z: 534.1 [M + H]$^+$; EC$_{50}$ = 17; $^1$H NMR (500 MHz, DMSO-d$_6$) δ 7.61-7.69 (m, 3H), 7.49-7.61 (m, 2H), 6.54 (br s, 1H), 6.46 (br s, 1H), 6.12 (br d, J = 16.17 Hz, 1H), 5.01-5.14 (m, 1H), 3.63 (br d, J = 4.58 Hz, 1H), 3.11-3.18 (m, 2H), 2.32 (br d, J = 3.36 Hz, 1H), 1.60 (br s, 2H), 1.41 (br d, J = 7.02 Hz, 1H), 1.15 (br d, J = 5.80 Hz, 2H), 1.05 (br d, J = 2.75 Hz, 2H) additional signals were lost due to water suppression. | A2 |
| 69 | 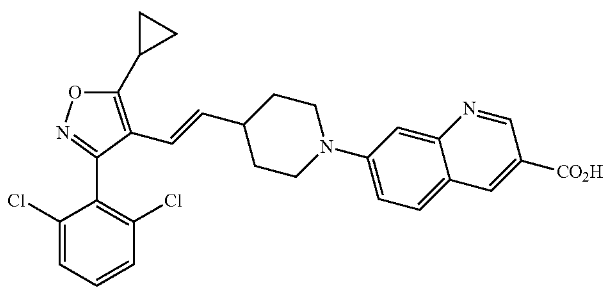 [SMILES: O=C(O)c1cnc2cc(N3CCC(/C=C/c4c(-c5c(Cl)cccc5Cl)noc4C4CC4)CC3)ccc2c1] | MS (ESI) m/z: 534.4 [M + H]$^+$; EC$_{50}$ = 31; $^1$H NMR (500 MHz, DMSO-d$_6$) δ 8.67 (br s, 1H), 7.92 (br s, 1H), 7.64-7.70 (m, 2H), 7.60 (br d, J = 7.32 Hz, 1H), 7.49 (br d, J = 9.16 Hz, 1H), 7.21 (br s, 1H), 6.20 (d, J = 16.17 Hz, 1H), 5.36 (dd, J = 6.71, 16.17 Hz, 1H), 3.93 (br d, J = 12.82 Hz, 2H), 2.95 (br s, 2H), 2.35-2.40 (m, 1H), 2.26-2.34 (m, 1H), 1.69 (br d, J = 11.60 Hz, 2H), 1.20-1.33 (m, 3H), 1.14-1.19 (m, 2H), 1.09 (br d, J = 2.75 Hz, 2H). | A2 |
| 70 | 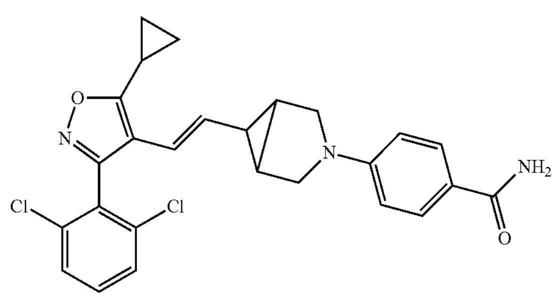 [SMILES: NC(=O)c1ccc(N2CC3C(/C=C/c4c(-c5c(Cl)cccc5Cl)noc4C4CC4)C3C2)cc1] | MS (ESI) m/z: 480.1 [M + H]$^+$; EC$_{50}$ = 377; $^1$H NMR (500 MHz, DMSO-d$_6$) δ 7.70 (d, J = 8.6 Hz, 2H), 7.67-7.62 (m, 2H), 7.59 (dd, J = 9.2, 6.8 Hz, 1H), 6.50 (d, J = 8.6 Hz, 2H), 6.12 (d, J = 16.1 Hz, 1H), 5.18 (dd, J = 16.1, 8.7 Hz, 1H), 3.56 (d, J = 9.9 Hz, 2H), 3.20-3.18 (two proton signals were lost due to water suppression), 2.32 (td, J = 8.5, 4.3 Hz, 1H), 1.71-1.62 (m, 2H), 1.36 (dt, J = 8.8, 3.3 Hz, 1H), 1.23-1.01 (m, 4H). | F |
| 71 | 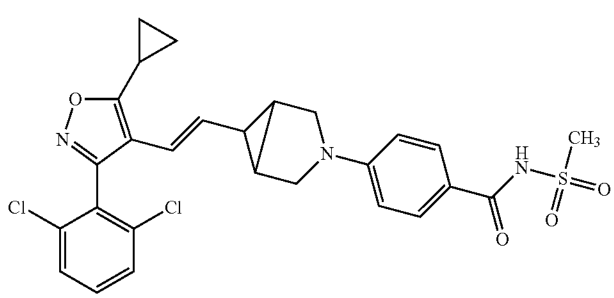 [SMILES: CS(=O)(=O)NC(=O)c1ccc(N2CC3C(/C=C/c4c(-c5c(Cl)cccc5Cl)noc4C4CC4)C3C2)cc1] | MS (ESI) m/z: 558.1 [M + H]$^+$; EC$_{50}$ = 83; $^1$H NMR (500 MHz, DMSO-d$_6$) δ 7.77 (d, J = 8.6 Hz, 2H), 7.66 (d, J = 8.0 Hz, 2H), 7.60 (dd, J = 9.1, 7.0 Hz, 1H), 6.54 (d, J = 8.7 Hz, 2H), 6.13 (d, J = 16.1 Hz, 1H), 5.14 (dd, J = 16.1, 8.9 Hz, 1H), 3.58 (d, J = 10.2 Hz, 2H), 3.31 (s, 3H), 3.20-3.18 (two protons signals were lost due to water suppression), 2.44-2.25 (m, 1H), 1.69 (s, 2H), 1.37-1.24 (m, 1H), 1.24-0.99 (m, 4H). | G |

TABLE 1-continued

| Ex. No. | Structure | LCMS, FXR EC$_{50}$ (nM) & NMR | Method |
|---|---|---|---|
| 72 | 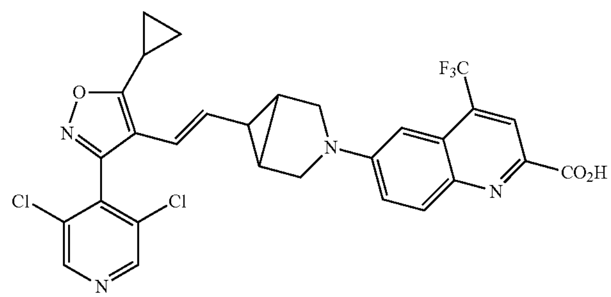 [SMILES: O=C(O)c1cc(C(F)(F)F)c2cc(N3CC4C(/C=C/c5c(-c6c(Cl)cncc6Cl)noc5C5CC5)C4C3)ccc2n1] | MS (ESI) m/z: 600.9 [M + H]$^+$; EC$_{50}$ = 98; $^1$H NMR (500 MHz, Methanol-d$_4$) δ 8.71 (s, 2H), 8.25 (s, 1H), 8.07 (d, J = 9.35 Hz, 1H), 7.36-7.52 (m, 1H), 6.79 (br s, 1H), 6.16 (d, J = 16.23 Hz, 1H), 5.27 (dd, J = 8.80, 15.96 Hz, 1H), 3.72 (s, 2H), 3.45-3.54 (m, 2H), 2.23-2.30 (m, 1H), 1.83-1.89 (m, 2H), 1.39-1.43 (m, 1H), 1.17-1.21 (m, 2H), 1.14-1.17 (m, 2H). | A2 |
| 73 | 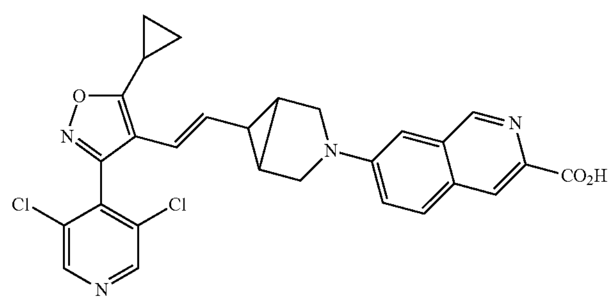 [SMILES: O=C(O)c1cc2ccc(N3CC4C(/C=C/c5c(-c6c(Cl)cncc6Cl)noc5C5CC5)C4C3)cc2cn1] | MS (ESI) m/z: 533.0 [M + H]$^+$; EC$_{50}$ = 673; $^1$H NMR (500 MHz, Methanol-d$_4$) δ 9.21 (s, 1H), 8.72 (s, 2H), 8.70 (s, 1H), 8.12 (s, 1H), 7.62 (br d, J = 7.43 Hz, 1H), 7.25 (br s, 1H), 6.16 (d, J = 16.23 Hz, 1H), 5.24-5.35 (m, 1H), 3.80 (d, J = 10.18 Hz, 2H), 3.57 (br d, J = 9.35 Hz, 2H), 2.27 (s, 1H), 1.18-1.22 (m, 2H), 1.13-1.18 (m, 2H). | A2 |
| 74 | 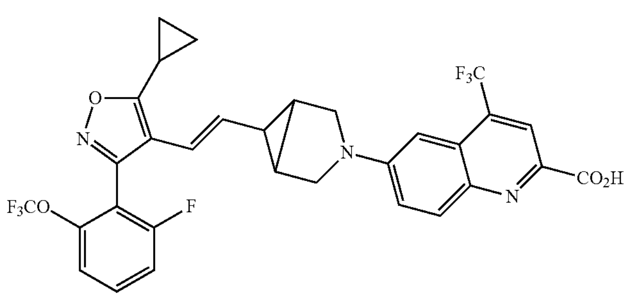 [SMILES: O=C(O)c1cc(C(F)(F)F)c2cc(N3CC4C(/C=C/c5c(-c6c(F)cccc6OC(F)(F)F)noc5C5CC5)C4C3)ccc2n1] | MS (ESI) m/z: 534.4 [M + H]$^+$; EC$_{50}$ = 308; $^1$H NMR (500 MHz, DMSO-d$_6$) δ 8.16 (s, 1H), 8.05 (d, J = 9.46 Hz, 1H), 7.76 (br d, J = 6.41 Hz, 1H), 7.43-7.54 (m, 3H), 6.68 (br s, 1H), 6.11 (d, J = 15.87 Hz, 1H), 5.31 (dd, J = 9.00, 16.02 Hz, 1H), 3.85 (br s, 1H), 3.70 (br d, J = 10.07 Hz, 1H), 2.98 (s, 1H), 2.92 (br d, J = 6.10 Hz, 1H), 2.32 (br d, J = 4.88 Hz, 1H), 1.47-1.56 (m, 1H), 1.39-1.45 (m, 1H), 1.36 (br d, J = 6.41 Hz, 1H), 1.12-1.18 (m, 2H), 1.02-1.10 (m, 2H). | A2 |
| 75 | 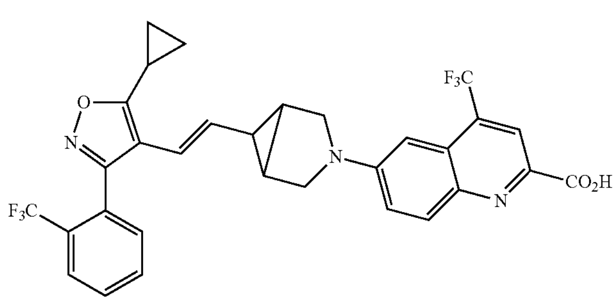 [SMILES: O=C(O)c1cc(C(F)(F)F)c2cc(N3CC4C(/C=C/c5c(-c6ccccc6C(F)(F)F)noc5C5CC5)C4C3)ccc2n1] | MS (ESI) m/z: 600.1 [M + H]$^+$; EC$_{50}$ = 577; $^1$H NMR (500 MHz, DMSO-d$_6$) δ 8.13 (s, 1H), 8.01 (br d, J = 9.34 Hz, 1H), 7.87 (br d, J = 7.74 Hz, 1H), 7.68-7.80 (m, 2H), 7.46 (br d, J = 7.41 Hz, 1H), 7.41 (dd, J = 1.85, 9.42 Hz, 1H), 6.66 (br s, 1H), 6.02 (d, J = 16.16 Hz, 1H), 5.13-5.24 (m, 1H), 3.65 (br d, J = 10.10 Hz, 2H), 3.45 (br d, J = 9.26 Hz, 2H), 2.24 (br s, 1H), 1.72 (br s, 2H), 1.33 (br d, J = 8.67 Hz, 1H), 1.11 (br dd, J = 2.57, 8.12 Hz, 2H), 0.99-1.04 (m, 2H). | A2 |
| 76 | 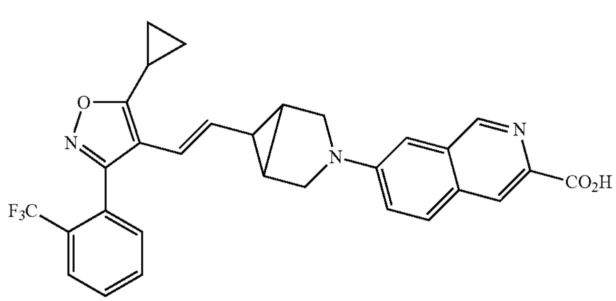 [SMILES: O=C(O)c1cc2ccc(N3CC4C(/C=C/c5c(-c6ccccc6C(F)(F)F)noc5C5CC5)C4C3)cc2cn1] | MS (ESI) m/z: 532.2 [M + H]$^+$; EC$_{50}$ = 413; $^1$H NMR (500 MHz, Methanol-d$_4$) δ 9.19 (s, 1H), 8.67 (s, 1H), 8.10 (d, J = 9.08 Hz, 1H), 7.88 (d, J = 7.43 Hz, 1H), 7.69-7.81 (m, 2H), 7.59 (dd, J = 1.65, 9.08 Hz, 1H), 7.45 (d, J = 7.15 Hz, 1H), 7.21 (s, 1H), 6.10 (d, J = 16.23 Hz, 1H), 5.21 (dd, J = 8.67, 16.09 Hz, 1H), 3.77 (d, J = 9.90 Hz, 2H), 3.55 (br s, 2H), 2.22 (s, 1H), 1.76 (br s, 2H), 1.35-1.39 (m, 1H), 1.12-1.19 (m, 4H). | A2 |

TABLE 1-continued

| Ex. No. | Structure | LCMS, FXR EC$_{50}$ (nM) & NMR | Method |
|---|---|---|---|
| 77 | 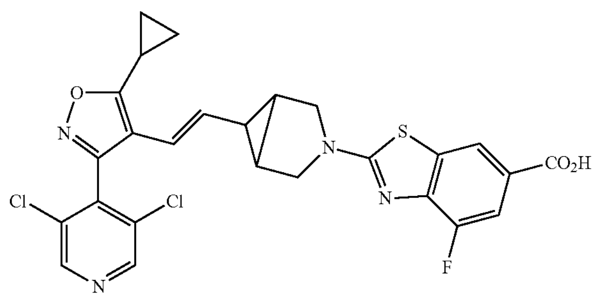 [SMILES: O=C(O)c1cc(F)c2nc(N3CC4C(/C=C/c5c(-c6c(Cl)cncc6Cl)noc5C5CC5)C4C3)sc2c1] | MS (ESI) m/z: 557.1 [M + H]$^+$; EC$_{50}$ = 786; $^1$H NMR (500 MHz, DMSO-d$_6$) δ 8.80 (s, 2H), 8.16 (s, 1H), 7.57 (br d, J = 11.61 Hz, 1H), 6.12 (d, J = 15.99 Hz, 1H), 5.30 (dd, J = 8.54, 16.11 Hz, 1H), 3.66-3.74 (m, 2H), 3.41-3.59 (m, 2H), 2.27-2.36 (m, 1H), 1.80 (br s, 2H), 1.38-1.46 (m, 1H), 1.17 (br dd, J = 2.57, 8.20 Hz, 2H), 1.03-1.12 (m, 2H). | A2 |
| 78 | 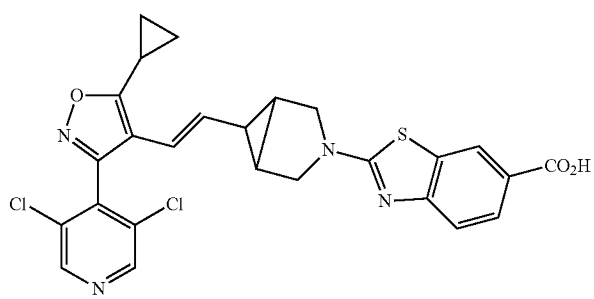 [SMILES: O=C(O)c1ccc2nc(N3CC4C(/C=C/c5c(-c6c(Cl)cncc6Cl)noc5C5CC5)C4C3)sc2c1] | MS (ESI) m/z: 538.8 [M + H]$^+$; EC$_{50}$ = 515; $^1$H NMR (500 MHz, DMSO-d$_6$) δ 8.76 (s, 2H), 8.26 (s, 1H), 7.80 (br d, J = 8.41 Hz, 1H), 7.41 (d, J = 8.41 Hz, 1H), 6.09 (d, J = 16.07 Hz, 1H), 5.25 (dd, J = 8.58, 16.07 Hz, 1H), 3.58-3.70 (m, 4H), 2.28 (br t, J = 4.88 Hz, 1H), 1.75 (br s, 2H), 1.36 (br d, J = 8.50 Hz, 1H), 1.13 (br dd, J = 2.61, 8.16 Hz, 2H), 1.00-1.06 (m, 2H). | A1 |
| 79 | 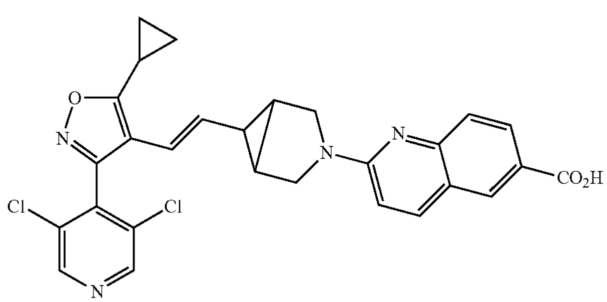 [SMILES: O=C(O)c1ccc2nc(N3CC4C(/C=C/c5c(-c6c(Cl)cncc6Cl)noc5C5CC5)C4C3)ccc2c1] | MS (ESI) m/z: 533.0 [M + H]$^+$; EC$_{50}$ = 1160; $^1$H NMR (500 MHz, DMSO-d$_6$) δ 8.85 (s, 2H), 8.47 (s, 1H), 8.37 (br d, J = 9.46 Hz, 1H), 8.15 (s, 1H), 7.85 (br d, J = 8.54 Hz, 1H), 7.15 (br d, J = 6.41 Hz, 1H), 6.09 (d, J = 16.17 Hz, 1H), 5.33 (dd, J = 8.85, 16.17 Hz, 1H), 3.98 (br d, J = 11.60 Hz, 2H), 3.77 (br s, 1H), 1.60-3.61 (m, 4H), 1.41-1.51 (m, 1H), 1.13-1.22 (m, 2H), 1.05-1.13 (m, 2H). | A2 |
| 80 | 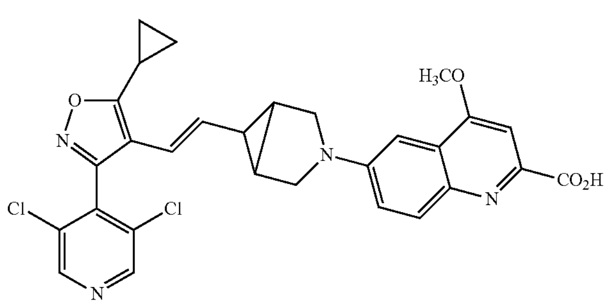 [SMILES: COc1cc(C(=O)O)nc2ccc(N3CC4C(/C=C/c5c(-c6c(Cl)cncc6Cl)noc5C5CC5)C4C3)cc12] | MS (ESI) m/z: 563.2 [M + H]$^+$; EC$_{50}$ = 38; $^1$H NMR (500 MHz, DMSO-d$_6$) δ 8.83 (s, 2H), 7.92 (br d, J = 9.17 Hz, 1H), 7.43 (s, 1H), 7.30 (br d, J = 9.17 Hz, 1H), 6.86 (s, 1H), 6.13 (d, J = 16.07 Hz, 1H), 5.31 (dd, J = 8.71, 16.03 Hz, 1H), 4.08 (s, 3H), 3.67 (br d, J = 9.76 Hz, 2H), 3.40 (br d, J = 8.92 Hz, 1H), 2.35 (br s, 1H), 1.91 (s, 1H), 1.80 (br s, 2H), 1.41-1.47 (m, 1H), 1.18 (br dd, J = 2.52, 8.16 Hz, 2H), 1.06-1.13 (m, 2H). | A2 |
| 81 | 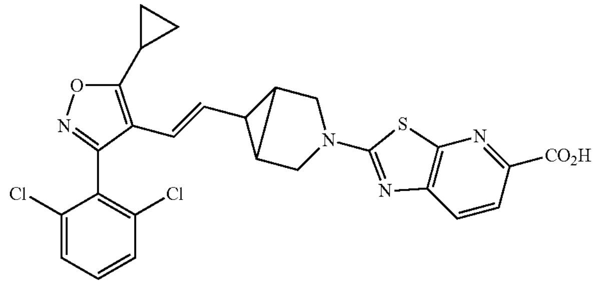 [SMILES: O=C(O)c1ccc2nc(N3CC4C(/C=C/c5c(-c6c(Cl)cccc6Cl)noc5C5CC5)C4C3)sc2n1] | MS (ESI) m/z: 539.0 [M + H]$^+$; EC$_{50}$ = 89. | A1 |

TABLE 1-continued

| Ex. No. | Structure | LCMS, FXR EC$_{50}$ (nM) & NMR | Method |
|---|---|---|---|
| 82 | 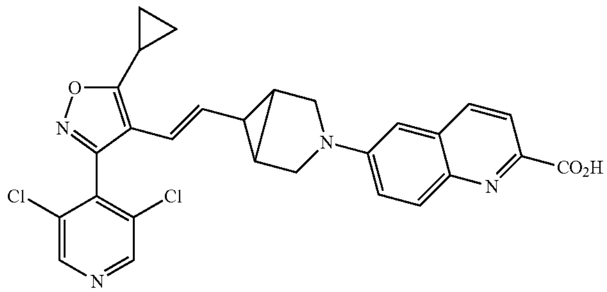 [SMILES: O=C(O)c1ccc2cc(N3CC4C(/C=C/c5c(-c6c(Cl)cncc6Cl)noc5C5CC5)C4C3)ccc2n1] | MS (ESI) m/z: 532.9 [M + H]$^+$; EC$_{50}$ = 267; $^1$H NMR (500 MHz, Methanol-d$_4$) δ 7.19 (s, 2H), 6.94 (br d, J = 8.53 Hz, 1H), 6.60 (dd, J = 4.26, 8.94 Hz, 2 H), 5.99 (br d, J = 9.63 Hz, 1H), 5.38 (s, 1H), 4.62 (d, J = 15.96 Hz, 1H), 3.75 (dd, J = 8.80, 15.96 Hz, 1H), 2.24 (d, J = 10.18 Hz, 2H), 1.98 (br d, J = 9.35 Hz, 2H), 0.73 (s, 1H), 0.27 (br s, 2H), −0.11 (br d, J = 8.80 Hz, 1H), −0.39- −0.32 (m, 4H). | A2 |
| 83 | 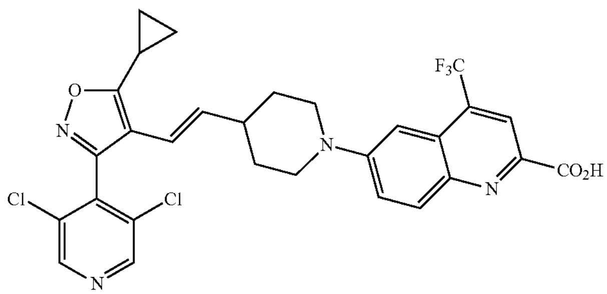 [SMILES: O=C(O)c1cc(C(F)(F)F)c2cc(N3CCC(/C=C/c4c(-c5c(Cl)cncc5Cl)noc4C4CC4)CC3)ccc2n1] | MS (ESI) m/z: 603.0 [M + H]$^+$; EC$_{50}$ = 42; $^1$H NMR (400 MHz, Methanol-d$_4$) δ 7.16 (s, 2H), 6.76 (s, 1H), 6.57 (d, J = 9.46 Hz, 1H), 6.21 (dd, J = 2.64, 9.68 Hz, 1H), 5.63 (br s, 1H), 4.65 (dd, J = 1.10, 16.29 Hz, 1H), 3.91-4.02 (m, 1H), 2.35-2.47 (m, 2H), 1.42-1.54 (m, 2H), 0.66-0.86 (m, 2H), 0.24 (br s, 2H), −0.21- −0.06 (m, 2H), −0.41- −0.32 (m, 4H). | A2 |
| 84 | 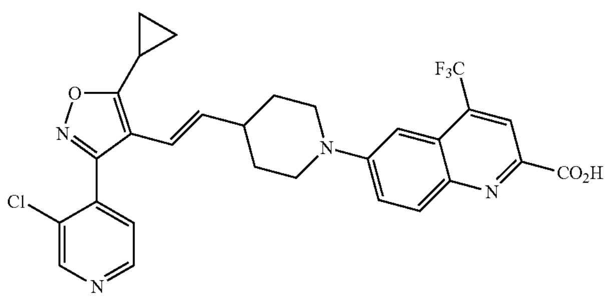 [SMILES: O=C(O)c1cc(C(F)(F)F)c2cc(N3CCC(/C=C/c4c(-c5ccncc5Cl)noc4C4CC4)CC3)ccc2n1] | MS (ESI) m/z: 569.0 [M + H]$^+$; EC$_{50}$ = 215; $^1$H NMR (400 MHz, Methanol-d$_4$) δ 7.19 (s, 1H), 7.06 (d, J = 4.84 Hz, 1H), 6.75 (s, 1H), 6.57 (d, J = 9.68 Hz, 1H), 6.21 (dd, J = 2.64, 9.68 Hz, 1H), 5.97 (d, J = 4.84 Hz, 1H), 5.65 (br s, 1H), 4.64 (dd, J = 1.10, 16.29 Hz, 1H), 4.05 (dd, J = 7.04, 16.29 Hz, 1H), 2.43 (br d, J = 13.20 Hz, 2H), 1.49 (br d, J = 1.32 Hz, 2H), 0.75-0.86 (m, 1H), 0.68 (s, 1H), 0.21-0.34 (m, 2H), −0.13 (br s, 2H), −0.46- −0.34 (m, 4H). | A2 |
| 85 | 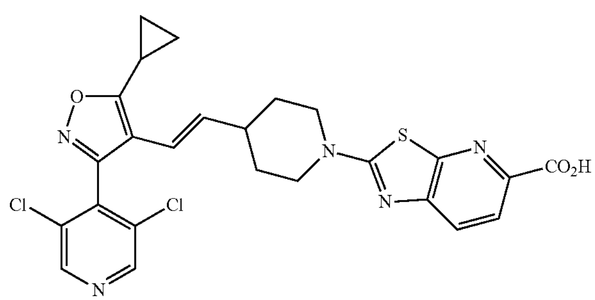 [SMILES: O=C(O)c1ccc2nc(N3CCC(/C=C/c4c(-c5c(Cl)cncc5Cl)noc4C4CC4)CC3)sc2n1] | MS (ESI) m/z: 542.0 [M + H]$^+$; EC$_{50}$ = 156; $^1$H NMR (500 MHz, Methanol-d$_4$) δ 8.73 (s, 2H), 8.11 (d, J = 8.3 Hz, 1H), 7.76 (d, J = 8.5 Hz, 1H), 6.23 (d, J = 16.2 Hz, 1H), 5.51 (dd, J = 16.2, 7.2 Hz, 1H), 4.19 (br d, J = 11.3 Hz, 2H), 3.31-3.26 (m, 2H), 2.44 (br dd, J = 6.9, 3.6 Hz, 2H), 2.34-2.22 (m, 1H), 1.82 (br d, J = 12.4 Hz, 2H), 1.50-1.32 (m, 2H), 1.26-1.15 (m, 4H). | A1 |
| 86 | 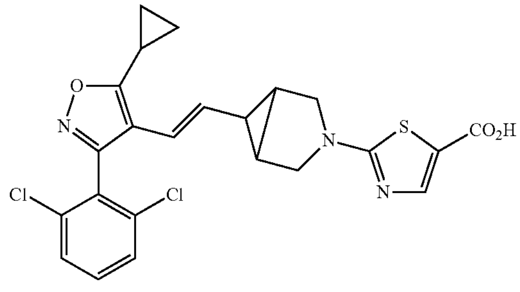 [SMILES: O=C(O)c1cnc(N2CC3C(/C=C/c4c(-c5c(Cl)cccc5Cl)noc4C4CC4)C3C2)s1] | MS (ESI) m/z: 487.9 [M + H]$^+$; EC$_{50}$ = 1013; $^1$H NMR (500 MHz, DMSO-d$_6$) δ 7.71 (s, 1H), 7.65-7.52 (m, 3H), 6.11 (d, J = 16.1 Hz, 1H), 5.16 (dd, J = 16.0, 8.6 Hz, 1H), 3.69-3.53 (m, 2H), 2.55 (m, 2H), 2.34-2.24 (m, 1H), 1.69 (br s, 2H), 1.37-1.29 (m, 1H), 1.21-1.12 (m, 2H), 1.09-1.01 (m, 2H). | A2 |

TABLE 1-continued

| Ex. No. | Structure | LCMS, FXR EC$_{50}$ (nM) & NMR | Method |
|---|---|---|---|
| 87 | 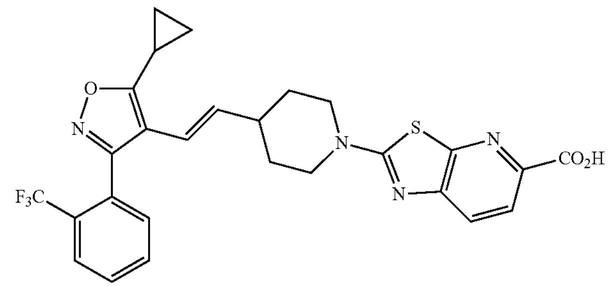 [SMILES: O=C(O)c1ccc2nc(N3CCC(/C=C/c4c(-c5ccccc5C(F)(F)F)noc4C4CC4)CC3)sc2n1] | MS (ESI) m/z: 541.0 [M + H]$^+$; EC$_{50}$ = 26; $^1$H NMR (500 MHz, DMSO-d$_6$) δ 7.97 (d, J = 8.4 Hz, 1H), 7.90 (br d, J = 7.7 Hz, 1H), 7.82-7.69 (m, 3H), 7.47 (br d, J = 7.5 Hz, 1H), 6.07 (d, J = 16.2 Hz, 1H), 5.39 (dd, J = 16.2, 6.8 Hz, 1H), 4.01 (br d, J = 13.3 Hz, 2H), 3.24 (br t, J = 11.6 Hz, 2H), 2.39-2.21 (m, 2H), 1.69 (br d, J = 10.9 Hz, 2H), 1.28-1.11 (m, 4H), 1.08-1.00 (m, 2H). | A1 |
| 88 | 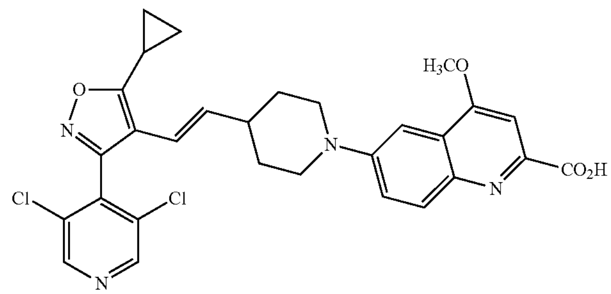 [SMILES: COc1cc(C(=O)O)nc2ccc(N3CCC(/C=C/c4c(-c5c(Cl)cncc5Cl)noc4C4CC4)CC3)cc12] | MS (ESI) m/z: 565.0 [M + H]$^+$; EC$_{50}$ = 5; $^1$H NMR (500 MHz, Methanol-d$_4$) δ 8.71 (s, 2H), 8.15 (d, J = 9.63 Hz, 1H), 7.89 (dd, J = 2.48, 9.63 Hz, 1H), 7.76 (s, 1H), 7.44 (d, J = 2.48 Hz, 1H), 6.20 (dd, J = 1.10, 16.23 Hz, 1H), 5.43-5.54 (m, 1H), 4.35 (s, 3H), 3.98 (br d, J = 13.20 Hz, 2H), 2.97-3.07 (m, 2H), 2.32-2.40 (m, 1H), 2.22-2.31 (m, 1H), 1.80 (br d, J = 11.00 Hz, 2H), 1.40 (br dd, J = 2.34, 11.42 Hz, 2H), 1.19-1.22 (m, 2H), 1.17 (td, J = 2.79, 5.16 Hz, 2H). | A2 |
| 89 | 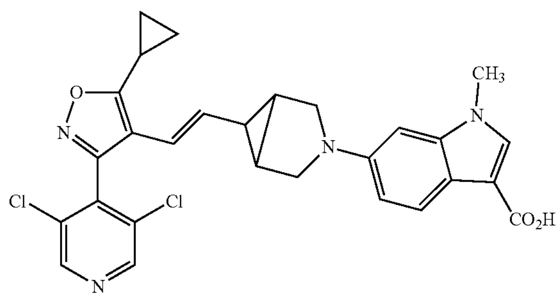 [SMILES: Cn1cc(C(=O)O)c2ccc(N3CC4C(/C=C/c5c(-c6c(Cl)cncc6Cl)noc5C5CC5)C4C3)cc21] | MS (ESI) m/z: 534.9 [M + H]$^+$; EC$_{50}$ = 31; $^1$H NMR (500 MHz, Methanol-d$_4$) δ 8.72 (s, 2H), 7.83 (d, J = 8.80 Hz, 1H), 7.69 (br s, 1H), 6.66 (br s, 1H), 6.50 (br s, 1H), 6.13 (d, J = 15.96 Hz, 1H), 5.19-5.31 (m, 1H), 3.75 (s, 3H), 3.68 (br d, J = 82.5 Hz, 2H), 3.27 (ddd, J = 1.10, 2.20, 7.15 Hz, 2H), 2.22-2.31 (m, 1H), 1.69 (br s, 2H), 1.48-1.55 (m, 1H), 1.18-1.22 (m, 2H), 1.16 (br s, 2H). | A2 |
| 90 | 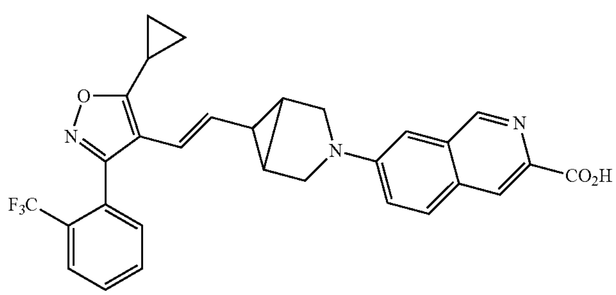 [SMILES: O=C(O)c1cc2ccc(N3CC4C(/C=C/c5c(-c6ccccc6C(F)(F)F)noc5C5CC5)C4C3)cc2cn1] | MS (ESI) m/z: 534.1 [M + H]$^+$; EC$_{50}$ = 74; $^1$H NMR (500 MHz, DMSO-d$_6$) δ 9.12 (s, 1H), 8.44 (s, 1H), 7.98 (d, J = 9.4 Hz, 1H), 7.93 (d, J = 7.7 Hz, 1H), 7.84-7.80 (m, 1H), 7.79-7.74 (m, 1H), 7.73-7.68 (m, 1H), 7.53 (d, J = 7.2 Hz, 1H), 7.41 (s, 1H), 6.11 (d, J = 16.2 Hz, 1H), 5.40 (dd, J = 16.4, 7.0 Hz, 1H), 3.91 (br d, J = 12.7 Hz, 2H), 2.90 (br t, J = 11.4 Hz, 2H), 2.35-2.30 (m, 1H), 2.29-2.22 (m, 1H), 1.67 (br d, J = 11.6 Hz, 2H), 1.32-1.22 (m, 2H), 1.18-1.13 (m, 2H), 1.10-1.05 (m, 2H). | A2 |
| 91 | 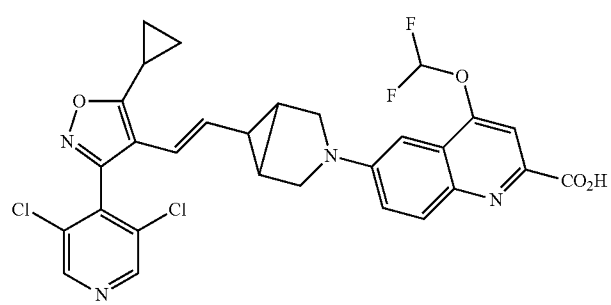 [SMILES: O=C(O)c1cc(OC(F)F)c2cc(N3CC4C(/C=C/c5c(-c6c(Cl)cncc6Cl)noc5C5CC5)C4C3)ccc2n1] | MS (ESI) m/z: 599.0 [M + H]$^+$; EC$_{50}$ = 4; $^1$H NMR (400 MHz, Methanol-d$_4$) δ 8.73 (s, 2H), 8.10 (d, J = 9.46 Hz, 1H), 7.80 (s, 1H), 7.45-7.53 (m, 1H), 6.91 (d, J = 2.42 Hz, 1H), 6.12-6.23 (m, 1H), 5.29 (dd, J = 8.80, 16.07 Hz, 1H), 3.77 (d, J = 10.12 Hz, 2H), 3.54 (br s, 2H), 2.28 (s, 1H), 1.82 (br s, 2H), 1.40-1.47 (m, 1H), 1.12-1.25 (m, 5H). | A2 |

TABLE 1-continued

| Ex. No. | Structure | LCMS, FXR EC$_{50}$ (nM) & NMR | Method |
|---|---|---|---|
| 92 | 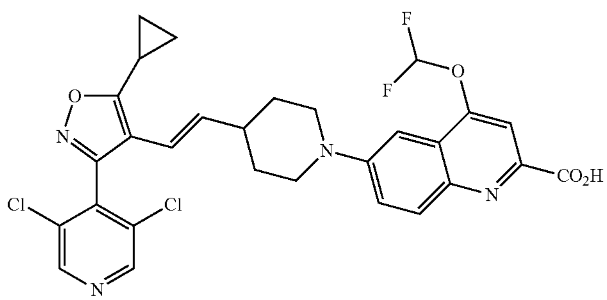 [SMILES: O=C(O)c1cc(OC(F)F)c2cc(N3CCC(/C=C/c4c(-c5c(Cl)cncc5Cl)noc4C4CC4)CC3)ccc2n1] | MS (ESI) m/z: 601.0 [M + H]$^+$; EC$_{50}$ = 3; $^1$H NMR (400 MHz, Methanol-d$_4$) δ 8.71 (s, 2H), 8.10 (br d, J = 2.64 Hz, 1H), 7.74-7.87 (m, 2H), 7.42 (s, 1H), 7.31 (d, J = 2.42 Hz, 1H), 6.20 (dd, J = 1.10, 16.07 Hz, 1H), 5.44-5.57 (m, 1H), 3.96 (br d, J = 12.98 Hz, 2H), 3.01 (br t, J = 11.33 Hz, 2H), 2.23-2.38 (m, 2H), 1.81 (br d, J = 11.00 Hz, 2H), 1.41-1.51 (m, 2H), 1.29 (s, 1H), 1.14-1.23 (m, 4H). | A2 |
| 93 | 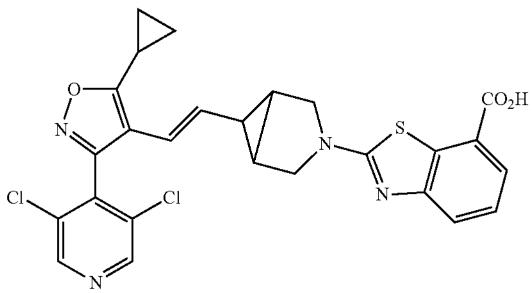 [SMILES: O=C(O)c1cccc2nc(N3CC4C(/C=C/c5c(-c6c(Cl)cncc6Cl)noc5C5CC5)C4C3)sc12] | MS (ESI) m/z: 539.0 [M + H]$^+$; EC$_{50}$ = 280; $^1$H NMR (500 MHz, DMOS-d$_6$) δ 8.86 (br s, 2H), 7.68 (br s, 2H), 7.41 (br s, 1H), 6.17 (br d, J = 15.1 Hz, 1H), 5.32 (br s, 1H), 3.81-3.61 (m, 4H), 2.38 (br s, 1H), 1.83 (br s, 2H), 1.45 (br s, 1H), 1.25-1.06 (m, 4H). | A1 |
| 94 | 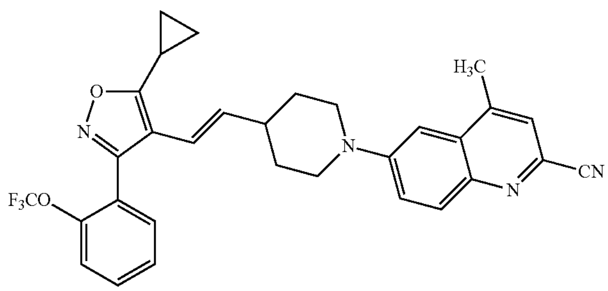 | MS (ESI) m/z: 536.1 [M + H]$^+$; EC$_{50}$ = 409; $^1$H NMR (400 MHz, CDCl$_3$) δ 7.48-7.75 (m, 3H), 7.34-7.43 (m, 2H), 7.17 (s, 1H), 6.60 (s, 1H), 6.03-6.15 (m, 1H), 5.69 (dd, J = 7.04, 16.07 Hz, 1H), 4.18-4.27 (m, 1H), 3.63 (br d, J = 12.32 Hz, 2H), 2.80 (br d, J = 1.98 Hz, 2H), 2.51 (s, 3H), 2.20 (tdd, J = 3.71, 7.37, 10.95 Hz, 1H), 2.11 (tt, J = 5.12, 8.42 Hz, 1H), 1.60 (br d, J = 2.42 Hz, 2H), 1.39-1.48 (m, 2H), 1.21-1.24 (m, 2H), 1.10-1.18 (m, 2H). | A2 |
| 95 | 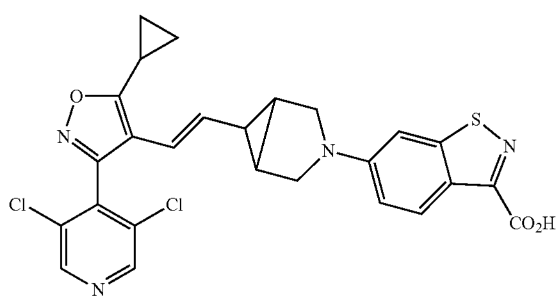 [SMILES: O=C(O)c1nsc2cc(N3CC4C(/C=C/c5c(-c6c(Cl)cncc6Cl)noc5C5CC5)C4C3)ccc12] | MS (ESI) m/z: 539.0 [M + H]$^+$; EC$_{50}$ = 108; $^1$H NMR (500 MHz, DMSO-d$_6$) δ 8.87 (s, 2H), 8.33 (br d, J = 9.1 Hz, 1H), 7.14 (s, 1H), 6.91 (dd, J = 9.1, 1.7 Hz, 1H), 6.16 (d, J = 16.2 Hz, 1H), 5.29 (dd, J = 16.1, 8.9 Hz, 1H), 3.64 (d, J = 9.9 Hz, 2H), 3.37 (br d, J = 9.1 Hz, 2H), 2.42-2.34 (m, 1H), 1.81 (br s, 2H), 1.46-1.39 (m, 1H), 1.22-1.15 (m, 2H), 1.14-1.08 (m, 2H). | A2 |
| 96 | 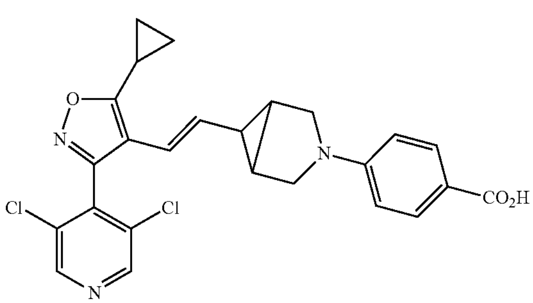 [SMILES: O=C(O)c1ccc(N2CC3C(/C=C/c4c(-c5c(Cl)cncc5Cl)noc4C4CC4)C3C2)cc1] | MS (ESI) m/z: 482.0 [M + H]$^+$; EC$_{50}$ = 66; $^1$H NMR (400 MHz, Methanol-d$_4$) δ 8.72 (s, 2H), 7.82 (d, J = 8.80 Hz, 2H), 6.55 (d, J = 9.02 Hz, 2H), 6.14 (d, J = 16.07 Hz, 1H), 5.19-5.31 (m, 1H), 3.63 (d, J = 9.90 Hz, 2H), 3.37 (br d, J = 1.10 Hz, 2H), 2.22-2.31 (m, 1H), 1.68-1.75 (m, 2H), 1.37 (br d, J = 8.80 Hz, 1H), 1.12-1.23 (m, 4H). | A1 |

TABLE 1-continued

| Ex. No. | Structure | LCMS, FXR EC$_{50}$ (nM) & NMR | Method |
|---|---|---|---|
| 97 | 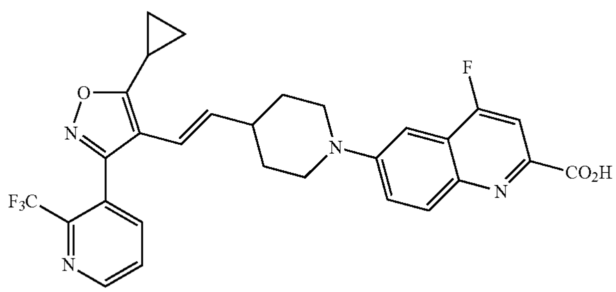 [SMILES: O=C(O)c1cc(F)c2cc(N3CCC(/C=C/c4c(-c5cccnc5C(F)(F)F)noc4C4CC4)CC3)ccc2n1] | MS (ESI) m/z: 603.1 [M + H]$^+$; EC$_{50}$ = 21; $^1$H NMR (400 MHz, DMSO-d$_6$) δ 8.85 (dd, J = 4.6, 1.6 Hz, 1H), 8.13 (s, 1H), 8.05-7.97 (m, 2H), 7.84-7.74 (m, 2H), 6.97 (s, 1H), 6.06 (dd, J = 16.3, 1.3 Hz, 1H), 5.36 (dd, J = 16.3, 6.9 Hz, 1H), 3.87 (d, J = 13.1 Hz, 2H), 2.93 (t, J = 12.3 Hz, 2H), 2.34-2.07 (m, 2H), 1.69-1.59 (m, 2H), 1.30-1.14 (m, 2H), 1.14-0.89 (m, 4H). | A2 |
| 98 | 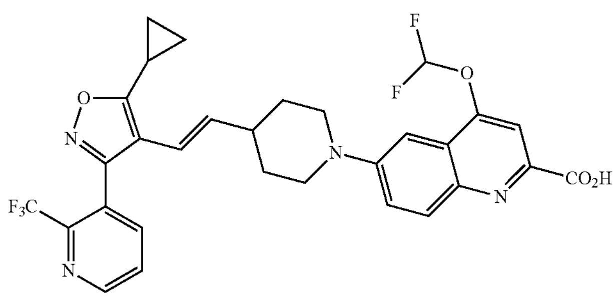 | MS (ESI) m/z: 601.1 [M + H]$^+$; EC$_{50}$ = 3; $^1$H NMR (400 MHz, DMSO-d$_6$) δ 8.85 (dd, J = 4.8, 1.5 Hz, 1H), 8.03 (dd, J = 8.0, 1.6 Hz, 1H), 7.89 (d, J = 9.4 Hz, 1H), 7.85-7.78 (m, 1H), 7.68 (dd, J = 9.5, 2.8 Hz, 1H), 7.65 (t, J = 72.6 Hz, 1H), 7.62 (s, 1H), 7.06 (d, J = 2.7 Hz, 1H), 6.07 (dd, J = 16.3, 1.3 Hz, 1H), 5.37 (dd, J = 16.3, 7.0 Hz, 1H), 3.83 (d, J = 12.7 Hz, 2H), 2.83 (t, J = 12.1 Hz, 2H), 2.33-2.13 (m, 2H), 1.63 (d, J = 12.8 Hz, 2H), 1.32-1.14 (m, 2H), 1.14-0.82 (m, 4H). | A2 |
| 99 | 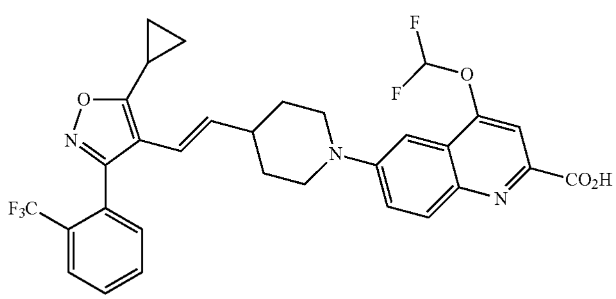 [SMILES: O=C(O)c1cc(OC(F)F)c2cc(N3CCC(/C=C/c4c(-c5ccccc5C(F)(F)F)noc4C4CC4)CC3)ccc2n1] | MS (ESI) m/z: 600.2 [M + H]$^+$; EC$_{50}$ = 3; $^1$H NMR (500 MHz, DMSO-d$_6$) δ 8.05-7.66 (m, 7H), 7.63-7.48 (m, 1H), 7.12 (br s, 1H), 6.11 (br d, J = 15.1 Hz, 1H), 5.41 (br d, J = 11.0 Hz, 1H), 3.86 (br s, 2H), 2.91 (br s, 2H), 2.36-2.25 (m, 2H), 1.69 (br d, J = 6.1 Hz, 2H), 1.27 (br d, J = 8.3 Hz, 2H), 1.19-1.05 (m, 4H). | A2 |
| 100 | 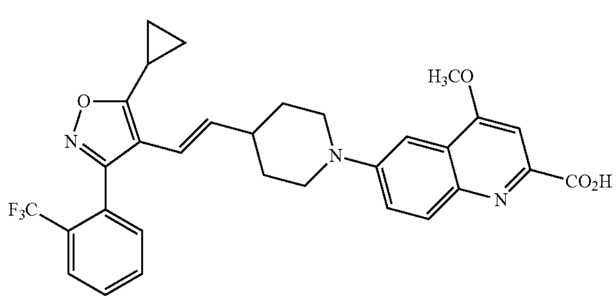 [SMILES: COc1cc(C(=O)O)nc2ccc(N3CCC(/C=C/c4c(-c5ccccc5C(F)(F)F)noc4C4CC4)CC3)cc12] | MS (ESI) m/z: 564.2 [M + H]$^+$; EC$_{50}$ = 4; $^1$H NMR (500 MHz, DMSO-d$_6$) δ 7.98-7.91 (m, 2H), 7.85-7.80 (m, 1H), 7.80-7.75 (m, 1H), 7.69 (dd, J = 9.5, 2.6 Hz, 1H), 7.53 (d, J = 7.4 Hz, 1H), 7.49 (s, 1H), 7.23 (d, J = 2.8 Hz, 1H), 6.11 (d, J = 15.7 Hz, 1H), 5.40 (dd, J = 16.4, 7.0 Hz, 1H), 4.12 (s, 3H), 3.83 (br d, J = 12.9 Hz, 2H), 2.85 (br t, J = 11.4 Hz, 2H), 2.36-2.30 (m, 1H), 2.27-2.19 (m, 1H), 1.68 (br d, J = 11.3 Hz, 2H), 1.32-1.23 (m, 2H), 1.18-1.13 (m, 2H), 1.10-1.04 (m, 2H). | A2 |
| 101 | 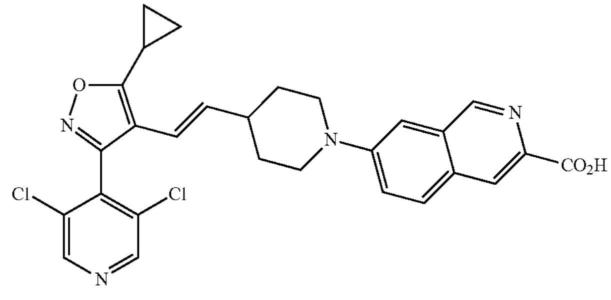 [SMILES: O=C(O)c1cc2ccc(N3CCC(/C=C/c4c(-c5c(Cl)cncc5Cl)noc4C4CC4)CC3)cc2cn1] | MS (ESI) m/z: 535.0 [M + H]$^+$; EC$_{50}$ = 47; $^1$H NMR (500 MHz, Methanol-d$_4$) δ 9.19 (br s, 1H), 8.73 (s, 2H), 8.63 (br s, 1H), 8.08 (br d, J = 9.1 Hz, 1H), 7.89 (br d, J = 8.3 Hz, 1H), 7.54 (br s, 1H), 6.23 (d, J = 16.2 Hz, 1H), 5.51 (dd, J = 16.2, 6.9 Hz, 1H), 4.04 (br d, J = 12.7 Hz, 2H), 3.06 (br t, J = 12.0 Hz, 2H), 2.39 (br d, J = 7.2 Hz, 1H), 2.33-2.25 (m, 1H), 1.82 (br d, J = 12.1 Hz, 2H), 1.49-1.37 (m, 2H), 1.26-1.15 (m, 2H). | A2 |

TABLE 1-continued

| Ex. No. | Structure | LCMS, FXR EC$_{50}$ (nM) & NMR | Method |
|---|---|---|---|
| 102 | 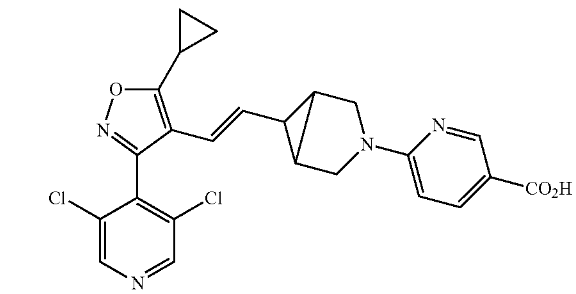 | MS (ESI) m/z: 483.0 [M + H]$^+$; EC$_{50}$ = 1270; $^1$H NMR (500 MHz, DMSO-d$_6$) δ 8.82 (s, 2H), 8.55 (s, 1H), 7.87 (br d, J = 8.84 Hz, 1H), 6.45 (br d, J = 8.92 Hz, 1H), 6.11 (br d, J = 16.07 Hz, 1H), 5.24 (br dd, J = 8.50, 15.99 Hz, 1H), 1.25-3.90 (8H), 1.12-1.21 (m, 2H), 1.07 (br d, J = 1.85 Hz, 2H). | A1 |
| 103 | 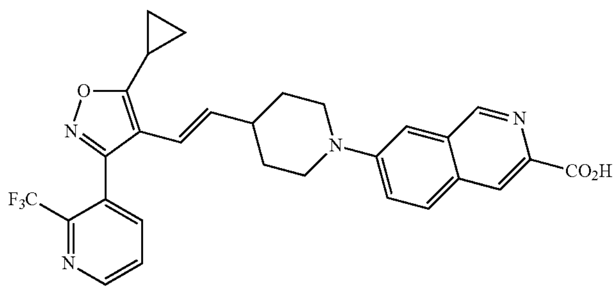 [SMILES: O=C(O)c1cc2ccc(N3CCC(/C=C/c4c(-c5cccnc5C(F)(F)F)noc4C4CC4)CC3)cc2cn1] | MS (ESI) m/z: 535.2 [M + H]$^+$; EC$_{50}$ = 189; $^1$H NMR (400 MHz, Methanol-d$_4$) δ 9.12 (s, 1H), 8.84-8.67 (m, 1H), 8.59 (s, 1H), 8.02 (d, J = 9.3 Hz, 1H), 7.89-7.79 (m, 2H), 7.68 (dd, J = 7.9, 4.7 Hz, 1H), 7.48 (s, 1H), 6.05 (dd, J = 16.3, 1.2 Hz, 1H), 5.37 (dd, J = 16.3, 7.0 Hz, 1H), 3.97 (d, J = 13.0 Hz, 2H), 2.96 (t, J = 12.4 Hz, 2H), 2.33-2.20 (m, 1H), 2.14 (td, J = 8.3, 4.2 Hz, 1H), 1.70 (d, J = 13.1 Hz, 2H), 1.38-1.17 (m, 2H), 1.13-1.00 (m, 4H). | A2 |
| 104 | 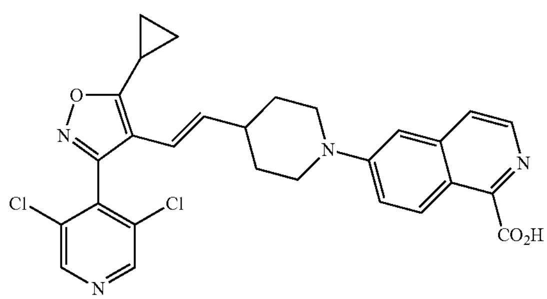 [SMILES: O=C(O)c1nccc2cc(N3CCC(/C=C/c4c(-c5c(Cl)cncc5Cl)noc4C4CC4)CC3)ccc12] | MS (ESI) m/z: 535.1 [M + H]$^+$; EC$_{50}$ = 219; $^1$H NMR (500 MHz, Methanol-d$_4$) δ 9.21 (d, J = 9.9 Hz, 1H), 8.72 (s, 2H), 7.99 (d, J = 6.6 Hz, 1H), 7.85 (d, J = 6.6 Hz, 1H), 7.70 (dd, J = 9.9, 2.2 Hz, 1H), 7.25 (d, J = 2.2 Hz, 1H), 6.22 (dd, J = 16.2, 0.8 Hz, 1H), 5.50 (dd, J = 16.2, 7.2 Hz, 1H), 4.26 (br d, J = 13.5 Hz, 2H), 3.21 (br t, J = 11.7 Hz, 2H), 2.53-2.40 (m, 1H), 2.35-2.19 (m, 1H), 1.84 (br d, J = 11.6 Hz, 2H), 1.47-1.31 (m, 2H), 1.27-1.12 (m, 4H). | A2 |
| 105 | 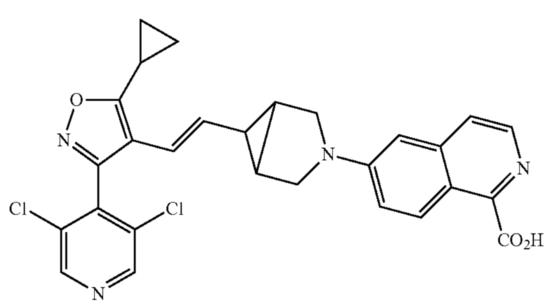 [SMILES: O=C(O)c1nccc2cc(N3CC4C(/C=C/c5c(-c6c(Cl)cncc6Cl)noc5C5CC5)C4C3)ccc12] | MS (ESI) m/z: 533.0 [M + H]$^+$; EC$_{50}$ = 310; $^1$H NMR (500 MHz, Methanol-d$_4$) δ 9.25 (br d, J = 9.4 Hz, 1H), 8.74 (s, 2H), 7.99 (br d, J = 6.6 Hz, 1H), 7.85 (br d, J = 6.3 Hz, 1H), 7.38 (br d, J = 9.4 Hz, 1H), 6.93 (br s, 1H), 6.19 (br d, J = 16.2 Hz, 1H), 5.31 (br dd, J = 16.0, 8.5 Hz, 1H), 3.86 (br d, J = 10.2 Hz, 2H), 3.68 (br d, J = 9.6 Hz, 2H), 2.30 (br d, J = 5.0 Hz, 1H), 1.87 (br s, 2H), 1.41 (br d, J = 8.0 Hz, 1H), 1.28-1.13 (m, 4H). | A2 |
| 106 | 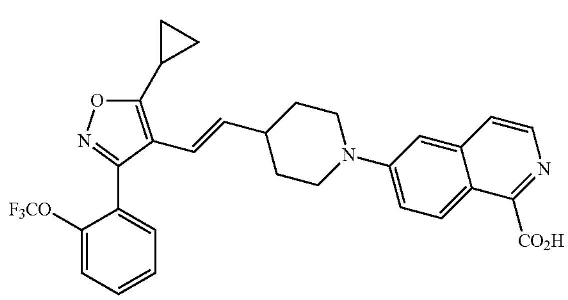 [SMILES: O=C(O)c1nccc2cc(N3CCC(/C=C/c4c(-c5ccccc5OC(F)(F)F)noc4C4CC4)CC3)ccc12] | MS (ESI) m/z: 550.2 [M + H]$^+$; EC$_{50}$ = 330; $^1$H NMR (500 MHz, DMSO-d$_6$) δ 9.10 (s, 1H), 8.42 (s, 1H), 7.96 (br d, J = 9.16 Hz, 1H), 7.69 (br d, J = 8.54 Hz, 1H), 7.61-7.65 (m, 1H), 7.46-7.53 (m, 3H), 7.41 (br s, 1H), 6.01-6.11 (m, 1H), 5.57 (br dd, J = 6.71, 16.17 Hz, 1H), 3.91 (br d, J = 12.21 Hz, 2H), 2.89 (br t, J = 11.60 Hz, 2H), 2.25 (br s, 2H), 1.68 (br d, J = 12.21 Hz, 2H), 1.28 (br d, J = 10.68 Hz, 2H), 1.09 (br d, J = 7.63 Hz, 2H), 0.97-1.02 (m, 2H). | A2 |

TABLE 1-continued

| Ex. No. | Structure | LCMS, FXR EC$_{50}$ (nM) & NMR | Method |
|---|---|---|---|
| 107 | 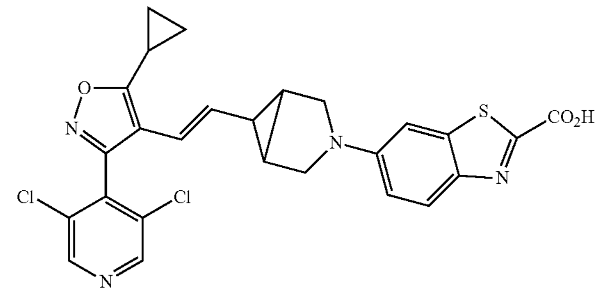 [SMILES: O=C(O)c1nc2ccc(N3CC4C(/C=C/c5c(-c6c(Cl)cncc6Cl)noc5C5CC5)C4C3)cc2s1] | MS (ESI) m/z: 539.0 [M + H]$^+$; EC$_{50}$ = 472; $^1$H NMR (500 MHz, Methanol-d$_4$) δ 8.74 (s, 2H), 7.90 (br d, J = 8.8 Hz, 1H), 7.07 (br s, 1H), 6.96 (br d, J = 8.8 Hz, 1H), 6.16 (d, J = 16.0 Hz, 1H), 5.28 (dd, J = 16.1, 8.7 Hz, 1H), 3.74-3.64 (m, 2H), 3.40 (br d, J = 9.1 Hz, 2H), 2.36-2.23 (m, 1H), 1.82-1.70 (m, 2H), 1.48-1.41 (m, 1H), 1.23-1.17 (m, 4H). | A2 |
| 108 | 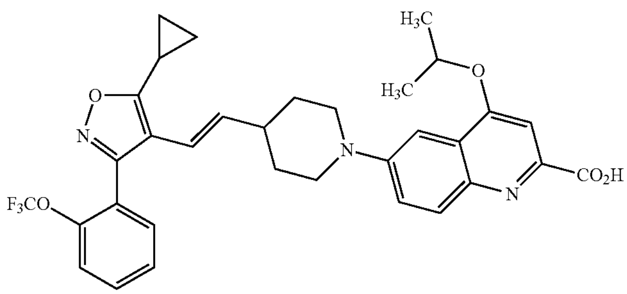 [SMILES: CC(C)Oc1cc(C(=O)O)nc2ccc(N3CCC(/C=C/c4c(-c5ccccc5OC(F)(F)F)noc4C4CC4)CC3)cc12] | MS (ESI) m/z: 608.2 [M + H]$^+$; EC$_{50}$ = 22; $^1$H NMR (500 MHz, DMSO-d$_6$) δ 8.03 (br d, J = 9.34 Hz, 1H), 7.60-7.73 (m, 2H), 7.46-7.52 (m, 4H), 7.25 (br s, 1H), 6.07 (br d, J = 16.24 Hz, 1H), 5.60 (br dd, J = 6.69, 16.28 Hz, 1H), 5.00-5.11 (m, 1H), 3.77-3.84 (m, 1H), 2.90 (br t, J = 11.53 Hz, 2H), 2.19-2.32 (m, 2H), 1.72 (br d, J = 11.86 Hz, 2H), 1.43 (br d, J = 5.89 Hz, 6H), 1.28-1.38 (m, 3H), 1.13 (br d, J = 5.81 Hz, 2H), 1.01 (br d, J = 2.61 Hz, 2H). | A2 |
| 109 | 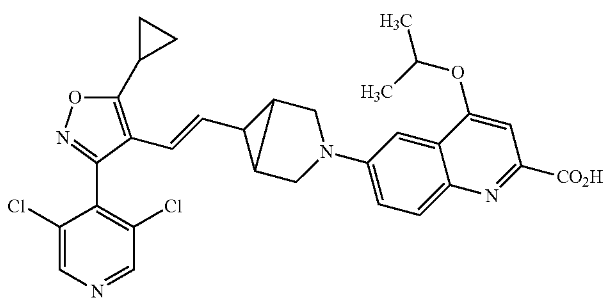 [SMILES: CC(C)Oc1cc(C(=O)O)nc2ccc(N3CC4C(/C=C/c5c(-c6c(Cl)cncc6Cl)noc5C5CC5)C4C3)cc12] | MS (ESI) m/z: 591.2 [M + H]$^+$; EC$_{50}$ = 25; $^1$H NMR (500 MHz, DMSO-d$_6$) δ 8.77 (s, 2H), 7.93-8.07 (m, 1H), 7.41 (s, 1H), 7.28 (br s, 1H), 6.78 (br s, 1H), 6.06 (br d, J = 16.17 Hz, 1H), 5.20 (br dd, J = 8.85, 15.87 Hz, 1H), 4.97 (br s, 1H), 3.32 (br s, 2H), 2.78-2.91 (m, 1H), 2.28 (br d, J = 4.58 Hz, 1H), 1.72 (br s, 2H), 1.36 (br d, J = 3.97 Hz, 6H), 1.19 (br d, J = 6.41 Hz, 2H), 1.02 (br d, J = 2.44 Hz, 2H) additional signals were lost due to water suppression. | A2 |
| 110 | 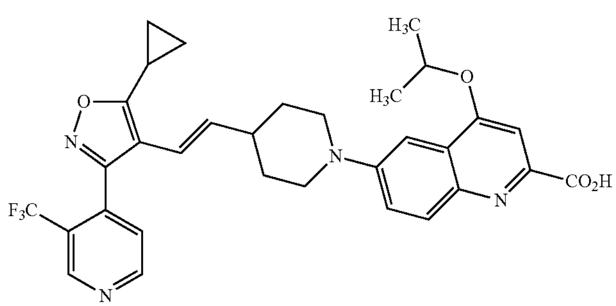 [SMILES: CC(C)Oc1cc(C(=O)O)nc2ccc(N3CCC(/C=C/c4c(-c5ccncc5C(F)(F)F)noc4C4CC4)CC3)cc12] | MS (ESI) m/z: 593.2 [M + H]$^+$; EC$_{50}$ = 5; $^1$H NMR (400 MHz, CDCl$_3$) δ 8.85 (dd, J = 4.9, 1.6 Hz, 1H), 8.68 (d, J = 4.9 Hz, 1H), 7.85-7.77 (m, 1H), 7.78-7.68 (m, 2H), 7.61 (dd, J = 7.8, 4.7 Hz, 1H), 7.31 (d, J = 2.5 Hz, 1H), 6.03 (dd, J = 16.3, 1.2 Hz, 1H), 5.48 (dd, J = 16.2, 7.0 Hz, 1H), 5.23-5.08 (m, 1H), 3.92 (d, J = 12.8 Hz, 2H), 2.96 (t, J = 12.3 Hz, 2H), 2.39-2.19 (m, 1H), 2.09 (tt, J = 8.3, 5.1 Hz, 1H), 1.81 (d, J = 13.0 Hz, 2H), 1.59 (d, J = 6.0 Hz, 6H) 1.53-1.35 (m, 2H), 1.31-1.06 (m, 4H). | A2 |
| 111 | 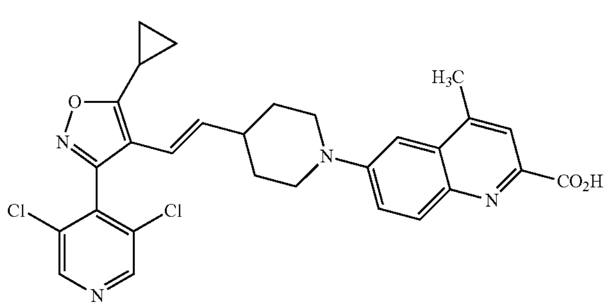 | MS (ESI) m/z: 547.1 [M + H]$^+$; EC$_{50}$ = 38; $^1$H NMR (400 MHz, CDCl$_3$) δ 8.63 (s, 2H), 8.05 (d, J = 9.3 Hz, 1H), 8.00 (s, 1H), 7.22 (d, J = 9.7 Hz, 1H), 6.61 (s, 1H), 6.04 (d, J = 16.0 Hz, 1H), 5.23 (dd, J = 16.0, 8.7 Hz, 1H), 3.75 (d, J = 9.7 Hz, 2H), 3.50 (d, J = 9.9 Hz, 2H), 2.63 (s, 3H), 2.09 (td, J = 8.4, 4.2 Hz, 1H), 1.75 (s, 2H), 1.51-1.38 (m, 1H), 1.30-1.00 (m, 4H). | A2 |

TABLE 1-continued

| Ex. No. | Structure | LCMS, FXR EC$_{50}$ (nM) & NMR | Method |
|---|---|---|---|
| 112 | 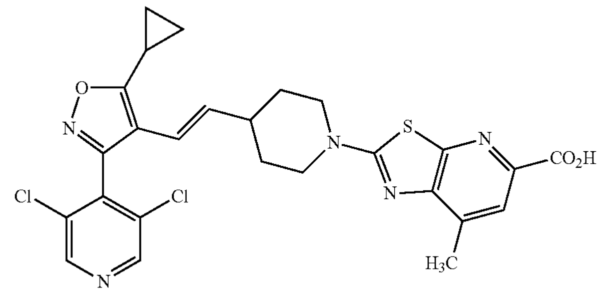 [SMILES: Cc1cc(C(=O)O)nc2sc(N3CCC(/C=C/c4c(-c5c(Cl)cncc5Cl)noc4C4CC4)CC3)nc12] | MS (ESI) m/z: 556.1 [M + H]$^+$; EC$_{50}$ = 155; $^1$H NMR (500 MHz, Methanol-d$_4$) δ 8.74 (s, 2H), 7.94 (s, 1H), 6.36-6.11 (m, 1H), 5.52 (dd, J = 16.2, 7.2 Hz, 1H), 4.22 (br d, J = 12.4 Hz, 2H), 3.31-3.24 (m, 2H), 2.56 (s, 3H), 2.49-2.38 (m, 1H), 2.35-2.25 (m, 1H), 1.81 (br d, J = 12.1 Hz, 2H), 1.46-1.33 (m, 2H), 1.28-1.14 (m, 4H). | A1 |
| 113 | 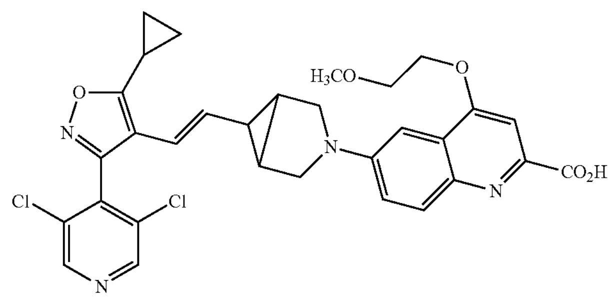 [SMILES: COCCOc1cc(C(=O)O)nc2ccc(N3CC4C(/C=C/c5c(-c6c(Cl)cncc6Cl)noc5C5CC5)C4C3)cc12] | MS (ESI) m/z: 607.1 [M + H]$^+$; EC$_{50}$ = 154; $^1$H NMR (500 MHz, DMSO-d6) δ 8.85 (s, 2H), 8.00 (d, J = 9.0 Hz, 1H), 7.48 (s, 1H), 7.39-7.30 (m, 1H), 6.87 (s, 1H), 6.15 (d, J = 16.0 Hz, 1H), 5.29 (dd, J = 16.1, 8.9 Hz, 1H), 4.47 (s, 2H), 3.84 (s, 2H), 3.75-3.5 (two proton signals were lost due to water suppression), 3.58-3.46 (m, 2H), 3.38 (s, 3H), 2.43-2.28 (m, 1H), 1.82 (s, 2H), 1.49-1.38 (m, 1H), 1.31-0.90 (m, 4H). | A2 |
| 114 | 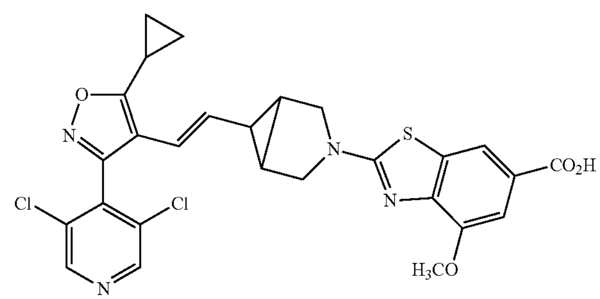 [SMILES: COc1cc(C(=O)O)cc2sc(N3CC4C(/C=C/c5c(-c6c(Cl)cncc6Cl)noc5C5CC5)C4C3)nc12] | MS (ESI): m/z 569.1 [M + H]$^+$; EC$_{50}$ = 131; $^1$H NMR (500 MHz, Methanol-d$_4$) δ 8.75 (br s, 2H), 8.00 (s, 1H), 7.55 (s, 1H), 6.19 (br d, J = 16.0 Hz, 1H), 5.29 (br dd, J = 16.0, 8.5 Hz, 1H), 4.01 (s, 3H), 3.82 (br d, J = 9.6 Hz, 2H), 3.72 (br d, J = 9.9 Hz, 2H), 2.37-2.23 (m, 1H), 1.80 (br s, 2H), 1.48-1.36 (m, 1H), 1.27-1.12 (m, 4H). | A1 |
| 115 | 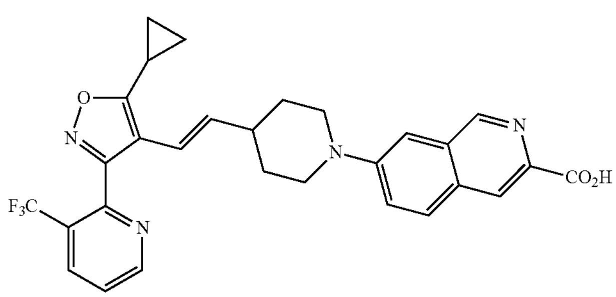 [SMILES: O=C(O)c1cc2ccc(N3CCC(/C=C/c4c(-c5ncccc5C(F)(F)F)noc4C4CC4)CC3)cc2cn1] | MS (ESI) m/z: 535.2 [M + H]$^+$; EC$_{50}$ = 112; $^1$H NMR (400 MHz, Methanol-d$_4$) δ 9.27 (s, 1H), 8.88-8.94 (m, 1H), 8.74 (s, 1H), 8.31-8.37 (m, 1H), 8.16 (d, J = 9.24 Hz, 1H), 7.98 (br d, J = 8.14 Hz, 1H), 7.76 (dd, J = 4.84, 7.48 Hz, 1H), 7.62 (br s, 1H), 6.20 (dd, J = 1.10, 16.29 Hz, 1H), 5.44 (dd, J = 7.15, 16.18 Hz, 1H), 4.10 (br d, J = 13.20 Hz, 2H), 3.09 (br s, 2H), 2.31-2.42 (m, 1H), 2.25 (s, 1H), 1.80 (br d, J = 11.44 Hz, 2H), 1.38 (br d, J = 9.46 Hz, 2H), 1.11-1.23 (m, 4H). | A2 |
| 116 | 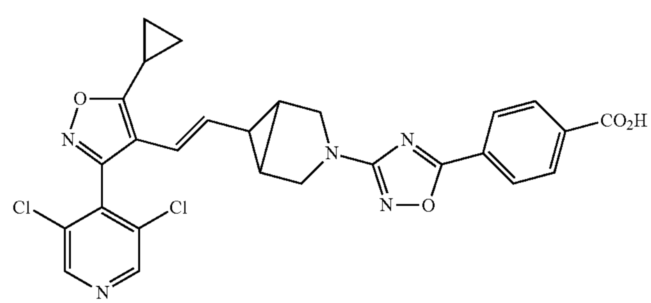 [SMILES: O=C(O)c1ccc(-c2nc(N3CC4C(/C=C/c5c(-c6c(Cl)cncc6Cl)noc5C5CC5)C4C3)no2)cc1] | MS (ESI): m/z 550.1 [M + H]$^+$; EC$_{50}$ = 862; $^1$H NMR (500 MHz, DMSO-d$_6$) δ 8.86 (s, 2H), 8.13 (s, 4H), 6.16 (d, J = 16.0 Hz, 1H), 5.29 (dd, J = 16.0, 8.8 Hz, 1H), 3.64 (d, J = 10.2 Hz, 2H), 3.48 (d, J = 9.7 Hz, 2H), 2.43-2.33 (m, 1H), 1.74 (s, 2H), 1.45-1.38 (m, 1H), 1.28-0.95 (m, 4H). | H |

TABLE 1-continued

| Ex. No. | Structure | LCMS, FXR EC$_{50}$ (nM) & NMR | Method |
|---|---|---|---|
| 117 | 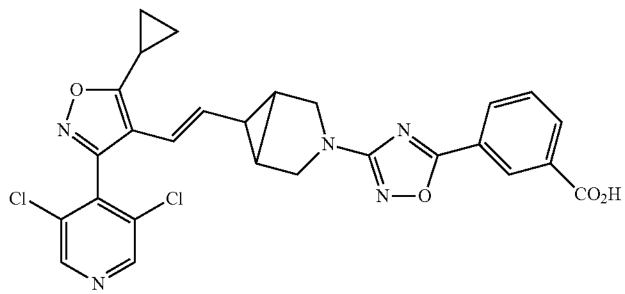 [SMILES: O=C(O)c1cccc(-c2nc(N3CC4C(/C=C/c5c(-c6c(Cl)cncc6Cl)noc5C5CC5)C4C3)no2)c1] | MS (ESI): m/z 550.1 [M + H]$^+$; EC$_{50}$ = 494; $^1$H NMR (400 MHz, DMSO-d$_6$) δ 8.86 (s, 2H), 8.50 (s, 1H), 8.24 (d, J = 7.7 Hz, 1H), 8.20 (d, J = 7.9 Hz, 1H), 7.74 (t, J = 7.8 Hz, 1H), 6.16 (d, J = 16.1 Hz, 1H), 5.29 (dd, J = 16.1, 8.8 Hz, 1H), 3.64 (d, J = 10.2 Hz, 2H), 3.48 (d, J = 11.3 Hz, 2H), 2.44-2.33 (m, 1H), 1.74 (s, 2H), 1.50-1.27 (m, 1H), 1.15 (m, 4H). | H |
| 118 | 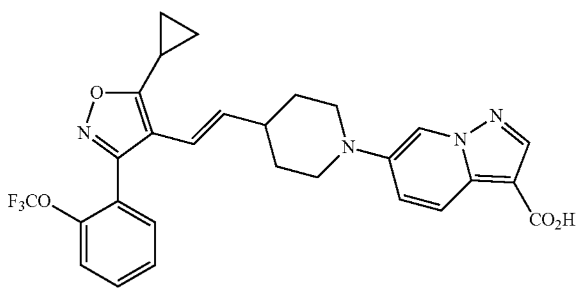 [SMILES: O=C(O)c1cnn2cc(N3CCC(/C=C/c4c(-c5ccccc5OC(F)(F)F)noc4C4CC4)CC3)ccc12] | MS (ESI) m/z: 539.1 [M + H]$^+$; EC$_{50}$ = 276; $^1$H NMR (500 MHz, DMSO-d$_6$) δ 8.19 (s, 1H), 8.11 (br s, 1H), 7.89 (br d, J = 9.76 Hz, 1H), 7.67 (br d, J = 3.53 Hz, 1H), 7.47-7.58 (m, 4H), 6.01-6.17 (m, 1H), 5.63 (br dd, J = 6.56, 16.24 Hz, 1H), 3.54 (br d, J = 12.45 Hz, 2H), 2.66-2.75 (m, 2H), 2.27 (br d, J = 4.46 Hz, 1H), 2.14-2.22 (m, 1H), 1.71 (br d, J = 12.37 Hz, 2H), 1.36 (br d, J = 11.36 Hz, 2H), 1.14 (br d, J = 8.16 Hz, 2H), 1.04 (br s, 2H). | A2 |
| 119 | 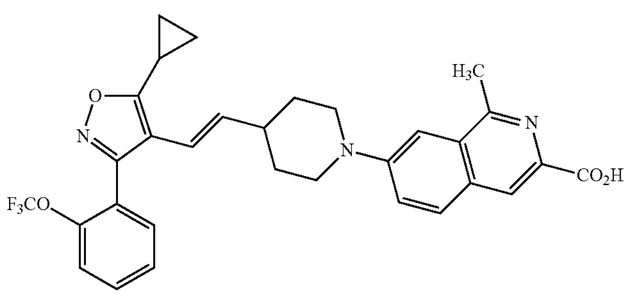 [SMILES: Cc1nc(C(=O)O)cc2ccc(N3CCC(/C=C/c4c(-c5ccccc5OC(F)(F)F)noc4C4CC4)CC3)cc12] | MS (ESI): m/z: 564.2 [M + H]$^+$; EC$_{50}$ = 96; $^1$H NMR (400 MHz, Methanol-d$_4$) δ 8.59 (s, 1H), 8.12 (d, J = 9.24 Hz, 1H), 7.96 (br d, J = 2.42 Hz, 1H), 7.57-7.66 (m, 1H), 7.44-7.54 (m, 4H), 6.09-6.23 (m, 1H), 5.68 (dd, J = 7.04, 16.07 Hz, 1H), 4.14 (br d, J = 12.98 Hz, 2H), 3.07-3.17 (m, 5H), 2.34-2.46 (m, 1H), 2.17-2.29 (m, 1H), 1.79-1.93 (m, 2H), 1.45 (br dd, J = 2.97, 12.21 Hz, 2H), 1.08-1.20 (m, 4H). | A2 |
| 120 | 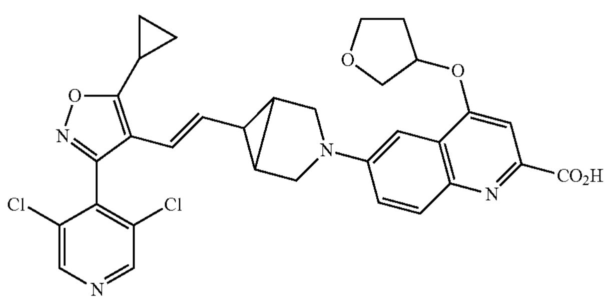 [SMILES: O=C(O)c1cc(OC2CCOC2)c2cc(N3CC4C(/C=C/c5c(-c6c(Cl)cncc6Cl)noc5C5CC5)C4C3)ccc2n1] | MS (ESI): m/z 619.1 [M + H]$^+$; EC$_{50}$ = 18; $^1$H NMR (400 MHz, DMSO-d$_6$) δ 8.87 (s, 2H), 8.02 (d, J = 9.2 Hz, 1H), 7.45 (s, 1H), 7.39 (dd, J = 9.4, 2.6 Hz, 1H), 6.87 (d, J = 2.6 Hz, 1H), 6.14 (d, J = 16.1 Hz, 1H), 5.52-5.43 (m, 1H), 5.31 (dd, J = 16.1, 8.9 Hz, 1H), 4.01 (d, J = 2.9 Hz, 2H), 3.94 (q, J = 7.7 Hz, 1H), 3.83 (td, J = 8.3, 4.6 Hz, 1H), 3.71 (d, J = 10.1 Hz, 2H), 3.43 (d, J = 9.5 Hz, 2H), 2.57-2.46 (m, 1H), 2.44-2.30 (m, 1H), 2.22-2.09 (m, 1H), 1.86-1.79 (m, 2H), 1.43 (dt, J = 9.0, 3.2 Hz, 1H), 1.26-0.97 (m, 4H). | A2 |
| 121 | 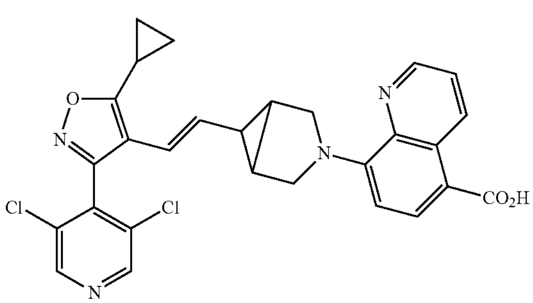 [SMILES: O=C(O)c1ccc(N2CC3C(/C=C/c4c(-c5c(Cl)cncc5Cl)noc4C4CC4)C3C2)c2ncccc12] | MS (ESI): m/z 533.1 [M + H]$^+$; EC$_{50}$ = 824; $^1$H NMR (500 MHz, Methanol-d$_4$) δ 9.55 (dd, J = 8.8, 1.1 Hz, 1H), 8.77-8.72 (m, 3H), 8.24 (d, J = 8.5 Hz, 1H), 7.50 (dd, J = 8.8, 3.9 Hz, 1H), 6.80 (d, J = 8.5 Hz, 1H), 6.17 (d, J = 16.0 Hz, 1H), 5.29 (dd, J = 16.0, 8.8 Hz, 1H), 4.52 (d, J = 11.0 Hz, 2H), 3.70 (br d, J = 10.7 Hz, 2H), 2.36-2.22 (m, 1H), 1.73 (br s, 2H), 1.65-1.55 (m, 1H), 1.25-1.15 (m, 4H). | A2 |

TABLE 1-continued

| Ex. No. | Structure | LCMS, FXR EC$_{50}$ (nM) & NMR | Method |
|---|---|---|---|
| 122 | 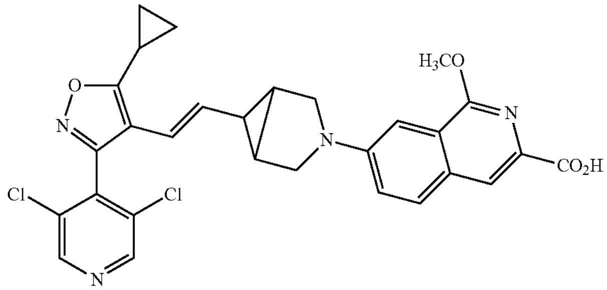 [SMILES: COc1nc(C(=O)O)cc2ccc(N3CC4C(/C=C/c5c(-c6c(Cl)cncc6Cl)noc5C5CC5)C4C3)cc12] | MS (ESI): m/z 563.1 [M + H]$^+$; EC$_{50}$ = 126; $^1$H NMR (400 MHz, Methanol-d$_4$) δ 8.72 (s, 2H), 8.05 (s, 1H), 7.77 (d, J = 9.0 Hz, 1H), 7.22 (dd, J = 8.9, 2.3 Hz, 1H), 7.10 (s, 1H), 6.15 (d, J = 16.1 Hz, 1H), 5.27 (dd, J = 16.1, 8.8 Hz, 1H), 4.16 (s, 3H), 3.72 (d, J = 9.7 Hz, 2H), 3.46-3.39 (m, 2H), 2.27 (tt, J = 8.1, 5.4 Hz, 1H), 1.77 (br s, 2H), 1.43 (dt, J = 8.8, 3.2 Hz, 1H), 1.26-1.10 (m, 4H). | A2 |
| 123 | 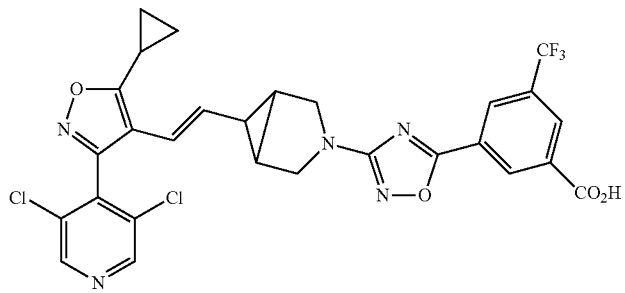 [SMILES: O=C(O)c1cc(-c2nc(N3CC4C(/C=C/c5c(-c6c(Cl)cncc6Cl)noc5C5CC5)C4C3)no2)cc(C(F)(F)F)c1] | MS (ESI): m/z 618.1 [M + H]$^+$; EC$_{50}$ = 206; $^1$H NMR (400 MHz, DMSO-d$_6$) δ 8.86 (s, 2H), 8.71 (s, 1H), 8.46 (s, 1H), 8.41 (s, 1H), 6.15 (d, J = 16.1 Hz, 1H), 5.30 (dd, J = 16.1, 8.9 Hz, 1H), 3.66 (d, J = 10.3 Hz, 2H), 3.56-3.48 (m, 2H), 2.43-2.33 (m, 1H), 1.81-1.68 (m, 2H), 1.41 (dt, J = 8.7, 3.3 Hz, 1H), 1.24-1.05 (m, 4H). | H |
| 124 | 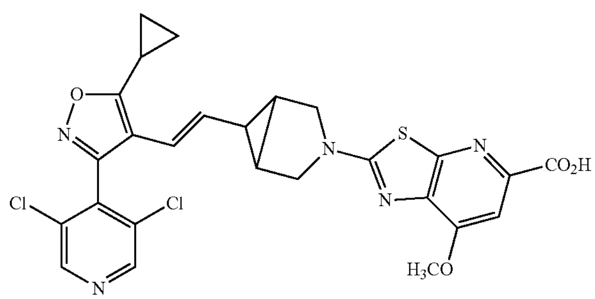 [SMILES: COc1cc(C(=O)O)nc2sc(N3CC4C(/C=C/c5c(-c6c(Cl)cncc6Cl)noc5C5CC5)C4C3)nc12] | MS (ESI): m/z 570.0 [M + H]$^+$; EC$_{50}$ = 284; $^1$H NMR (500 MHz, Methanol-d$_4$) δ 8.73 (s, 2H), 7.75 (s, 1H), 6.19 (d, J = 16.0 Hz, 1H), 5.29 (dd, J = 16.0, 8.5 Hz, 1H), 4.10 (s, 3H), 3.89-3.78 (m, 2H), 3.73 (br d, J = 9.4 Hz, 2H), 2.36-2.22 (m, 1H), 1.81 (br s, 2H), 1.47-1.39 (m, 1H), 1.24-1.16 (m, 4H). | A1 |
| 125 | 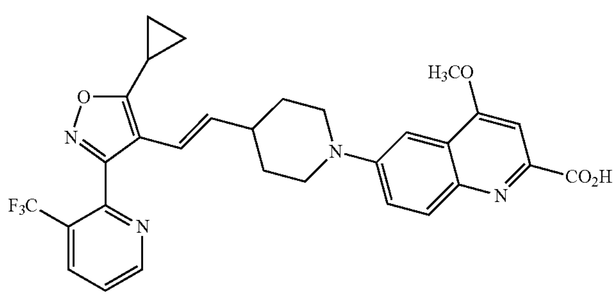 | MS (ESI) m/z: 565.2 [M + H]$^+$; EC$_{50}$ = 14; $^1$H NMR (500 MHz, Methanol-d$_4$) δ 8.92 (br d, J = 4.40 Hz, 1H), 8.34 (d, J = 7.98 Hz, 1H), 8.09-8.24 (m, 1H), 7.79-7.92 (m, 1H), 7.75 (br d, J = 2.75 Hz, 2H), 7.41 (br s, 1H), 6.19 (d, J = 16.23 Hz, 1H), 5.37-5.48 (m, 1H), 4.31 (br s, 3H), 3.95 (br d, J = 1.93 Hz, 2H), 2.90-3.03 (m, 2H), 2.21-2.33 (m, 2H), 1.77 (br d, J = 12.10 Hz, 2H), 1.33-1.43 (m, 2H), 1.10-1.21 (m, 4H). | A2 |
| 126 | 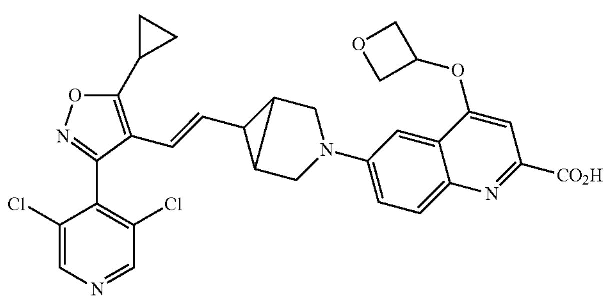 [SMILES: O=C(O)c1cc(OC2COC2)c2cc(N3CC4C(/C=C/c5c(-c6c(Cl)cncc6Cl)noc5C5CC5)C4C3)ccc2n1] | MS (ESI): m/z 605.2 [M + H]$^+$; EC$_{50}$ = 18; $^1$H NMR (400 MHz, DMSO-d$_6$) δ 8.80 (s, 2H), 7.88 (d, J = 9.3 Hz, 1H), 7.28 (dd, J = 9.4, 2.7 Hz, 1H), 6.96 (s, 1H), 6.89 (d, J = 2.7 Hz, 1H), 6.08 (d, J = 16.1 Hz ,1H), 5.58 (q, J = 5.3 Hz, 1H), 5.24 (dd, J = 1.61, 8.9 Hz, 1H), 4.98 (t, J = 6.7 Hz, 2H), 4.64 (dd, J = 7.5, 4.5 Hz, 2H), 3.67 (d, J = 10.1 Hz, 2H), 3.40-3.30 (m, 2H), 2.31 (tt, J = 8.5, 5.2 Hz, 1H), 1.83-1.71 (m, 2H), 1.37 (dt, J = 8.9, 3.2 Hz, 1H), 1.19-0.96 (m, 4H). | A2 |

TABLE 1-continued

| Ex. No. | Structure | LCMS, FXR EC$_{50}$ (nM) & NMR | Method |
|---|---|---|---|
| 127 | 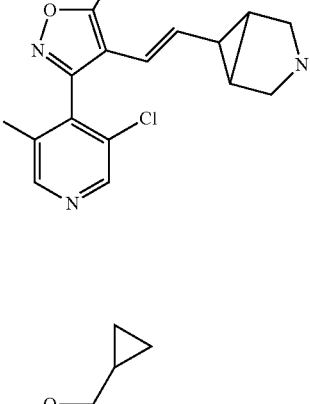 | MS (ESI): m/z 619.2 [M + H]$^+$; EC$_{50}$ = 30; $^1$H NMR (400 MHz, DMSO-d$_6$) δ 8.79 (s, 2H), 7.91 (d, J = 9.3 Hz, 1H), 7.35 (s, 1H), 7.29 (dd, J = 9.4, 2.8 Hz, 1H), 6.79 (d, J = 2.7 Hz, 1H), 6.07 (d, J = 16.0 Hz, 1H), 5.41-5.34 (m, 1H), 5.23 (dd, J = 16.1, 8.9 Hz, 1H), 3.99-3.90 (m, 2H), 3.87 (q, J = 7.9 Hz, 1H),3 .75 (td, J = 8.3, 4.6 Hz, 1H), 3.64 (d, J = 10.1 Hz, 2H), 3.37-3.31 (m, 2H), 2.36-2.23 (m, 2H), 2.12-2.01 (m, 1H), 1.81-1.71 (m, 2H), 1.36 (dt, J = 8.9, 3.3 Hz, 1H), 1.18-0.96 (m, 4H). | A2 |
| 128 | 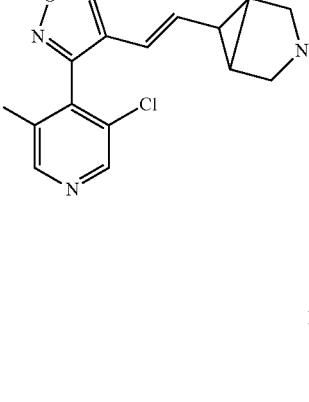 | MS (ESI): m/z 619.3 [M + H]$^+$; EC$_{50}$ = 27; $^1$H NMR (400 MHz, DMSO-d$_6$) δ 8.79 (s, 2H), 7.91 (d, J = 9.3 Hz, 1H), 7.35 (s, 1H), 7.29 (dd, J = 9.3, 2.8 Hz, 1H), 6.79 (d, J = 2.7 Hz, 1H), 6.07 (d, J = 16.1 Hz, 1H), 5.42-4.35 (m, 1H), 5.23 (dd, J = 16.1, 8.9 Hz, 1H), 3.98-3.90 (m, 2H), 3.87 (q, J = 7.9 Hz, 1H), 3.75 (td, J = 8.3, 4.6 Hz, 1H), 3.64 (d, J = 10.1 Hz, 2H), 3.35 (d, J = 10.0 Hz, 2H), 2.36-2.20 (m, 2H), 2.13-2.00 (m, 1H), 1.81-1.68 (m, 2H), 1.36 (dt, J = 9.0, 3.2 Hz, 1H), 1.21-0.91 (m, 4H). | A2 |
| 129 | 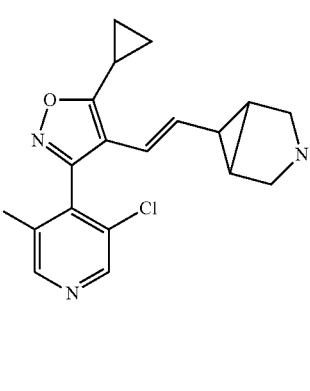 | MS (ESI) m/z: 669.3 [M + H]$^+$; EC$_{50}$ = 240; $^1$H NMR (500 MHz, DMSO-d$_6$) δ 8.83 (s, 2H), 7.93-8.02 (m, 1H), 7.46 (br d, J = 8.24 Hz, 2H), 7.28-7.36 (m, 1H), 6.98 (br d, J = 8.54 Hz, 2H), 6.07-6.18 (m, 1H), 5.39 (s, 2H), 5.20-5.31 (m, 1H), 3.88 (s, 1H), 3.76 (s, 3H), 3.64 (br d, J = 10.07 Hz, 1H), 3.37 (br d, J = 8.54 Hz, 1H), 2.30-2.38 (m, 1H), 1.78 (br s, 2H), 1.37-1.43 (m, 1H), 1.15-2.0 (m, 2H), 1.08 (br d, J = 2.44 Hz, 2H) additional signals were lost due to water suppression. | A2 |
| 130 | 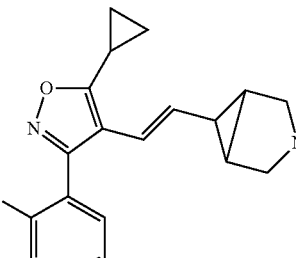 | MS (ESI) m/z: 602.2 [M + H]$^+$; EC$_{50}$ = 50; $^1$H NMR (400 MHz, Methanol-d$_4$) δ 8.13 (d, J = 9.46 Hz, 1H), 7.86-7.91 (m, 1H), 7.68-7.80 (m, 2H), 7.51-7.57 (m, 2H), 7.45 (d, J = 6.82 Hz, 1H), 7.03 (d, J = 2.64 Hz, 1H), 6.04-6.16 (m, 1H), 5.28 (t, J = 7.26 Hz, 1H), 3.75 (d, J = 9.90 Hz, 2H), 3.46-3.55 (m, 2H), 2.66-2.76 (m, 2H), 2.36-2.48 (m, 2H), 2.20-2.28 (m, 1H), 1.97-2.07 (m, 1H), 1.86-1.96 (m, 1H), 1.76 (br s, 2H), 1.33-1.40 (m, 2H), 1.11-1.20 (m, 4H). | A2 |

TABLE 1-continued

| Ex. No. | Structure | LCMS, FXR EC$_{50}$ (nM) & NMR | Method |
|---|---|---|---|
| 131 | 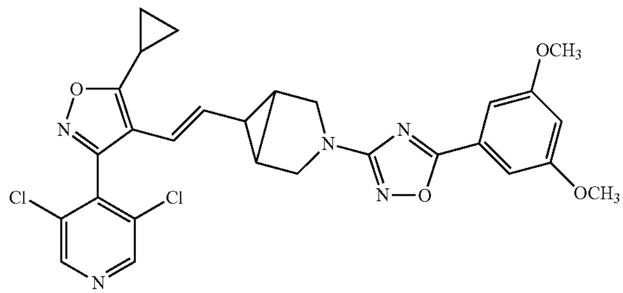 [SMILES: COc1cc(OC)cc(-c2nc(N3CC4C(/C=C/c5c(-c6c(Cl)cncc6Cl)noc5C5CC5)C4C3)no2)c1] | MS (ESI): m/z 580.1 [M + H]$^+$; EC$_{50}$ = 73; $^1$H NMR (400 MHz, Methanol-d$_4$) δ 8.62 (s, 2H), 8.14 (t, J = 1.4 Hz, 1H), 7.76-7.51 (m, 2H), 6.05 (d, J = 15.9 Hz, 1H), 5.16 (dd, J = 16.0, 8.7 Hz, 1H), 3.83 (s, 3H), 3.63 (d, J = 10.2 Hz, 2H), 3.45-3.39 (m, 2H), 2.21-2.10 (m, 1H), 1.63-1.55 (m, 2H), 1.35-1.26 (m, 1H), 1.16-0.99 (m, 4H). | H |
| 132 | 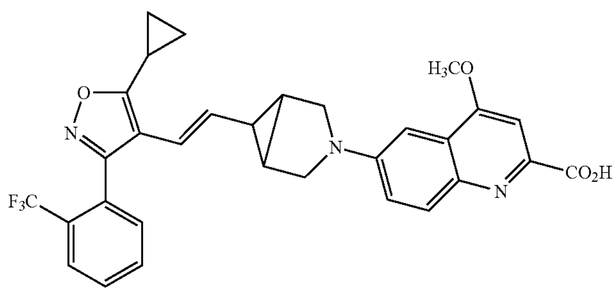 [SMILES: COc1cc(C(=O)O)nc2ccc(N3CC4C(/C=C/c5c(-c6ccccc6C(F)(F)F)noc5C5CC5)C4C3)cc12] | MS (ESI) m/z: 562.2 [M + H]$^+$; EC$_{50}$ = 16; $^1$H NMR (400 MHz, DMSO-d$_6$) δ 8.02 (d, J = 9.24 Hz, 1H), 7.92 (d, J = 7.48 Hz, 1H), 7.73-7.85 (m, 2H), 7.47-7.54 (m, 2H), 7.37 (dd, J = 2.53, 9.35 Hz, 1H), 6.83 (d, J = 2.42 Hz, 1H), 6.07 (d, J = 16.07 Hz, 1H), 5.17 (dd, J = 8.91, 16.18 Hz, 1H), 4.14 (s, 3H), 3.66 (d, J = 9.90 Hz, 2H), 3.39 (br d, J = 9.24 Hz, 2H), 2.31 (s, 1H), 1.72 (br s, 2H), 1.32-1.39 (m, 1H), 1.10-1.18 (m, 2H), 1.06 (dd, J = 2.20, 5.06 Hz, 2H). | A2 |
| 133 | 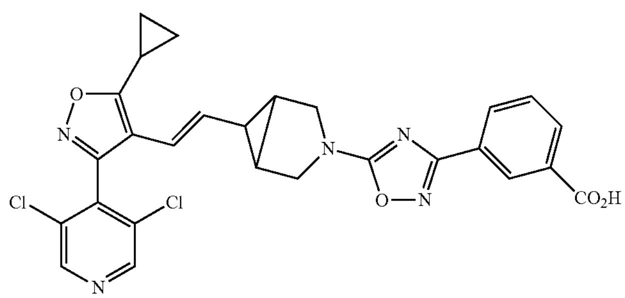 [SMILES: O=C(O)c1cccc(-c2noc(N3CC4C(/C=C/c5c(-c6c(Cl)cncc6Cl)noc5C5CC5)C4C3)n2)c1] | MS (ESI): m/z 550.2 [M + H]$^+$; EC$_{50}$ = 1292; $^1$H NMR (500 MHz, DMSO-d6) δ 8.86 (s, 2H), 8.44 (t, J = 1.8 Hz, 1H), 8.10 (ddt, J = 10.9, 7.8, 1.4 Hz, 2H), 7.65 (t, J = 7.8 Hz, 1H), 6.14 (d, J = 16.0 Hz, 1H), 5.32 (dd, J = 16.1, 8.8 Hz, 1H), 3.76 (d, J = 10.5 Hz, 2H), 3.70 (dt, J = 10.5, 1.8 Hz, 2H), 2.38 (tt, J = 8.6, 5.2 Hz, 1H), 1.83-1.78 (m, 2H), 1.46 (dt, J = 8.7, 3.4 Hz, 1H), 1.26-1.01 (m, 4H). | I |
| 134 | 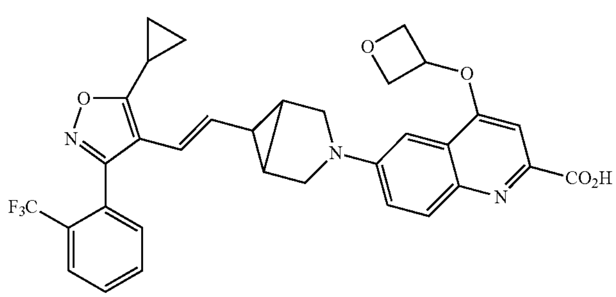 | MS (ESI): m/z: 604.2 [M + H]$^+$; EC$_{50}$ = 15; $^1$H NMR (500 MHz, Methanol-d$_4$) δ 8.14 (br d, J = 8.53 Hz, 1H), 7.88 (d, J = 7.70 Hz, 1H), 7.70-7.79 (m, 2H), 7.55 (br d, J = 9.08 Hz, 1H), 7.45 (br d, J = 7.15 Hz, 1H), 7.28 (s, 1H), 7.10 (br s, 1H), 6.06-6.14 (m, 1H), 5.82 (br s, 1H), 5.15-5.26 (m, 3H), 4.90 (br dd, J = 4.54, 7.29 Hz, 2H), 3.76 (br d, J = 10.18 Hz, 2H), 3.52 (br d, J = 9.08 Hz, 2H), 2.22 (br s, 1H), 1.75 (br s, 2H), 1.34-1.39 (m, 1H), 1.10-1.19 (m, 4H). | A2 |
| 135 | 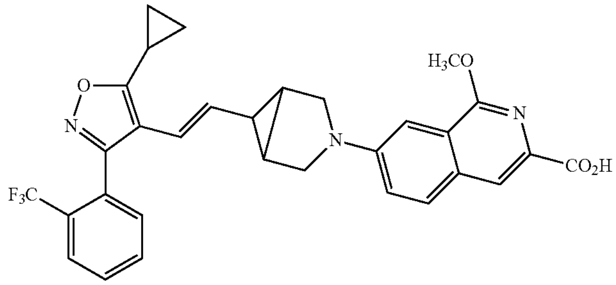 | MS (ESI): m/z: 562.2 [M + H]$^+$; EC$_{50}$ = 416; $^1$H NMR (500 MHz, DMSO-d$_6$) δ 8.04 (s, 1H), 7.93 (br d, J = 7.70 Hz, 1H), 7.87 (d, J = 9.08 Hz, 1H), 7.79-7.84 (m, 1H), 7.78 (br d, J = 7.70 Hz, 1H), 7.52 (br d, J = 7.43 Hz, 1H), 7.22 (br d, J = 7.70 Hz, 1H), 6.93 (s, 1H), 6.03-6.11 (m, 1H), 5.17 (dd, J = 8.94, 16.09 Hz, 1H), 4.07 (s, 3H), 3.65 (br d, J = 9.90 Hz, 2H), 3.37 (br d, J = 8.80 Hz, 2H), 2.31 (br d, J = 4.95 Hz, 1H), 1.71 (br s, 2H), 1.30-1.39 (m, 1H), 1.11-1.18 (m, 2H), 1.06 (br d, J = 2.48 Hz, 2H). | A2 |

TABLE 1-continued

| Ex. No. | Structure | LCMS, FXR EC$_{50}$ (nM) & NMR | Method |
|---|---|---|---|
| 136 | 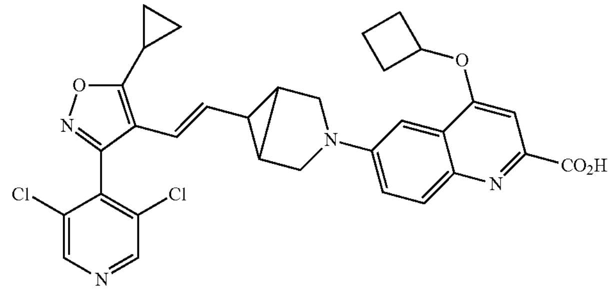 [SMILES: O=C(O)c1cc(OC2CCC2)c2cc(N3CC4C(/C=C/c5c(-c6c(Cl)cncc6Cl)noc5C5CC5)C4C3)ccc2n1] | MS (ESI): m/z 603.2 [M + H]$^+$; EC$_{50}$ = 20; $^1$H NMR (400 MHz, Methanol-d$_4$) δ 8.72 (s, 2H), 8.28-7.99 (m, 1H), 7.62-7.34 (m, 2H), 7.02 (br s, 1H), 6.15 (d, J = 16.1 Hz, 1H), 5.28 (dd, J = 16.1, 8.8 Hz, 1H), 3.75 (d, J = 10.1 Hz, 2H), 3.48 (td, J = 3.4, 2.0 Hz, 2H), 3.13 (dt, J = 3.2, 1.6 Hz, 1H), 2.76-2.67 (m, 2H), 2.44-2.33 (m, 2H), 2.31-2.22 (m, 1H), 1.81 (br s, 2H), 1.46-1.40 (m, 1H), 1.29 (br s, 2H), 1.22-1.16 (m, 4H). | A2 |
| 137 | 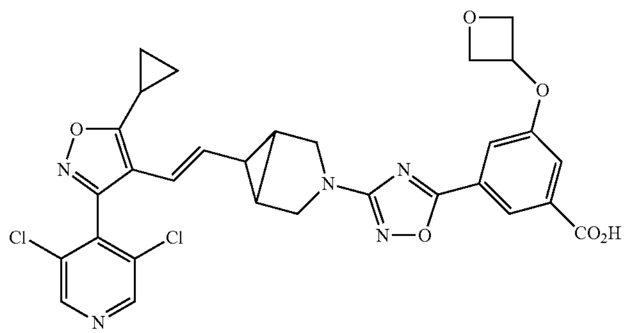 [SMILES: O=C(O)c1cc(OC2COC2)cc(-c2nc(N3CC4C(/C=C/c5c(-c6c(Cl)cncc6Cl)noc5C5CC5)C4C3)no2)c1] | MS (ESI): m/z 622.3 [M + H]$^+$; EC$_{50}$ = 932; $^1$H NMR (400 MHz, CDCl$_3$) δ 8.66 (s, 2H), 8.41 (s, 1H), 7.63 (s, 1H), 7.57 (s, 1H), 6.04 (d, J = 15.9 Hz, 1H), 5.42-5.31 (m, 1H), 5.24 (dd, J = 16.0, 8.7 Hz, 1H), 5.11-5.00 (m, 2H), 4.87-4.76 (m, 2H), 3.81 (d, J = 10.3 Hz, 2H), 3.55 (d, J = 10.0 Hz, 2H), 2.21-2.06 (m, 1H), 1.69-1.61 (m, 2H), 1.44-1.37 (m, 1H), 1.22-0.72 (m, 4H). | H |
| 138 | 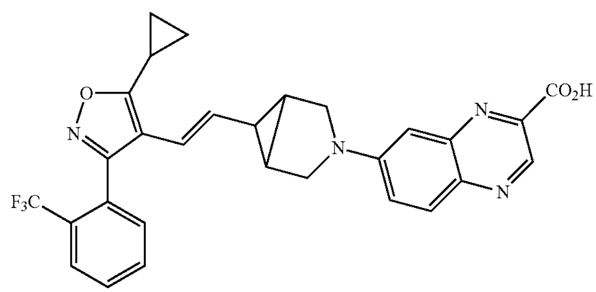 [SMILES: O=C(O)c1cnc2ccc(N3CC4C(/C=C/c5c(-c6ccccc6C(F)(F)F)noc5C5CC5)C4C3)cc2n1] | MS (ESI) m/z: 533.2 [M + H]$^+$; EC$_{50}$ = 2470; $^1$H NMR (400 MHz, Methanol-d$_4$) δ 9.07 (s, 1H), 7.84-7.94 (m, 2H), 7.67-7.81 (m, 2H), 7.41-7.54 (m, 2H), 6.98 (br s, 1H), 6.02-6.17 (m, 1H), 5.20 (dd, J = 8.80, 16.07 Hz, 1H), 3.75 (d, J = 10.12 Hz, 2H), 3.46-3.56 (m, 2H), 2.23 (s, 1H), 1.73 (br s, 2H), 1.35-1.42 (m, 1H), 1.08-1.22 (m, 4H). | A2 |
| 139 | 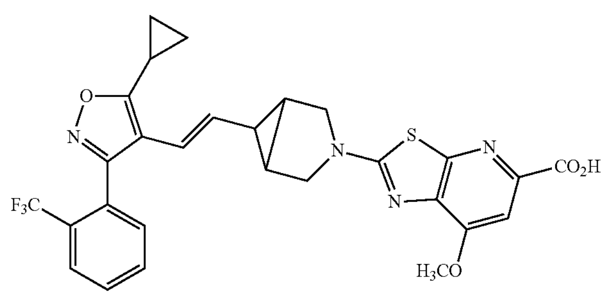 [SMILES: COc1cc(C(=O)O)nc2sc(N3CC4C(/C=C/c5c(-c6ccccc6C(F)(F)F)noc5C5CC5)C4C3)nc12] | MS (ESI): m/z 569.2 [M + H]$^+$; EC$_{50}$ = 163; $^1$H NMR (500 MHz, Methanol-d$_4$) δ 7.89 (d, J = 7.4 Hz, 1H), 7.79-7.71 (m, 3H), 7.46 (d, J = 7.4 Hz, 1H), 6.14 (d, J = 16.2 Hz, 1H), 5.20 (dd, J = 16.0, 8.5 Hz, 1H), 4.09 (s, 3H), 3.81 (br s, 2H), 3.71 (br d, J = 10.2 Hz, 2H), 2.24 (br s, 1H), 1.73 (br s, 2H), 1.39-1.30 (m, 1H), 1.21-1.11 (m, 4H). | A1 |
| 140 | 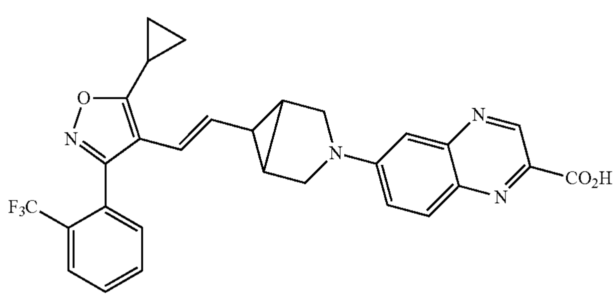 [SMILES: O=C(O)c1cnc2cc(N3CC4C(/C=C/c5c(-c6ccccc6C(F)(F)F)noc5C5CC5)C4C3)ccc2n1] | MS (ESI) m/z: 533.2 [M + H]$^+$; EC$_{50}$ = 142; $^1$H NMR (400 MHz, Methanol-d$_4$) δ 9.19 (s, 1H), 7.96 (br d, J = 9.02 Hz, 1H), 7.83-7.90 (m, 1H), 7.66-7.79 (m, 2H), 7.39-7.48 (m, 2H), 6.85 (d, J = 2.64 Hz, 1H), 6.04-6.14 (m, 1H), 5.21 (d, J = 8.80 Hz, 1H), 3.76 (d, J = 10.56 Hz, 2H), 3.55 (dd, J = 1.76, 8.36 Hz, 2H), 2.17-2.26 (m, 1H), 1.74 (br s, 2H), 1.32-1.39 (m, 1H), 1.10-1.19 (m, 4H). | A2 |

TABLE 1-continued

| Ex. No. | Structure | LCMS, FXR EC$_{50}$ (nM) & NMR | Method |
|---|---|---|---|
| 141 | 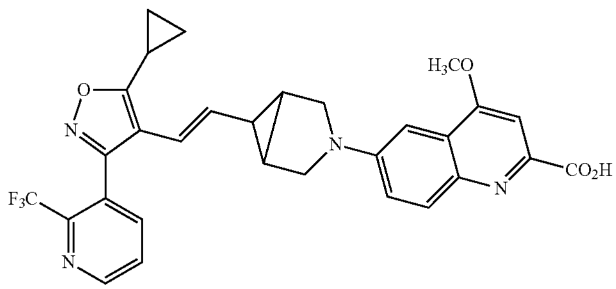 [SMILES: COc1cc(C(=O)O)nc2ccc(N3CC4C(/C=C/c5c(-c6cccnc6C(F)(F)F)noc5C5CC5)C4C3)cc12] | MS (ESI): m/z 563.3 [M + H]$^+$; EC$_{50}$ = 98; $^1$H NMR (400 MHz, DMSO-d$_6$) δ 8.93 (dd, J = 4.7, 1.5 Hz, 1H), 8.09 (dd, J = 7.9, 1.5 Hz, 1H), 8.03 (d, J = 9.5 Hz, 1H), 7.89 (dd, J = 7.9, 4.8 Hz, 1H), 7.51 (s, 1H), 7.40 (dd, J = 9.4, 2.7 Hz, 1H), 6.85 (d, J = 2.7 Hz, 1H), 6.12 (d, J = 16.1 Hz, 1H), 5.25 (dd, J = 16.1, 8.9 Hz, 1H), 4.15 (s, 3H), 3.68 (d, J = 10.0 Hz, 2H), 3.45-3.33 (m, 2H), 2.40-2.21 (m, 1H), 1.82-1.73 (m, 2H), 1.41 (dt, J = 9.1, 3.2 Hz, 1H), 1.31-0.95 (m, 4H). | A2 |
| 142 | 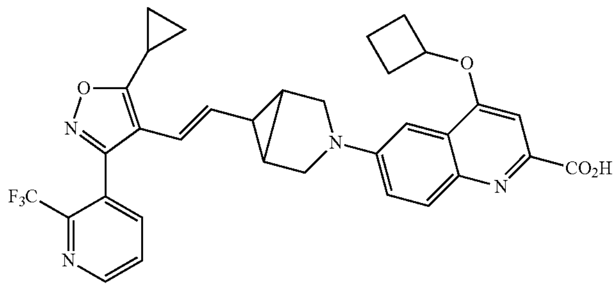 [SMILES: O=C(O)c1cc(OC2CCC2)c2cc(N3CC4C(/C=C/c5c(-c6cccnc6C(F)(F)F)noc5C5CC5)C4C3)ccc2n1] | MS (ESI): m/z 603.3 [M + H]$^+$; EC$_{50}$ = 54; $^1$H NMR (400 MHz, DMSO-d$_6$) δ 8.93 (dd, J = 4.7, 1.5 Hz, 1H), 8.09 (dd, J = 8.0, 1.6 Hz, 1H), 8.03 (d, J = 9.3 Hz, 1H), 7.90 (dd, J = 7.9, 4.7 Hz, 1H), 7.40 (dd, J = 9.4, 2.7 Hz, 1H), 6.87 (d, J = 2.6 Hz, 1H), 7.31 (s, 1H), 6.11 (d, J = 16.1 Hz, 1H), 5.26 (dd, J = 16.1, 8.9 Hz, 1H), 5.15 (p, J = 7.2 Hz, 1H), 3.70 (d, J = 10.1 Hz, 2H), 3.48-3.39 (m, 2H), 2.62-2.42 (m, 2H), 2.38-2.39 (m, 1H), 2.30-2.18 (m, 2H), 1.97-1.6 (m, 4H), 1.40 (dt, J = 8.9, 3.2 Hz, 1H), 1.25-1.00 (m, 4H). | A2 |
| 143 | 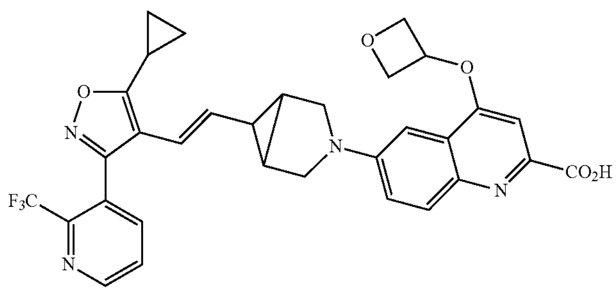 [SMILES: O=C(O)c1cc(OC2COC2)c2cc(N3CC4C(/C=C/c5c(-c6cccnc6C(F)(F)F)noc5C5CC5)C4C3)ccc2n1] | MS (ESI): m/z 605.3 [M + H]$^+$; EC$_{50}$ = 88; $^1$H NMR (400 MHz, DMSO-d$_6$) δ 8.86 (dd, J = 4.7, 1.6 Hz, 1H), 8.02 (dd, J = 7.9, 1.5 Hz, 1H), 7.89 (d, J = 9.3 Hz, 1H), 7.82 (dd, J = 7.9, 4.8 Hz, 1H), 7.28 (dd, J = 9.3, 2.7 Hz, 1H), 6.96 (s, 1H), 6.89 (d, J = 2.7 Hz, 1H), 6.05 (d, J = 16.0 Hz, 1H), 5.59 (p, J = 5.2 Hz, 1H), 5.18 (dd, J = 16.1, 8.9 Hz, 1H), 5.04-4.90 (m, 2H), 4.64 (dd, J = 7.6, 4.5 Hz, 2H), 3.65 (d, J = 10.1 Hz, 2H), 3.41-3.27 (m, 2H), 2.33-2.21 (m, 1H), 1.78-1.64 (m, 2H), 1.34 (dt, J = 8.9, 3.2 Hz, 1H), 1.18-0.88 (m, 4H). | A2 |
| 144 | 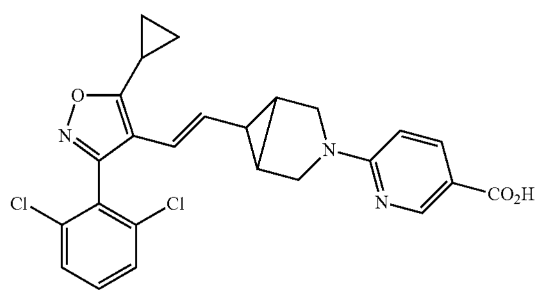 [SMILES: O=C(O)c1ccc(N2CC3C(/C=C/c4c(-c5c(Cl)cccc5Cl)noc4C4CC4)C3C2)nc1] | MS (ESI) m/z: 482.1 [M + H]$^+$; EC$_{50}$ = 424; $^1$H NMR (500 MHz, DMSO-d$_6$) δ 8.58 (d, J = 1.8 Hz, 1H), 7.90 (dd, J = 9.0, 2.0 Hz, 1H), 7.70-7.63 (m, 2H), 7.63-7.56 (m, 1H), 7.28-7.99 (m, 1H), 6.47 (d, J = 9.2 Hz, 1H), 6.14 (d, J = 15.9 Hz, 1H), 5.15 (dd, J = 16.0, 9.0 Hz, 1H), 3.82-3.66 (m, 1H), 2.42-2.26 (m, 1H), 1.69 (br s, 2H), 1.37-1.29 (m, 1H), 1.22-1.14 (m, 2H), 1.12-1.02 (m, 2H) additional signals were lost due to water suppression. | A1 |
| 145 | 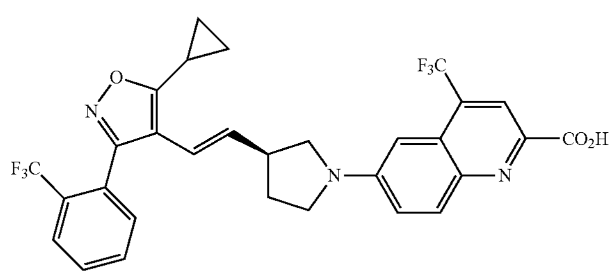 [SMILES: O=C(O)c1cc(C(F)(F)F)c2cc(N3CC[C@@H](/C=C/c4c(-c5ccccc5C(F)(F)F)noc4C4CC4)C3)ccc2n1] | MS (ESI) m/z: 588.3 [M + H]$^+$; EC$_{50}$ = 419; $^1$H NMR (500 MHz, DMSO-d$_6$) δ 8.32 (br s, 1H), 7.29-7.92 (m, 6H), 6.48-6.64 (m, 1H), 6.13-6.24 (m, 1H), 5.35-5.52 (m, 1H), 2.99 (br s, 2H), 2.34 (br dd, J = 4.27, 8.85 Hz, 1H), 2.05-2.14 (m, 1H), 1.68 (br s, 1H), 1.13-1.18 (m, 2H), 1.07 (br d, J = 2.44 Hz, 2H) additional signals were lost due to water suppression. | A2 |

TABLE 1-continued

| Ex. No. | Structure | LCMS, FXR EC$_{50}$ (nM) & NMR | Method |
|---|---|---|---|
| 146 | 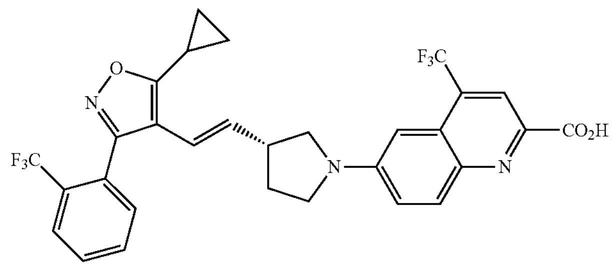 [SMILES: O=C(O)c1cc(C(F)(F)F)c2cc(N3CC[C@H](/C=C/c4c(-c5ccccc5C(F)(F)F)noc4C4CC4)C3)ccc2n1] | MS (ESI) m/z: 588.4 [M + H]$^+$; EC$_{50}$ = 22; $^1$H NMR (500 MHz, DMSO-d$_6$) δ 8.15 (br s, 1H), 8.03 (br s, 1H), 7.78 (br d, J = 7.63 Hz, 1H), 7.70 (br d, J = 7.63 Hz, 1H), 7.61 (br d, J = 7.32 Hz, 1H), 7.47 (br d, J = 7.32 Hz, 1H), 7.37 (br d, J = 6.10 Hz, 1H), 6.58 (br s, 1H), 6.17 (br d, J = 16.17 Hz, 1H), 5.37-5.49 (m, 1H), 2.98 (br d, J = 4.58 Hz, 2H), 2.32 (br d, J = 4.27 Hz, 1H), 2.04-2.13 (m, 1H), 1.62-1.72 (m, 1H), 1.12 (br d, J = 7.93 Hz, 2H), 1.04 (br s, 2H) additional signals were lost due to water suppression. | A2 |
| 147 | 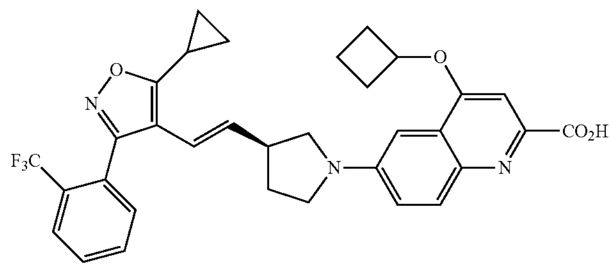 [SMILES: O=C(O)c1cc(OC2CCC2)c2cc(N3CC[C@@H](/C=C/c4c(-c5ccccc5C(F)(F)F)noc4C4CC4)C3)ccc2n1] | MS (ESI) m/z: 590.2 [M + H]$^+$; EC$_{50}$ = 139; $^1$H NMR (400 MHz, Methanol-d$_4$) δ 8.11 (br d, J = 9.24 Hz, 1H), 7.78 (d, J = 7.70 Hz, 1H), 7.66-7.72 (m, 1H), 7.57-7.64 (m, 1H), 7.51 (s, 1H), 7.42-7.47 (m, 1H), 6.88-6.97 (m, 1H), 6.23 (d, J = 16.07 Hz, 1H), 5.49-5.60 (m, 1H), 5.27 (br t, J = 7.15 Hz, 1H), 3.58 (br s, 1H), 3.43 (br t, J = 6.71 Hz, 2H), 3.08 (br d, J = 5.72 Hz, 2H), 2.67-2.78 (m, 2H), 2.42 (ddd, J = 2.64, 7.43, 9.96 Hz, 2H), 2.16-2.30 (m, 2H), 1.98-2.07 (m, 1H), 1.86-1.97 (m, 1H), 1.80 (br dd, J = 8.14, 12.32 Hz, 1H), 1.12-1.22 (m, 5H). | A2 |
| 148 | 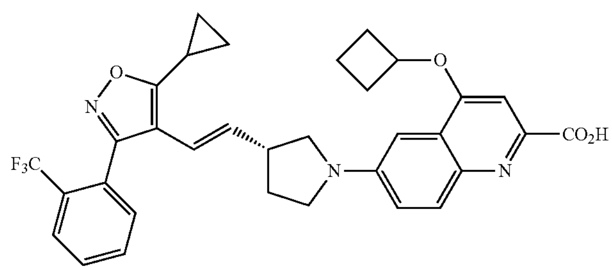 [SMILES: O=C(O)c1cc(OC2CCC2)c2cc(N3CC[C@H](/C=C/c4c(-c5ccccc5C(F)(F)F)noc4C4CC4)C3)ccc2n1] | MS (ESI) m/z: 590.2 [M + H]$^+$; EC$_{50}$ = 2; $^1$H NMR( 400 MHz, Methanol-d$_4$) δ 8.11 (d, J = 9.46 Hz, 1H), 7.79 (d, J = 7.92 Hz, 1H), 7.70 (s, 1H), 7.57-7.65 (m, 1H), 7.41-7.50 (m, 2H), 6.93 (d, J = 2.42 Hz, 1H), 6.23 (d, J = 16.07 Hz, 1H), 5.49-5.60 (m, 1H), 5.27 (br t, J = 7.15 Hz, 1H), 3.59 (br d, J = 1.76 Hz, 1H), 3.43 (br dd, J = 5.94, 7.70 Hz, 2H), 3.03-3.11 (m, 2H), 2.68-2.78 (m, 2H), 2.42 (br s, 2H), 2.16-2.31 (m, 2H), 1.98-2.08 (m, 1H), 1.87-1.98 (m, 1H), 1.74-1.86 (m, 1H), 1.17 (dtd, J = 2.42, 5.45, 11.11 Hz, 5H). | A2 |
| 149 | 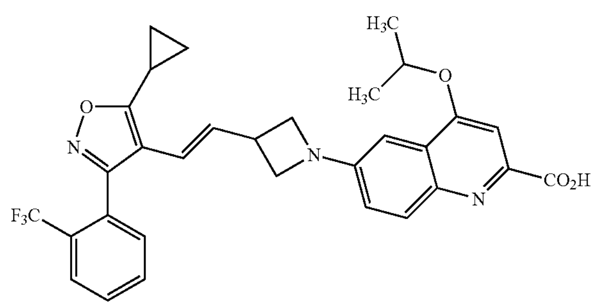 [SMILES: CC(C)Oc1cc(C(=O)O)nc2ccc(N3CC(/C=C/c4c(-c5ccccc5C(F)(F)F)noc4C4CC4)C3)cc12] | MS (ESI) m/z: 564.2 [M + H]$^+$; EC$_{50}$ = 164; $^1$H NMR (500 MHz, Methanol-d$_4$) δ 8.14 (br d, J = 9.1 Hz, 1H), 7.90 (d, J = 7.7 Hz, 1H), 7.81-7.76 (m, 1H), 7.75-7.69 (m, 2H), 7.49 (br d, J = 7.7 Hz, 1H), 7.30 (br d, J = 8.5 Hz, 1H), 6.89 (s, 1H), 6.25 (d, J = 16.0 Hz, 1H), 5.81 (dd, J = 16.1, 8.4 Hz, 1H), 5.26 (dt, J = 12.0, 5.8 Hz, 1H), 4.27 (br t, J = 7.8 Hz, 2H), 3.72 (br t, J = 6.6 Hz, 2H), 3.59-3.50 (m, 1H), 2.35-2.27 (m, 1H), 1.59 (d, J = 6.1 Hz, 6H), 1.25-1.14 (m, 4H). | A2 |
| 150 | 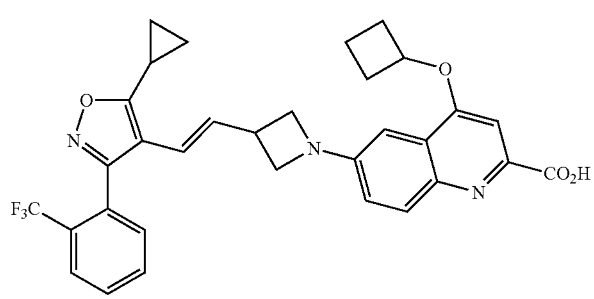 [SMILES: O=C(O)c1cc(OC2CCC2)c2cc(N3CC(/C=C/c4c(-c5ccccc5C(F)(F)F)noc4C4CC4)C3)ccc2n1] | MS (ESI) m/z: 576.3 [M + H]$^+$; EC$_{50}$ = 58; $^1$H NMR (500 MHz, Methanol-d$_4$) δ 8.13 (br d, J = 8.8 Hz, 1H), 7.90 (d, J = 7.7 Hz, 1H), 7.78 (t, J = 7.7 Hz, 1H), 7.72 (t, J = 7.6 Hz, 1H), 7.54 (s, 1H), 7.50 (d, J = 7.5 Hz, 1H), 7.29 (br d, J = 8.8 Hz, 1H), 6.90 (s, 1H), 6.26 (d, J = 16.0 Hz, 1H), 5.82 (dd, J = 16.0, 8.3 Hz, 1H), 5.26 (quin, J = 7.0 Hz, 1H), 4.28 (br t, J = 7.7 Hz, 2H), 3.72 (br t, J = 6.3 Hz, 2H), 3.58-3.51 (m, 1H), 2.77-2.68 (m, 2H), 2.47-2.37 (m, 2H), 2.34-2.25 (m, 1H), 2.03 (q, J = 10.3 Hz, 1H), 1.96-1.87 (m, 1H), 1.24-1.14 (m, 4H). | A2 |

TABLE 1-continued

| Ex. No. | Structure | LCMS, FXR EC$_{50}$ (nM) & NMR | Method |
|---|---|---|---|
| 151 | 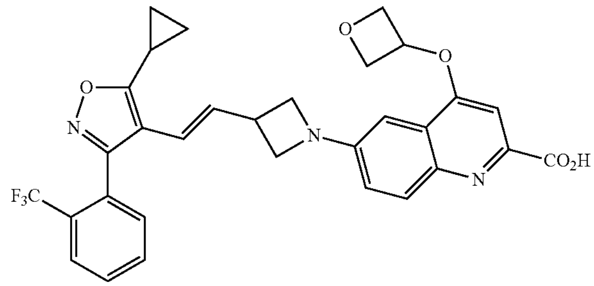 [SMILES: O=C(O)c1cc(OC2COC2)c2cc(N3CC(/C=C/c4c(-c5ccccc5C(F)(F)F)noc4C4CC4)C3)ccc2n1] | MS (ESI) m/z: 578.3 [M + H]$^+$; EC$_{50}$ = 96; $^1$H NMR (500 MHz, DMSO-d$_6$) δ 11.82 (br s, 1H), 7.95 (br d, J = 9.1 Hz, 1H), 7.79 (br d, J = 7.2 Hz, 1H), 7.73-7.58 (m, 2H), 7.48 (br d, J = 7.2 Hz, 1H), 7.21 (br d, J = 8.5 Hz, 1H), 7.03 (s, 1H), 6.95 (br s, 1H), 6.71 (br s, 1H), 5.64 (br s, 1H), 5.05 (br t, J = 5.8 Hz, 2H), 4.71 (br s, 2H), 4.42 (br s, 2H), 4.07 (br s, 4H), 2.14-2.06 (m, 1H), 0.78-0.57 (m, 4H). | A2 |
| 152 | 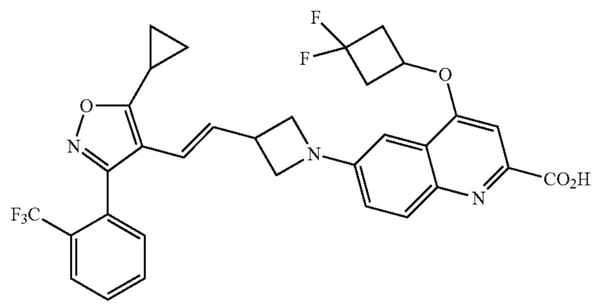 [SMILES: O=C(O)c1cc(OC2CC(F)(F)C2)c2cc(N3CC(/C=C/c4c(-c5ccccc5C(F)(F)F)noc4C4CC4)C3)ccc2n1] | MS (ESI) m/z: 612.4 [M + H]$^+$; EC$_{50}$ = 228; $^1$H NMR (500 MHz, Methanol-d$_4$) δ 8.13 (br d, J = 9.1 Hz, 1H), 7.90 (d, J = 8.0 Hz, 1H), 7.81-7.75 (m, 1H), 7.75-7.70 (m, 1H), 7.53 (s, 1H), 7.49 (d, J = 7.4 Hz, 1H), 7.26 (br d, J = 8.8 Hz, 1H), 6.91 (d, J = 1.4 Hz, 1H), 6.25 (d, J = 16.2 Hz, 1H), 5.81 (dd, J = 16.1, 8.4 Hz, 1H), 5.25 (br s, 1H), 4.27 (t, J = 7.8 Hz, 2H), 3.71 (br t, J = 6.7 Hz, 2H), 3.58-3.50 (m, 1H), 3.45-3.38 (m, 2H), 3.09-2.97 (m, 2H), 2.35-2.26 (m, 1H), 1.25-1.15 (m, 4H). | A2 |
| 153 | 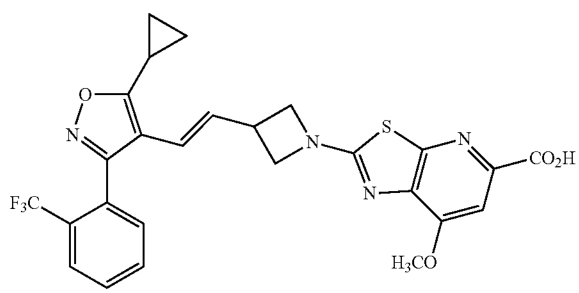 [SMILES: COc1cc(C(=O)O)nc2sc(N3CC(/C=C/c4c(-c5ccccc5C(F)(F)F)noc4C4CC4)C3)nc12] | MS (ESI) m/z: 543.3 [M + H]$^+$; EC$_{50}$ = 473; $^1$H NMR (500 MHz, Methanol-d$_4$) δ 7.89 (d, J = 7.7 Hz, 1H), 7.80-7.75 (m, 2H), 7.75-7.70 (m, 1H), 7.49 (d, J = 7.4 Hz, 1H), 6.25 (d, J = 16.0 Hz, 1H), 5.81 (br dd, J = 15.8, 8.4 Hz, 1H), 4.40 (br t, J = 8.4 Hz, 2H), 4.09 (s, 3H), 3.89 (br t, J = 6.9 Hz, 2H), 3.65-3.57 (m, 1H), 2.36-2.28 (m, 1H), 1.25-1.14 (m, 4H). | A1 |
| 154 | 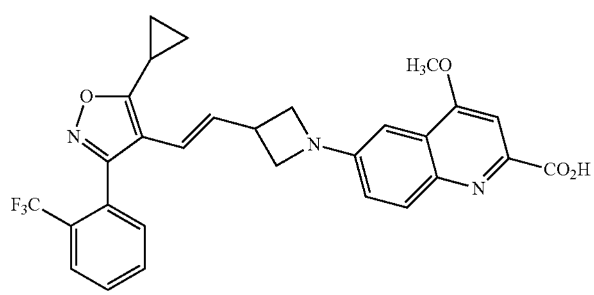 | MS (ESI) m/z: 536.3 [M + H]$^+$; EC$_{50}$ = 63; $^1$H NMR (500 MHz, Methanol-d$_4$) δ 8.13 (d, J = 9.4 Hz, 1H), 7.89 (d, J = 7.7 Hz, 1H), 7.80-7.75 (m, 1H), 7.74-7.70 (m, 2H), 7.49 (d, J = 7.4 Hz, 1H), 7.28 (dd, J = 9.1, 2.5 Hz, 1H), 6.92 (d, J = 2.5 Hz, 1H), 6.25 (d, J = 16.0 Hz, 1H), 5.81 (dd, J = 16.1, 8.4 Hz, 1H), 4.33 (s, 3H), 4.26 (t, J = 7.8 Hz, 2H), 3.74-3.67 (m, 2H), 3.58-3.50 (m, 1H), 2.35-2.26 (m, 1H), 1.25-1.15 (m, 4H). | A2 |
| 155 | 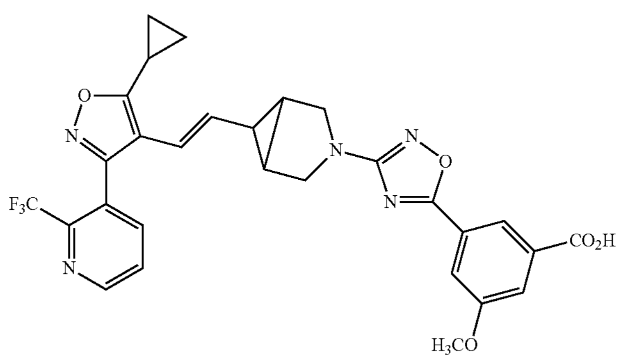 [SMILES: COc1cc(C(=O)O)cc(-c2nc(N3CC4C(/C=C/c5c(-c6cccnc6C(F)(F)F)noc5C5CC5)C4C3)no2)c1] | EC$_{50}$ = 784; H NMR (400 MHz, DMSO-d$_6$) δ 13.48 (s, 1H), 8.92 (dd, J = 4.8, 1.5 Hz, 1H), 8.13-8.05 (m, 2H), 7.89 (dd, J = 7.9, 4.7 Hz, 1H), 7.68 (d, J = 1.5 Hz, 2H), 6.12 (d, J = 16.1 Hz, 1H), 5.24 (dd, J = 16.1, 8.9 Hz, 1H), 3.91 (s, 3H), 3.62 (d, J = 10.2 Hz, 2H), 3.46 (dt, J = 10.1, 2.0 Hz, 2H), 2.33 (tt, J = 8.3, 5.1 Hz, 1H), 1.69 (d, J = 3.2 Hz, 2H), 1.38 (dt, J = 8.9, 3.3 Hz, 1H), 1.30-0.83 (m, 4H). | H |

TABLE 1-continued

| Ex. No. | Structure | LCMS, FXR EC$_{50}$ (nM) & NMR | Method |
|---|---|---|---|
| 156 | 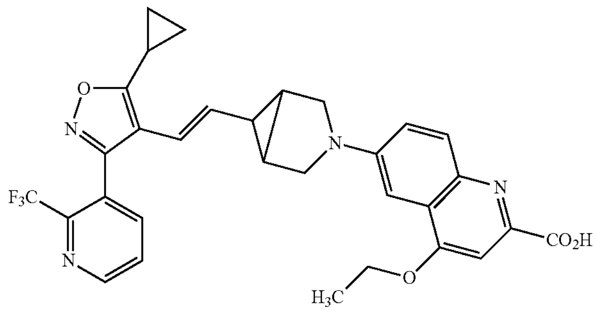 [SMILES: CCOc1cc(C(=O)O)nc2ccc(N3CC4C(/C=C/c5c(-c6cccnc6C(F)(F)F)noc5C5CC5)C4C3)cc12] | MS (ESI) m/z: 577.5 [M + H]$^+$; EC$_{50}$ = 43; $^1$H NMR (400 MHz, DMSO-d$_6$) δ 8.86 (dd, J = 4.8, 1.5 Hz, 1H), 8.02 (dd, J = 7.9, 1.5 Hz, 1H), 7.95 (d, J = 9.3 Hz, 1H), 7.82 (dd, J = 7.9, 4.7 Hz, 1H), 7.40 (s, 1H), 7.32 (dd, J = 9.4, 2.7 Hz, 1H), 6.79 (d, J = 2.6 Hz, 1H), 6.04 (d, J = 16.1 Hz, 1H), 5.18 (dd, J = 16.1, 8.9 Hz, 1H), 4.36 (q, J = 7.0 Hz, 2H), 3.61 (d, J = 10.1 Hz, 2H), 3.47-3.15 (m, 2H), 2.26 (ddt, J = 10.1, 8.2, 4.2 Hz, 1H), 1.71 (d, J = 3.1 Hz, 2H), 1.42 (t, J = 7.0 Hz, 3H), 1.33 (dt, J = 9.0, 3.2 Hz, 1H), 1.17-1.05 (m, 2H), 1.05-0.92 (m, 2H). | A2 |
| 157 | 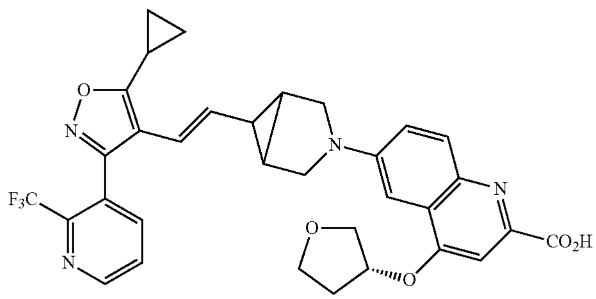 [SMILES: O=C(O)c1cc(O[C@@H]2CCOC2)c2cc(N3CC4C(/C=C/c5c(-c6cccnc6C(F)(F)F)noc5C5CC5)C4C3)ccc2n1] | MS (ESI) m/z: 619.5 [M + H]$^+$; EC$_{50}$ = 165; $^1$H NMR (400 MHz, DMSO-d$_6$) δ 8.86 (dd, J = 4.8, 1.5 Hz, 1H), 8.02 (dd, J = 7.9, 1.5 Hz, 1H), 7.97 (d, J = 9.4 Hz, 1H), 7.82 (dd, J = 7.9, 4.7 Hz, 1H), 5.39 (s, 1H), 7.33 (dd, J = 9.4, 2.7 Hz, 1H), 6.79 (d, J = 2.7 Hz, 1H), 6.03 (d, J = 16.1 Hz, 1H), 5.48-5.39 (m, 1H), 5.18 (dd, J = 16.1, 8.9 Hz, 1H), 3.94 (d, J = 3.0 Hz, 2H), 3.87 (q, J = 7.9 Hz, 1H), 3.76 (td, J = 8.3, 4.7 Hz, 1H), 3.62 (d, J = 10.1 Hz, 2H), 3.45-3.28 (m, 2H), 2.38-2.17 (m, 2H), 2.13-2.02 (m, 1H), 1.75-1.68 (m, 2H), 1.32 (dt, J = 9.0, 3.2 Hz, 2H), 1.19-1.05 (m, 2H), 1.05-0.94 (m, 2H). | A2 |
| 158 | 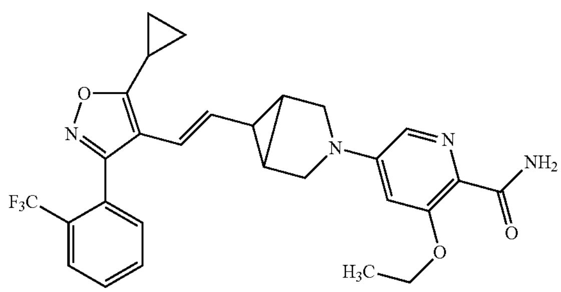 [SMILES: CCOc1cc(N2CC3C(/C=C/c4c(-c5ccccc5C(F)(F)F)noc4C4CC4)C3C2)cnc1C(N)=O] | MS (ESI) m/z: 525.2 [M + H]$^+$; EC$_{50}$ = 555; $^1$H NMR (500 MHz, Methanol-d$_4$) δ 7.87 (d, J = 7.70 Hz, 1H), 7.69-7.78 (m, 2H), 7.53 (d, J = 2.20 Hz, 1H), 7.44 (d, J = 7.15 Hz, 1H), 6.42-6.45 (m, 1H), 6.08 (d, J = 16.23 Hz, 1H), 5.18 (dd, J = 8.80, 15.96 Hz, 1H), 4.17 (q, J = 7.15 Hz, 2H), 3.62 (d, J = 10.18 Hz, 2H), 3.43 (br d, J = 9.90 Hz, 2H), 2.18-2.25 (m, 1H), 1.70 (br s, 2H), 1.44 (t, J = 702 Hz, 3H), 1.27-1.41 (m, 1H), 1.10-1.19 (m, 4H). | A2 |
| 159 | 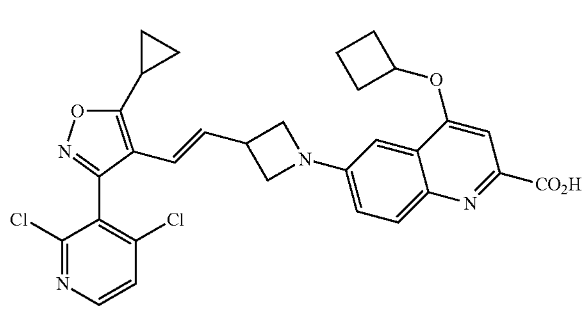 [SMILES: O=C(O)c1cc(OC2CCC2)c2cc(N3CC(/C=C/c4c(-c5c(Cl)ccnc5Cl)noc4C4CC4)C3)ccc2n1] | MS (ESI) m/z: 577.2 [M + H]$^+$; EC$_{50}$ = 39; $^1$H NMR (500 MHz, Methanol-d$_4$) δ 8.68 (s, 2H), 8.06-8.16 (m, 1H), 7.52 (s, 1H), 7.27 (br d, J = 7.70 Hz, 1H), 6.89 (d, J = 2.20 Hz, 1H), 6.28 (d, J = 15.96 Hz, 1H), 5.84 (dd, J = 8.25, 15.96 Hz, 1H), 5.23 (s, 1H), 4.31 (s, 2H), 3.79 (br t, J = 6.74 Hz, 2H), 3.59 (br d, J = 7.70 Hz, 1H), 2.66-2.76 (m, 2H), 2.41 (br s, 2H), 2.25-2.33 (m, 1H), 2.03 (s, 1H), 1.89 (br d, J = 10.18 Hz, 1H), 1.15-1.28 (m, 4H). | A2 |
| 160 | 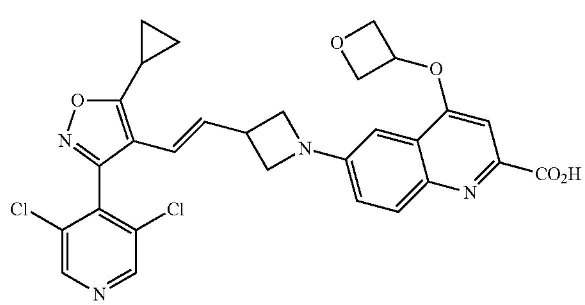 [SMILES: O=C(O)c1cc(OC2COC2)c2cc(N3CC(/C=C/c4c(-c5c(Cl)cncc5Cl)noc4C4CC4)C3)ccc2n1] | MS (ESI) m/z: 579.2 [M + H]$^+$; EC$_{50}$ = 65; $^1$H NMR (500 MHz, Methanol-d$_4$) δ 8.64 (s, 2H), 8.08 (br d, J = 7.98 Hz, 1H), 7.22 (br s, 1H), 7.14-7.20 (m, 1H), 6.92 (br s, 1H), 6.21 (br d, J = 15.13 Hz, 1H), 5.79-5.87 (m, 1H), 5.69 (br s, 1H), 5.20 (br s, 2H), 4.88 (br s, 2H), 4.30 (br s, 2H), 3.78 (br s, 2H), 3.57 (br s, 1H), 2.17-2.24 (m, 1H), 1.22 (br s, 4H). | A2 |

TABLE 1-continued

| Ex. No. | Structure | LCMS, FXR EC$_{50}$ (nM) & NMR | Method |
|---|---|---|---|
| 161 | 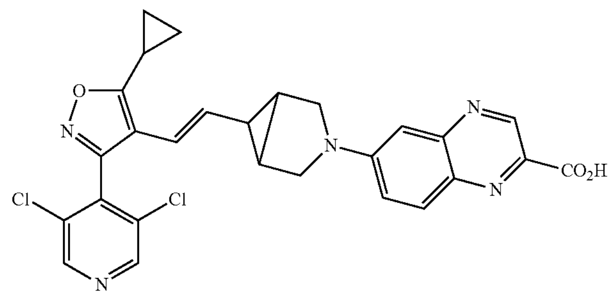 [SMILES: O=C(O)c1cnc2cc(N3CC4C(/C=C/c5c(-c6c(Cl)cncc6Cl)noc5C5CC5)C4C3)ccc2n1] | MS (ESI) m/z: 534.1 [M + H]$^+$; EC$_{50}$ = 192; $^1$H NMR (500 MHz, Methanol-d$_4$) δ 9.22 (s, 1H), 8.66 (s, 2H), 7.98 (br d, J = 9.46 Hz, 1H), 7.69 (s, 1H), 7.37 (dd, J = 2.64, 9.46 Hz, 1H), 6.85 (d, J = 2.20 Hz, 1H), 6.08 (d, J = 15.85 Hz, 1H), 5.29 (dd, J = 8.58, 16.07 Hz, 1H), 3.79 (d, J = 10.34 Hz, 2H), 3.59 (br d, J = 10.12 Hz, 2H), 2.15-2.24 (m, 1H), 1.82 (br s, 2H), 1.35-1.45 (m, 1H), 1.19 (d, J = 6.82 Hz, 4H). | A2 |
| 162 | 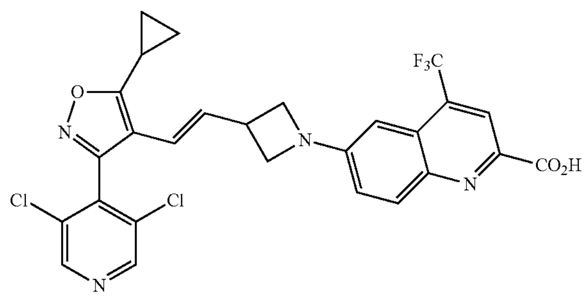 [SMILES: O=C(O)c1cc(C(F)(F)F)c2cc(N3CC(/C=C/c4c(-c5c(Cl)cncc5Cl)noc4C4CC4)C3)ccc2n1] | MS (ESI) m/z: 575.1 [M + H]$^+$; EC$_{50}$ = 150; $^1$H NMR (400 MHz, Methanol-d$_4$) δ 8.71 (s, 2H), 8.28 (s, 1H), 8.09 (d, J = 9.24 Hz, 1H), 7.19 (dd, J = 2.42, 9.24 Hz, 1H), 6.63 (s, 1H), 6.30 (dd, J = 0.88, 16.07 Hz, 1H), 5.90 (dd, J = 8.14, 16.07 Hz, 1H), 4.29 (t, J = 8.03 Hz, 2H), 3.78 (dd, J = 5.94, 7.92 Hz, 2H), 3.52-3.62 (m, 1H), 2.30-2.37 (m, 1H), 1.13-1.28 (m, 4H). | A2 |
| 163 | 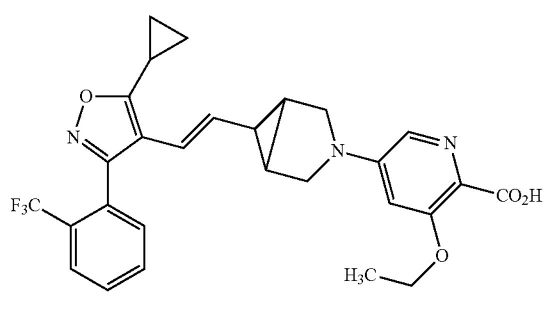 [SMILES: CCOc1cc(N2CC3C(/C=C/c4c(-c5ccccc5C(F)(F)F)noc4C4CC4)C3C2)cnc1C(=O)O] | MS (ESI) m/z: 526.2 [M + H]$^+$; EC$_{50}$ = 424; $^1$H NMR (500 MHz, Methanol-d$_4$) δ 8.29 (s, 1H), 7.87 (br d, J = 7.43 Hz, 1H), 7.68-7.79 (m, 2H), 7.44 (br d, J = 7.15 Hz, 1H), 6.18 (s, 1H), 6.10 (d, J = 15.96 Hz, 1H), 5.22 (dd, J = 8.80, 15.96 Hz, 1H), 4.29 (q, J = 6.88 Hz, 2H), 3.78 (br d, J = 10.73 Hz, 2H), 3.68-3.75 (m, 2H), 2.21 (br t, J = 4.95 Hz, 1H), 1.84 (br s, 2H), 1.49 (t, J = 7.02 Hz, 3H), 1.34-1.39 (m, 1H), 1.11-1.19 (m, 4H). | A2 |
| 164 | 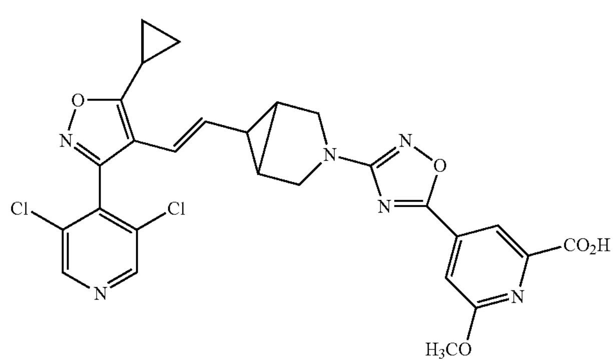 [SMILES: COc1cc(-c2nc(N3CC4C(/C=C/c5c(-c6c(Cl)cncc6Cl)noc5C5CC5)C4C3)no2)cc(C(=O)O)n1] | MS (ESI) m/z: 581.3 [M + H]$^+$; EC$_{50}$ = 297; $^1$H NMR (400 MHz, DMSO-d$_6$) δ 8.78 (s, 2H), 8.00 (d, J = 1.2 Hz, 1H), 7.45 (d, J = 1.2 Hz, 1H), 6.07 (d, J = 16.1 Hz, 1H), 5.22 (dd, J = 16.1, 8.9 Hz, 1H), 3.92 (s, 3H), 3.56 (d, J = 10.2 Hz, 2H), 3.41 (dt, J = 10.1, 1.9 Hz, 2H), 2.34-2.27 (m, 1H), 1.73-1.61 (m, 2H), 1.33 (dt, J = 8.8, 3.3 Hz, 1H), 1.18-1.06 (m, 2H), 1.06-0.98 (m, 2H). | H |

TABLE 1-continued

| Ex. No. | Structure | LCMS, FXR EC$_{50}$ (nM) & NMR | Method |
|---|---|---|---|
| 165 | 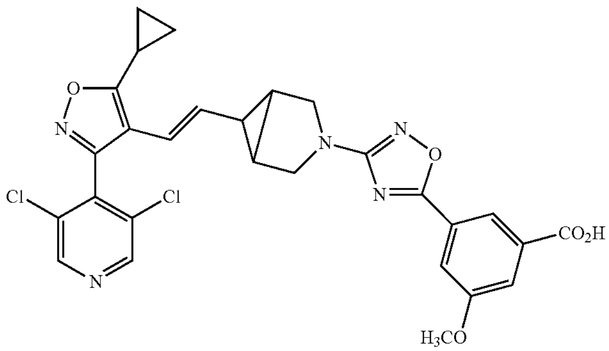 [SMILES: COc1cc(C(=O)O)cc(-c2nc(N3CC4C(/C=C/c5c(-c6c(Cl)cncc6Cl)noc5C5CC5)C4C3)no2)c1] | MS (ESI) mz: 582.3 [M + H]$^+$; EC$_{50}$ = 222; $^1$H NMR (400 MHz, DMSO-d$_6$) δ 8.80 (s, 2H), 8.04 (t, J = 1.5 Hz, 1H), 7.64 (dd, J = 2.6, 1.5 Hz, 1H), 7.61 (dd, J = 2.7, 1.4 Hz, 1H), 6.12 (dd, J = 16.4, 1.3 Hz, 1H), 5.37 (dd, J = 16.3, 6.8 Hz, 1H), 3.84 (s, 3H), 3.83-3.75 (m, 2H), 2.91 (td, J = 12.6, 2.7 Hz, 2H), 2.32 (tt, J = 8.3, 5.1 Hz, 1H), 2.25-2.12 (m, 1H), 1.68-1.44 (m, 2H), 1.28-1.06 (m, 4H), 1.06-0.99 (m, 2H). | H |
| 166 | 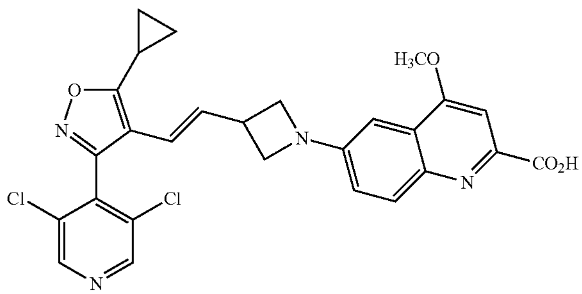 [SMILES: COc1cc(C(=O)O)nc2ccc(N3CC(/C=C/c4c(-c5c(Cl)cncc5Cl)noc4C4CC4)C3)cc12] | MS (ESI) m/z: 537.1 [M + H]$^+$; EC$_{50}$ = 29; $^1$H NMR (500 MHz, Methanol-d$_4$) δ 8.62 (s, 2H), 8.06 (s, 1H), 7.68 (s, 1H), 7.16 (br d, J = 8.25 Hz, 1H), 6.88 (br s, 1H), 6.18 (br d, J = 15.96 Hz, 1H), 5.80 (dd, J = 8.25, 15.96 Hz, 1H), 4.20-4.33 (m, 5H), 3.75 (br t, J = 6.46 Hz, 2H), 3.56 (br d, J = 6.88 Hz, 1H), 2.11-2.22 (m, 1H), 1.18-1.25 (m, 4H). | A2 |
| 167 | 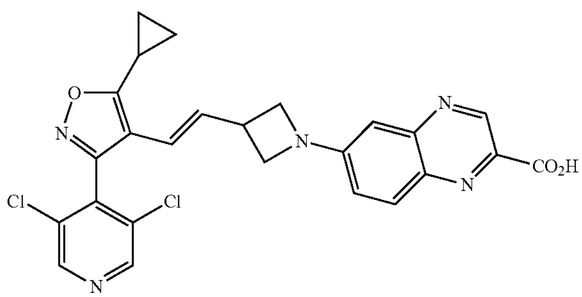 [SMILES: O=C(O)c1cnc2cc(N3CC(/C=C/c4c(-c5c(Cl)cncc5Cl)noc4C4CC4)C3)ccc2n1] | MS (ESI) m/z: 508.2 [M + H]$^+$; EC$_{50}$ = 308; $^1$H NMR (400 MHz, Methanol-d$_4$) δ 9.21 (s, 1H), 8.72 (s, 2H), 7.98 (d, J = 9.24 Hz, 1H), 7.22 (dd, J =2.64, 9.24 Hz, 1H), 6.68 (d, J = 2.42 Hz, 1H), 6.32 (dd, J = 0.88, 16.07 Hz, 1H), 5.92 (d, J = 8.36 Hz, 1H), 4.35 (t, J = 8.47 Hz, 2H), 3.85 (dd, J = 6.05, 8.47 Hz, 2H), 3.60 (br d, J = 7.48 Hz, 1H), 2.30-2.40 (m, 1H), 1.16-1.25 (m, 4H). | A2 |
| 168 | 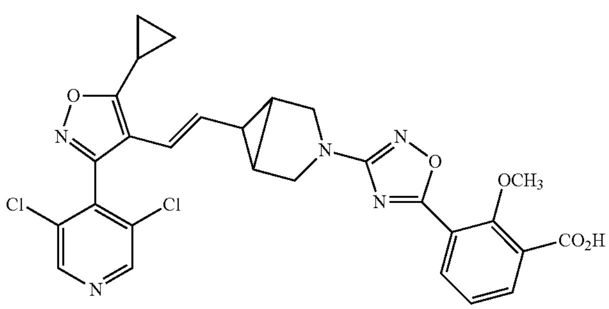 [SMILES: COc1c(C(=O)O)cccc1-c1nc(N2CC3C(/C=C/c4c(-c5c(Cl)cncc5Cl)noc4C4CC4)C3C2)no1] | MS (ESI) m/z: 580.3 [M + H]$^+$; EC$_{50}$ = 1101; $^1$H NMR (400 MHz, DMSO-d$_6$) δ 8.86 (s, 2H), 8.06 (dd, J = 7.8, 1.8 Hz, 1H), 7.95 (dd, J = 7.7, 1.8 Hz, 1H), 7.39 (t, J = 7.7 Hz, 1H), 6.16 (d, J = 16.0 Hz, 1H), 5.29 (dd, J = 16.1, 8.9 Hz, 1H), 3.82 (s, 3H), 3.63 (d, J = 10.2 Hz, 2H), 3.47 (dt, J = 10.0, 1.9 Hz, 2H), 2.44-2.26 (m, 1H), 1.79-1.68 (m, 2H), 1.43 (dt, J = 8.9, 3.3 Hz, 1H), 1.27-0.95 (m, 4H). | H |
| 169 | 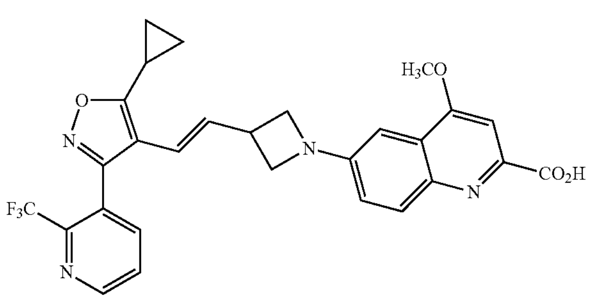 | MS (ESI) m/z: 537.2 [M + H]$^+$; EC$_{50}$ = 223; $^1$H NMR (400 MHz, Methanol-d$_4$) δ 8.83 (dd, J = 1.10, 4.84 Hz, 1H), 8.10 (d, J = 9.24 Hz, 1H), 7.98 (dd, J = 1.10, 7.92 Hz, 1H), 7.78 (dd, J = 4.73, 7.81 Hz, 1H), 7.71 (s, 1H), 7.28 (dd, J = 2.53, 9.35 Hz, 1H) ,6.86 (d, J = 2.42 Hz, 1H), 6.25 (dd, J = 0.88, 16.07 Hz, 1H), 5.83 (dd, J = 8.36, 16.07 Hz, 1H), 4.32 (s, 3H), 4.26 (t, J = 8.03 Hz, 2H), 3.74 (dd, J = 5.94, 7.92 Hz, 2H), 3.48-3.62 (m, 1H), 2.25-2.34 (m, 1H), 1.12-1.24 (m, 4H). | A2 |

TABLE 1-continued

| Ex. No. | Structure | LCMS, FXR EC$_{50}$ (nM) & NMR | Method |
|---|---|---|---|
| 170 | 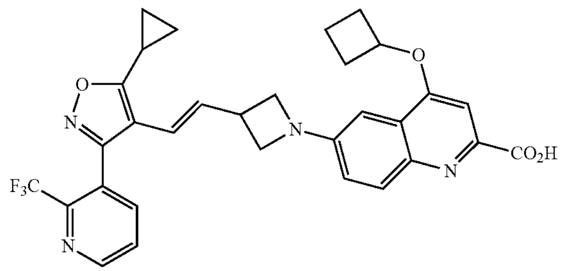 [SMILES: O=C(O)c1cc(OC2CCC2)c2cc(N3CC(/C=C/c4c(-c5cccnc5C(F)(F)F)noc4C4CC4)C3)ccc2n1] | MS (ESI) m/z: 577.2 [M + H]$^+$; EC$_{50}$ = 50; $^1$H NMR (400 MHz, Methanol-d$_4$) δ 8.83 (br s, 1H), 7.93-8.18 (m, 2H), 7.79 (br s, 1H), 7.48 (br s, 1H), 7.23 (br s, 1H), 6.78 (br s, 1H), 6.25 (br d, J = 15.85 Hz, 1H), 5.85 (br s, 1H), 5.22 (br s, 1H), 4.24 (br s, 2H), 3.72 (br s, 2H), 3.46-3.64 (m, 1H), 2.70 (br s, 2H), 2.39 (br s, 2H), 2.18-2.35 (m, 1H), 1.81-2.09 (m, 2H), 1.06-1.29 (m, 4H). | A2 |
| 171 | 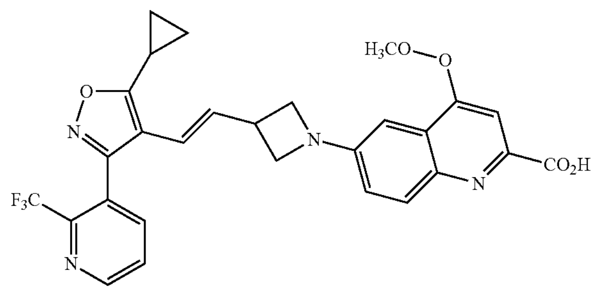 [SMILES: COOc1cc(C(=O)O)nc2ccc(N3CC(/C=C/c4c(-c5cccnc5C(F)(F)F)noc4C4CC4)C3)cc12] | MS (ESI) m/z: 551.2 [M + H]$^+$; EC$_{50}$ = 65; $^1$H NMR( 400 MHz, Methanol-d$_4$) δ 8.84 (br d, J = 4.18 Hz, 1H), 8.24 (s, 1H), 8.13 (br d, J = 8.80 Hz, 1H), 7.99 (br d, J = 7.70 Hz, 1H), 7.79 (dd, J = 4.73, 7.81 Hz, 1H), 7.19-7.26 (m, 1H), 6.59 (d, J = 1.98 Hz, 1H), 6.22-6.31 (m, 1H), 5.81-5.89 (m, 1H), 4.94 (s, 2H), 4.28 (t, J = 8.03 Hz, 2H), 3.76 (br t, J = 6.82 Hz, 2H), 3.58 (s, 4H), 2.30 (s, 2H), 1.11-1.26 (m, 4H). | A2 |
| 172 | 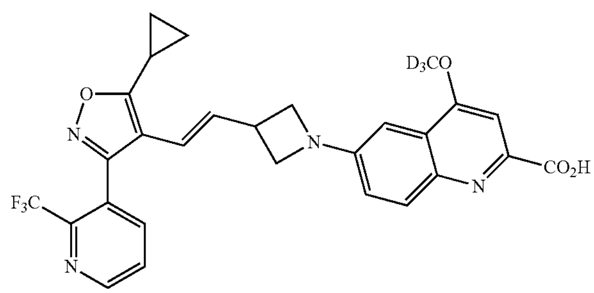 | MS (ESI) m/z: 539.3 [M + H]$^+$; EC$_{50}$ = 29; $^1$H NMR (400 MHz, Methanol-d$_4$) δ 7.99 (br d, J = 9.2 Hz, 1H), 7.77 (d, J = 7.7 Hz, 1H), 7.70-7.56 (m, 3H), 7.37 (d, J = 7.3 Hz, 1H), 7.13 (br d, J = 8.1 Hz, 1H), 6.79 (br s, 1H), 6.12 (d, J = 16.1 Hz, 1H), 5.68 (dd, J = 16.0, 8.5 Hz, 1H), 4.12 (br t, J = 7.8 Hz, 2H), 3.57 (br t, J = 6.5 Hz, 2H), 3.46-3.35 (m, 1H), 2.23-2.13 (m, 1H), 1.13-1.02 (m, 4H). | A2 |
| 173 | 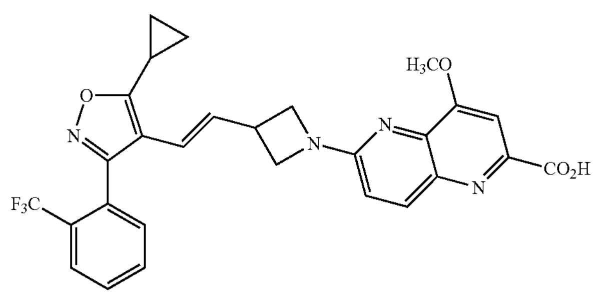 [SMILES: COc1cc(C(=O)O)nc2ccc(N3CC(/C=C/c4c(-c5ccccc5C(F)(F)F)noc4C4CC4)C3)nc12] | MS (ESI) m/z: 537.3 [M + H]$^+$; EC$_{50}$ = 375; $^1$H NMR (500 MHz, Methanol-d$_4$) δ 8.28 (d, J = 9.4 Hz, 1H), 7.95-7.86 (m, 2H), 7.81-7.76 (m, 1H), 7.75-7.70 (m, 1H), 7.50 (d, J = 7.5 Hz, 1H), 7.14 (d, J = 9.7 Hz, 1H), 6.29 (d, J = 16.1 Hz, 1H), 5.83 (dd, J = 15.8, 8.3 Hz, 1H), 4.55 (br t, J = 9.0 Hz, 2H), 4.25 (s, 3H), 4.05 (br dd, J = 9.3, 6.2 Hz, 2H), 3.63-3.54 (m, 1H), 2.35-2.28 (m, 1H), 1.25-1.16 (m, 4H). | A2 |
| 174 | 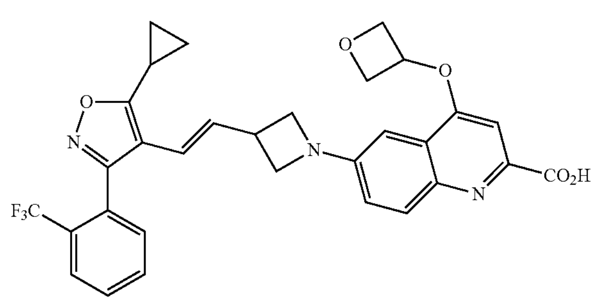 | MS (ESI) m/z: 579.2 [M + H]$^+$; EC$_{50}$ = 324; $^1$H NMR (500 MHz, Methanol-d$_4$) δ 8.84 (br d, J = 4.13 Hz, 1H), 8.13 (br d, J = 8.80 Hz, 1H), 7.99 (br d, J = 7.43 Hz, 1H), 7.79 (dd, J = 4.68, 7.70 Hz, 1H), 7.31 (br s, 1H), 7.29 (s, 1H), 6.94 (d, J = 1.38 Hz, 1H), 6.27 (d, J = 15.96 Hz, 1H), 5.78-5.89 (m, 2H), 5.20 (t, J = 6.74 Hz, 2H), 4.89 (br dd, J = 4.54, 7.57 Hz, 2H), 4.29 (br t, J = 7.84 Hz, 2H), 3.77 (br d, J = 6.88 Hz, 2H), 3.51-3.63 (m, 1H), 2.30 (br s, 2H), 1.18-1.22 (m, 2H), 1.16 (br d, J = 3.03 Hz, 2H). | A2 |

TABLE 1-continued

| Ex. No. | Structure | LCMS, FXR EC$_{50}$ (nM) & NMR | Method |
|---|---|---|---|
| 175 | 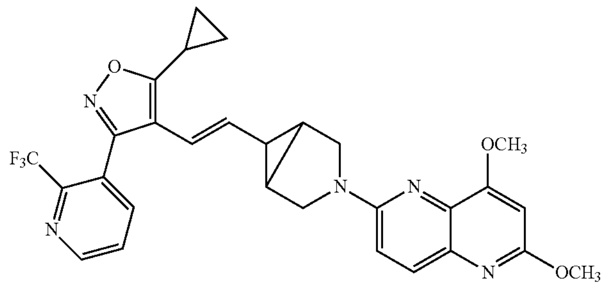 [SMILES: COc1cc(OC)c2nc(N3CC4C(/C=C/c5c(-c6cccnc6C(F)(F)F)noc5C5CC5)C4C3)ccc2n1] | MS (ESI) m/z: 564.3 [M + H]$^+$; EC$_{50}$ = 1891; $^1$H NMR (400 MHz, Methanol-d$_4$) δ 8.88-8.76 (m, 1H), 8.25 (d, J = 9.5 Hz, 1H), 8.02-7.93 (m, 1H), 7.87 (s, 1H), 7.81 (dd, J = 7.9, 4.8 Hz, 1H), 7.30 d, J = 9.5 Hz, 1H), 6.13 (d, J = 16.1 Hz, 1H), 5.27 (dd, J = 16.1, 8.8 Hz, 1H), 4.26 (s, 3H), 4.11-3.85 (m, 2H), 3.72 (dt, J = 11.3, 2.0 Hz, 2H), 2.25 (tt, J = 8.2, 5.2 Hz, 1H), 1.86-1.74 (m, 2H), 1.36 (dt, J = 8.8, 3.3 Hz, 1H), 1.31-0.96 (m, 4H). | A2 |
| 176 | 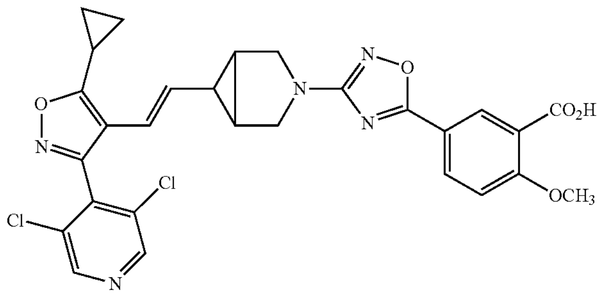 [SMILES: COc1ccc(-c2nc(N3CC4C(/C=C/c5c(-c6c(Cl)cncc6Cl)noc5C5CC5)C4C3)no2)cc1C(=O)O] | MS (ESI) m/z: 564.3 [M + H]$^+$; EC$_{50}$ = 1347; $^1$H NMR (400 MHz, DMSO-d$_6$) δ 8.86 (s, 2H), 8.24 (dd, J = 2.2 Hz, 1H), 8.12 (dd, J = 8.8, 2.3 Hz, 1H), 7.33 (d, J = 8.8 Hz, 1H), 6.15 (d, J = 16.1 Hz, 1H), 5.28 (dd, J = 16.1, 8.8 Hz, 1H), 3.92 (s, 3H), 3.62 (d, J = 10.1 Hz, 2H), 3.45 (d, J = 9.9 Hz, 2H), 2.43-2.26 (m, 1H), 1.72 (s, 2H), 1.47-1.35 (m, 1H), 1.22-0.94 (m, 4H). | H |
| 178 | 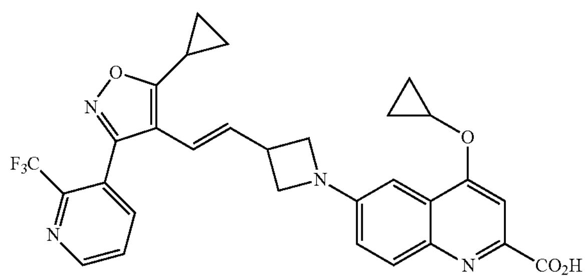 [SMILES: O=C(O)c1cc(OC2CC2)c2cc(N3CC(/C=C/c4c(-c5cccnc5C(F)(F)F)noc4C4CC4)C3)ccc2n1] | MS (ESI) m/z: 563.3 [M + H]$^+$; EC$_{50}$ = 37; $^1$H NMR (400 MHz, Methanol-d$_4$) δ 8.84 (d, J = 3.74 Hz, 1H), 8.14 (br d, J = 8.80 Hz, 1H), 8.05 (s, 1H), 7.96-8.02 (m, 1H), 7.80 (dd, J = 4.84, 7.92 Hz, 1H), 7.31 (br d, J = 8.14 Hz, 1H), 6.80 (d, J = 2.20 Hz, 1H), 6.19-6.34 (m, 1H), 5.83 (dd, J = 8.14, 16.07 Hz, 1H), 4.41 (br s, 1H), 4.27 (br t, J = 8.03 Hz, 2H), 3.74 (br s, 2H), 3.51-3.61 (m, 1H), 2.25-2.35 (m, 1H), 1.15-1.25 (m, 4H), 1.08-1.14 (m, 2H), 1.04 (br s, 2H). | A2 |
| 180 | 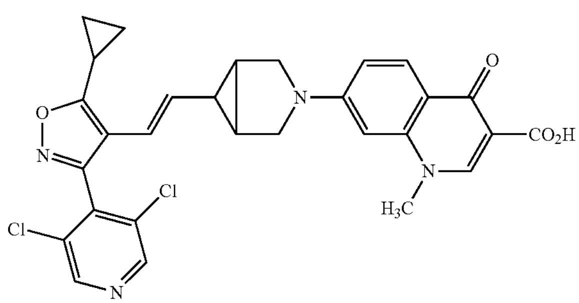 [SMILES: Cn1cc(C(=O)O)c(=O)c2ccc(N3CC4C(/C=C/c5c(-c6c(Cl)cncc6Cl)noc5C5CC5)C4C3)cc21] | MS (ESI) m/z: 563.3 [M + H]$^+$; EC$_{50}$ = 276; $^1$H NMR (400 MHz, DMSO-d$_6$) δ 8.87 (s, 2H), 8.83 (s, 1H), 8.10 (d, J = 9.0 Hz, 1H), 6.93 (dd, J = 9.2, 2.1 Hz, 1H), 6.48 (d, J = 2.1 Hz, 1H), 6.15 (d, J = 16.1 Hz, 1H), 5.31 (dd, J = 16.1, 8.9 Hz, 1H), 3.96 (s, 3H), 3.75 (d, J = 10.0 Hz, 2H), 3.51-3.46 (m, 2H), 2.38 (ddd, J = 8.3, 6.9, 4.1 Hz, 1H), 1.90-1.79 (m, 2H), 1.39 (dt, J = 9.0, 3.3 Hz, 1H), 1.26-0.99 (m, 4H). | A2 |
| 181 | 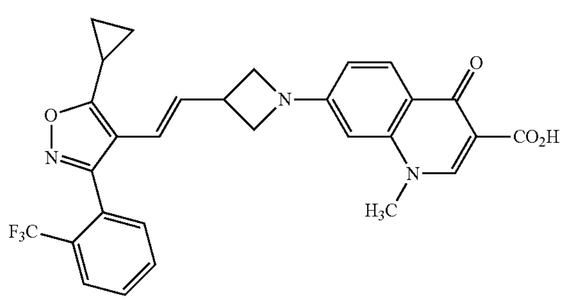 [SMILES: Cn1cc(C(=O)O)c(=O)c2ccc(N3CC(/C=C/c4c(-c5ccccc5C(F)(F)F)noc4C4CC4)C3)cc21] | MS (ESI) m/z: 536.2 [M + H]$^+$; EC$_{50}$ = 400; $^1$H NMR (400 MHz, DMSO-d$_6$) δ 8.83 (s, 1H), 8.11 (d, J = 8.9 Hz, 1H), 7.94 (dd, J = 7.8, 1.4 Hz, 1H), 7.87-7.71 (m, 2H), 7.55 (d, J = 7.4 Hz, 1H), 6.71 (dd, J = 9.0, 2.0 Hz, 1H), 6.37 (d, J = 2.0 Hz, 1H), 6.23 (dd, J = 16.1, 1.0 Hz, 1H), 5.76 (dd, J = 16.1, 8.9 Hz, 1H), 4.22 (t, J = 8.2 Hz, 2H), 3.94 (s, 3H), 3.71 (dd, J = 8.2, 6.0 Hz, 2H), 3.52 (h, J = 7.5 Hz, 1H), 2.41 (tt, J = 8.3, 5.1 Hz, 1H), 1.23-0.92 (m, 4H). | A2 |

TABLE 1-continued

| Ex. No. | Structure | LCMS, FXR EC$_{50}$ (nM) & NMR | Method |
|---|---|---|---|
| 182 | 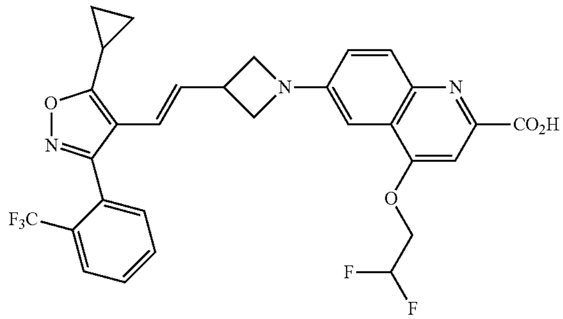 [SMILES: O=C(O)c1cc(OCC(F)F)c2cc(N3CC(/C=C/c4c(-c5ccccc5C(F)(F)F)noc4C4CC4)C3)ccc2n1] | MS (ESI) m/z: 586.3 [M + H]$^+$; EC$_{50}$ = 72; $^1$H NMR (500 MHz, Methanol-d$_4$) δ 8.18-8.09 (m, 1H), 7.89 (d, J = 7.7 Hz, 1H), 7.81-7.68 (m, 3H), 7.49 (br d, J = 7.4 Hz, 1H), 7.25 (br d, J = 8.3 Hz, 1H), 6.88 (br s, 1H), 6.60-6.31 (m, 1H), 6.25 (br d, J = 16.0 Hz, 1H), 5.81 (br dd, J = 15.8, 8.4 Hz, 1H), 4.81-4.72 (m, 2H), 4.26 (br t, J = 7.7 Hz, 2H), 3.70 (br t, J = 6.3 Hz, 2H), 3.58-3.49 (m, 1H), 2.34-2.26 (m, 1H), 1.24-1.15 (m, 4H). | A2 |
| 183 | 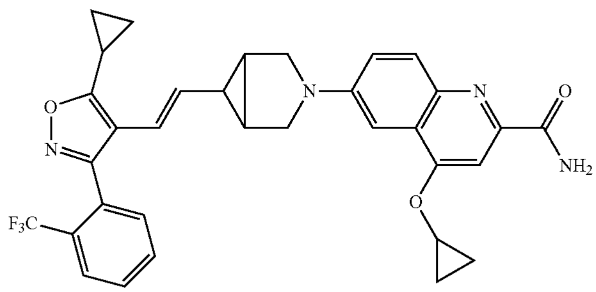 [SMILES: NC(=O)c1cc(OC2CC2)c2cc(N3CC4C(/C=C/c5c(-c6ccccc6C(F)(F)F)noc5C5CC5)C4C3)ccc2n1] | MS (ESI) m/z: 587.2 [M + H]$^+$; EC$_{50}$ = 908; $^1$H NMR (500 MHz, DMSO-d$_6$) δ 8.00 (bs, 1H), 7.91 (d, J = 7.8 Hz, 1H), 7.87-7.62 (m, 4H), 7.48 (d, J = 7.5 Hz, 1H), 7.34 (bs, 1H), 7.24 (dd, J = 9.3, 2.7 Hz, 1H), 6.75 (d, J = 2.7 Hz, 1H), 6.04 (d, J = 16.1 Hz, 1H), 5.19 (dd, J = 16.1, 8.8 Hz, 1H), 4.27-3.97 (m, 1H), 3.62 (d, J = 9.8 Hz, 2H), 3.41-3.27 (m, 2H), 2.26 (td, J = 8.5, 4.3 Hz, 1H), 1.73-1.64 (m, 2H), 1.36-1.31 (m, 1H), 1.15-1.11 (m, 2H), 1.07-1.01 (m, 2H), 0.97-0.90 (m, 2H), 0.84-0.77 (m, 2H). | J1 |
| 184 | 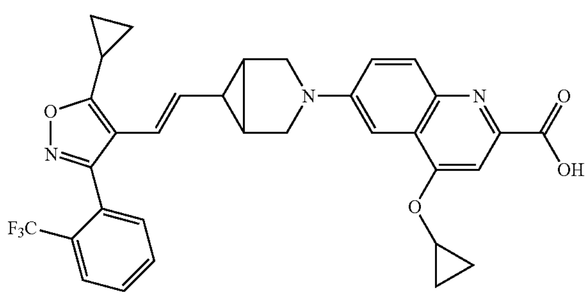 [SMILES: O=C(O)c1cc(OC2CC2)c2cc(N3CC4C(/C=C/c5c(-c6ccccc6C(F)(F)F)noc5C5CC5)C4C3)ccc2n1] | MS (ESI) m/z: 588.3 [M + H]$^+$; HLE GAL-FXR EC$_{50}$ = 50; $^1$H NMR (400 MHz, Methanol-d$_4$) δ 8.16 (d, J = 9.1 Hz, 1H), 8.06 (s, 1H), 7.98-7.83 (m, 1H), 7.83-7.66 (m, 2H), 7.58 (d, J = 8.8 Hz, 1H), 7.46 (d, J = 7.2 Hz, 1H), 7.03-6.80 (m, 1H), 6.11 (d, J = 16.1 Hz, 1H), 5.22 (dd, J = 16.0, 8.7 Hz, 1H), 4.47-4.40 (m, 1H), 3.74 (d, J = 9.9 Hz, 2H), 3.52 (d, J = 10.1 Hz, 2H), 2.24 (tt, J = 8.0, 5.2 Hz, 1H), 1.82-1.67 (m, 2H), 1.49-1.25 (m, 1H), 1.28-0.79 (m, 8H). | J2 |
| 185 | 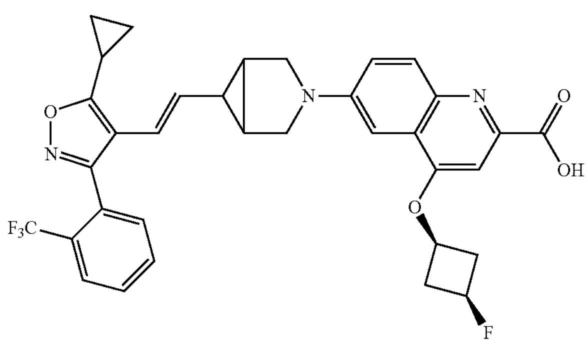 [SMILES: O=C(O)c1cc(O[C@H]2C[C@@H](F)C2)c2cc(N3CC4C(/C=C/c5c(-c6ccccc6C(F)(F)F)noc5C5CC5)C4C3)ccc2n1] | MS (ESI) m/z: 620.3 [M + H]; EC$_{50}$ = 11; $^1$H NMR (400 MHz, Methanol-d$_4$) δ 8.15 (d, J = 9.4 Hz, 1H), 7.90 (dd, J = 7.6, 1.6 Hz, 1H), 7.83-7.67 (m, 2H), 7.56 (dd, J = 9.5, 2.6 Hz, 1H), 7.53 (s, 1H), 7.49-7.43 (m, 1H), 7.06 (d, J = 2.6 Hz, 1H), 6.12 (d, J = 16.1 Hz, 1H), 5.22 (dd, J = 1.61, 8.8 Hz, 1H), 5.06 (p, J = 6.3 Hz, 1H), 5.00-4.89 (m, 2H), 3.77 (d, J = 10.1 Hz, 2H), 3.66-3.48 (m, 2H), 3.31-3.22 (m, 2H), 2.72-2.52 (m, 1H), 2.24 (tt, J = 8.2, 5.3 Hz, 1H), 1.82-1.72 (m, 2H), 1.38 (dt, J = 8.8, 3.3 Hz, 1H), 1.29-0.97 (m, 4H). | A2 |
| 186 | 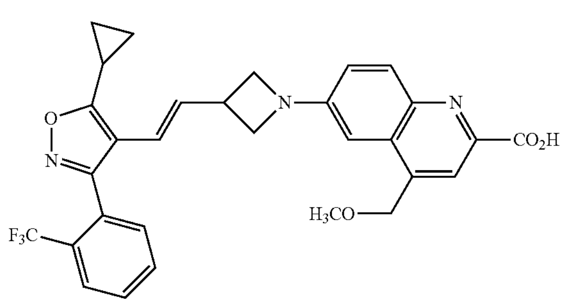 [SMILES: COCc1cc(C(=O)O)nc2ccc(N3CC(/C=C/c4c(-c5ccccc5C(F)(F)F)noc4C4CC4)C3)cc12] | MS (ESI) m/z: 550.2 [M + H]$^+$; EC$_{50}$ = 228; $^1$H NMR (500 MHz, Methanol-d$_4$) δ 8.22 (br s, 1H), 8.17-8.08 (m, 1H), 7.89 (d, J = 8.0 Hz, 1H), 7.81-7.75 (m, 1H), 7.75-7.69 (m, 1H), 7.49 (d, J = 7.4 Hz, 1H), 7.17 (br d, J = 8.5 Hz, 1H), 6.61 (br s, 1H), 6.25 (br d, J = 16.0 Hz, 1H), 5.82 (br dd, J = 15.7, 8.3 Hz, 1H), 4.93 (br s, 2H), 4.26 (br t, J = 7.4 Hz, 2H), 3.75-3.66 (m, 2H), 3.57 (s, 3H), 3.55-3.50 (m, 1H), 2.34-2.27 (m, 1H), 1.25-1.16 (m, 4H). | A2 |

TABLE 1-continued

| Ex. No. | Structure | LCMS, FXR EC$_{50}$ (nM) & NMR | Method |
|---|---|---|---|
| 187 | 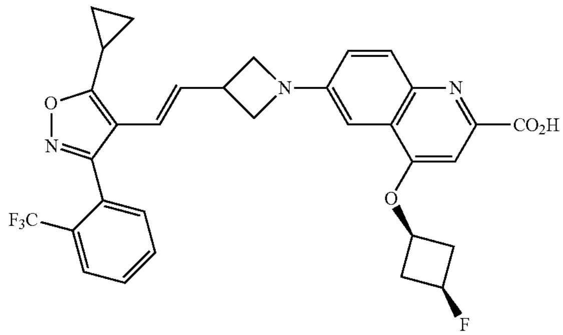 | MS (ESI) m/z: 594.2 [M + H]+; EC$_{50}$ = 348; $^1$H NMR (500 MHz, Methanol-d$_4$) δ 8.14 (br d, J = 9.4 Hz, 1H), 7.90 (d, J = 7.7 Hz, 1H), 7.82-7.75 (m, 1H), 7.75-7.69 (m, 1H), 7.53 (s, 1H), 7.50 (d, J = 7.4 Hz, 1H), 7.29 (br d, J = 7.4 Hz, 1H), 6.92 (d, J = 1.7 Hz, 1H), 6.26 (d, J = 16.0 Hz, 1H), 5.82 (dd, J = 16.1, 8.4 Hz, 1H), 5.08-4.90 (m, 2H), 4.28 (t, J = 7.8 Hz, 2H), 3.73 (t, J = 6.7 Hz, 2H), 3.60-3.50 (m, 1H), 3.29 (td, J = 7.0, 3.9 Hz, 2H), 2.68-2.55 (m, 2H), 2.35-2.26 (m, 1H), 1.24-1.16 (m, 4H). | A2 |
| 188 | 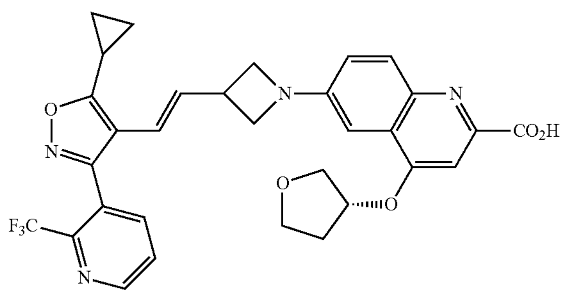 [SMILES: O=C(O)c1cc(O[C@@H]2CCOC2)c2cc(N3CC(/C=C/c4c(-c5cccnc5C(F)(F)F)noc4C4CC4)C3)ccc2n1] | MS (ESI) m/z: 593.3 [M + H]$^+$; EC$_{50}$ = 1690; $^1$H NMR (400 MHz, Methanol-d$_4$) δ 8.84 (d, J = 3.96 Hz, 1H), 8.13 (br d, J = 8.58 Hz, 1H), 7.98 (d, J = 7.04 Hz, 1H), 7.79 (dd, J = 4.73, 7.81 Hz, 1H), 7.68 (s, 1H), 7.30 (br d, J = 8.36 Hz, 1H), 6.88 (s, 1H), 6.26 (d, J = 16.07 Hz, 1H), 5.85 (br d, J = 8.14 Hz, 1H), 5.61 (br s, 1H), 4.23-4.33 (m, 2H), 4.16-4.23 (m, 1H), 4.02-4.15 (m, 2H), 3.96 (br d, J = 4.84 Hz, 1H), 3.75 (br t, J = 6.38 Hz, 2H), 3.56 (br d, J = 6.16 Hz, 1H), 2.47-2.61 (m, 1H), 2.24-2.36 (m, 2H), 1.12-1.23 (m, 4H). | A2 |
| 189 | 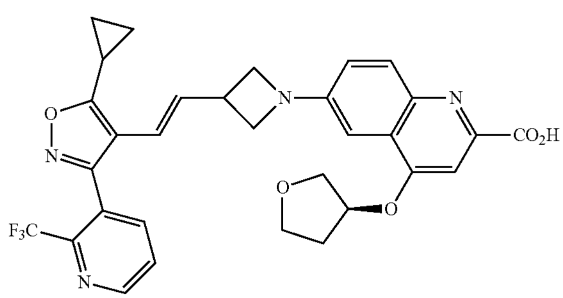 [SMILES: O=C(O)c1cc(O[C@H]2CCOC2)c2cc(N3CC(/C=C/c4c(-c5cccnc5C(F)(F)F)noc4C4CC4)C3)ccc2n1] | MS (ESI) m/z: 593.2 [M + H]$^+$; EC$_{50}$ = 650; $^1$H NMR (400 MHz, Methanol-d$_4$) δ 8.80-8.87 (m, 1H), 8.14 (br d, J = 9.24 Hz, 1H), 7.95-8.02 (m, 1H), 7.80 (dd, J = 4.73, 8.03 Hz, 1H), 7.69 (s, 1H), 7.30 (dd, J = 2.0, 9.24 Hz, 1H), 6.90 (d, J = 2.42 Hz, 1H), 6.27 (dd, J = 0.88, 16.07 Hz, 1H), 5.84 (dd, J = 8.36, 16.07 Hz, 1H), 5.61 (br s, 1H), 4.28 (t, J = 8.03 Hz, 2H), 4.18-4.23 (m, 1H), 4.05-4.16 (m, 2H), 3.96 (br d, J = 4.84 Hz, 1H), 3.71-3.80 (m, 2H), 3.53-3.62 (m, 1H), 2.49-2.62 (m, 1H), 2.25-2.37 (m, 2H), 1.15-1.24 (m, 4H). | A2 |
| 190 | 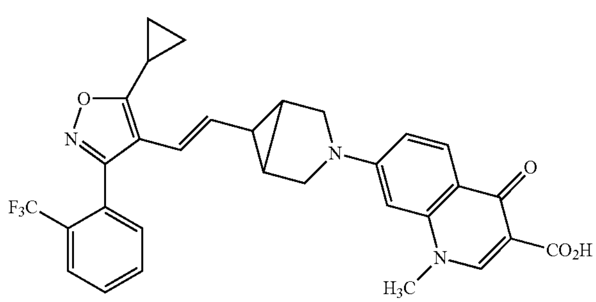 [SMILES: Cn1cc(C(=O)O)c(=O)c2ccc(N3CC4C(/C=C/c5c(-c6ccccc6C(F)(F)F)noc5C5CC5)C4C3)cc21] | MS (ESI) m/z: 562.3 [M + H]$^+$; EC$_{50}$ = 376; $^1$H NMR (400 MHz, DMSO-d$_6$) δ 8.75 (s, 1H), 8.01 (d, J = 9.1 Hz, 1H), 7.86 (dd, J = 7.7, 1.5 Hz, 1H), 7.80-7.66 (m, 2H), 7.48-7.41 (m, 1H), 6.84 (dd, J = 9.2, 2.0 Hz, 1H), 6.39 (d, J = 2.1 Hz, 1H), 6.00 (d, J = 16.1 Hz, 1H), 5.12 (dd, J = 16.1, 9.0 Hz, 1H), 3.88 (s, 3H), 3.65 (d, J = 10.5 Hz, 2H), 3.43-3.35 (m, 2H), 2.25-2.15 (m, 1H), 1.73-1.60 (m, 2H), 1.29-1.14 (m, 1H), 1.12-1.03 (m, 2H), 1.06-0.95 (m, 2H). | A2 |

TABLE 1-continued

| Ex. No. | Structure | LCMS, FXR EC$_{50}$ (nM) & NMR | Method |
|---|---|---|---|
| 191 | 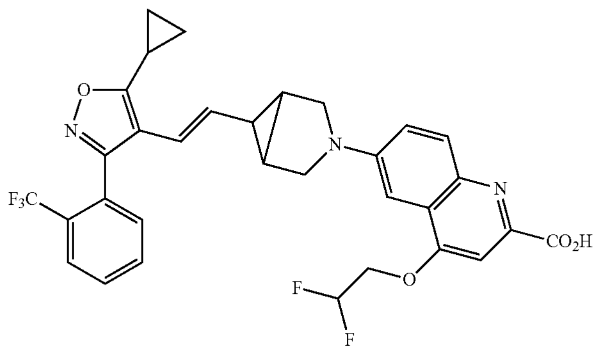 [SMILES: O=C(O)c1cc(OCC(F)F)c2cc(N3CC4C(/C=C/c5c(-c6ccccc6C(F)(F)F)noc5C5CC5)C4C3)ccc2n1] | MS (ESI) m/z: 512.2 [M + H]$^+$; EC$_{50}$ = 40; $^1$H NMR (400 MHz, Methanol-d$_4$) δ 8.16 (d, J = 9.4 Hz, 1H), 7.90 (dd, J = 7.7, 1.6 Hz, 1H), 7.84-7.69 (m, 3h), 7.61-7.51 (m, 1H), 7.46 (dd, J = 7.5, 1.6 Hz, 1H), 7.04 (s, 1H), 6.73-6.27 (m, 1H), 6.12 (d, J = 16.1 Hz, 1H), 5.22 (dd, J = 16.1, 8.7 Hz, 1H), 4.81 (dd, J = 13.8, 3.4 Hz, 2H), 3.75 (d, J = 10.0 Hz, 2H), 3.60-3.45 (m, 2H), 2.24 (tt, J = 8.2, 5.3 Hz, 1H), 1.72-1.82 (m, J = 3.1 Hz, 2H), 1.37 (dt, J = 8.9, 3.3 Hz, 1H), 1.20-1.12 (m, 4H). | A2 |
| 192 | 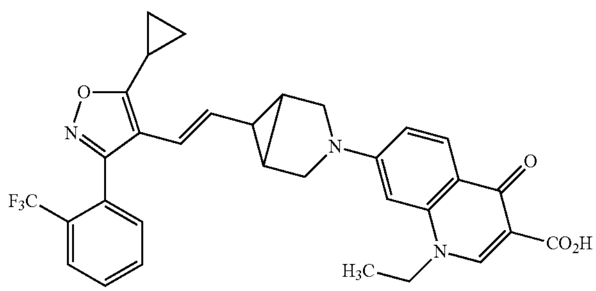 [SMILES: CCn1cc(C(=O)O)c(=O)c2ccc(N3CC4C(/C=C/c5c(-c6ccccc6C(F)(F)F)noc5C5CC5)C4C3)cc21] | MS (ESI) m/z: 576.3 [M + H]$^+$; EC$_{50}$ = 132.0; $^1$H NMR (400 MHz, DMSO-d$_6$) δ 8.82 (s, 1H), 8.10 (d, J = 9.1 Hz, 1H), 7.94 (dd, J = 7.8, 1.6 Hz, 1H), 7.88-7.67 (m, 2H), 7.56-7.40 (m, 1H), 6.91 (dd, J = 9.1, 2.0 Hz, 1H), 6.51 (d, J = 2.1 Hz, 1H), 6.07 (d, J = 16.1 Hz, 1H), 5.20 (dd, J = 16.1, 8.9 Hz, 1H), 4.47 (q, J = 7.1 Hz, 2H), 3.72 (d, J = 10.4 Hz, 2H), 3.50-3.42 (m, 2H), 2.36-2.27 (m, 1H), 1.81-1.68 (m, 2H), 1.39 (t, J = 7.0 Hz, 3H), 1.38 (dt, J = 8.8, 3.3 Hz, 1H), 1.20-1.10 (m, 2H), 1.11-0.94 (m, 2H). | A2 |
| 193 | 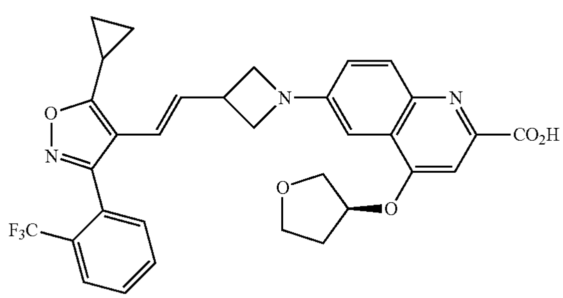 | MS (ESI) m/z: 592.3 [M + H]$^+$; EC$_{50}$ = 343; $^1$H NMR (500 MHz, Methanol-d$_4$) δ 8.15 (br d, J = 8.8 Hz, 1H), 7.89 (d, J = 7.7 Hz, 1H), 7.81-7.67 (m, 3H), 7.49 (d, J = 7.7 Hz, 1H), 7.30 (br d, J = 8.5 Hz, 1H), 6.90 (s, 1H), 6.25 (d, J = 16.0 Hz, 1H), 5.81 (dd, J = 16.1, 8.4 Hz, 1H), 5.61 (br s, 1H), 4.32-4.19 (m, 3H), 4.18-4.06 (m, 2H), 3.98 (td, J = 8.4, 5.0 Hz, 1H), 3.72 (br t, J = 6.5 Hz, 2H), 3.59-3.50 (m, 1H), 2.62-2.51 (m, 1H), 2.38-2.26 (m, 2H), 1.24-1.16 (m, 4H). | A2 |
| 194 | 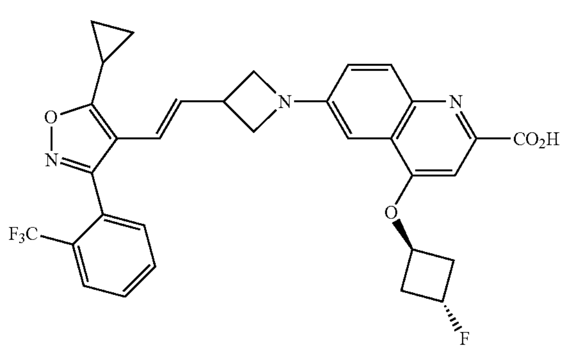 [SMILES: O=C(O)c1cc(O[C@H]2C[C@H](F)C2)c2cc(N3CC(/C=C/c4c(-c5ccccc5C(F)(F)F)noc4C4CC4)C3)ccc2n1] | MS (ESI) m/z: 594.2 [M + H]$^+$; EC$_{50}$ = 159; $^1$H NMR (400 MHz, Methanol-d$_4$) δ 8.01 (br d, J = 9.2 Hz, 1H), 7.78 (d, J = 7.7 Hz, 1H), 7.71-7.56 (m, 2H), 7.42-7.32 (m, 2H), 7.16 (br d, J = 8.1 Hz, 1H), 6.78 (d, J = 1.1 Hz, 1H), 6.14 (d, J = 16.1 Hz, 1H), 5.69 (dd, J = 16.1, 8.4 Hz, 1H), 5.36 (td, J = 6.7, 3.3 Hz, 2H), 4.15 (br t, J = 7.8 Hz, 2H), 3.60 (br t, J = 6.6 Hz, 2H), 2.93-2.62 (m, 4H), 2.25-2.12 (m, 1H), 1.15-1.01 (m, 5H). | A2 |

TABLE 1-continued

| Ex. No. | Structure | LCMS, FXR EC$_{50}$ (nM) & NMR | Method |
|---|---|---|---|
| 195 | 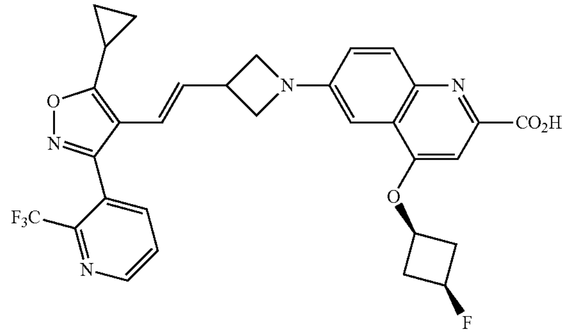 [SMILES: O=C(O)c1cc(O[C@H]2C[C@@H](F)C2)c2cc(N3CC(/C=C/c4c(-c5cccnc5C(F)(F)F)noc4C4CC4)C3)ccc2n1] | MS (ESI) m/z: 595.3 [M + H]$^+$; EC$_{50}$ = 286; $^1$H NMR (500 MHz, Methanol-d$_4$) δ 8.80-8.87 (m, 1H), 8.13 (br d, J = 7.98 Hz, 1H), 7.98 (d, J = 7.43 Hz, 1H), 7.79 (dd, J = 4.68, 7.70 Hz, 1H), 7.52 (s, 1H), 7.31 (br d, J = 7.43 Hz, 1H), 6.91 (br s, 1H), 6.26 (d, J = 15.96 Hz, 1H), 5.84 (dd, J = 8.25, 15.96 Hz, 1H), 5.03 (quin, J = 6.33 Hz, 1H), 4.87-4.96 (m, 2H), 4.29 (br t, J = 7.43 Hz, 2H), 3.76 (br s, 2H), 3.56 (br d, J = 7.15 Hz, 1H), 3.21-3.26 (m, 1H), 2.52-2.66 (m, 2H), 2.26-2.34 (m, 1H), 1.18-1.23 (m, 2H), 1.16 (br d, J = 3.03 Hz, 2H). | A2 |
| 196 | 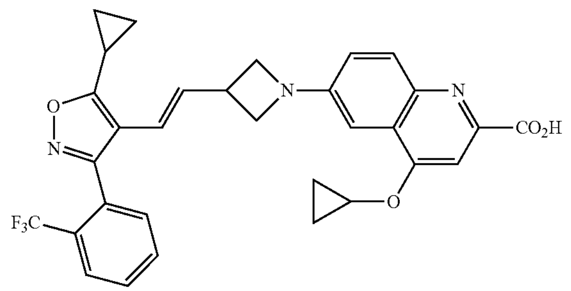 [SMILES: O=C(O)c1cc(OC2CC2)c2cc(N3CC(/C=C/c4c(-c5ccccc5C(F)(F)F)noc4C4CC4)C3)ccc2n1] | MS (ESI) m/z: 562.2 [M + H]$^+$; EC$_{50}$ = 53; $^1$H NMR (400 MHz, Methanol-d$_4$) δ 8.01 (br d, J = 9.2 Hz, 1H), 7.93 (s, 1H), 7.77 (d, J = 7.5 Hz, 1H), 7.70-7.55 (m, 2H), 7.37 (d, J = 7.3 Hz, 1H), 7.15 (dd, J = 8.5, 1.4 Hz, 1H), 6.69 (d, J = 2.0 Hz, 1H), 6.12 (d, J = 16.1 Hz, 1H), 5.68 (dd, J = 15.8, 8.4 Hz, 1H), 4.30-4.22 (m, 1H), 4.13 (t, J = 7.8 Hz, 2H), 3.57 (t, J = 6.7 Hz, 2H), 3.45-3.36 (m, 1H), 2.23-2.13 (m, 1H), 1.12-1.04 (m, 4H), 1.02-0.96 (m, 2H), 0.95-0.88 (m, 2H). | A2 |
| 197 | 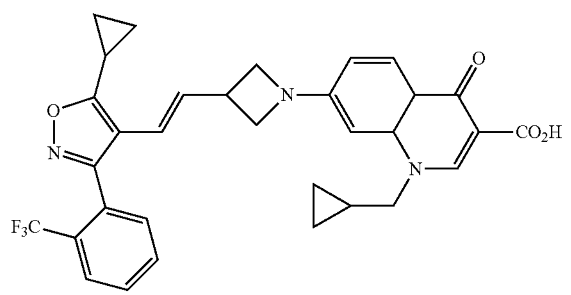 [SMILES: O=C(O)C1=CN(CC2CC2)C2C=C(N3CC(/C=C/c4c(-c5ccccc5C(F)(F)F)noc4C4CC4)C3)C=CC2C1=O] | MS (ESI) m/z: 602.3 [M + H]$^+$; EC$_{50}$ = 373; $^1$H NMR (400 MHz, DMSO-d$_6$) δ 8.85 (s, 1H), 8.11 (d, J = 9.1 Hz, 1H), 7.93 (dd, J = 7.7, 1.5 Hz, 1H), 7.88-7.70 (m, 2H), 7.59-7.42 (m, 1H), 6.92 (dd, J = 9.2, 2.0 Hz, 1H), 6.62 (d, J = 2.1 Hz, 1H), 6.07 (d, J = 16.1 Hz, 1H), 5.20 (dd, J = 16.1, 8.9 Hz, 1H), 4.32 (d, J = 7.2 Hz, 2H), 3.73 (d, J = 10.3 Hz, 2H), 3.54-3.38 (m, 2H), 2.38-2.18 (m, 1H), 1.81-1.72 (m, 2H), 1.55-1.37 (m, 1H), 1.34 (dt, J = 9.0, 3.2 Hz, 1H), 1.22-1.10 (m, 2H), 1.11-0.98 (m, 2H), 0.66-0.51 (m, 2H), 0.51-0.41 (m, 2H). | A2 |
| 198 | 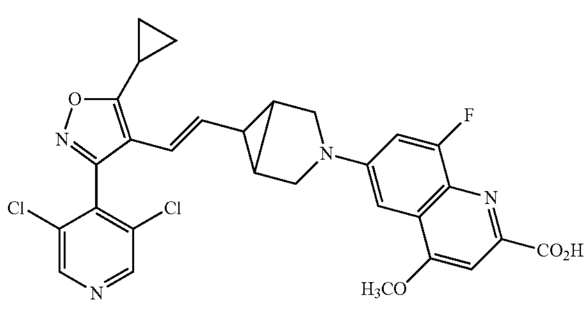 [SMILES: COc1cc(C(=O)O)nc2c(F)cc(N3CC4C(/C=C/c5c(-c6c(Cl)cncc6Cl)noc5C5CC5)C4C3)cc12] | MS (ESI) m/z: 581.2 [M + H]$^+$; EC$_{50}$ = 71; $^1$H NMR (400 MHz, Methanol-d$_4$) δ 8.74 (s, 2H), 7.59 (s, 1H), 7.24-6.94 (m, 1H), 6.81 (s, 1H), 6.17 (d, J = 16.0 Hz, 1H), 5.29 (dd, J = 16.0, 8.8 Hz, 1H), 4.17 (s, 3H), 3.71 (d, J = 9.8 Hz, 2H), 3.61-3.39 (m, 2H), 2.33-2.24 (m, 1H), 1.79 (d, J = 3.3 Hz, 2H), 1.50-1.39 (m, 1H), 1.26-1.09 (m, 4H). | A2 |
| 199 | 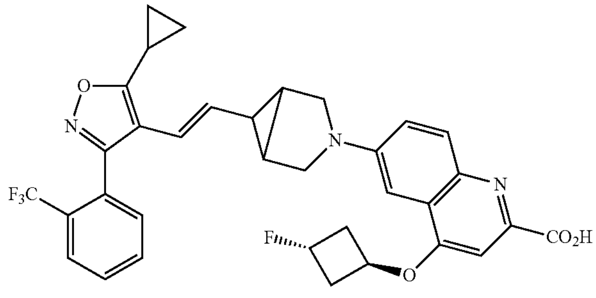 [SMILES: O=C(O)c1cc(O[C@H]2C[C@H](F)C2)c2cc(N3CC4C(/C=C/c5c(-c6ccccc6C(F)(F)F)noc5C5CC5)C4C3)ccc2n1] | MS (ESI) m/z: 620.3 [M + H]$^+$; EC$_{50}$ = 63; $^1$H NMR (400 MHz, Methanol-d$_4$) δ 8.15 (d, J = 9.4 Hz, 1H), 7.90 (dd, J = 7.6, 1.6 Hz, 1H), 7.84-7.62 (m, 2H), 7.56 (dd, J = 9.5, 2.7 Hz, 1H), 7.50 (s, 1H), 7.47 (dd, J = 7.5, 1.6 Hz, 1H), 7.04 (d, J = 2.6 Hz, 1H), 6.11 (d, J = 16.0 Hz, 1H), 5.62-5.29 (m, 3H), 5.22 (dd, J = 16.1, 8.7 Hz, 1H), 3.77 (d, J = 10.1 Hz, 2H), 3.58-3.38 (m, 2H), 3.07-2.90 (m, 2H), 2.90-2.76 (m, 2H), 2.31-2.16 (m, 1H), 1.83-1.71 (m, 2H), 1.37 (dt, J = 8.7, 3.3 Hz, 1H), 1.25-1.08 (m, 4H). | A2 |

TABLE 1-continued

| Ex. No. | Structure | LCMS, FXR EC$_{50}$ (nM) & NMR | Method |
|---|---|---|---|
| 200 | 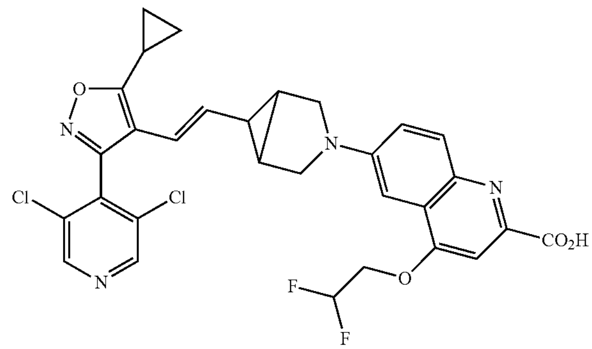 [SMILES: O=C(O)c1cc(OCC(F)F)c2cc(N3CC4C(/C=C/c5c(-c6c(Cl)cncc6Cl)noc5C5CC5)C4C3)ccc2n1] | MS (ESI) m/z: 613.2 [M + H]$^+$; EC$_{50}$ = 21; $^1$H NMR (400 MHz, Methanol-d$_4$) δ 8.74 (s, 2H), 8.18 (d, J = 9.4 Hz, 1H), 7.79 (s, 1H), 7.59 (d, J = 9.3 Hz, 1H), 7.06 (d, J = 2.4 Hz, 1H), 6.77-6.28 (m, 1H), 6.17 (d, J = 16.1 Hz, 1H), 5.30 (dd, J = 16.0, 8.7 Hz, 1H), 4.90-4.90 (m, 2H), 3.78 (d, J = 10.1 Hz, 2H), 3.55 (d, J = 10.2 Hz, 2H), 2.29 (tt, J = 8.1, 5.3 Hz, 1H), 1.91-1.77 (m, 2H), 1.52-1.33 (m, 1H), 1.30-1.00 (m, 4H). | A2 |
| 201 | 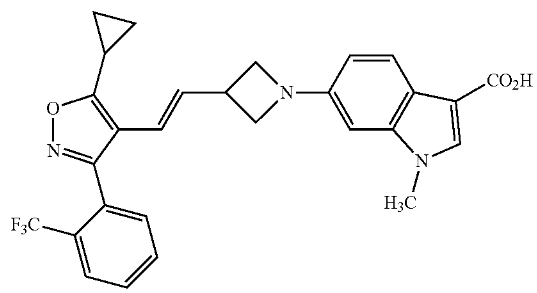 [SMILES: Cn1cc(C(=O)O)c2ccc(N3CC(/C=C/c4c(-c5ccccc5C(F)(F)F)noc4C4CC4)C3)cc21] | MS (ESI) m/z: 508.2 [M + H]$^+$; EC$_{50}$ = 178; $^1$H NMR (500 MHz, Methanol-d$_4$) δ 7.95 (d, J = 8.5 Hz, 1H), 7.90 (d, J = 7.4 Hz, 1H), 7.83-7.70 (m, 3H), 7.49 (d, J = 7.4 Hz, 1H), 6.68-6.60 (m, 2H), 6.23 (d, J = 16.5 Hz, 1H), 5.80 (dd, J = 16.1, 8.4 Hz, 1H), 4.19 (br t, J = 7.6 Hz, 2H), 3.81 (s, 3H), 3.69-3.63 (m, 2H), 3.52-3.45 (m, 1H), 2.34-2.27 (m, 1H), 1.24-1.15 (m, 4H). | A2 |
| 202 | 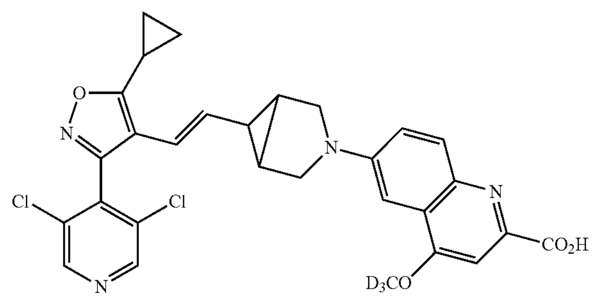 | MS (ESI) m/z: 566.2 [M + H]$^+$; EC$_{50}$ = 30; $^1$H NMR (400 MHz, Methanol-d$_4$) δ 8.74 (s, 2H), 8.16 (d, J = 9.5 Hz, 1H), 7.74 (s, 1H), 7.56 (dd, J = 9.5, 2.6 Hz, 1H), 7.07 (d, J = 2.6 Hz, 1H), 6.17 (d, J = 16.0 Hz, 1H), 5.30 (dd, J = 16.0, 8.7 Hz, 1H), 3.78 (d, J = 10.0 Hz, 2H), 3.53 (d, J = 9.8 Hz, 2H), 2.35-2.23 (m, 1H), 1.88-1.79 (m, 2H), 1.44 (dt, J = 8.1, 4.2 Hz, 1H), 1.28-0.96 (m, 4H). | A2 |
| 203 | 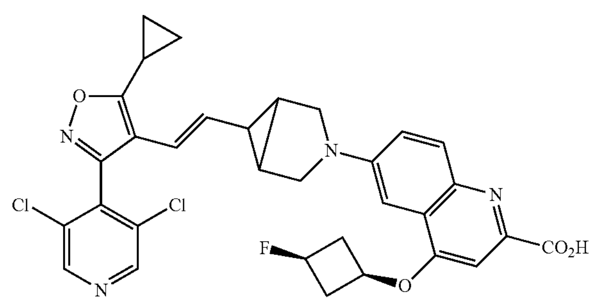 [SMILES: O=C(O)c1cc(O[C@H]2C[C@@H](F)C2)c2cc(N3CC4C(/C=C/c5c(-c6c(Cl)cncc6Cl)noc5C5CC5)C4C3)ccc2n1] | MS (ESI) m/z: 621.2 [M + H]$^+$; EC$_{50}$ = 16; $^1$H NMR (400 MHz, Methanol-d$_4$) δ 8.63 (s, 2H), 8.04 (d, J = 9.3 Hz, 1H), 7.45 (dd, J = 8.5, 2.6 Hz, 1H), 7.42 (s, 1H), 6.96 (d, J = 2.8 Hz, 1H), 6.06 (d, J = 16.0 Hz, 1H), 5.19 (dd, J = 16.1, 8.7 Hz, 1H), 5.04-4.78 (m, 2H), 3.68 (d, J = 10.0 Hz, 2H), 3.51-3.30 (m, 2H), 3.08-3.31 (m, 2H), 2.62-2.33 (m, 2H), 2.17 (tt, J = 8.2, 5.2 Hz, 1H), 1.76-1.69 (m, 2H), 1.33 (dt, J = 8.7, 3.2 Hz, 1H), 1.28-0.96 (m, 4H). | A2 |
| 204 | 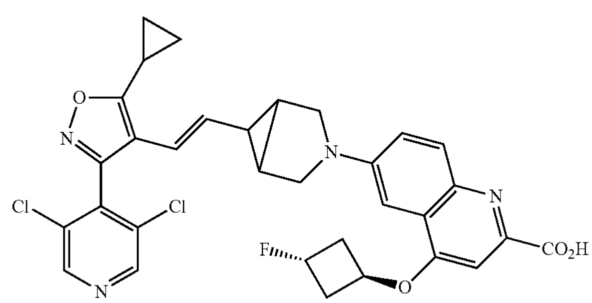 [SMILES: O=C(O)c1cc(O[C@H]2C[C@H](F)C2)c2cc(N3CC4C(/C=C/c5c(-c6c(Cl)cncc6Cl)noc5C5CC5)C4C3)ccc2n1] | MS (ESI) m/z: 621.3 [M + H]$^+$; EC$_{50}$ = 19; $^1$H NMR (500 MHz, Methanol-d$_4$) δ 8.74 (s, 2H), 8.17 (d, J = 9.4 Hz, 1H), 7.59 (dd, J = 9.4, 2.6 Hz, 1H), 7.52 (s, 1H), 7.07 (d, J = 2.7 Hz, 1H), 6.17 (d, J = 16.1 Hz, 1H), 5.60-5.35 (m, 2H), 5.31 (dd, J = 16.0, 8.7 Hz, 1H), 3.80 (d, J = 10.1 Hz, 2H), 3.56 (d, J = 10.1, 2H), 3.05-2.91 (m, 2H), 2.92-2.76 (m, 2H), 2.29 (tt, J = 8.2, 5.2 Hz, 1H), 1.89-1.78 (m, 2H), 1.52-1.37 (m, 1H), 1.31-0.99 (m, 4H). | A2 |

TABLE 1-continued

| Ex. No. | Structure | LCMS, FXR EC$_{50}$ (nM) & NMR | Method |
|---|---|---|---|
| 205 | 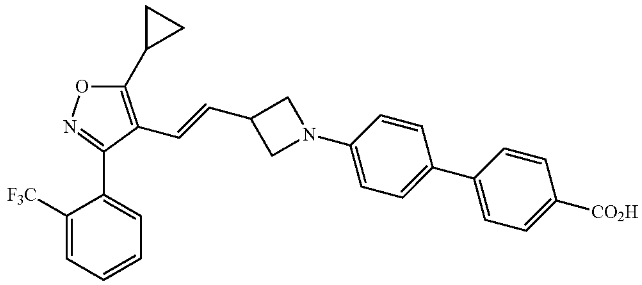 [SMILES: O=C(O)c1ccc(-c2ccc(N3CC(/C=C/c4c(-c5ccccc5C(F)(F)F)noc4C4CC4)C3)cc2)cc1] | MS (ESI) m/z: 531.2 [M + H]$^+$; EC$_{50}$ = 189; $^1$H NMR (500 MHz, DMSO-d$_6$) δ 7.97-7.93 (m, 3H), 7.86-7.81 (m, 1H), 7.80-7.75 (m, 1H), 7.70 (d, J = 8.5 Hz, 2H), 7.61-7.52 (m, 3H), 6.49 (d, J = 8.5 Hz, 2H), 6.19 (d, J = 16.0 Hz, 1H), 5.72 (dd, J = 16.1, 7.8 Hz, 1H), 4.05-4.00 (m, 2H), 3.50-3.41 (m, 3H), 2.43-2.36 (m, 1H), 1.20-1.14 (m, 2H), 1.11-1.06 (m, 2H). | A2 |
| 206 | 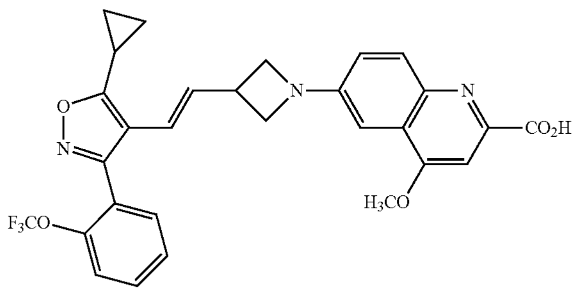 [SMILES: COc1cc(C(=O)O)nc2ccc(N3CC(/C=C/c4c(-c5ccccc5OC(F)(F)F)noc4C4CC4)C3)cc12] | MS (ESI) m/z: 552.2 [M + H]$^+$; EC$_{50}$ = 216; $^1$H NMR (400 MHz, Methanol-d$_4$) δ 8.09-8.17 (m, 1H), 7.73 (s, 1H), 7.59-7.66 (m, 1H), 7.45-7.56 (m, 3H), 7.31 (br dd, J = 1.87, 9.13 Hz, 1H), 6.90 (d, J = 2.20 Hz, 1H), 6.27 (d, J = 16.07 Hz, 1H), 6.00 (dd, J = 8.36, 16.07 Hz, 1H), 4.33 (s, 3H), 4.27-4.31 (m, 2H), 3.78 (br t, J = 6.82 Hz, 2H), 3.54-3.64 (m, 1H), 2.24-2.33 (m, 1H), 1.11-1.22 (m, 4H). | A2 |
| 207 | 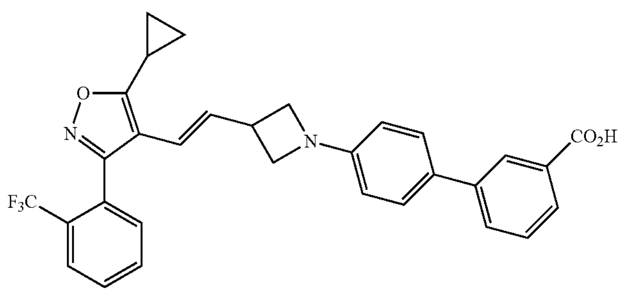 [SMILES: O=C(O)c1cccc(-c2ccc(N3CC(/C=C/c4c(-c5ccccc5C(F)(F)F)noc4C4CC4)C3)cc2)c1] | MS (ESI) m/z: 531.2 [M + H]$^+$; EC$_{50}$ = 64; $^1$H NMR (500 MHz, DMSO-d$_6$) δ 8.09 (t, J = 1.7 Hz, 1H), 7.95 (d, J = 7.4 Hz, 1H), 7.87-7.74 (m, 4H), 7.57-7.49 (m, 4H), 6.49 (d, J = 8.8 Hz, 2H), 6.19 (d, J = 16.0 Hz, 1H), 5.72 (dd, J = 16.0, 7.7 Hz, 1H), 4.06-3.98 (m, 2H), 3.49-3.41 (m, 3H), 2.44-2.35 (m, 1H), 1.21-1.14 (m, 2H), 1.12-1.05 (m, 2H). | A2 |
| 208 | 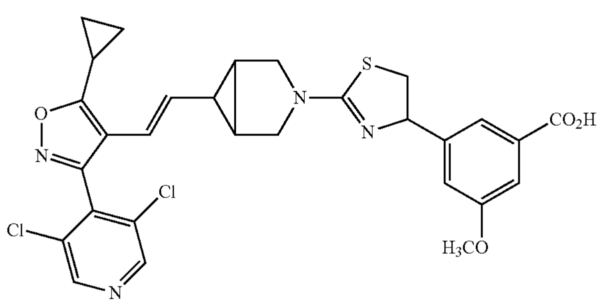 [SMILES: COc1cc(C(=O)O)cc(C2CSC(N3CC4C(/C=C/c5c(-c6c(Cl)cncc6Cl)noc5C5CC5)C4C3)=N2)c1] | MS (ESI) m/z: 595.1 [M + H]$^+$; EC$_{50}$ = 247; $^1$H NMR (400 MHz, Methanol-d$_4$) δ 8.73 (s, 2H), 7.98 (t, J = 1.5 Hz, 1H), 7.60 (dd, J = 2.6, 1.4 Hz, 1H), 7.53 (dd, J = 2.5, 1.6 Hz, 1H), 7.10 (s, 1H), 6.19 (d, J = 16.0 Hz, 1H), 5.30 (dd, J = 16.0, 8.5 Hz, 1H), 3.91 (s, 3H), 3.80 (d, J = 10.5 Hz, 2H), 3.78-3.72 (m, 2H), 2.28 (tt, J = 8.2, 5.3 Hz, 1H), 1.90-1.81 (m, 2H), 1.47 (dt, J = 8.6, 3.5 Hz, 1H), 1.29-0.93 (m, 4H). | K |
| 209 | 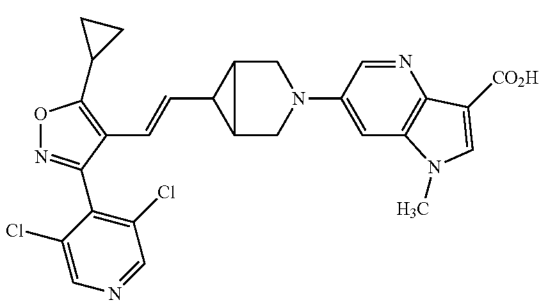 [SMILES: Cn1cc(C(=O)O)c2ncc(N3CC4C(/C=C/c5c(-c6c(Cl)cncc6Cl)noc5C5CC5)C4C3)cc21] | MS (ESI) m/z: 536.1 [M + H]$^+$; EC$_{50}$ = 472; $^1$H NMR (400 MHz, Methanol-d$_4$) δ 8.62 (s, 2H), 8.16 (br s, 1H), 7.85-7.70 (m, 1H), 7.68-7.52 (m, 1H), 6.04 (d, J = 16.1 Hz, 1H), 5.20 (br dd, J = 15.8, 8.4 Hz, 1H), 3.85 (br s, 3H), 3.63 (br d, J = 7.7 Hz, 2H), 3.43-3.31 (m, 2H), 2.23-2.11 (m, 1H), 1.73 (br s, 2H), 1.42-1.31 (m, 1H), 1.12-1.05 (m, 4H). | A2 |

TABLE 1-continued

| Ex. No. | Structure | LCMS, FXR EC$_{50}$ (nM) & NMR | Method |
|---|---|---|---|
| 210 | 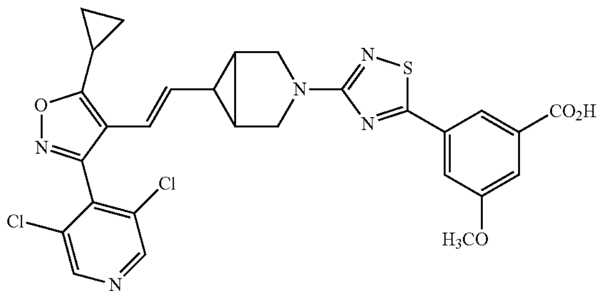 [SMILES: COc1cc(C(=O)O)cc(-c2nc(N3CC4C(/C=C/c5c(-c6c(Cl)cncc6Cl)noc5C5CC5)C4C3)ns2)c1] | MS (ESI) m/z: 596.1 [M + H]$^+$; EC$_{50}$ = 670; $^1$H NMR (400 MHz, Methanol-d$_4$) δ 8.74 (s, 2H), 8.10 (t, J = 1.5 Hz, 1H), 7.73 (dd, J = 2.6, 1.4 Hz, 1H), 7.68 (dd, J = 2.6, 1.5 Hz, 1H), 6.16 (d, J = 16.1 Hz, 1H), 5.27 (dd, J = 16.0, 8.7 Hz, 1H), 3.97 (d, J = 10.6 Hz, 2H), 3.94 (s, 3H), 3.66 (dt, J = 10.6, 2.0 Hz, 2H), 2.28 (tt, J = 8.2, 5.2 Hz, 1H), 1.76-1.60 (m, 2H), 1.50-1.36 (m, 1H), 1.27-1.09 (m, 4H). | L |
| 211 | 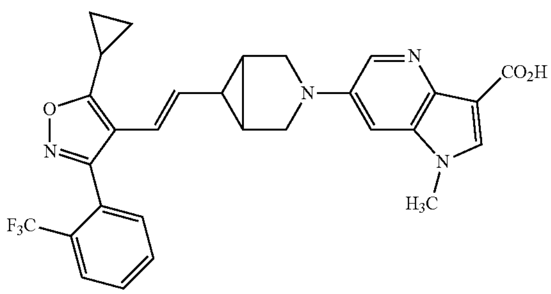 [SMILES: Cn1cc(C(=O)O)c2ncc(N3CC4C(/C=C/c5c(-c6ccccc6C(F)(F)F)noc5C5CC5)C4C3)cc21] | MS (ESI) m/z: 535.3 [M + H]$^+$; EC$_{50}$ = 154; $^1$H NMR (500 MHz, Methanol-d$_4$) δ 8.29 (s, 1H), 7.90 (d, J = 7.4 Hz, 1H), 7.86 (br s, 1H), 7.81-7.71 (m, 3H), 7.47 (d, J = 7.2 Hz, 1H), 6.11 (d, J = 16.0 Hz, 1H), 5.24 (dd, J = 15.8, 8.7 Hz, 1H), 3.97 (s, 3H),3 .73 (br d, J = 9.4 Hz, 2H), 3.49-3.42 (m, 2H), 2.28-2.20 (m, 1H), 1.79 (br s, 2H), 1.46-1.40 (m, 1H), 1.22-1.13 (m, 4H). | A2 |
| 212 | 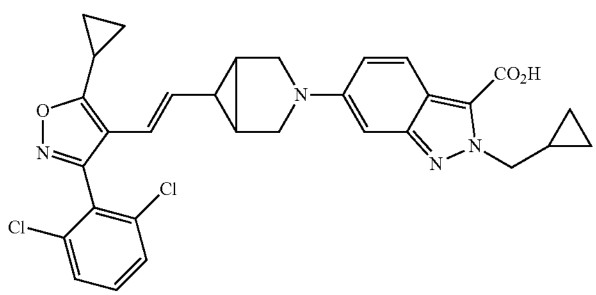 [SMILES: O=C(O)c1c2ccc(N3CC4C(/C=C/c5c(-c6c(Cl)cccc6Cl)noc5C5CC5)C4C3)cc2nn1CC1CC1] | MS (ESI) m/z: 575.2 [M + H]$^+$; EC$_{50}$ = 21; $^1$H NMR (500 MHz, Methanol-d$_4$) δ 7.92 (br d, J = 9.1 Hz, 1H), 7.59-7.56 (m, 2H), 7.55-7.51 (m, 1H), 6.88 (br d, J = 8.0 Hz, 1H), 6.50 (d, J = 1.4 Hz, 1H), 6.16 (d, J = 16.0 Hz, 1H), 5.19 (dd, J = 16.0, 8.8 Hz, 1H), 4.69 (d, J = 7.4 Hz, 2H), 3.68 (d, J = 9.4 Hz, 2H), 3.32-3.30 (m, 2H), 2.31-2.23 (m, 1H), 1.65 (br s, 2H), 1.51-1.44 (m, 2H), 1.23-1.15 (m, 4H), 0.56-0.48 (m, 4H). | A2 |
| 213 | 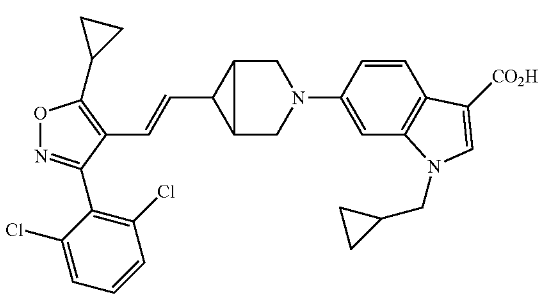 [SMILES: O=C(O)c1cn(CC2CC2)c2cc(N3CC4C(/C=C/c5c(-c6c(Cl)cccc6Cl)noc5C5CC5)C4C3)ccc12] | MS (ESI) m/z: 575.2; [M + H]$^+$; EC$_{50}$ = 18; $^1$H NMR (500 MHz, DMSO-d$_6$) δ 7.79 (d, J = 8.8 Hz, 1H), 7.69-7.66 (m, 2H), 7.64-7.58 (m, 1H), 6.72 (dd, J = 8.9, 1.8 Hz, 1H), 6.56 (s, 1H), 6.16 (d, J = 16.0 Hz, 1H), 5.15 (dd, J = 16.0, 9.1 Hz, 1H), 4.24 (d, J = 6.9 Hz, 2H), 3.64 (d, J = 9.6 Hz, 2H), 3.30-3.26 (m, 2H), 2.39-2.34 (m, 1H), 1.69 (br s, 2H), 1.43 (dt, J = 8.8, 3.0 Hz, 1H), 1.33-1.26 (m, 1H), 1.20-1.15 (m, 2H), 1.12-1.07 (m, 2H), 0.52-0.47 (m, 2H), 0.43-0.38 (m, 2H). | A2 |
| 214 | 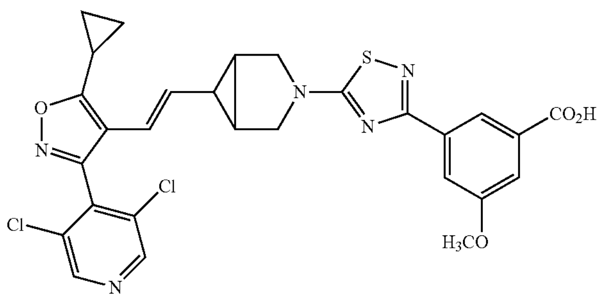 | MS (ESI) m/z: 596.1 [M + H]$^+$; EC$_{50}$ = 107; $^1$H NMR (400 MHz, DMSO-d$_6$) δ 8.86 (s, 2H), 8.25 (t, J = 1.5 Hz, 1H), 7.81 (dd, J = 2.6, 1.4 Hz, 1H), 7.52 (dd, J = 2.6, 1.5 Hz, 1H), 6.15 (d, J = 16.0 Hz, 1H), 5.33 (dd, J = 16.1, 8.8 Hz, 1H), 3.87 (s, 3H), 3.81-3.51 (m, 4H), 2.46-2.28 (m, 1H), 1.87-1.77 (m, 2H), 1.44 (dt, J = 8.9, 3.4 Hz, 1H), 1.23-1.02 (m, 4H). | M |

TABLE 1-continued

| Ex. No. | Structure | LCMS, FXR EC$_{50}$ (nM) & NMR | Method |
|---|---|---|---|
| 215 | 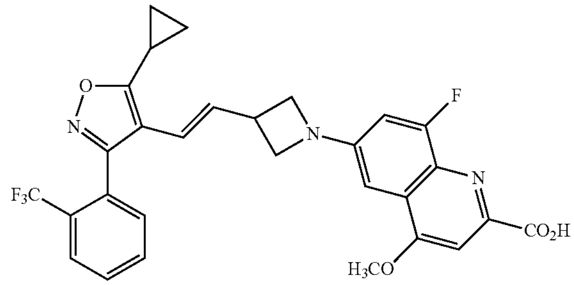 [SMILES: COc1cc(C(=O)O)nc2c(F)cc(N3CC(/C=C/c4c(-c5ccccc5C(F)(F)F)noc4C4CC4)C3)cc12] | MS (ESI) m/z: 554.2 [M + H]$^+$; EC$_{50}$ = 199; $^1$H NMR (500 MHz, Methanol-d$_4$) δ 7.90 (d, J = 7.7 Hz, 1H), 7.81-7.75 (m, 1H), 7.75-7.70 (m, 1H), 7.60 (s, 1H), 7.49 (d, J = 7.4 Hz, 1H), 6.87 (br d, J = 11.6 Hz, 1H), 6.66 (br s, 1H), 6.23 (d, J = 16.2 Hz, 1H), 5.80 (dd, J = 16.1, 8.4 Hz, 1H), 4.20 (t, J = 7.8 Hz, 2H), 4.16 (s, 3H), 3.65 (t, J = 6.6 Hz, 2H), 3.53-3.46 (m, 1H), 2.34-2.27 (m, 1H), 1.21 (dt, J = 8.3, 2.8 Hz, 2H), 1.19-1.16 (m, 2H). | A2 |
| 216 | 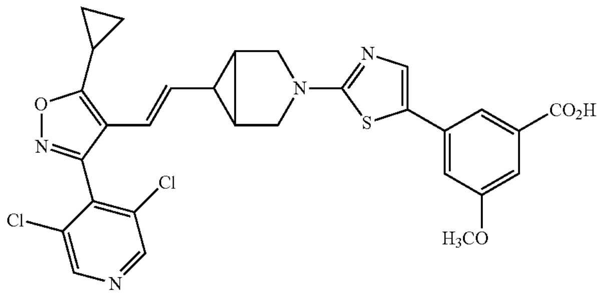 [SMILES: COc1cc(C(=O)O)cc(-c2cnc(N3CC4C(/C=C/c5c(-c6c(Cl)cncc6Cl)noc5C5CC5)C4C3)s2)c1] | MS (ESI) m/z: 595.1 [M + H]$^+$; EC$_{50}$ = 202; $^1$H NMR (400 MHz, Methanol-d$_4$) δ 8.62 (s, 2H), 7.65 (s, 1H), 7.60 (t, J = 1.5 Hz, 1H), 7.45-7.41 (m, 1H), 7.20 (t, J = 2.1 Hz, 1H), 6.08 (d, J = 16.0 Hz, 1H), 5.20 (dd, J = 16.0, 8.5 Hz, 1H), 3.79 (s, 3H), 3.69 (d, J = 11.5 Hz, 2H), 3.65 (d, J = 10.5 Hz, 2H), 2.16 (tt, J = 8.2, 5.3 Hz, 1H), 1.82-1.76 (m, 2H), 1.38 (dt, J = 8.8, 3.5 Hz, 1H), 1.17-0.87 (m, 4H). | A2 |
| 217 | 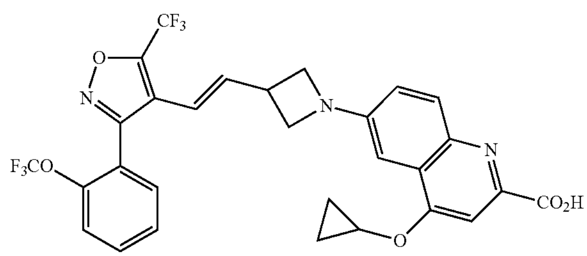 [SMILES: O=C(O)c1cc(OC2CC2)c2cc(N3CC(/C=C/c4c(-c5ccccc5OC(F)(F)F)noc4C(F)(F)F)C3)ccc2n1] | MS (ESI) m/z: 606.0 [M + H]$^+$; EC$_{50}$ = 1400; $^1$H NMR (500 MHz, Methanol-d$_4$) δ 8.13 (d, J = 9.08 Hz, 1H), 8.04 (s, 1H), 7.70 (s, 1H), 7.64 (s, 1H), 7.50-7.59 (m, 2H), 7.27 (dd, J = 2.20, 8.80 Hz, 1H), 6.78-6.85 (m, 1H), 6.40 (br d, J = 16.23 Hz, 1H), 5.90-6.05 (m, 1H), 4.38 (br d, J = 3.30 Hz, 1H), 4.23-4.29 (m, 2H), 3.66-3.73 (m, 2H), 3.57-3.63 (m, 1H), 1.06-1.13 (m, 2H), 1.03 (br s, 2H). | A2 |
| 218 | 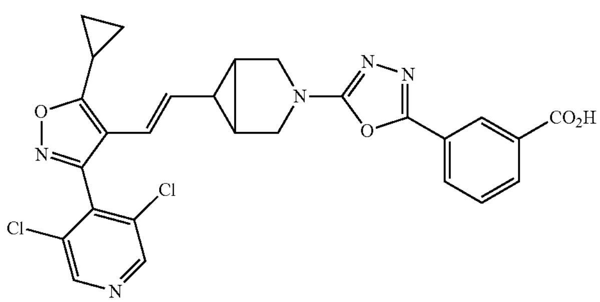 [SMILES: O=C(O)c1cccc(-c2nnc(N3CC4C(/C=C/c5c(-c6c(Cl)cncc6Cl)noc5C5CC5)C4C3)o2)c1] | MS (ESI) m/z: 550.0 [M + H]$^+$; EC$_{50}$ = 1600; $^1$H NMR (400 MHz, Methanol-d$_4$) δ 8.67 (s, 2H), 8.48-8.51 (m, 1H), 8.14 (td, J = 1.35, 7.87 Hz, 1H), 8.07-8.11 (m, 1H), 7.60 (t, J = 7.81 Hz, 1H), 6.10 (d, J = 15.85 Hz, 1H), 5.29 (dd, J = 8.47, 15.96 Hz, 1H), 3.84 (d, J = 10.12 Hz, 2H), 3.71 (br d, J = 10.56 Hz, 2H), 2.17-2.25 (m, 1H), 1.77 (br s, 2H), 1.44 (td, J = 3.22, 8.53 Hz, 1H), 1.20 (s, 2H), 1.18 (s, 2H). | A2 |
| 219 | 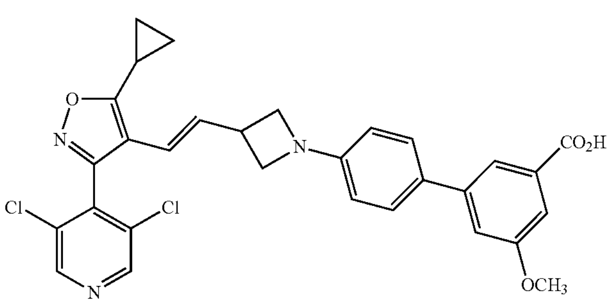 [SMILES: COc1cc(C(=O)O)cc(-c2ccc(N3CC(/C=C/c4c(-c5c(Cl)cncc5Cl)noc4C4CC4)C3)cc2)c1] | MS (ESI) m/z: 562.0 [M + H]$^+$; EC$_{50}$ = 117; $^1$H NMR (500 MHz, Methanol-d$_4$) δ 8.72 (s, 2H), 7.79 (s, 1H), 7.47-7.54 (m, 2H), 7.44 (s, 1H), 7.30 (s, 1H), 6.57 (br d, J = 8.53 Hz, 2H), 6.26 (d, J = 15.96 Hz, 1H), 5.84 (dd, J = 8.25, 15.96 Hz, 1H), 4.09 (br t, J = 7.43 Hz, 2H), 3.88 (s, 3H), 3.56 (br t, J = 6.46 Hz, 2H), 3.46 (br d, J = 7.98 Hz, 1H), 2.28-2.36 (m, 1H), 1.15-1.25 (m, 4H). | A2 |

TABLE 1-continued

| Ex. No. | Structure | LCMS, FXR EC$_{50}$ (nM) & NMR | Method |
|---|---|---|---|
| 220 | 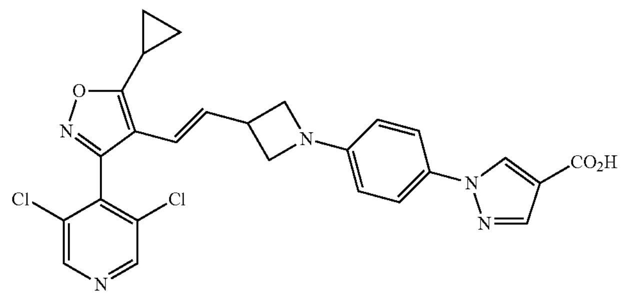 [SMILES: O=C(O)c1cnn(-c2ccc(N3CC(/C=C/c4c(-c5c(Cl)cncc5Cl)noc4C4CC4)C3)cc2)c1] | MS (ESI) m/z: 522.0 [M + H]$^+$; EC$_{50}$ = 107; $^1$H NMR (500 MHz, Methanol-d$_4$) δ 8.72 (s, 2H), 8.50( s, 1H), 8.01 (s, 1H), 7.55 (d, J = 8.80 Hz, 2H), 6.55 (d, J = 8.80 Hz, 2H), 6.21-6.31 (m, 1H), 5.84 (dd, J = 8.25, 15.96 Hz, 1H), 4.09 (t, J = 7.43 Hz, 2H), 3.55 (t, J = 6.46 Hz, 2H), 3.42-3.50 (m, 1H), 2.27-2.37 (m, 1H), 1.17-1.24 (m, 4H). | A2 |
| 221 | 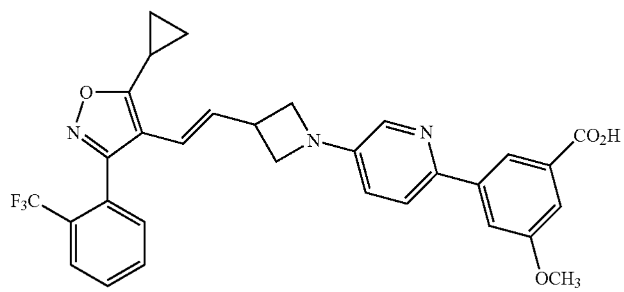 | MS (ESI) m/z: 562.1 [M + H]$^+$; EC$_{50}$ 56; $^1$H NMR (500 MHz, DMSO-d$_6$) δ 8.13 (t, J = 1.4 Hz, 1H), 7.95 (d, J = 7.4 Hz, 1H), 7.88 (d, J = 2.5 Hz, 1H), 7.86-7.81 (m, 2H), 7.80-7.76 (m, 1H), 7.75-7.72 (m, 1H), 7.55 (d, J = 7.4 Hz, 1H), 7.39 (dd, J = 2.5, 1.4 Hz, 1H), 6.89 (dd, J = 8.7, 2.9 Hz, 1H), 6.20 (d, J = 16.0 Hz, 1H), 5.75 (dd, J = 16.0, 8.3 Hz, 1H), 4.10 (t, J = 7.6 Hz, 2H), 3.87 (s, 3H), 3.59-3.45 (m, 3H), 2.44-2.36 (m, 1H), 1.20-1.15 (m, 2H), 1.12-1.07 (m, 2H). | |
| 222 | 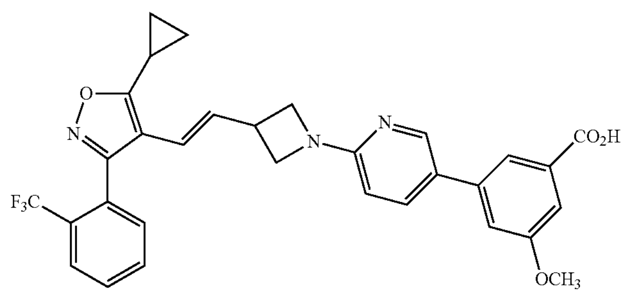 | MS (ESI) m/z: 562.2 [M + H]$^+$; EC$_{50}$ 34; $^1$H NMR (500 MHz, DMSO-d$_6$) δ 8.39 (d, J = 2.2 Hz, 1H), 8.00 (br d, J = 8.0 Hz, 1H), 7.95 (d, J = 7.7 Hz, 1H), 7.87-7.81 (m, 1H), 7.81-7.76 (m, 1H), 7.71 (t, J = 1.5 Hz, 1H), 7.55 (d, J = 7.4 Hz, 1H), 7.40 (s, 2H), 6.57 (br d, J = 8.8 Hz, 1H), 6.20 (dd, J = 16.0, 0.8 Hz, 1H), 5.77 (dd, J = 16.1, 8.4 Hz, 1H), 4.21 (t, J = 8.3 Hz, 2H), 3.87 (s, 3H), 3.74-3.70 (m, 2H), 3.47-3.40 (m, 1H), 2.45-2.36 (m, 1H), 1.21-1.15 (m, 2H), 1.12-1.07 (m, 2H). | |
| 223 | 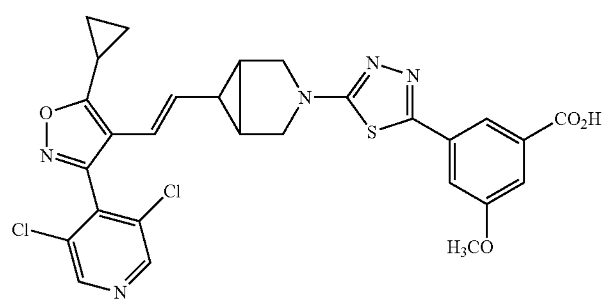 [SMILES: COc1cc(C(=O)O)cc(-c2nnc(N3CC4C(/C=C/c5c(-c6c(Cl)cncc6Cl)noc5C5CC5)C4C3)s2)c1] | MS (ESI) m/z: 596.0 [M + H]$^+$; EC$_{50}$ = 1400; $^1$H NMR (500 MHz, Methanol-d$_4$) δ 8.70-8.75 (m, 2H), 7.94 (t, J = 1.38 Hz, 1H), 7.61 (dd, J = 1.38, 2.48 Hz, 1H), 7.59 (d, J = 1.38 Hz, 1H), 6.18 (d, J = 15.96 Hz, 1H), 5.27 (dd, J = 8.67, 16.09 Hz, 1H), 3.90 (s, 3H), 3.68-3.73 (m, 4H), 2.23-2.30 (m, 1H), 1.79 (br s, 2H), 1.42-1.47 (m, 1H), 1.20 (td, J = 2.68, 8.39 Hz, 2H), 1.16 (td, J = 2.68, 5.09 Hz, 2H). | A2 |
| 224 | 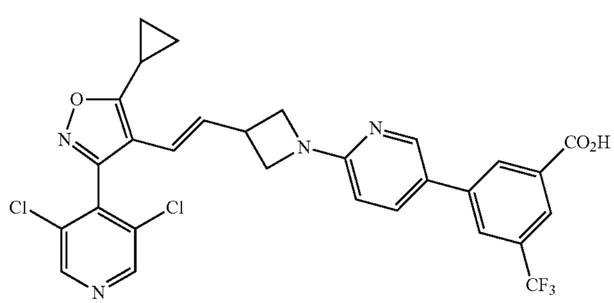 [SMILES: O=C(O)c1cc(-c2ccc(N3CC(/C=C/c4c(-c5c(Cl)cncc5Cl)noc4C4CC4)C3)nc2)cc(C(F)(F)F)c1] | MS (ESI) m/z: 601.0 [M + H]$^+$; EC$_{50}$ = 166; $^1$H NMR (400 MHz, Methanol-d$_4$) 8.73 (s, 2H), 8.46 (s, 1H), 8.26-8.31 (m, 2H), 8.21 (dd, J = 2.31, 9.13 Hz, 1H), 8.13 (s, 1H), 6.81-6.87 (m, 1H), 6.35 (dd, J = 0.88, 16.07 Hz, 1H), 5.89 (dd, J = 8.47, 15.96 Hz, 1H), 4.46 (t, J = 8.80 Hz, 2H), 3.99 (dd, J = 6.16, 9.02 Hz, 2H), 3.61-3.72 (m, 1H), 2.34 (ddd, J = 2.86, 5.39, 8.25 Hz, 1H), 1.18-1.26 (m, 4H). | A2 |

TABLE 1-continued

| Ex. No. | Structure | LCMS, FXR $EC_{50}$ (nM) & NMR | Method |
|---|---|---|---|
| 225 | 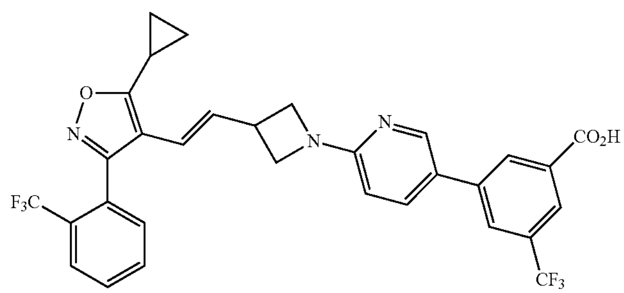 | MS (ESI) m/z: 600.0 [M + H]$^+$; $EC_{50}$ = 6; $^1$H NMR (500 MHz, Methanol-d$_4$) δ 8.44-8.48 (m, 1H), 8.25-8.30 (m, 2H), 8.20-8.25 (m, 1H), 8.14 (s, 1H), 7.89 (d, J = 7.70 Hz, 1H), 7.70-7.80 (m, 2H), 7.48 (d, J = 7.43 Hz, 1H), 6.84 (d, J = 9.08 Hz, 1H), 6.24-6.30 (m, 1H), 5.83 (dd, J = 8.53, 15.96 Hz, 1H), 4.45 (t, J = 8.80 Hz, 2H), 3.95 (dd, J = 6.19, 8.94 Hz, 2H), 3.62 (br d, J = 7.98 Hz, 1H), 2.26-2.35 (m, 1H), 1.13-1.25 (m, 4H). | A2 |
| 226 | 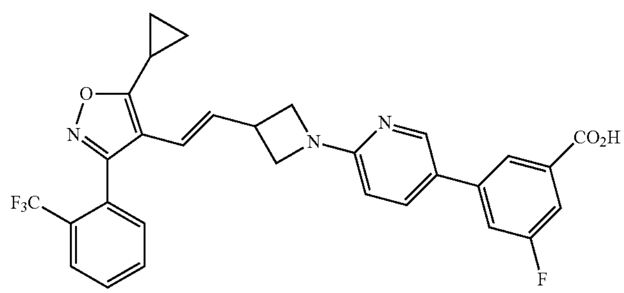 [SMILES: O=C(O)c1cc(F)cc(-c2ccc(N3CC(/C=C/c4c(-c5ccccc5C(F)(F)F)noc4C4CC4)C3)nc2)c1] | MS (ESI) m/z: 550.1 [M + H]$^+$; $EC_{50}$ = 14; $^1$H NMR (400 MHz, Methanol-d$_4$) δ 8.19-8.26 (m, 2H), 8.07 (t, J = 1.43 Hz, 1H), 7.90 (d, J = 7.48 Hz, 1H), 7.70-7.80 (m, 3H), 7.66 (dd, J = 1.76, 9.68 Hz, 1H), 7.46-7.51 (m, 1H), 6.85-6.90 (m, 1H), 6.28 (dd, J = 0.88, 16.07 Hz, 1H), 5.84 (dd, J = 8.36, 16.07 Hz, 1H), 4.47 (t, J = 8.91 Hz, 2H), 3.99 (dd, J = 6.16, 9.24 Hz, 2H), 3.58-3.6 (m, 1H), 2.31 (s, 1H), 1.16-1.23 (m, 4H). | A2 |
| 227 | 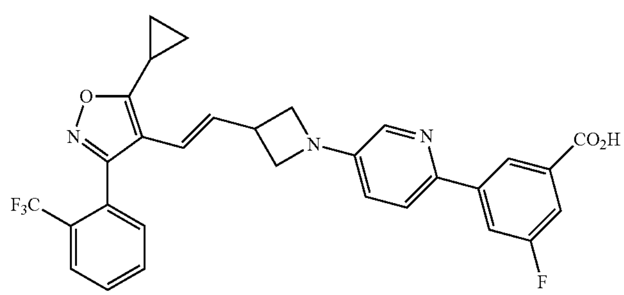 [SMILES: O=C(O)c1cc(F)cc(-c2ccc(N3CC(/C=C/c4c(-c5ccccc5C(F)(F)F)noc4C4CC4)C3)cn2)c1] | MS (ESI) m/z: 600.1 [M + H]$^+$; $EC_{50}$ = 4; $^1$H NMR( 400 MHz, Methanol-d$_4$) δ 8.69 (s, 1H), 8.37 (s, 1H), 8.31 (s, 1H), 7.96 (d, J = 8.80 Hz, 1H), 7.88 (d, J = 7.48 Hz, 1H), 7.83-7.86 (m, 1H), 7.68-7.80 (m, 2H), 7.47 (d, J = 7.26 Hz, 1H), 7.24 (dd, J = 2.86, 8.80 Hz, 1H), 6.23 (d, J = 16.07 Hz, 1H), 5.81 (d, J = 8.36 Hz, 1H), 4.23 (t, J = 7.92 Hz, 2H), 3.67-3.74 (m, 2H), 3.49-3.60 (m, 1H), 2.24-2.33 (m, 1H), 1.18 (tdd, J = 2.45, 8.31, 11.22 Hz, 4H). | A2 |

Biological Evaluation

The exemplified compounds of the present invention were tested in the transient human FXR/Gal4-luciferase reporter assay, and assay results were described in Table 1.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 µg/mL Zeocin and 10% charcoal/dextran-treated fetal bovine serum (cs-FBS) at 37° C. in a humidified 5% $CO_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 µg of the pcDNA3.1-Gal4-FXR plasmid into 1.87 mL of Opti-MEM (Thermo-Fisher), and 40 µL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% $CO_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 µL are plated into each well of the 384-well compound assay plate. The compound-treated cells are incubated overnight at 37° C. in a humidified 5% $CO_2$ atmosphere. The next morning 25 µL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 µM GW-4064. These data are fit to a 4-parameter log agonist-response equation to calculate an $EC_{50}$ value.

Acute Mouse In Vivo Assay:

Male, C57BL6/NTac mice, weighing 25-28 g, are purchased from Taconic Labs (Hudson, N.Y.) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and $CYP_{7A1}$ expression as a percent reduction relative to vehicle control.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

Biological Evaluation

The exemplified compounds of the present invention were tested in the transient human FXR/Gal4-luciferase reporter assay, and assay results were described in the EXAMPLES section hereinbefore.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 µg/mL Zeocin and 10% charcoal/dextran-treated fetal bovine serum (cs-FBS) at 37° C. in a humidified 5% $CO_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 µg of the pcDNA3.1-Gal4-FXR plasmid into 1.87 mL of Opti-MEM (Thermo-Fisher), and 40 µL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% $CO_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 µL are plated into each well of the 384-well compound assay plate. The compound-treated cells are incubated overnight at 37° C. in a humidified 5% $CO_2$ atmosphere. The next morning 25 µL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 µM GW-4064. These data are fit to a 4-parameter log agonist-response equation to calculate an $EC_{50}$ value.

In Vivo Testing Example: Acute Mouse PK/PD

Male, C57BL6/NTac mice, weighing 25-28 g, are purchased from Taconic Labs (Hudson, N.Y.) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb1 1 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51 b (which encodes organic solute transporter beta subunit, OSTB) in the ileum. The statistical significant changes in FGF15 gene expression are expressed as fold increase and $CYP_{7A1}$ expression as a percent reduction relative to vehicle control.

TABLE A

| | | Mouse PD | |
|---|---|---|---|
| Example # | Dose (mg/kg) | Cyp7a1 (fold change@ 6 h relative to Vehicle) | Fgf15 (fold change@ 6 h relative to Vehicle) |
| 27 | 30 | 0.10 | 2.8 |
| 101 | 3 | 0.06 | 21 |

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:
1. A compound of Formula (I):

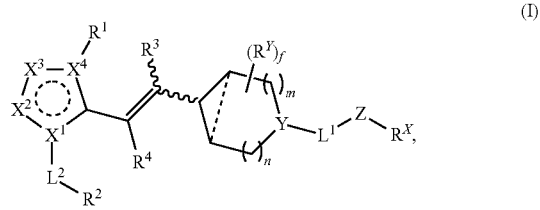

(I)

or a stereoisomer, a tautomer, or a pharmaceutically acceptable salt thereof; wherein:
$X^1$ and $X^4$ are each independently C or N;
$X^2$ and $X^3$ are each independently $CR^5$, N, $NR^6$, O, or S;
Y is $CR^7$, or N;
the dashed straight line is an optional covalent bond;
m and n are each independently an integer of 0, 1, or 2; provided that when m and n are both 0, then the optional covalent bond of the dashed line is absent;
f is an integer of 0, 1, 2, or 3;
Z is 6- to 10-membered aryl, 5- to 10-membered heteroaryl, 3- to 10-membered carbocyclyl, or 4- to 10-membered heterocyclyl, wherein the aryl, heteroaryl, carbocyclyl, and heterocyclyl are independently substituted with 0 to 5 $R^8$;
$L^1$ is a covalent bond, O, S, NR", $S(O)_2$, $C_{1-3}$ alkylene, $C_{1-3}$ heteroalkylene, $C_{2-4}$ alkenylene, $C_{2-4}$ alkynylene, aryl, or a 5- to 6-membered heteroaryl containing 1 to 4 heteroatoms independently selected from N, O, and S; wherein the alkylene, heteroalkylene, aryl, and heteroaryl are each independently substituted with 0 to 3 $R^{11}$;
$L^2$ is a covalent bond, O, S, $NR^{18}$, $C_{1-3}$ alkylene, or $C_{1-3}$ heteroalkylene, wherein the alkylene and heteroalkylene are independently substituted with 0 to 3 $R^{16}$;
$R^X$ is $-L^3-R^Z$;
$L^3$ is a covalent bond, a $C_{1-3}$ alkylene, or —C(O)$NR^{12}$— $CH_2$—, wherein the $C_{1-3}$ alkylene is substituted with 0 to 3 $R^{15}$;
$R^Z$ is —CN, —C(O)$OR^{13}$, —C(O)$NR^{14a}R^{14b}$,

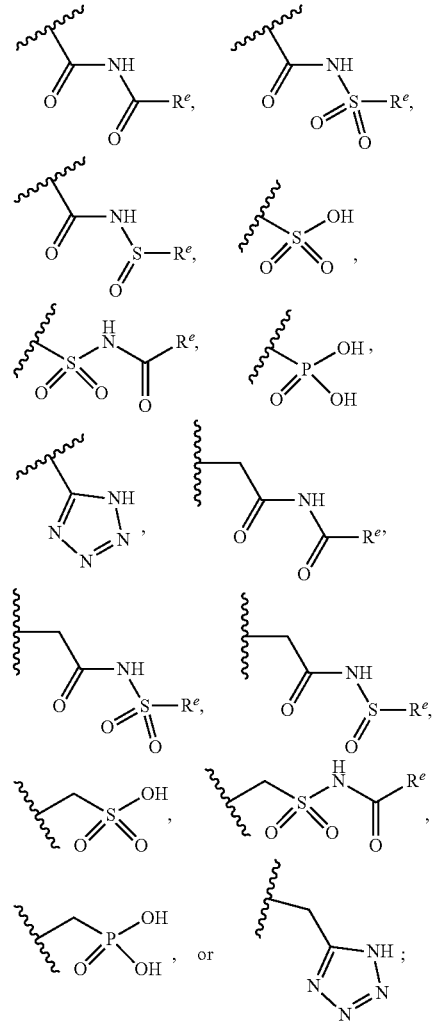

$R^e$ is $C_{1-6}$ alkyl, $C_{3-6}$ cycloalkyl, haloalkyl, hydroxyalkyl, aminoalkyl, alkoxyalkyl, or haloalkoxyalkyl;
each $R^Y$ is independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy; or alternatively two $R^Y$, together with the carbon atoms to which they are attached, form a bridge moiety; and with the proviso that when Y is N and $R^Y$ is attached to a carbon atom adjacent to Y, then $R^Y$ is not halo, cyano, hydroxyl, amino, alkoxy, or haloalkoxy;

$R^1$ is $C_{1-6}$ alkyl, $C_{3-5}$ cycloalkyl, or $C_{4-6}$ heterocyclyl, wherein the alkyl and cycloalkyl are substituted with 0 to 3 $R^9$;

$R^2$ is 6- to 10-membered aryl, 5- to 10-membered heteroaryl, 3- to 10-membered carbocyclyl, or 4- to 10-membered heterocyclyl, wherein the aryl, heteroaryl, carbocyclyl, and heterocyclyl are independently substituted with 0 to 5 $R^{10}$;

$R^3$ and $R^4$ are each independently hydrogen, $C_{1-6}$ alkyl, haloalkyl, hydroxyalkyl, aminoalkyl, alkoxyalkyl, or haloalkoxyalkyl;

$R^5$ and $R^7$ are each independently hydrogen, halo, cyano, hydroxyl, amino, $C_{1-6}$ alkyl, alkylamino, haloalkyl, hydroxyalkyl, aminoalkyl, alkoxyalkyl, haloalkoxyalkyl, alkoxy, or haloalkoxy;

$R^6$, $R^{17}$ and $R^{18}$ are each independently is hydrogen, $C_{1-6}$ alkyl, haloalkyl, hydroxyalkyl, aminoalkyl, alkoxyalkyl, or haloalkoxyalkyl;

$R^8$ and $R^{10}$ are each independently halo, cyano, hydroxyl, amino, oxo, —$OR^a$, —$SR^a$, =S, —$NR^cR^c$, =NH, =N—OH, =$NR^a$, =N—$OR^a$, —$NO_2$, —$S(O)_2R^a$, —$S(O)_2NHR^b$, —$S(O)_2NR^cR^c$, —$S(O)_2OR^b$, —OS(O)$_2R^b$, —OS(O)$_2OR^b$, —P(O)(O$R^b$)(O$R^b$), —C(O)$R^b$, —C(N$R^b$)$R^b$, —C(O)O$R^b$, —C(O)N$R^cR^c$, —C(N$R^b$)N$R^cR^c$, —OC(O)$R^b$, —N$R^b$C(O)$R^b$, —OC(O)O$R^b$, —N$R^b$C(O)O$R^b$, —OC(O)N$R^cR^c$, —N$R^b$C(O)N$R^cR^c$, —N$R^b$C(N$R^b$)$R^b$, —N$R^b$C(N$R^b$)N$R^cR^c$, $C_{1-6}$ alkyl, $C_{1-6}$ haloalkyl, aryl, arylalkyl, heteroaryl, carbocyclyl, or heterocyclyl; wherein the alkyl, aryl, heteroaryl, carbocyclyl, and heterocyclyl, by themselves or as part of another group, are each independently substituted with 0 to 5 $R^d$;

$R^b$ is each independently hydrogen or $R^a$;

$R^c$ is each independently $R^b$ or alternatively, the two $R^c$ are taken together with the nitrogen atom to which they are bonded form a 4, 5, 6 or 7-membered heterocyclyl;

$R^d$ is each independently $R^a$, alkoxy, haloalkoxy, alkylamino, cycloalkylamino, heterocyclylamino, haloalkyl, hydroxyalkyl, aminoalkyl, cycloalkoxy, heterocyclyloxy, haloalkoxy, alkoxyalkoxy, haloalkylamino, alkoxyalkylamino, haloalkoxyalkylamino, arylamino, aralkylamino, aryloxy, aralkyloxy, heteroaryloxy, heteroarylalkyloxy, alkylthio, halo, cyano, hydroxyl, amino, oxo, —$OR^a$, —$SR^a$, =S, —$NR^cR^c$, =NH, =N—OH, =$NR^a$, =N—$OR^a$, —$NO_2$, —$S(O)_2R^a$, —$S(O)_2NHR^b$, —$S(O)_2NR^cR^c$, —$S(O)_2OR^b$, —OS(O)$_2R^b$, —OS(O)$_2OR^b$, —P(O)(O$R^b$)(O$R^b$), —C(O)$R^b$, —C(N$R^b$)$R^b$, —C(O)O$R^b$, —C(O)N$R^cR^c$, —C(N$R^b$)N$R^cR^c$, —OC(O)$R^b$, N$R^b$C(O)$R^b$; —OC(O)O$R^b$, —N$R^b$C(O)O$R^b$, —N$R^b$C(O)N$R^cR^c$, —N$R^b$C(N$R^b$)$R^b$, or N$R^b$C(N$R^b$)N$R^cR^c$;

$R^9$ is each independently halo, cyano, hydroxyl, amino, or $C_{1-6}$ alkyl;

$R^{11}$ and $R^{16}$ are each independently halo, oxo, cyano, hydroxyl, amino, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy;

$R^{12}$ are each independently hydrogen or $C_{1-4}$ alkyl;

$R^{13}$ is hydrogen, $C_{1-10}$ alkyl, or glycosyl;

$R^{14a}$ and $R^{14b}$ are each independently hydrogen, $C_{1-6}$ alkyl, $C_{3-6}$ cycloalkyl, $C_{4-6}$ heterocyclyl, alkylamino, haloalkyl, hydroxyalkyl, aminoalkyl, alkoxyalkyl, haloalkoxyalkyl, alkoxy, or haloalkoxy; and $R^{15}$ are each independently halo, oxo, cyano, hydroxyl, amino, alkyl, alkoxy, or alkylamino; or alternatively, two $R^{15}$, taken together with the atom(s) to which they are attached, form a carbocyclyl or heterocyclyl moiety.

2. The compound of claim 1, or a tautomer, or a pharmaceutically acceptable salt thereof, which is represented by Formula (Ia):

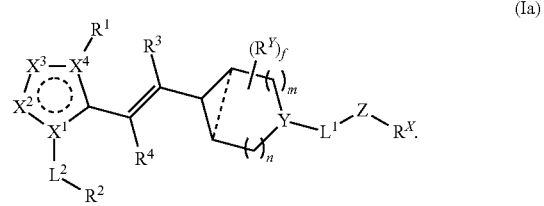

3. The compound according to claim 1, or a stereoisomer, a tautomer, or a pharmaceutically acceptable salt thereof, wherein the

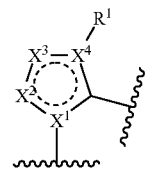

moiety is

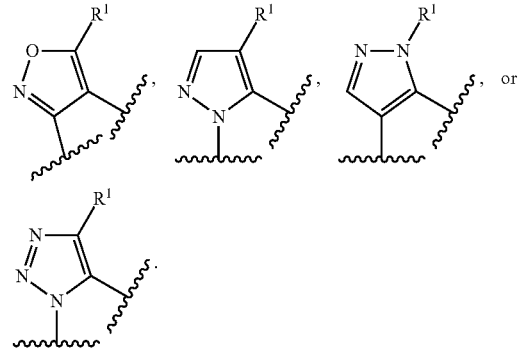

4. The compound according to claim 1, or a stereoisomer, a tautomer, or a pharmaceutically acceptable salt thereof, wherein the

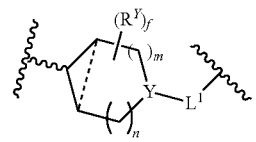

moiety is:

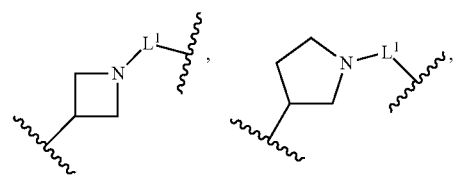

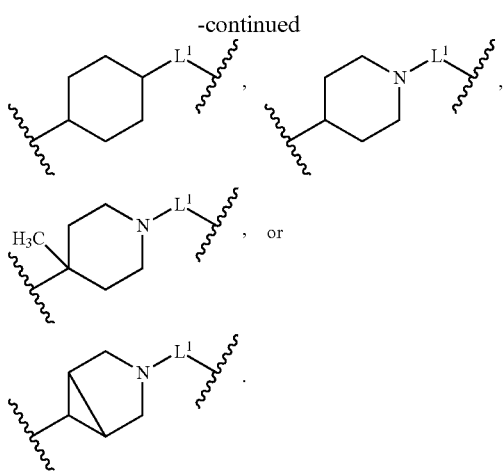

5. The compound according to claim 1, or a stereoisomer, a tautomer, or a pharmaceutically acceptable salt thereof, wherein:
$L^1$ is a covalent bond, phenyl, thiazolyl, oxadiazolyl, thiadiazolyl, or pyridinyl; and
Z is phenyl or 5- to 10-membered heteroaryl, wherein the phenyl and heteroaryl are independently substituted with 0 to 5 $R^8$.

6. The compound according to claim 1, or a stereoisomer, a tautomer, or a pharmaceutically acceptable salt thereof, wherein:
$L^3$ is a covalent bond or a $C_{1-2}$ alkylene, wherein the $C_{1-2}$ alkylene is substituted with 0 to 3 $R^{15}$; and
$R^Z$ is —CN, —C(O)O$R^{13}$, —C(O)N$R^{14a}R^{14b}$,

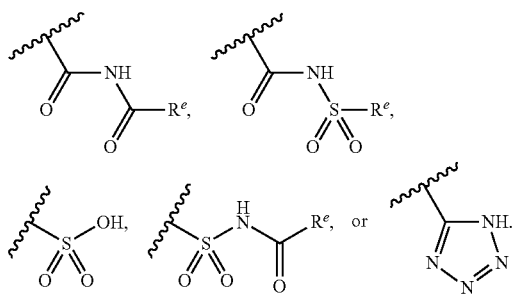

7. The compound according to claim 1, or a stereoisomer, a tautomer, or a pharmaceutically acceptable salt thereof, wherein:
$L^2$ is a covalent bond; and
$R^2$ is phenyl or 6-membered heteroaryl, wherein the phenyl and the heteroaryl are substituted with 0 to 3 $R^{10}$.

8. The compound according to claim 1, or a stereoisomer, a tautomer, or a pharmaceutically acceptable salt thereof, wherein:
the

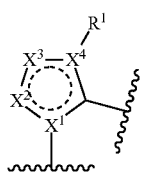

moiety is

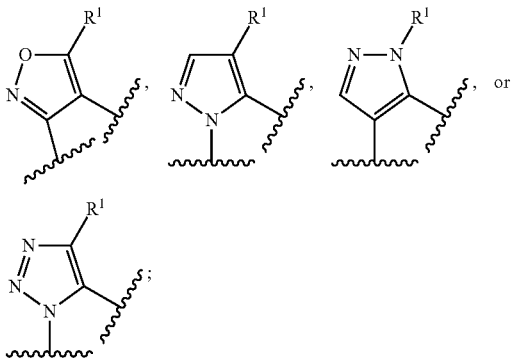

the

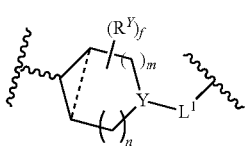

moiety is:

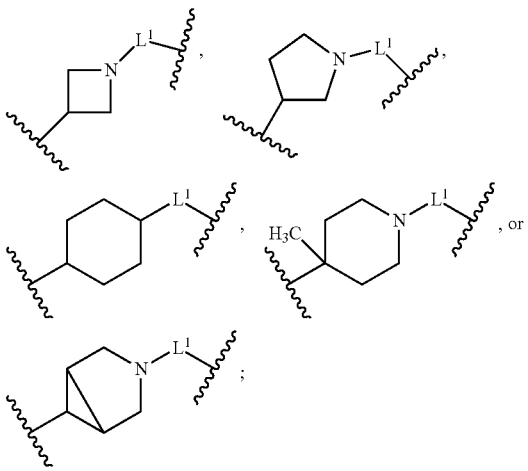

$L^1$ is a covalent bond, phenyl, thiazolyl, oxadiazolyl, thiadiazolyl, or pyridinyl;
Z is 1,5-naphthyridinyl, benzo[d]imidazolyl, benzo[d]isothiazolyl, benzo[d]oxazolyl, benzo[d]thiazolyl, cinnolinyl, imidazo[3,4-a]pyridinyl, indazolyl, indolyl, isoquinolinyl, phenyl, pyrazinyl, pyrazolo[1,5-a]pyridinyl, pyrazolo[4,3-b]pyridinyl, pyrazolyl, pyridazinyl, pyridinyl, pyrimidinyl, pyrrolo[2,1-f]triazinyl, pyrrolo[2,3-b] pyridinyl, pyrrolo[2,3-d]pyrimidinyl, pyrrolo[3,2-b]pyridinyl, quinolinonyl, quinolinyl, quinoxalinyl, thiazolo[5,4-b]pyridinyl, or thiazolyl, each independently substituted with 0 to 2 $R^8$;
$R^X$ is —CN, —C(O)OH, —CH$_2$C(O)OH, —C(O)NH$_2$, —C(O)NHS(O)$_2$CH$_3$,

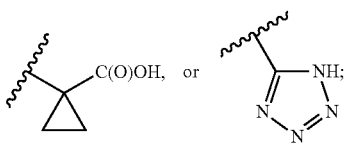

R¹ is cyclopropyl;
R² is phenyl or pyridinyl, each independently substituted with 1 to 2 R¹⁰;
R³ is hydrogen;
R⁴ is hydrogen or —CH₃;
R⁸ is each independently F, Cl, —CH₃, —CH₂CH₃, —CH₂OCH₃, —CF₃, —OCH₃, —OCD₃, —OCH₂CH₃, —CH(CH₃)₂, —OCH₂CH₂OCH₃, —OCHF₂, —OCH₂CHF₂, —CH₂(cyclopropyl), —O(cyclopropyl), —O(cyclobutyl), —O(difluorocyclobutyl), —O(fluorocyclobutyl), —O(oxetanyl), —O(tetrahydrofuranyl), or —OCH₂(methoxyphenyl);
L² is a covalent bond; and
R¹⁰ is each independently Cl, —CF₃, or —OCF₃.

9. The compound of claim 1 or a salt thereof, wherein said compound is:
(E)-6-(4-(2-(5-cyclopropyl-3-(2,6-dichlorophenyl)isoxazol-4-yl)vinyl)piperidin-1-yl) nicotinic acid (1);
(E)-6-(4-(2-(5-cyclopropyl-3-(2,6-dichlorophenyl)isoxazol-4-yl)vinyl)piperidin-1-yl)-1-methyl-1H-indole-3-carboxylic acid (2);
(Z)-6-(4-(2-(5-cyclopropyl-3-(2,6-dichlorophenyl)isoxazol-4-yl)vinyl)piperidin-1-yl) nicotinic acid (3);
(E)-2-(4-(1-(5-cyclopropyl-3-(2,6-dichlorophenyl)isoxazol-4-yl)prop-1-en-2-yl)piperidin-1-yl)-4-fluorobenzo[d]thiazole-6-carboxylic acid (4);
(E)-6-(4-(1-(5-cyclopropyl-3-(2,6-dichlorophenyl)isoxazol-4-yl)prop-1-en-2-yl)piperidin-1-yl)quinoline-2-carboxylic acid (5);
(E)-2-(4-(2-(5-cyclopropyl-3-(2,6-dichlorophenyl)isoxazol-4-yl)vinyl)-4-methylpiperidin-1-yl)-4-fluorobenzo[d]thiazole-6-carboxylic acid (6);
(E)-6-(4-(2-(5-cyclopropyl-3-(2,6-dichlorophenyl)isoxazol-4-yl)vinyl)-4-methylpiperidin-1-yl)quinoline-2-carboxylic acid (7);
(E)-2-(6-(2-(5-cyclopropyl-3-(2,6-dichlorophenyl)isoxazol-4-yl)vinyl)-3-azabicyclo[3.1.0]hexan-3-yl)-4-fluorobenzo[d]thiazole-6-carboxylic acid (8);
(E)-6-(6-(2-(5-cyclopropyl-3-(2,6-dichlorophenyl)isoxazol-4-yl)vinyl)-3-azabicyclo[3.1.0]hexan-3-yl)quinoline-2-carboxylic acid (9);
(E)-2-(4-(2-(4-cyclopropyl-1-(2,6-dichlorophenyl)-1H-1,2,3-triazol-5-yl)vinyl)piperidin-1-yl)-4-fluorobenzo[d]thiazole-6-carboxylic acid (10);
(E)-6-(4-(2-(4-cyclopropyl-1-(2,6-dichlorophenyl)-1H-pyrazol-5-yl)vinyl)piperidin-1-yl) nicotinic acid (11);
(E)-2-(4-(2-(1-cyclopropyl-4-(2,6-dichlorophenyl)-1H-pyrazol-5-yl)vinyl)piperidin-1-yl)-4-fluorobenzo[d]thiazole-6-carboxylic acid (12);
(E)-6-(4-(2-(5-cyclopropyl-3-(2,6-dichlorophenyl)isoxazol-4-yl)vinyl)piperidin-1-yl) picolinic acid (13);
(E)-2-(4-(2-(5-cyclopropyl-3-(2,6-dichlorophenyl)isoxazol-4-yl)vinyl)piperidin-1-yl)-4-fluorobenzo[d]thiazole-6-carboxylic acid (14);
(Z)-2-(4-(2-(5-cyclopropyl-3-(2,6-dichlorophenyl)isoxazol-4-yl)vinyl)piperidin-1-yl)-4-fluorobenzo[d]thiazole-6-carboxylic acid (15);
(E)-6-(4-(2-(4-cyclopropyl-1-(2,6-dichlorophenyl)-1H-1,2,3-triazol-5-yl)vinyl)piperidin-1-yl)nicotinic acid (16);
(Z)-2-(3-(2-(5-cyclopropyl-3-(2,6-dichlorophenyl)isoxazol-4-yl)vinyl)-8-azabicyclo[3.2.1]octan-8-yl)-4-fluorobenzo[d]thiazole-6-carboxylic acid (17);
(E)-6-(4-(2-(5-cyclopropyl-3-(2,6-dichlorophenyl)isoxazol-4-yl)vinyl)piperidin-1-yl) pyridazine-3-carboxylic acid (18);
(E)-2-(4-(2-(5-cyclopropyl-3-(2,6-dichlorophenyl)isoxazol-4-yl)vinyl)piperidin-1-yl)-7-methyl-7H-pyrrolo[2,3-d]pyrimidine-5-carboxylic acid (19);
(E)-6-(4-(2-(5-cyclopropyl-3-(2,6-dichlorophenyl)isoxazol-4-yl)vinyl)piperidin-1-yl)-1-methyl-1H-pyrrolo[2,3-b]pyridine-3-carboxylic acid (20);
(E)-6-(4-(2-(5-cyclopropyl-3-(2,6-dichlorophenyl)isoxazol-4-yl)vinyl)piperidin-1-yl)-5-fluoronicotinic acid (21);
(E)-2-(4-(2-(5-cyclopropyl-3-(2,6-dichlorophenyl)isoxazol-4-yl)vinyl)piperidin-1-yl) benzo[d]thiazole-6-carboxylic acid (22);
(E)-2-(4-(2-(5-cyclopropyl-3-(2,6-dichlorophenyl)isoxazol-4-yl)vinyl)piperidin-1-yl) benzo[d]oxazole-5-carboxylic acid (23);
(E)-5-(4-(2-(5-cyclopropyl-3-(2,6-dichlorophenyl)isoxazol-4-yl)vinyl)piperidin-1-yl) pyrazine-2-carboxylic acid (24);
(E)-2-(4-(2-(5-cyclopropyl-3-(2,6-dichlorophenyl)isoxazol-4-yl)vinyl)piperidin-1-yl) pyrimidine-5-carboxylic acid (25);
(E)-6-(4-(2-(5-cyclopropyl-3-(2,6-dichlorophenyl)isoxazol-4-yl)vinyl)piperidin-1-yl) quinoline-2-carboxylic acid (26);
(E)-5-(4-(2-(5-cyclopropyl-3-(2,6-dichlorophenyl)isoxazol-4-yl)vinyl)piperidin-1-yl) pyrimidine-2-carboxylic acid (27);
(E)-2-(4-(2-(5-cyclopropyl-3-(2,6-dichlorophenyl)isoxazol-4-yl)vinyl)piperidin-1-yl)-1-methyl-1H-benzo[d]imidazole-5-carboxylic acid (28);
(E)-2-(4-(2-(5-cyclopropyl-3-(2,6-dichlorophenyl)isoxazol-4-yl)vinyl)piperidin-1-yl) pyrrolo[2,1-f][1,2,4]triazine-5-carboxylic acid (29);
(E)-5-(4-(2-(5-cyclopropyl-3-(2,6-dichlorophenyl)isoxazol-4-yl)vinyl)piperidin-1-yl) picolinic acid (30);
(E)-3-(4-(2-(5-cyclopropyl-3-(2,6-dichlorophenyl)isoxazol-4-yl)vinyl)piperidin-1-yl)-1-methyl-1H-pyrazolo[4,3-b]pyridine-6-carboxylic acid (31);
(E)-2-(4-(2-(4-cyclopropyl-1-(2,6-dichlorophenyl)-1H-pyrazol-5-yl)vinyl)piperidin-1-yl)-4-fluorobenzo[d]thiazole-6-carboxylic acid (32);
(E)-2-(4-(2-(5-cyclopropyl-3-(2,6-dichlorophenyl)isoxazol-4-yl)vinyl)piperidin-1-yl) quinoline-6-carboxylic acid (33);
(E)-6-(4-(2-(5-cyclopropyl-3-(2,6-dichlorophenyl)isoxazol-4-yl)vinyl)-4-methylpiperidin-1-yl)nicotinic acid (34);
(E)-6-(4-(2-(5-cyclopropyl-3-(2,6-dichlorophenyl)isoxazol-4-yl)vinyl)piperidin-1-yl)-1-methyl-1H-indole-2-carboxylic acid (35);
(E)-2-(4-(2-(5-cyclopropyl-3-(2,6-dichlorophenyl)isoxazol-4-yl)vinyl)piperidin-1-yl) isonicotinic acid (36);
(E)-7-(4-(2-(5-cyclopropyl-3-(2,6-dichlorophenyl)isoxazol-4-yl)vinyl)piperidin-1-yl) isoquinoline-3-carboxylic acid (37);
(E)-6-(4-(2-(5-cyclopropyl-3-(2,6-dichlorophenyl)isoxazol-4-yl)vinyl)piperidin-1-yl)-4-(trifluoromethyl)quinoline-2-carboxylic acid (38);

(E)-6-(4-(2-(5-cyclopropyl-3-(2,6-dichlorophenyl)isoxazol-4-yl)vinyl)piperidin-1-yl)-3-(trifluoromethyl)imidazo[1,5-a]pyridine-1-carboxylic acid (39);

(E)-2-(2-(4-(2-(5-cyclopropyl-3-(2,6-dichlorophenyl)isoxazol-4-yl)vinyl)piperidin-1-yl) pyridin-4-yl)acetic acid (40);

(E)-6-(4-(2-(5-cyclopropyl-3-(2,6-dichlorophenyl)isoxazol-4-yl)vinyl)piperidin-1-yl)-1-methyl-1H-indazole-3-carboxylic acid (41);

(E)-6-(4-(2-(5-cyclopropyl-3-(2-(trifluoromethoxy)phenyl)isoxazol-4-yl)vinyl)piperidin-1-yl) nicotinic acid (42);

(E)-2-(4-(2-(5-cyclopropyl-3-(2-(trifluoromethoxy)phenyl)isoxazol-4-yl)vinyl)piperidin-1-yl)-4-fluorobenzo[d]thiazole-6-carboxylic acid (43);

(E)-6-(4-(2-(5-cyclopropyl-3-(2-(trifluoromethoxy)phenyl)isoxazol-4-yl)vinyl)piperidin-1-yl)-4-(trifluoromethyl)quinoline-2-carboxylic acid (44);

(E)-6-(4-(2-(5-cyclopropyl-3-(2-(trifluoromethyl)phenyl)isoxazol-4-yl)vinyl)piperidin-1-yl)-4-(trifluoromethyl)quinoline-2-carboxylic acid (45);

(E)-2-(6-(2-(5-cyclopropyl-3-(2,6-dichlorophenyl)isoxazol-4-yl)vinyl)-3-azabicyclo[3.1.0]hexan-3-yl)benzo[d]thiazole-6-carboxylic acid (46);

(E)-4-(6-(2-(5-cyclopropyl-3-(2,6-dichlorophenyl)isoxazol-4-yl)vinyl)-3-azabicyclo[3.1.0]hexan-3-yl)benzoic acid (47);

(E)-7-(6-(2-(5-cyclopropyl-3-(2,6-dichlorophenyl)isoxazol-4-yl)vinyl)-3-azabicyclo[3.1.0]hexan-3-yl)isoquinoline-3-carboxylic acid (48);

(E)-2-(4-(2-(5-cyclopropyl-3-(2-(trifluoromethyl)phenyl)isoxazol-4-yl)vinyl)piperidin-1-yl)-4-fluorobenzo[d]thiazole-6-carboxylic acid (49);

(E)-4-(4-(2-(5-cyclopropyl-3-(2,6-dichlorophenyl)isoxazol-4-yl)vinyl)piperidin-1-yl) benzonitrile (50);

(E)-4-(4-(2-(5-cyclopropyl-3-(2,6-dichlorophenyl)isoxazol-4-yl)vinyl)piperidin-1-yl)-2-fluorobenzoic acid (51);

(E)-6-(6-(2-(5-cyclopropyl-3-(2,6-dichlorophenyl)isoxazol-4-yl)vinyl)-3-azabicyclo[3.1.0]hexan-3-yl)-4-(trifluoromethyl)quinoline-2-carboxylic acid (52);

(E)-2-chloro-4-(4-(2-(5-cyclopropyl-3-(2,6-dichlorophenyl)isoxazol-4-yl)vinyl)piperidin-1-yl)benzoic acid (53);

(E)-4-(4-(2-(5-cyclopropyl-3-(2,6-dichlorophenyl)isoxazol-4-yl)vinyl)piperidin-1-yl)benzoic acid (54);

(E)-6-(4-(2-(5-cyclopropyl-3-(2,6-dichlorophenyl)isoxazol-4-yl)vinyl)piperidin-1-yl)-2-(trifluoromethyl)nicotinic acid (55);

(E)-4-(2-(1-(4-(1H-tetrazol-5-yl)phenyl)piperidin-4-yl)vinyl)-5-cyclopropyl-3-(2,6-dichlorophenyl)isoxazole (56);

(E)-4-(4-(2-(5-cyclopropyl-3-(2,6-dichlorophenyl)isoxazol-4-yl)vinyl)piperidin-1-yl)-2-(trifluoromethyl)benzoic acid (57);

(E)-6-(4-(2-(4-cyclopropyl-1-(2,6-dichlorophenyl)-1H-1,2,3-triazol-5-yl)vinyl)piperidin-1-yl)-4-(trifluoromethyl)quinoline-2-carboxylic acid (58);

(E)-1-(4-(4-(2-(5-cyclopropyl-3-(2,6-dichlorophenyl)isoxazol-4-yl)vinyl)piperidin-1-yl) phenyl)cyclopropane-1-carboxylic acid (59);

(E)-6-(4-(2-(4-cyclopropyl-1-(2,6-dichlorophenyl)-1H-1,2,3-triazol-5-yl)vinyl)piperidin-1-yl)quinoline-2-carboxylic acid (60);

(E)-4-(2-(3-(4-(2H-tetrazol-5-yl)phenyl)-3-azabicyclo[3.1.0]hexan-6-yl)vinyl)-5-cyclopropyl-3-(2,6-dichlorophenyl)isoxazole (61);

(E)-4-(2-(1-(4-(2H-tetrazol-5-yl)phenyl)piperidin-4-yl)vinyl)-5-cyclopropyl-3-(2-(trifluoromethoxy)phenyl)isoxazole (62);

(E)-4-(2-(1-(3-(2H-tetrazol-5-yl)phenyl)piperidin-4-yl)vinyl)-5-cyclopropyl-3-(2,6-dichlorophenyl)isoxazole (63);

(E)-4-(2-(1-(5-(2H-tetrazol-5-yl)pyridin-2-yl)piperidin-4-yl)vinyl)-5-cyclopropyl-3-(2,6-dichlorophenyl)isoxazole (64);

(E)-4-(2-(3-(2-(1H-tetrazol-5-yl)quinolin-6-yl)-3-azabicyclo[3.1.0]hexan-6-yl)vinyl)-5-cyclopropyl-3-(2,6-dichlorophenyl)isoxazole (65);

(E)-7-(6-(2-(5-cyclopropyl-3-(2,6-dichlorophenyl)isoxazol-4-yl)vinyl)-3-azabicyclo[3.1.0]hexan-3-yl)cinnoline-3-carboxylic acid (66);

(E)-7-(4-(2-(5-cyclopropyl-3-(2-(trifluoromethoxy)phenyl)isoxazol-4-yl)vinyl)piperidin-1-yl)cinnoline-3-carboxylic acid (67);

(E)-6-(6-(2-(5-cyclopropyl-3-(2,6-dichlorophenyl)isoxazol-4-yl)vinyl)-3-azabicyclo[3.1.0]hexan-3-yl)-1-methyl-1H-indole-3-carboxylic acid (68);

(E)-7-(4-(2-(5-cyclopropyl-3-(2,6-dichlorophenyl)isoxazol-4-yl)vinyl)piperidin-1-yl) quinoline-3-carboxylic acid (69);

(E)-4-(6-(2-(5-cyclopropyl-3-(2,6-dichlorophenyl)isoxazol-4-yl)vinyl)-3-azabicyclo[3.1.0]hexan-3-yl)benzamide (70);

(E)-4-(6-(2-(5-cyclopropyl-3-(2,6-dichlorophenyl)isoxazol-4-yl)vinyl)-3-azabicyclo[3.1.0]hexan-3-yl)-N-(methylsulfonyl)benzamide (71);

(E)-6-(6-(2-(5-cyclopropyl-3-(3,5-dichloropyridin-4-yl)isoxazol-4-yl)vinyl)-3-azabicyclo[3.1.0]hexan-3-yl)-4-(trifluoromethyl)quinoline-2-carboxylic acid (72);

(E)-7-(6-(2-(5-cyclopropyl-3-(3,5-dichloropyridin-4-yl)isoxazol-4-yl)vinyl)-3-azabicyclo[3.1.0]hexan-3-yl)isoquinoline-3-carboxylic acid (73);

(E)-6-(6-(2-(5-cyclopropyl-3-(2-fluoro-6-(trifluoromethoxy)phenyl)isoxazol-4-yl)vinyl)-3-azabicyclo[3.1.0]hexan-3-yl)-4-(trifluoromethyl)quinoline-2-carboxylic acid (74);

(E)-6-(6-(2-(5-cyclopropyl-3-(2-(trifluoromethyl)phenyl)isoxazol-4-yl)vinyl)-3-azabicyclo[3.1.0]hexan-3-yl)-4-(trifluoromethyl)quinoline-2-carboxylic acid (75);

(E)-7-(6-(2-(5-cyclopropyl-3-(2-(trifluoromethyl)phenyl)isoxazol-4-yl)vinyl)-3-azabicyclo[3.1.0]hexan-3-yl)isoquinoline-3-carboxylic acid (76);

(E)-2-(6-(2-(5-cyclopropyl-3-(3,5-dichloropyridin-4-yl)isoxazol-4-yl)vinyl)-3-azabicyclo[3.1.0]hexan-3-yl)-4-fluorobenzo[d]thiazole-6-carboxylic acid (77);

(E)-2-(6-(2-(5-cyclopropyl-3-(3,5-dichloropyridin-4-yl)isoxazol-4-yl)vinyl)-3-azabicyclo[3.1.0]hexan-3-yl)benzo[d]thiazole-6-carboxylic acid (78);

(E)-2-(6-(2-(5-cyclopropyl-3-(3,5-dichloropyridin-4-yl)isoxazol-4-yl)vinyl)-3-azabicyclo[3.1.0]hexan-3-yl)quinoline-6-carboxylic acid (79);

(E)-6-(6-(2-(5-cyclopropyl-3-(3,5-dichloropyridin-4-yl)isoxazol-4-yl)vinyl)-3-azabicyclo[3.1.0]hexan-3-yl)-4-methoxyquinoline-2-carboxylic acid (80);

(E)-2-(6-(2-(5-cyclopropyl-3-(2,6-dichlorophenyl)isoxazol-4-yl)vinyl)-3-azabicyclo[3.1.0]hexan-3-yl)thiazolo[5,4-b]pyridine-5-carboxylic acid (81);

(E)-6-(6-(2-(5-cyclopropyl-3-(3,5-dichloropyridin-4-yl)isoxazol-4-yl)vinyl)-3-azabicyclo[3.1.0]hexan-3-yl)quinoline-2-carboxylic acid (82);

(E)-6-(4-(2-(5-cyclopropyl-3-(3,5-dichloropyridin-4-yl)isoxazol-4-yl)vinyl)piperidin-1-yl)-4-(trifluoromethyl)quinoline-2-carboxylic acid (83);

(E)-6-(4-(2-(3-(3-chloropyridin-4-yl)-5-cyclopropylisoxazol-4-yl)vinyl)piperidin-1-yl)-4-(trifluoromethyl)quinoline-2-carboxylic acid (84);

(E)-2-(4-(2-(5-cyclopropyl-3-(3,5-dichloropyridin-4-yl)isoxazol-4-yl)vinyl)piperidin-1-yl) thiazolo[5,4-b]pyridine-5-carboxylic acid (85);

(E)-2-(6-(2-(5-cyclopropyl-3-(2,6-dichlorophenyl)isoxazol-4-yl)vinyl)-3-azabicyclo[3.1.0]hexan-3-yl)thiazole-5-carboxylic acid (86);

(E)-2-(4-(2-(5-cyclopropyl-3-(2-(trifluoromethyl)phenyl)isoxazol-4-yl)vinyl)piperidin-1-yl) thiazolo[5,4-b]pyridine-5-carboxylic acid (87);

(E)-6-(4-(2-(5-cyclopropyl-3-(3,5-dichloropyridin-4-yl)isoxazol-4-yl)vinyl)piperidin-1-yl)-4-methoxyquinoline-2-carboxylic acid (88);

(E)-6-(6-(2-(5-cyclopropyl-3-(3,5-dichloropyridin-4-yl)isoxazol-4-yl)vinyl)-3-azabicyclo[3.1.0]hexan-3-yl)-1-methyl-1H-indole-3-carboxylic acid (89);

(E)-7-(4-(2-(5-cyclopropyl-3-(2-(trifluoromethyl)phenyl)isoxazol-4-yl)vinyl)piperidin-1-yl)isoquinoline-3-carboxylic acid (90);

(E)-6-(6-(2-(5-cyclopropyl-3-(3,5-dichloropyridin-4-yl)isoxazol-4-yl)vinyl)-3-azabicyclo[3.1.0]hexan-3-yl)-4-(difluoromethoxy)quinoline-2-carboxylic acid (91);

(E)-6-(4-(2-(5-cyclopropyl-3-(3,5-dichloropyridin-4-yl)isoxazol-4-yl)vinyl)piperidin-1-yl)-4-(difluoromethoxy)quinoline-2-carboxylic acid (92);

(E)-2-(6-(2-(5-cyclopropyl-3-(3,5-dichloropyridin-4-yl)isoxazol-4-yl)vinyl)-3-azabicyclo[3.1.0]hexan-3-yl) benzo[d]thiazole-7-carboxylic acid (93);

(E)-6-(4-(2-(5-cyclopropyl-3-(2-(trifluoromethoxy)phenyl)isoxazol-4-yl)vinyl)piperidin-1-yl)-4-methylquinoline-2-carbonitrile (94);

(E)-6-(6-(2-(5-cyclopropyl-3-(3,5-dichloropyridin-4-yl)isoxazol-4-yl)vinyl)-3-azabicyclo[3.1.0]hexan-3-yl) benzo[d]isothiazole-3-carboxylic acid (95);

(E)-4-(6-(2-(5-cyclopropyl-3-(3,5-dichloropyridin-4-yl)isoxazol-4-yl)vinyl)-3-azabicyclo[3.1.0]hexan-3-yl) benzoic acid (96);

(E)-6-(4-(2-(5-cyclopropyl-3-(2-(trifluoromethyl)pyridin-3-yl)isoxazol-4-yl)vinyl)piperidin-1-yl)-4-(trifluoromethyl)quinoline-2-carboxylic acid (97);

(E)-6-(4-(2-(5-cyclopropyl-3-(2-(trifluoromethyl)pyridin-3-yl)isoxazol-4-yl)vinyl)piperidin-1-yl)-4-(difluoromethoxy)quinoline-2-carboxylic acid (98);

(E)-6-(4-(2-(5-cyclopropyl-3-(2-(trifluoromethyl)phenyl)isoxazol-4-yl)vinyl)piperidin-1-yl)-4-(difluoromethoxy)quinoline-2-carboxylic acid (99);

(E)-6-(4-(2-(5-cyclopropyl-3-(2-(trifluoromethyl)phenyl)isoxazol-4-yl)vinyl)piperidin-1-yl)-4-methoxyquinoline-2-carboxylic acid (100);

(E)-7-(4-(2-(5-cyclopropyl-3-(3,5-dichloropyridin-4-yl)isoxazol-4-yl)vinyl)piperidin-1-yl) isoquinoline-3-carboxylic acid (101);

(E)-6-(6-(2-(5-cyclopropyl-3-(3,5-dichloropyridin-4-yl)isoxazol-4-yl)vinyl)-3-azabicyclo[3.1.0]hexan-3-yl) nicotinic acid (102);

(E)-7-(4-(2-(5-cyclopropyl-3-(2-(trifluoromethyl)pyridin-3-yl)isoxazol-4-yl)vinyl)piperidin-1-yl)isoquinoline-3-carboxylic acid (103);

(E)-6-(4-(2-(5-cyclopropyl-3-(3,5-dichloropyridin-4-yl)isoxazol-4-yl)vinyl)piperidin-1-yl) isoquinoline-1-carboxylic acid (104)

(E)-6-(6-(2-(5-cyclopropyl-3-(3,5-dichloropyridin-4-yl)isoxazol-4-yl)vinyl)-3-azabicyclo[3.1.0]hexan-3-yl) isoquinoline-1-carboxylic acid (105);

(E)-6-(4-(2-(5-cyclopropyl-3-(2-(trifluoromethoxy)phenyl)isoxazol-4-yl)vinyl)piperidin-1-yl) isoquinoline-1-carboxylic acid (106);

(E)-6-(6-(2-(5-cyclopropyl-3-(3,5-dichloropyridin-4-yl)isoxazol-4-yl)vinyl)-3-azabicyclo[3.1.0]hexan-3-yl) benzo[d]thiazole-2-carboxylic acid (107);

(E)-6-(4-(2-(5-cyclopropyl-3-(2-(trifluoromethoxy)phenyl)isoxazol-4-yl)vinyl)piperidin-1-yl)-4-isopropoxyquinoline-2-carboxylic acid (108);

(E)-6-(6-(2-(5-cyclopropyl-3-(3,5-dichloropyridin-4-yl)isoxazol-4-yl)vinyl)-3-azabicyclo[3.1.0]hexan-3-yl)-4-isopropoxyquinoline-2-carboxylic acid (109);

(E)-6-(4-(2-(5-cyclopropyl-3-(2-(trifluoromethyl)pyridin-3-yl)isoxazol-4-yl)vinyl)piperidin-1-yl)-4-isopropoxyquinoline-2-carboxylic acid (110);

(E)-6-(6-(2-(5-cyclopropyl-3-(3,5-dichloropyridin-4-yl)isoxazol-4-yl)vinyl)-3-azabicyclo[3.1.0]hexan-3-yl)-4-methylquinoline-2-carboxylic acid (111);

(E)-2-(4-(2-(5-cyclopropyl-3-(3,5-dichloropyridin-4-yl)isoxazol-4-yl)vinyl)piperidin-1-yl)-7-methylthiazolo[5,4-b]pyridine-5-carboxylic acid (112);

(E)-6-(6-(2-(5-cyclopropyl-3-(3,5-dichloropyridin-4-yl)isoxazol-4-yl)vinyl)-3-azabicyclo[3.1.0]hexan-3-yl)-4-(2-methoxyethoxy)quinoline-2-carboxylic acid (113);

(E)-2-(6-(2-(5-cyclopropyl-3-(3,5-dichloropyridin-4-yl)isoxazol-4-yl)vinyl)-3-azabicyclo[3.1.0]hexan-3-yl)-4-methoxybenzo[d]thiazole-6-carboxylic acid (114);

(E)-7-(4-(2-(5-cyclopropyl-3-(3-(trifluoromethyl)pyridin-2-yl)isoxazol-4-yl)vinyl)piperidin-1-yl)isoquinoline-3-carboxylic acid (115);

(E)-4-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)benzoic acid (116);

(E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)benzoic acid (117);

(E)-6-(4-(2-(5-cyclopropyl-3-(2-(trifluoromethoxy)phenyl)isoxazol-4-yl)vinyl)piperidin-1-yl) pyrazolo[1,5-a]pyridine-3-carboxylic acid (118);

(E)-7-(4-(2-(5-cyclopropyl-3-(2-(trifluoromethoxy)phenyl)isoxazol-4-yl)vinyl)piperidin-1-yl)-1-methylisoquinoline-3-carboxylic acid (119);

(E)-6-(6-(2-(5-cyclopropyl-3-(3,5-dichloropyridin-4-yl)isoxazol-4-yl)vinyl)-3-azabicyclo[3.1.0]hexan-3-yl)-4-((tetrahydrofuran-3-yl)oxy)quinoline-2-carboxylic acid (120);

(E)-8-(6-(2-(5-cyclopropyl-3-(3,5-dichloropyridin-4-yl)isoxazol-4-yl)vinyl)-3-azabicyclo[3.1.0]hexan-3-yl) quinoline-5-carboxylic acid (121);

(E)-7-(6-(2-(5-cyclopropyl-3-(3,5-dichloropyridin-4-yl)isoxazol-4-yl)vinyl)-3-azabicyclo[3.1.0]hexan-3-yl)-1-methoxyisoquinoline-3-carboxylic acid (122);

(E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)-5-(trifluoromethyl)benzoic acid (123);

(E)-2-(6-(2-(5-cyclopropyl-3-(3,5-dichloropyridin-4-yl)isoxazol-4-yl)vinyl)-3-azabicyclo[3.1.0]hexan-3-yl)-7-methoxythiazolo[5,4-b]pyridine-5-carboxylic acid (124);

(E)-6-(4-(2-(5-cyclopropyl-3-(3-(trifluoromethyl)pyridin-2-yl)isoxazol-4-yl)vinyl)piperidin-1-yl)-4-methoxyquinoline-2-carboxylic acid (125);

(E)-6-(6-(2-(5-cyclopropyl-3-(3,5-dichloropyridin-4-yl)isoxazol-4-yl)vinyl)-3-azabicyclo[3.1.0]hexan-3-yl)-4-(oxetan-3-yloxy)quinoline-2-carboxylic acid (126);

6-(6-((E)-2-(5-cyclopropyl-3-(3,5-dichloropyridin-4-yl)isoxazol-4-yl)vinyl)-3-azabicyclo[3.1.0]hexan-3-yl)-4-(((R)-tetrahydrofuran-3-yl)oxy)quinoline-2-carboxylic acid (127);

6-(6-((E)-2-(5-cyclopropyl-3-(3,5-dichloropyridin-4-yl)isoxazol-4-yl)vinyl)-3-azabicyclo[3.1.0]hexan-3-yl)-4-(((S)-tetrahydrofuran-3-yl)oxy)quinoline-2-carboxylic acid (128);

(E)-6-(6-(2-(5-cyclopropyl-3-(3,5-dichloropyridin-4-yl)isoxazol-4-yl)vinyl)-3-azabicyclo[3.1.0]hexan-3-yl)-4-((4-methoxybenzyl)oxy)quinoline-2-carboxylic acid (129);

(E)-4-cyclobutoxy-6-(6-(2-(5-cyclopropyl-3-(2-(trifluoromethyl)phenyl)isoxazol-4-yl)vinyl)-3-azabicyclo[3.1.0]hexan-3-yl)quinoline-2-carboxylic acid (130);

(E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)-5-methoxybenzoic acid (131);

(E)-6-(6-(2-(5-cyclopropyl-3-(2-(trifluoromethyl)phenyl)isoxazol-4-yl)vinyl)-3-azabicyclo[3.1.0]hexan-3-yl)-4-methoxyquinoline-2-carboxylic acid (132);

(E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-3-yl)benzoic acid (133);

(E)-6-(6-(2-(5-cyclopropyl-3-(2-(trifluoromethyl)phenyl)isoxazol-4-yl)vinyl)-3-azabicyclo[3.1.0]hexan-3-yl)-4-(oxetan-3-yloxy)quinoline-2-carboxylic acid (134);

(E)-7-(6-(2-(5-cyclopropyl-3-(2-(trifluoromethyl)phenyl)isoxazol-4-yl)vinyl)-3-azabicyclo[3.1.0]hexan-3-yl)-1-methoxyisoquinoline-3-carboxylic acid (135);

(E)-4-cyclobutoxy-6-(6-(2-(5-cyclopropyl-3-(3,5-dichloropyridin-4-yl)isoxazol-4-yl)vinyl)-3-azabicyclo[3.1.0]hexan-3-yl)quinoline-2-carboxylic acid (136);

(E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)-5-(oxetan-3-yloxy)benzoic acid (137);

(E)-7-(6-(2-(5-cyclopropyl-3-(2-(trifluoromethyl)phenyl)isoxazol-4-yl)vinyl)-3-azabicyclo[3.1.0]hexan-3-yl)quinoxaline-2-carboxylic acid (138);

(E)-2-(6-(2-(5-cyclopropyl-3-(2-(trifluoromethyl)phenyl)isoxazol-4-yl)vinyl)-3-azabicyclo[3.1.0]hexan-3-yl)-7-methoxythiazolo[5,4-b]pyridine-5-carboxylic acid (139);

(E)-6-(6-(2-(5-cyclopropyl-3-(2-(trifluoromethyl)phenyl)isoxazol-4-yl)vinyl)-3-azabicyclo[3.1.0]hexan-3-yl)quinoxaline-2-carboxylic acid (140);

(E)-6-(6-(2-(5-cyclopropyl-3-(2-(trifluoromethyl)pyridin-3-yl)isoxazol-4-yl)vinyl)-3-azabicyclo[3.1.0]hexan-3-yl)-4-methoxyquinoline-2-carboxylic acid (141);

(E)-4-cyclobutoxy-6-(6-(2-(5-cyclopropyl-3-(2-(trifluoromethyl)pyridin-3-yl)isoxazol-4-yl)vinyl)-3-azabicyclo[3.1.0]hexan-3-yl)quinoline-2-carboxylic acid (142);

(E)-6-(6-(2-(5-cyclopropyl-3-(2-(trifluoromethyl)pyridin-3-yl)isoxazol-4-yl)vinyl)-3-azabicyclo[3.1.0]hexan-3-yl)-4-(oxetan-3-yloxy)quinoline-2-carboxylic acid (143);

(E)-6-(6-(2-(5-cyclopropyl-3-(2,6-dichlorophenyl)isoxazol-4-yl)vinyl)-3-azabicyclo[3.1.0]hexan-3-yl)nicotinic acid (144);

(S,E)-6-(3-(2-(5-cyclopropyl-3-(2-(trifluoromethyl)phenyl)isoxazol-4-yl)vinyl)pyrrolidin-1-yl)-4-(trifluoromethyl)quinoline-2-carboxylic acid (145);

(R,E)-6-(3-(2-(5-cyclopropyl-3-(2-(trifluoromethyl)phenyl)isoxazol-4-yl)vinyl)pyrrolidin-1-yl)-4-(trifluoromethyl)quinoline-2-carboxylic acid (146);

(S,E)-4-cyclobutoxy-6-(3-(2-(5-cyclopropyl-3-(2-(trifluoromethyl)phenyl)isoxazol-4-yl)vinyl)pyrrolidin-1-yl)quinoline-2-carboxylic acid (147);

(R,E)-4-cyclobutoxy-6-(3-(2-(5-cyclopropyl-3-(2-(trifluoromethyl)phenyl)isoxazol-4-yl)vinyl)pyrrolidin-1-yl)quinoline-2-carboxylic acid (148);

(E)-6-(3-(2-(5-cyclopropyl-3-(2-(trifluoromethyl)phenyl)isoxazol-4-yl)vinyl)azetidin-1-yl)-4-isopropoxyquinoline-2-carboxylic acid (149);

(E)-4-cyclobutoxy-6-(3-(2-(5-cyclopropyl-3-(2-(trifluoromethyl)phenyl)isoxazol-4-yl)vinyl)azetidin-1-yl)quinoline-2-carboxylic acid (150);

(E)-6-(3-(2-(5-cyclopropyl-3-(2-(trifluoromethyl)phenyl)isoxazol-4-yl)vinyl)azetidin-1-yl)-4-(oxetan-3-yloxy)quinoline-2-carboxylic acid (151);

(E)-6-(3-(2-(5-cyclopropyl-3-(2-(trifluoromethyl)phenyl)isoxazol-4-yl)vinyl)azetidin-1-yl)-4-(3,3-difluorocyclobutoxy)quinoline-2-carboxylic acid (152);

(E)-2-(3-(2-(5-cyclopropyl-3-(2-(trifluoromethyl)phenyl)isoxazol-4-yl)vinyl)azetidin-1-yl)-7-methoxythiazolo[5,4-b]pyridine-5-carboxylic acid (153);

(E)-6-(3-(2-(5-cyclopropyl-3-(2-(trifluoromethyl)phenyl)isoxazol-4-yl)vinyl)azetidin-1-yl)-4-methoxyquinoline-2-carboxylic acid (154);

(E)-3-(3-(6-(2-(5-cyclopropyl-3-(2-(trifluoromethyl)pyridin-3-yl)isoxazol-4-yl)vinyl)-3-azabicyclo[3.1.0]hexan-3-yl)-1,2,4-oxadiazol-5-yl)-5-methoxybenzoic acid (155);

(E)-6-(6-(2-(5-cyclopropyl-3-(2-(trifluoromethyl)pyridin-3-yl)isoxazol-4-yl)vinyl)-3-azabicyclo[3.1.0]hexan-3-yl)-4-ethoxyquinoline-2-carboxylic acid (156);

6-(6-((E)-2-(5-cyclopropyl-3-(2-(trifluoromethyl)pyridin-3-yl)isoxazol-4-yl)vinyl)-3-azabicyclo[3.1.0]hexan-3-yl)-4-(((R)-tetrahydrofuran-3-yl)oxy)quinoline-2-carboxylic acid (157);

(E)-5-(6-(2-(5-cyclopropyl-3-(2-(trifluoromethyl)phenyl)isoxazol-4-yl)vinyl)-3-azabicyclo[3.1.0]hexan-3-yl)-3-ethoxypicolinamide (158);

(E)-4-cyclobutoxy-6-(3-(2-(5-cyclopropyl-3-(3,5-dichloropyridin-4-yl)isoxazol-4-yl)vinyl)azetidin-1-yl)quinoline-2-carboxylic acid (159);

(E)-6-(3-(2-(5-cyclopropyl-3-(3,5-dichloropyridin-4-yl)isoxazol-4-yl)vinyl)azetidin-1-yl)-4-(oxetan-3-yloxy)quinoline-2-carboxylic acid (160);

(E)-6-(6-(2-(5-cyclopropyl-3-(3,5-dichloropyridin-4-yl)isoxazol-4-yl)vinyl)-3-azabicyclo[3.1.0]hexan-3-yl)quinoxaline-2-carboxylic acid (161);

(E)-6-(3-(2-(5-cyclopropyl-3-(3,5-dichloropyridin-4-yl)isoxazol-4-yl)vinyl)azetidin-1-yl)-4-(trifluoromethyl)quinoline-2-carboxylic acid (162);

(E)-5-(6-(2-(5-cyclopropyl-3-(2-(trifluoromethyl)phenyl)isoxazol-4-yl)vinyl)-3-azabicyclo[3.1.0]hexan-3-yl)-3-ethoxypicolinic acid (163);

(E)-4-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)-6-methoxypicolinic acid (164);

(E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)-5-methoxybenzoic acid (165);

(E)-6-(3-(2-(5-cyclopropyl-3-(3,5-dichloropyridin-4-yl)isoxazol-4-yl)vinyl)azetidin-1-yl)-4-methoxyquinoline-2-carboxylic acid (166);

(E)-6-(3-(2-(5-cyclopropyl-3-(3,5-dichloropyridin-4-yl)isoxazol-4-yl)vinyl)azetidin-1-yl) quinoxaline-2-carboxylic acid (167);

(E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)-2-methoxybenzoic acid (168);

(E)-6-(3-(2-(5-cyclopropyl-3-(2-(trifluoromethyl)pyridin-3-yl)isoxazol-4-yl)vinyl)azetidin-1-yl)-4-methoxyquinoline-2-carboxylic acid (169);

(E)-4-cyclobutoxy-6-(3-(2-(5-cyclopropyl-3-(2-(trifluoromethyl)pyridin-3-yl)isoxazol-4-yl) vinyl)azetidin-1-yl)quinoline-2-carboxylic acid (170);

(E)-6-(3-(2-(5-cyclopropyl-3-(2-(trifluoromethyl)pyridin-3-yl)isoxazol-4-yl)vinyl)azetidin-1-yl)-4-(methoxymethyl)quinoline-2-carboxylic acid (171);

(E)-6-(3-(2-(5-cyclopropyl-3-(2-(trifluoromethyl)phenyl)isoxazol-4-yl)vinyl)azetidin-1-yl)-4-(methoxy-d3)quinoline-2-carboxylic acid (172);

(E)-6-(3-(2-(5-cyclopropyl-3-(2-(trifluoromethyl)phenyl)isoxazol-4-yl)vinyl)azetidin-1-yl)-4-methoxy-1,5-naphthyridine-2-carboxylic acid (173);

(E)-6-(3-(2-(5-cyclopropyl-3-(2-(trifluoromethyl)pyridin-3-yl)isoxazol-4-yl)vinyl)azetidin-1-yl)-4-(oxetan-3-yloxy)quinoline-2-carboxylic acid (174);

(E)-6-(6-(2-(5-cyclopropyl-3-(2-(trifluoromethyl)pyridin-3-yl)isoxazol-4-yl)vinyl)-3-azabicyclo[3.1.0]hexan-3-yl)-4-methoxy-1,5-naphthyridine-2-carboxylic acid (175);

(E)-5-(3-(6-(2-(5-cyclopropyl-3-(3,5-dichloropyridin-4-yl)isoxazol-4-yl)vinyl)-3-azabicyclo[3.1.0]hexan-3-yl)-1,2,4-oxadiazol-5-yl)-2-methoxybenzoic acid (176);

(E)-4-cyclopropoxy-6-(3-(2-(5-cyclopropyl-3-(2-(trifluoromethyl)pyridin-3-yl)isoxazol-4-yl)vinyl)azetidin-1-yl)quinoline-2-carboxylic acid (178);

(E)-7-(6-(2-(5-cyclopropyl-3-(3,5-dichloropyridin-4-yl)isoxazol-4-yl)vinyl)-3-azabicyclo[3.1.0]hexan-3-yl)-1-methyl-4-oxo-1,4-dihydroquinoline-3-carboxylic acid (180);

(E)-7-(3-(2-(5-cyclopropyl-3-(2-(trifluoromethyl)phenyl)isoxazol-4-yl)vinyl)azetidin-1-yl)-1-methyl-4-oxo-1,4-dihydroquinoline-3-carboxylic acid (181);

(E)-6-(3-(2-(5-cyclopropyl-3-(2-(trifluoromethyl)phenyl)isoxazol-4-yl)vinyl)azetidin-1-yl)-4-(2,2-difluoroethoxy)quinoline-2-carboxylic acid (182);

(E)-4-cyclopropoxy-6-(6-(2-(5-cyclopropyl-3-(2-(trifluoromethyl)phenyl)isoxazol-4-yl) vinyl)-3-azabicyclo[3.1.0]hexan-3-yl)quinoline-2-carboxamide (183);

(E)-4-cyclopropoxy-6-(6-(2-(5-cyclopropyl-3-(2-(trifluoromethyl)phenyl)isoxazol-4-yl) vinyl)-3-azabicyclo[3.1.0]hexan-3-yl)quinoline-2-carboxylic acid (184);

6-(6-((E)-2-(5-cyclopropyl-3-(2-(trifluoromethyl)phenyl)isoxazol-4-yl)vinyl)-3-azabicyclo[3.1.0]hexan-3-yl)-4-((1S,3S)-3-fluorocyclobutoxy)quinoline-2-carboxylic acid (185);

(E)-6-(3-(2-(5-cyclopropyl-3-(2-(trifluoromethyl)phenyl)isoxazol-4-yl)vinyl)azetidin-1-yl)-4-(methoxymethyl)quinoline-2-carboxylic acid (186);

6-(3-((E)-2-(5-cyclopropyl-3-(2-(trifluoromethyl)phenyl)isoxazol-4-yl)vinyl)azetidin-1-yl)-4-((1S,3S)-3-fluorocyclobutoxy)quinoline-2-carboxylic acid (187);

(R,E)-6-(3-(2-(5-cyclopropyl-3-(2-(trifluoromethyl)pyridin-3-yl)isoxazol-4-yl)vinyl)azetidin-1-yl)-4-((tetrahydrofuran-3-yl)oxy)quinoline-2-carboxylic acid (188);

(S,E)-6-(3-(2-(5-cyclopropyl-3-(2-(trifluoromethyl)pyridin-3-yl)isoxazol-4-yl)vinyl)azetidin-1-yl)-4-((tetrahydrofuran-3-yl)oxy)quinoline-2-carboxylic acid (189);

(E)-7-(6-(2-(5-cyclopropyl-3-(2-(trifluoromethyl)phenyl)isoxazol-4-yl)vinyl)-3-azabicyclo[3.1.0]hexan-3-yl)-1-methyl-4-oxo-1,4-dihydroquinoline-3-carboxylic acid (190);

(E)-6-(6-(2-(5-cyclopropyl-3-(2-(trifluoromethyl)phenyl)isoxazol-4-yl)vinyl)-3-azabicyclo[3.1.0]hexan-3-yl)-4-(2,2-difluoroethoxy)quinoline-2-carboxylic acid (191);

(E)-7-(6-(2-(5-cyclopropyl-3-(2-(trifluoromethyl)phenyl)isoxazol-4-yl)vinyl)-3-azabicyclo[3.1.0]hexan-3-yl)-1-ethyl-4-oxo-1,4-dihydroquinoline-3-carboxylic acid (192);

(S,E)-6-(3-(2-(5-cyclopropyl-3-(2-(trifluoromethyl)phenyl)isoxazol-4-yl)vinyl)azetidin-1-yl)-4-((tetrahydrofuran-3-yl)oxy)quinoline-2-carboxylic acid (193);

6-(3-((E)-2-(5-cyclopropyl-3-(2-(trifluoromethyl)phenyl)isoxazol-4-yl)vinyl)azetidin-1-yl)-4-((1R,3R)-3-fluorocyclobutoxy)quinoline-2-carboxylic acid (194);

6-(3-((E)-2-(5-cyclopropyl-3-(2-(trifluoromethyl)pyridin-3-yl)isoxazol-4-yl)vinyl)azetidin-1-yl)-4-((1S,3S)-3-fluorocyclobutoxy)quinoline-2-carboxylic acid (195);

(E)-4-cyclopropoxy-6-(3-(2-(5-cyclopropyl-3-(2-(trifluoromethyl)phenyl)isoxazol-4-yl) vinyl)azetidin-1-yl) quinoline-2-carboxylic acid (196);

(E)-7-(3-(2-(5-cyclopropyl-3-(2-(trifluoromethyl)phenyl)isoxazol-4-yl)vinyl)azetidin-1-yl)-1-(cyclopropylmethyl)-4-oxo-1,4-dihydroquinoline-3-carboxylic acid (197);

(E)-6-(6-(2-(5-cyclopropyl-3-(3,5-dichloropyridin-4-yl)isoxazol-4-yl)vinyl)-3-azabicyclo[3.1.0]hexan-3-yl)-8-fluoro-4-methoxyquinoline-2-carboxylic acid (198);

6-(6-((E)-2-(5-cyclopropyl-3-(2-(trifluoromethyl)phenyl)isoxazol-4-yl)vinyl)-3-azabicyclo[3.1.0]hexan-3-yl)-4-((1R,3R)-3-fluorocyclobutoxy)quinoline-2-carboxylic acid (199);

(E)-6-(6-(2-(5-cyclopropyl-3-(3,5-dichloropyridin-4-yl)isoxazol-4-yl)vinyl)-3-azabicyclo[3.1.0]hexan-3-yl)-4-(2,2-difluoroethoxy)quinoline-2-carboxylic acid (200);

(E)-6-(3-(2-(5-cyclopropyl-3-(2-(trifluoromethyl)phenyl)isoxazol-4-yl)vinyl)azetidin-1-yl)-1-methyl-1H-indole-3-carboxylic acid (201);

(E)-6-(6-(2-(5-cyclopropyl-3-(3,5-dichloropyridin-4-yl)isoxazol-4-yl)vinyl)-3-azabicyclo[3.1.0]hexan-3-yl)-4-(methoxy-d3)quinoline-2-carboxylic acid (202);

6-(6-((E)-2-(5-cyclopropyl-3-(3,5-dichloropyridin-4-yl)isoxazol-4-yl)vinyl)-3-azabicyclo[3.1.0]hexan-3-yl)-4-((1S,3S)-3-fluorocyclobutoxy)quinoline-2-carboxylic acid (203);

6-(6-((E)-2-(5-cyclopropyl-3-(3,5-dichloropyridin-4-yl)isoxazol-4-yl)vinyl)-3-azabicyclo[3.1.0]hexan-3-yl)-4-((1R,3R)-3-fluorocyclobutoxy)quinoline-2-carboxylic acid (204);

(E)-4'-(3-(2-(5-cyclopropyl-3-(2-(trifluoromethyl)phenyl)isoxazol-4-yl)vinyl)azetidin-1-yl)-[1,1'-biphenyl]-4-carboxylic acid (205);

(E)-6-(3-(2-(5-cyclopropyl-3-(2-(trifluoromethoxy)phenyl)isoxazol-4-yl)vinyl)azetidin-1-yl)-4-methoxyquinoline-2-carboxylic acid (206);

(E)-4'-(3-(2-(5-cyclopropyl-3-(2-(trifluoromethyl)phenyl)isoxazol-4-yl)vinyl)azetidin-1-yl)-[1,1'-biphenyl]-3-carboxylic acid (207);

(E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-4-yl)-5-methoxybenzoic acid (208);

(E)-6-(6-(2-(5-cyclopropyl-3-(3,5-dichloropyridin-4-yl)isoxazol-4-yl)vinyl)-3-azabicyclo[3.1.0]hexan-3-yl)-1-methyl-1H-pyrrolo[3,2-b]pyridine-3-carboxylic acid (209);

(E)-3-(3-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-5-yl)-5-methoxybenzoic acid (210);

(E)-6-(6-(2-(5-cyclopropyl-3-(2-(trifluoromethyl)phenyl)isoxazol-4-yl)vinyl)-3-azabicyclo[3.1.0]hexan-3-yl)-1-methyl-1H-pyrrolo[3,2-b]pyridine-3-carboxylic acid (211);

(E)-6-(6-(2-(5-cyclopropyl-3-(2,6-dichlorophenyl)isoxazol-4-yl)vinyl)-3-azabicyclo[3.1.0]hexan-3-yl)-2-(cyclopropylmethyl)-2H-indazole-3-carboxylic acid (212);

(E)-6-(6-(2-(5-cyclopropyl-3-(2,6-dichlorophenyl)isoxazol-4-yl)vinyl)-3-azabicyclo[3.1.0]hexan-3-yl)-1-(cyclopropylmethyl)-1H-indazole-3-carboxylic acid (213);

(E)-3-(5-(6-(2-(5-cyclopropyl-3-(3,5-dichloropyridin-4-yl)isoxazol-4-yl)vinyl)-3-azabicyclo[3.1.0]hexan-3-yl)-1,2,4-thiadiazol-3-yl)-5-methoxybenzoic acid (214);

(E)-6-(3-(2-(5-cyclopropyl-3-(2-(trifluoromethyl)phenyl)isoxazol-4-yl)vinyl)azetidin-1-yl)-8-fluoro-4-methoxyquinoline-2-carboxylic acid (215);

(E)-3-(2-(6-(2-(5-cyclopropyl-3-(3,5-dichloropyridin-4-yl)isoxazol-4-yl)vinyl)-3-azabicyclo[3.1.0]hexan-3-yl)thiazol-5-yl)-5-methoxybenzoic acid (216);

(E)-4-cyclopropoxy-6-(3-(2-(3-(2-(trifluoromethoxy)phenyl)-5-(trifluoromethyl)isoxazol-4-yl)vinyl)azetidin-1-yl)quinoline-2-carboxylic acid (217);

(E)-3-(5-(6-(2-(5-cyclopropyl-3-(3,5-dichloropyridin-4-yl)isoxazol-4-yl)vinyl)-3-azabicyclo[3.1.0]hexan-3-yl)-1,3,4-oxadiazol-2-yl)benzoic acid (218);

(E)-4'-(3-(2-(5-cyclopropyl-3-(3,5-dichloropyridin-4-yl)isoxazol-4-yl)vinyl)azetidin-1-yl)-5-methoxy-[1,1'-biphenyl]-3-carboxylic acid (219);

(E)-1-(4-(3-(2-(5-cyclopropyl-3-(3,5-dichloropyridin-4-yl)isoxazol-4-yl)vinyl)azetidin-1-yl) phenyl)-1H-pyrazole-4-carboxylic acid (220);

(E)-3-(5-(3-(2-(5-cyclopropyl-3-(2-(trifluoromethyl)phenyl)isoxazol-4-yl)vinyl)azetidin-1-yl) pyridin-2-yl)-5-methoxybenzoic acid (221);

(E)-3-(6-(3-(2-(5-cyclopropyl-3-(2-(trifluoromethyl)phenyl)isoxazol-4-yl)vinyl)azetidin-1-yl) pyridin-3-yl)-5-methoxybenzoic acid (222)

(E)-3-(5-(6-(2-(5-cyclopropyl-3-(3,5-dichloropyridin-4-yl)isoxazol-4-yl)vinyl)-3-azabicyclo[3.1.0]hexan-3-yl)-1,3,4-thiadiazol-2-yl)-5-methoxybenzoic acid (223);

(E)-3-(6-(3-(2-(5-cyclopropyl-3-(3,5-dichloropyridin-4-yl)isoxazol-4-yl)vinyl)azetidin-1-yl) pyridin-3-yl)-5-(trifluoromethyl)benzoic acid (224);

(E)-3-(6-(3-(2-(5-cyclopropyl-3-(2-(trifluoromethyl)phenyl)isoxazol-4-yl)vinyl)azetidin-1-yl) pyridin-3-yl)-5-(trifluoromethyl)benzoic acid (225);

(E)-3-(6-(3-(2-(5-cyclopropyl-3-(2-(trifluoromethyl)phenyl)isoxazol-4-yl)vinyl)azetidin-1-yl) pyridin-3-yl)-5-fluorobenzoic acid (226); or (E)-3-(5-(3-(2-(5-cyclopropyl-3-(2-(trifluoromethyl)phenyl)isoxazol-4-yl)vinyl)azetidin-1-yl) pyridin-2-yl)-5-(trifluoromethyl)benzoic acid (227).

10. A pharmaceutical composition comprising a pharmaceutically acceptable carrier and a compound according to claim 1, or a pharmaceutically acceptable salt thereof.

11. The compound according to claim 1 or a salt thereof, wherein:

the

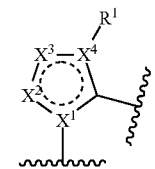

moiety is

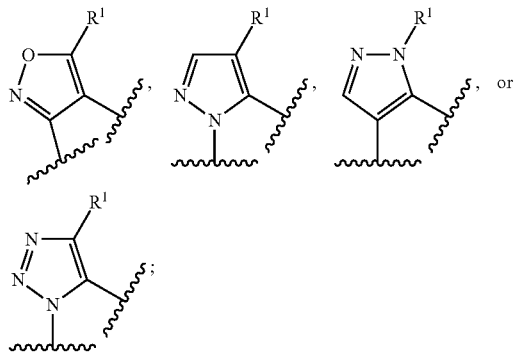

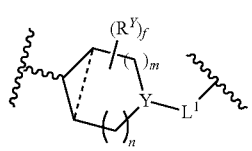

moiety is:

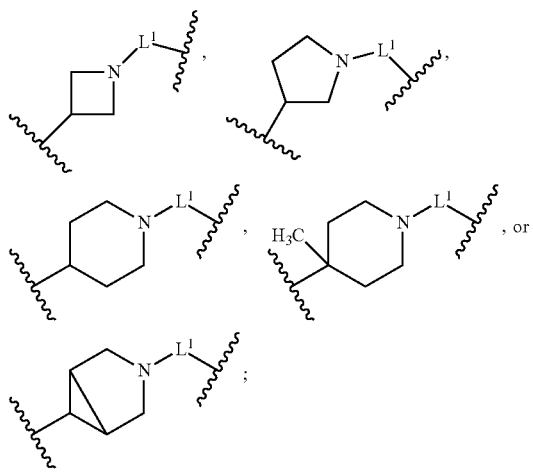

Z is cyclopropyl, phenyl, pyrazolyl, thiazolyl, pyridinyl, pyridazinyl, pyrazinyl, pyrimidinyl, indolyl, indazolyl, benzo[d]thiazolyl, pyrrolo[2,3-d]pyrimidinyl, pyrrolo[2,3-b]pyridinyl, pyrrolo[3,2-b]pyridinyl, benzo[d]oxazolyl, benzo[d]imidazolyl, pyrrolo[2,1-f]triazinyl, pyrazolo[4,3-b]pyridinyl, pyrrolo[2,1-f]triazinyl, pyrazolo[4,3-b]pyridinyl, thiazolo[5,4-b] pyridinyl, benzo[d]isothiazolyl, pyrazolo[1,5-a]pyridinyl, quinolinyl, isoquinolinyl, quinolinonyl, cinnolinyl, quinoxalinyl or 1,5-naphthyridinyl, $L^1$ is a covalent bond, phenyl, thiazolyl, oxadiazolyl, or thiadiazolyl;

$L^2$ is a covalent bond;

$L^3$ is a covalent bond or —$CH_2$—;

$R^Z$ is —CN, —C(O)$NH_2$, —C(O)NHS(O)$_2CH_3$, or

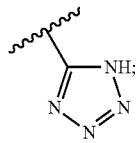

$R^1$ is —$CF_3$ or cyclopropyl;

$R^2$ is phenyl, pyridinyl, independently substituted with 0 to 5 $R^{10}$;

$R^3$ is hydrogen;

$R^4$ is hydrogen or —$CH_3$;

each $R^8$ is independently F, Cl, —$CH_3$, or —$CF_3$; and each $R^{10}$ is independently Cl, —$CH_3$, —$CH_2CH_3$, —$CH_2$(cyclopropyl), —$CF_3$, —$CH_2OCH_3$, —$OCH_3$, —$OCD_3$, —$OCH_2CH_3$, —$OCH(CH_3)_2$, —$O(CH(CH_3)_2)$, —$OCHF_2$, —$OCF_3$, —$OCH_2CHF_2$, —$OCH_2CH_2OCH_3$, —O(cyclopropyl), —O(cyclobutyl), —O(fluorocyclobutyl), —O(difluorocyclobutyl), —O(oxetanyl), —O(tetrahydrofuranyl), or —$OCH_2$(methoxphenyl).

* * * * *

UNITED STATES PATENT AND TRADEMARK OFFICE
CERTIFICATE OF CORRECTION

PATENT NO. : 11,168,079 B2
APPLICATION NO. : 16/759660
DATED : November 9, 2021
INVENTOR(S) : Joseph Carpenter et al.

It is certified that error appears in the above-identified patent and that said Letters Patent is hereby corrected as shown below:

On the Title Page

Column 2 (Abstract), delete "famesoid" and insert -- farnesoid --, therefor.

In the Claims

Claim 1, Column 204, Line 3, delete "NR", S(O)₂," and insert -- $NR^{17}$, —S(O)$_2$—, --, therefor.

Claim 1, Column 205, Line 51, delete "$NR^bC(O)R^b$;" and insert -- —$NR^bC(O)R^b$, --, therefor.

Claim 1, Column 205, Line 53, delete "$NR^bC(NR^b)NR^cR^c$;" and insert -- —$NR^bC(NR^b)NR^cR^c$; --, therefor.

Claim 7, Column 207, Line 51 (Approx.), delete "bond:" and insert -- bond; --, therefor.

Claim 8, Column 208, Lines 39-43 (Approx.), delete

"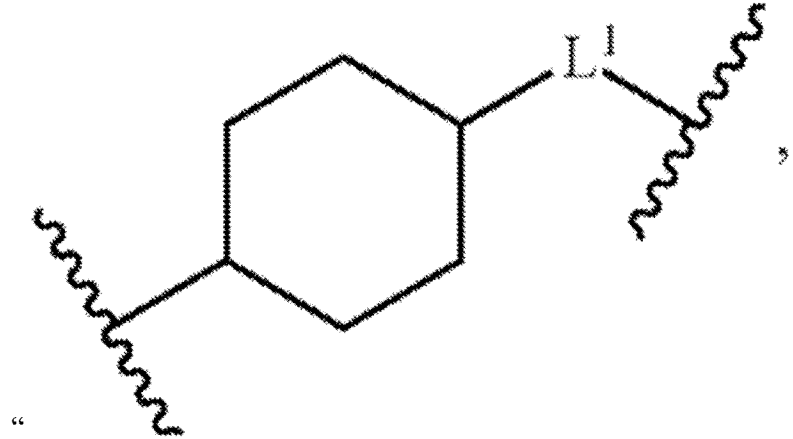" insert

Signed and Sealed this
Sixteenth Day of September, 2025

Coke Morgan Stewart
*Acting Director of the United States Patent and Trademark Office*

-- 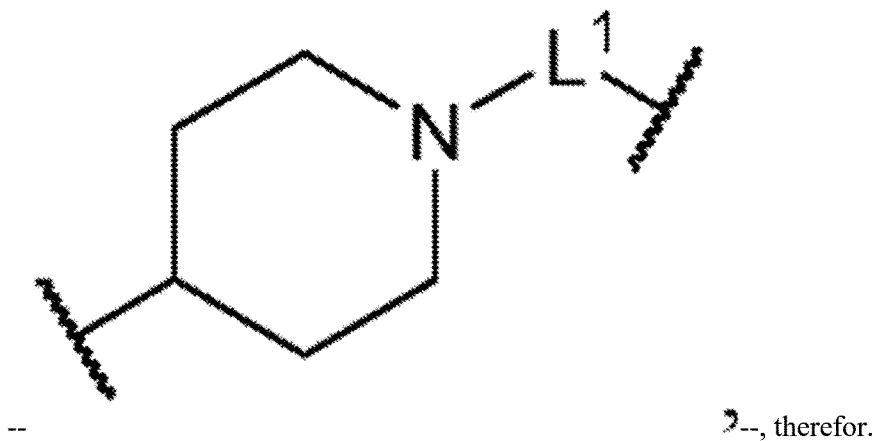 --, therefor.
Claim 8, Column 208, Line 60 (Approx.), delete "pyrrolo[2,3-b] pyridinyl," and insert -- pyrrolo[2,3-b]pyridinyl, --, therefor.
Claim 9, Column 213, Line 64, after "(104)" insert -- ; --.
Claim 9, Column 219, Line 51, after "(222)" insert -- ; --.
Claim 11, Column 221, Line 1, delete "thiazolo[5,4-b] pyridinyl," and insert -- thiazolo[5,4-b]pyridinyl, --, therefor.
Claim 11, Column 221, Line 32 (Approx.), delete "(methoxphenyl)." and insert -- (methoxyphenyl). --, therefor.